(12) United States Patent
Romo et al.

(10) Patent No.: US 11,839,704 B2
(45) Date of Patent: *Dec. 12, 2023

(54) ADAPTIVE MULTIVECTOR ILLUMINATION DELIVERY SYSTEM

(71) Applicant: Leviant, Inc., Hawthorne, NY (US)

(72) Inventors: Luis F. Romo, New York,, NY (US); Wladyslaw Kowalski, Long Island City, NY (US); Audrey McNicholas, Long Island City, NY (US)

(73) Assignee: Leviant, Inc., Hawthorne, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/058,261

(22) Filed: Nov. 22, 2022

(65) Prior Publication Data

US 2023/0149590 A1 May 18, 2023

Related U.S. Application Data

(63) Continuation of application No. 16/962,466, filed as application No. PCT/US2019/013817 on Jan. 16, 2019, now Pat. No. 11,511,012.

(60) Provisional application No. 62/617,755, filed on Jan. 16, 2018.

(51) Int. Cl.
*A61L 9/18* (2006.01)

(52) U.S. Cl.
CPC ............. *A61L 9/18* (2013.01); *A61L 2209/12* (2013.01); *A61L 2209/15* (2013.01)

(58) Field of Classification Search
CPC ..... A61L 2/08; A61L 2/10; A61L 9/18; A61L 9/20; A61L 2209/12; A61L 2209/15
See application file for complete search history.

(56) References Cited

U.S. PATENT DOCUMENTS

| | | |
|---|---|---|
| 4,448,750 A | 5/1984 | Fuesting |
| 5,080,209 A | 1/1992 | Yurko |
| 5,145,366 A | 9/1992 | Janhunen |
| 5,272,848 A | 12/1993 | Maas |
| 5,533,305 A | 7/1996 | Bielecki |
| 5,891,399 A | 4/1999 | Owesen |
| 6,656,424 B1 | 12/2003 | Deal |
| 6,911,177 B2 | 6/2005 | Deal |

(Continued)

FOREIGN PATENT DOCUMENTS

| | | |
|---|---|---|
| AU | 2013361188 | 7/2015 |
| AU | 2013361188 | 5/2017 |

(Continued)

OTHER PUBLICATIONS

International Search Report and Written Opinion in PCT/US2019/013817 dated May 13, 2019, 26 pages.

(Continued)

*Primary Examiner* — Timothy C Cleveland

(74) *Attorney, Agent, or Firm* — Nixon Peabody LLP

(57) ABSTRACT

An ultraviolet emitting system for sanitizing a target volume can include a plurality of adjustably positionable light sources having a collapsed position and the expanded position. The light sources of the plurality of adjustably positionable light sources can be configured to emit ultraviolet light in a substantially homogenous irradiance within the target volume in any position between the collapsed position and the expanded position.

20 Claims, 129 Drawing Sheets

(56) References Cited

U.S. PATENT DOCUMENTS

| | | |
|---|---|---|
| 6,911,178 B2 | 6/2005 | Rodkey |
| 6,911,179 B2 | 6/2005 | Ando |
| 7,459,964 B2 | 12/2008 | Dosho |
| 7,829,016 B2 | 11/2010 | Deal |
| 8,067,750 B2 | 11/2011 | Deal |
| D684,671 S | 6/2013 | Betancourt |
| 8,575,567 B2 | 11/2013 | Lyslo |
| 8,907,304 B2 | 12/2014 | Kreitenberg |
| 9,044,521 B2 | 6/2015 | Farren |
| 9,107,973 B1 | 8/2015 | Robinson |
| 9,165,756 B2 | 10/2015 | Stibich |
| 9,345,798 B2 | 5/2016 | Rapani |
| 9,675,720 B2 | 6/2017 | Romo |
| 10,376,604 B2 | 8/2019 | Romo |
| 10,894,102 B2 | 1/2021 | Romo |
| 11,511,012 B2 * | 11/2022 | Romo ................. A61L 2/10 |
| 2002/0085947 A1 | 7/2002 | Deal |
| 2003/0018373 A1 | 1/2003 | Eckhardt |
| 2003/0202902 A1 | 10/2003 | Elliott |
| 2004/0056201 A1 | 3/2004 | Fink |
| 2005/0201910 A1 | 9/2005 | Shou |
| 2006/0175554 A1 | 8/2006 | Riddell |
| 2007/0157385 A1 | 7/2007 | Lemire |
| 2007/0194255 A1 | 8/2007 | Garcia |
| 2007/0274879 A1 | 11/2007 | Milikin |
| 2008/0056933 A1 | 3/2008 | Moore |
| 2008/0178543 A1 | 7/2008 | Maas |
| 2008/0213128 A1 | 9/2008 | Rudy |
| 2009/0272029 A1 | 11/2009 | Aiking |
| 2011/0044848 A1 | 2/2011 | Wright |
| 2011/0069646 A1 | 3/2011 | Murray et al. |
| 2011/0172810 A1 | 7/2011 | Milodzinski |
| 2011/0215261 A1 | 9/2011 | Lyslo |
| 2011/0243789 A1 | 10/2011 | Roberts |
| 2011/0259864 A1 | 10/2011 | Galietti |
| 2012/0074334 A1 | 3/2012 | Milligan |
| 2012/0305787 A1 | 12/2012 | Henson |
| 2013/0002445 A1 | 1/2013 | Stibich |
| 2015/0086420 A1 | 3/2015 | Trapani |
| 2015/0192689 A1 | 7/2015 | Li |
| 2015/0246148 A1 | 9/2015 | Blechschmidt |
| 2015/0284206 A1 | 10/2015 | Michelena |
| 2015/0367008 A1 | 12/2015 | Romo |
| 2016/0021860 A1 | 1/2016 | Fortney |
| 2016/0128526 A1 | 5/2016 | Dobrinsky |
| 2016/0354503 A1 | 12/2016 | Hutchens |
| 2017/0049915 A1 | 2/2017 | Brais |
| 2017/0112953 A1 | 4/2017 | Dayton |
| 2017/0112954 A1 | 4/2017 | Dayton |
| 2017/0216468 A1 | 8/2017 | Romo |
| 2017/0246331 A1 * | 8/2017 | Lloyd ................. A61L 2/10 |
| 2017/0304473 A1 | 10/2017 | Farren |
| 2017/0367785 A1 | 12/2017 | Munari |
| 2018/0140727 A1 | 5/2018 | Romo |
| 2018/0256764 A1 | 9/2018 | Kreitenberg |
| 2019/0365938 A1 | 12/2019 | Romo |

FOREIGN PATENT DOCUMENTS

| | | |
|---|---|---|
| AU | 20017213522 | 3/2019 |
| CN | 2155875 | 2/1994 |
| CN | 2621044 | 6/2004 |
| CN | 2688291 | 3/2005 |
| CN | 206063449 | 4/2017 |
| DE | 20016160 | 11/2000 |
| EP | 2934606 | 10/2015 |
| EP | 2772272 | 3/2017 |
| EP | 3354289 | 8/2018 |
| JP | 04091794 | 8/1992 |
| JP | H07289616 | 11/1995 |
| JP | 2001327590 | 11/2001 |
| JP | 2005168858 | 6/2005 |
| JP | 2009504244 | 2/2009 |
| JP | 2014162474 | 8/2014 |
| JP | 2014523257 | 9/2014 |
| JP | 2016506274 | 3/2016 |
| JP | 2017532138 | 11/2017 |
| JP | 6385363 | 9/2018 |
| KR | 20150028153 | 3/2015 |
| KR | 101767055 | 8/2017 |
| TW | 381489 Y | 6/1999 |
| TW | 556556 Y | 10/2003 |
| WO | WO 199317195 | 9/1993 |
| WO | WO 199639820 | 12/1996 |
| WO | WO 2001051098 | 7/2001 |
| WO | WO 2008010684 | 1/2008 |
| WO | WO 2010115183 | 10/2010 |
| WO | WO 2012142427 | 10/2012 |
| WO | WO 2014100493 | 6/2014 |
| WO | WO 2015012592 | 1/2015 |
| WO | WO 2019143699 | 8/2019 |

OTHER PUBLICATIONS

Authorized office Blaine R. Copenheaver, International Search Report/Written Opinion in PCT/US2019/013817 dated May 13, 2019, 27 pages.

Authorized office Walter Griffin, International Preliminary Report on Patentability under Chapter 2 in PCT/US2019/013817 dated Apr. 2, 2020, 155 pages.

* cited by examiner

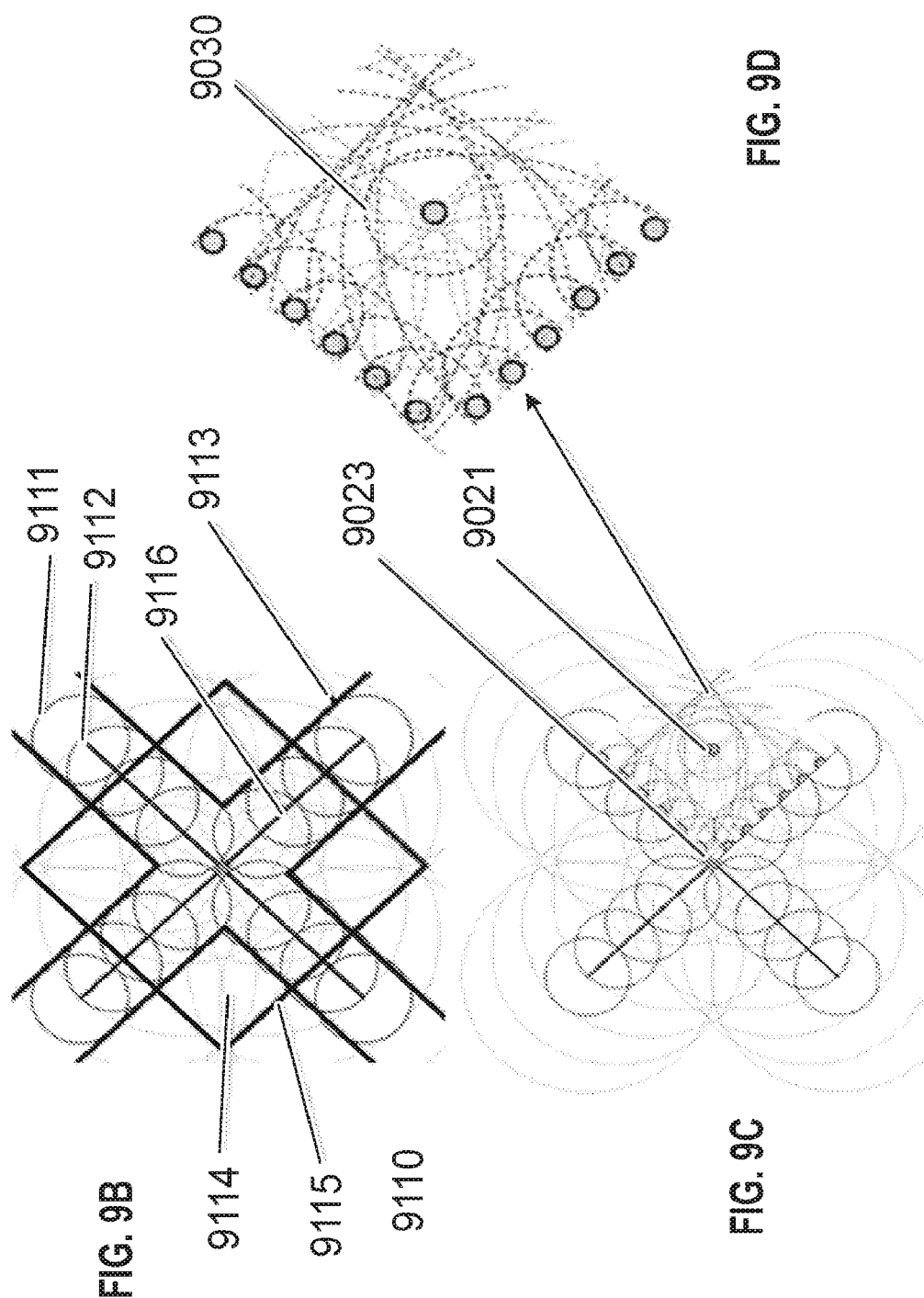

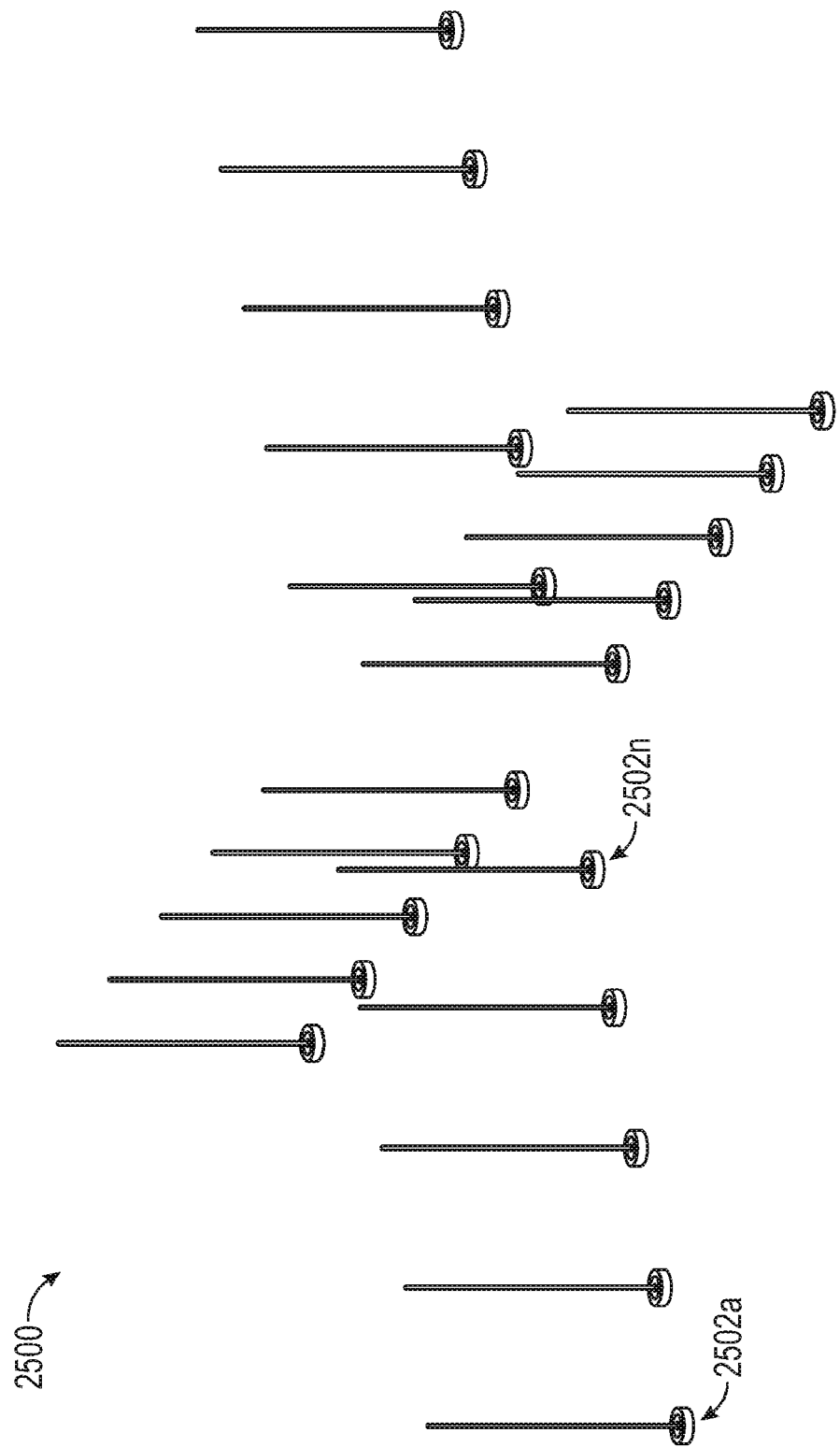

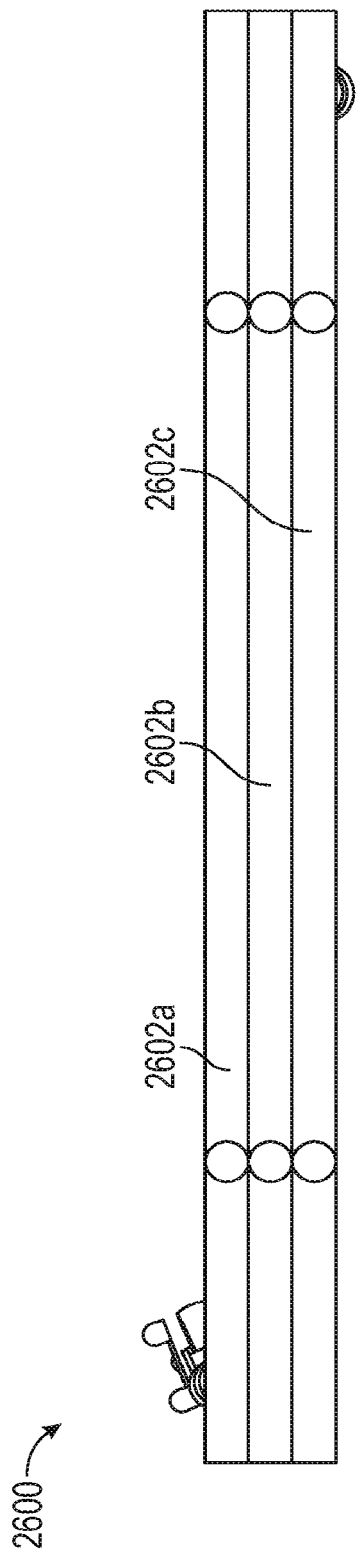

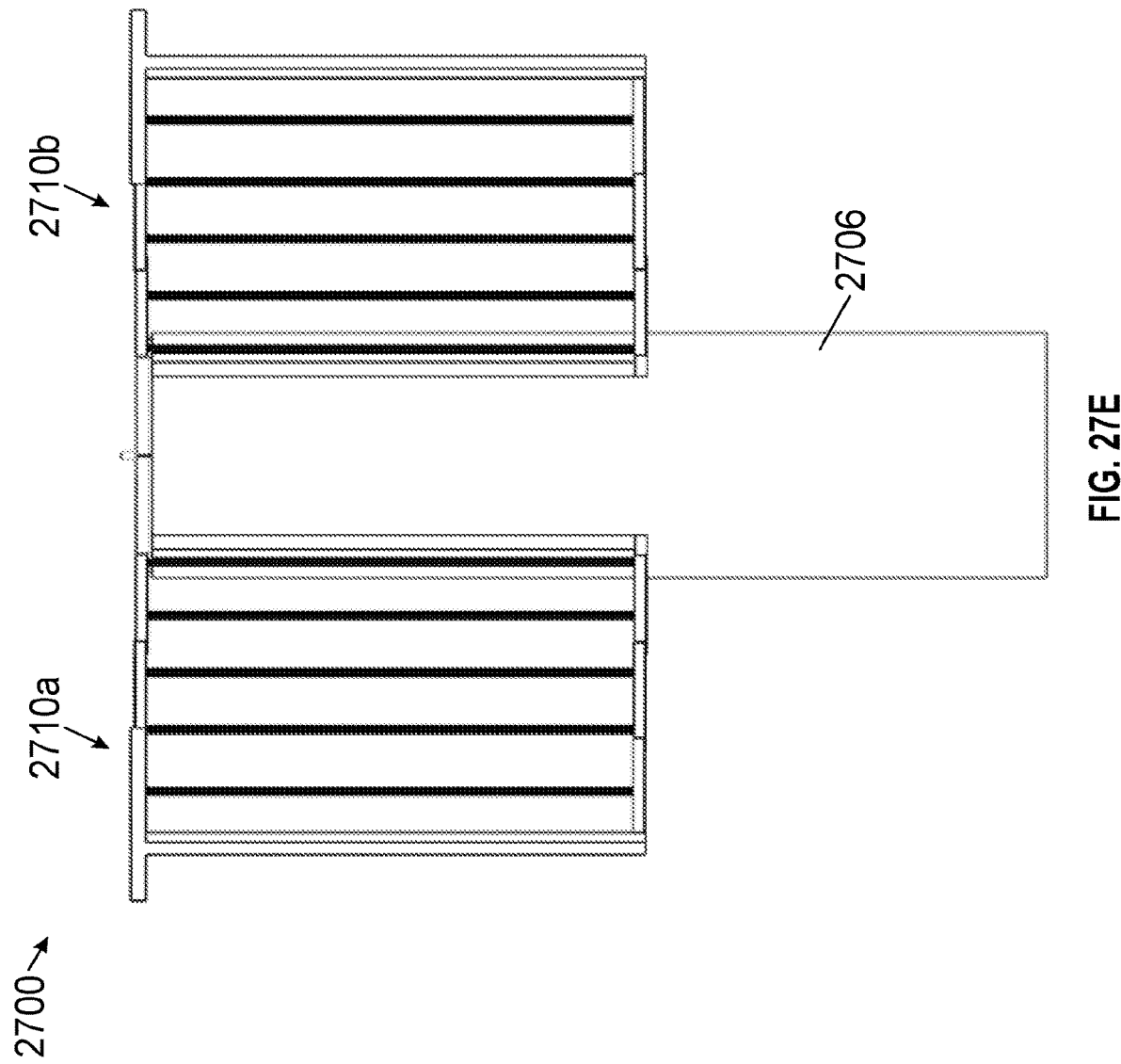

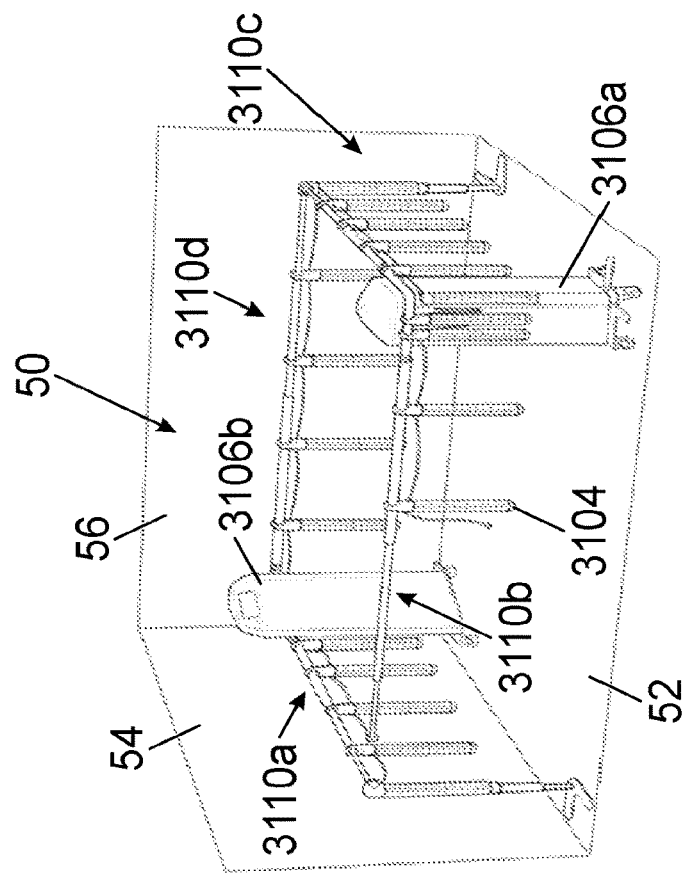
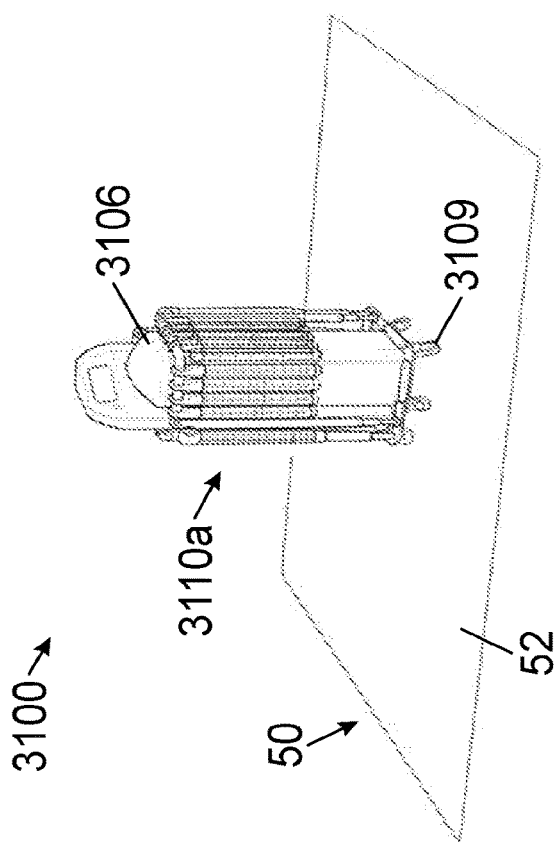
FIG. 31B
FIG. 31A

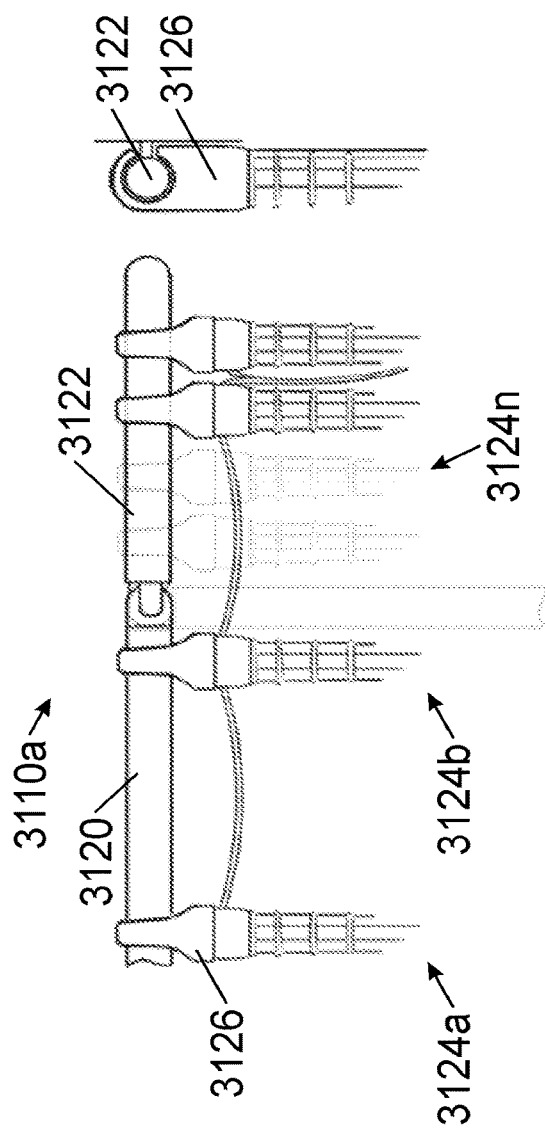
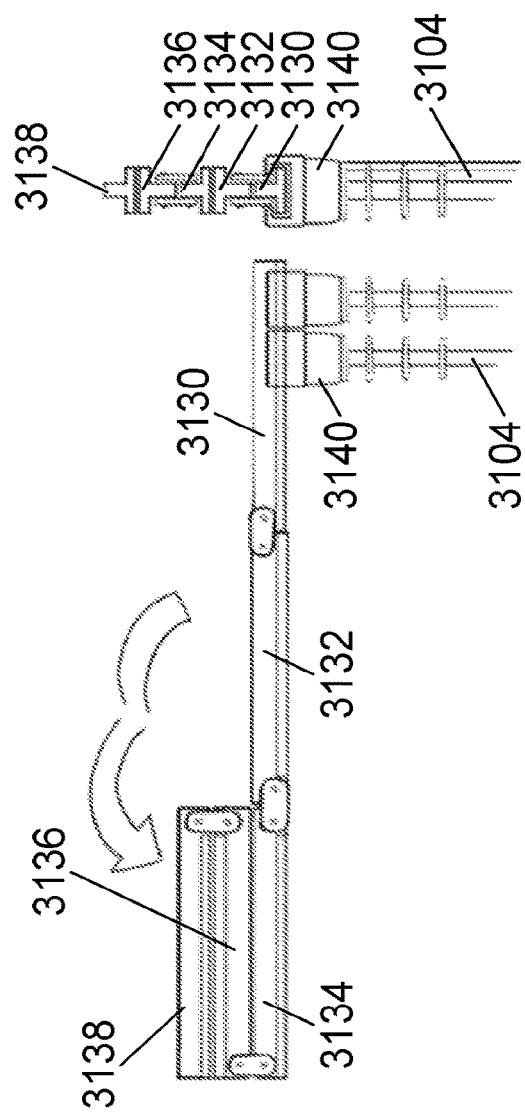

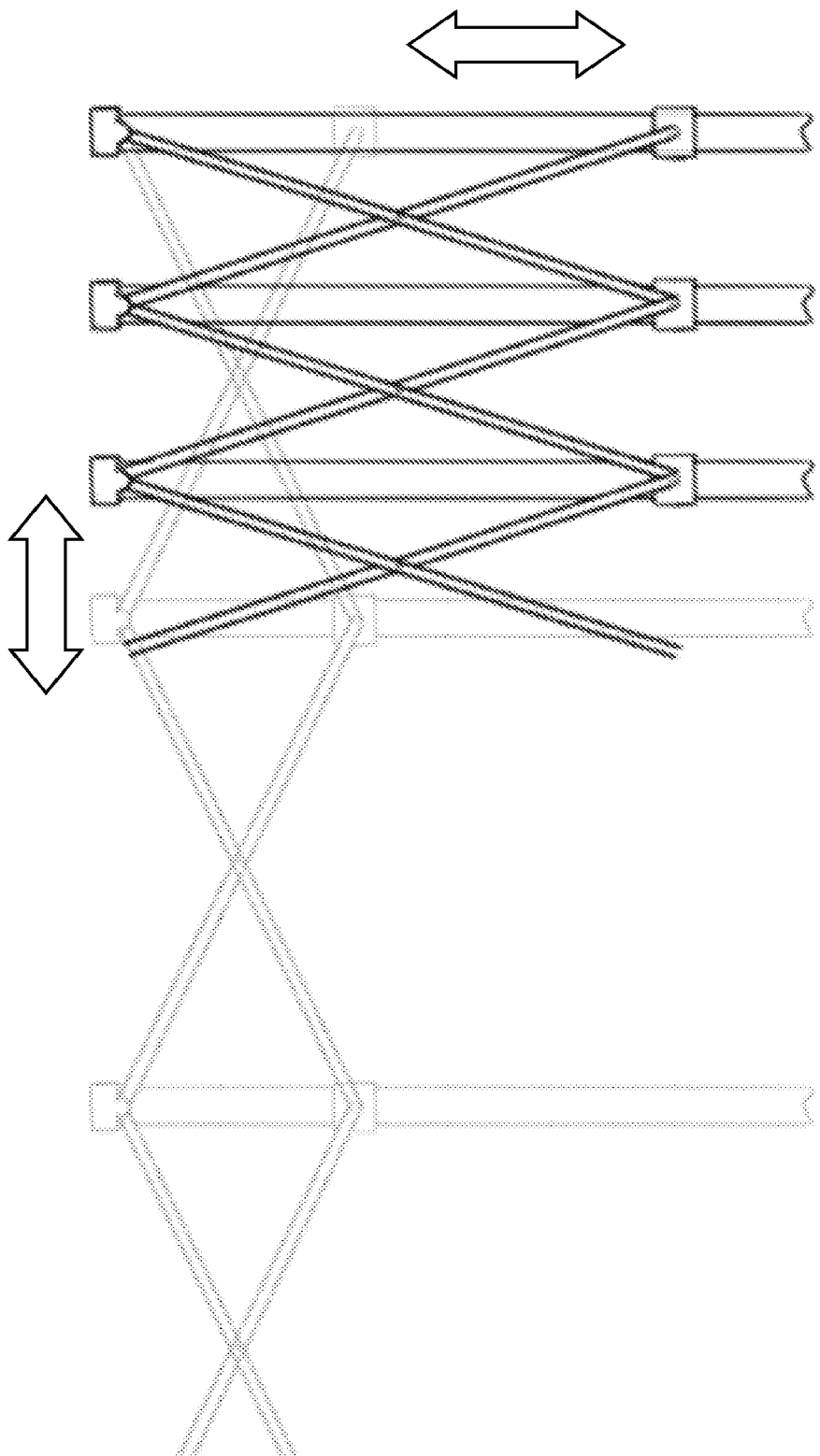

| Organisms | Time 0 (no exposure) | Time 15 sec | Time 30 sec | Time 60 sec | Time 90 sec | Time 180 sec |
|---|---|---|---|---|---|---|
| Carbapenem-resistant Klebsiella pneumoniae | $7.1 \pm 0.03 \times 10^4$ | $2.1 \pm 0.2 \times 10^3$ | $0.9 \pm 0.1 \times 10^3$ | 0 | 0 | 0 |
| Multidrug-resistant Pseudomonas aeruginosa | $1.7 \pm 0.5 \times 10^3$ | $5.0 \pm 2.9$ | 0 | 0 | 0 | 0 |
| C. auris | $3.4 \pm 0.8 \times 10^3$ | $2.1 \pm 0.05 \times 10^3$ | $1.1 \pm 0.2 \times 10^3$ | $20 \pm 11$ | 0 | 0 |

FIG.40C

| Organisms | Time 0 (no exposure) | Time 15 sec | Time 30 sec | Time 60 sec | Time 90 sec | Time 180 sec |
|---|---|---|---|---|---|---|
| Carbapenem-resistant Klebsiella pneumoniae | $7.1 \pm 0.03 \times 10^4$ | $8.3 \pm 1.0 \times 10^3$ | $8.0 \pm 0.9 \times 10^3$ | $0.5 \pm 0.1 \times 10^3$ | $110 \pm 51$ | 0 |
| Multidrug-resistant Pseudomonas aeruginosa | $1.7 \pm 0.5 \times 10^3$ | $0.12 \pm 0.03 \times 10^3$ | $40 \pm 18$ | 0 | 0 | 0 |
| C. auris | $3.4 \pm 0.8 \times 10^3$ | $3.3 \pm 0.4 \times 10^3$ | $2.2 \pm 0.1 \times 10^3$ | $0.5 \pm 0.02 \times 10^3$ | $145 \pm 49$ | 0 |

FIG.40D

Table 1: Summary of Photometric Readings on Vertical Wall

| WALL | Side 1 | | Side 2 | | Side 3 | | Side 4 | |
|---|---|---|---|---|---|---|---|---|
| Location | B | A | B | A | B | A | B | A |
| | uW/cm2 | uW/cm2 | uW/cm2 | uW/cm2 | uW/cm2 | uW/cm2 | uW/cm2 | uW/cm2 |
| ILT Avg | 492 | 520 | 423 | 532 | 356 | 408 | 494 | 471 |
| General Avg | 457 | 520 | 471 | 551 | 450 | 476 | 420 | 402 |
| Total Average ILT Readings for Wall | | | | | | 462 | uW/cm2 | |
| Total Average General UVC DLM Readings for Wall | | | | | | 468 | uW/cm2 | |

FIG. 41C

Table 2: Summary of Photometric Readings on Floor

| FLOOR | Side 1 | | Side 2 | | Side 3 | | Side 4 | |
|---|---|---|---|---|---|---|---|---|
| Location | C | D | C | D | C | D | C | D |
| | uW/cm2 | uW/cm2 | uW/cm2 | uW/cm2 | uW/cm2 | uW/cm2 | uW/cm2 | uW/cm2 |
| ILT Avg | * | 300 | 279 | 379 | 250 | 368 | 235 | 390 |
| General Avg | 190 | 356 | 240 | 376 | 193 | 372 | 177 | 373 |
| Total Average ILT 2400 Readings for Floor | | | | | | 314 | uW/cm2 | |
| Total Average General UVC DLM Readings for Floor | | | | | | 285 | uW/cm2 | |

FIG. 41D

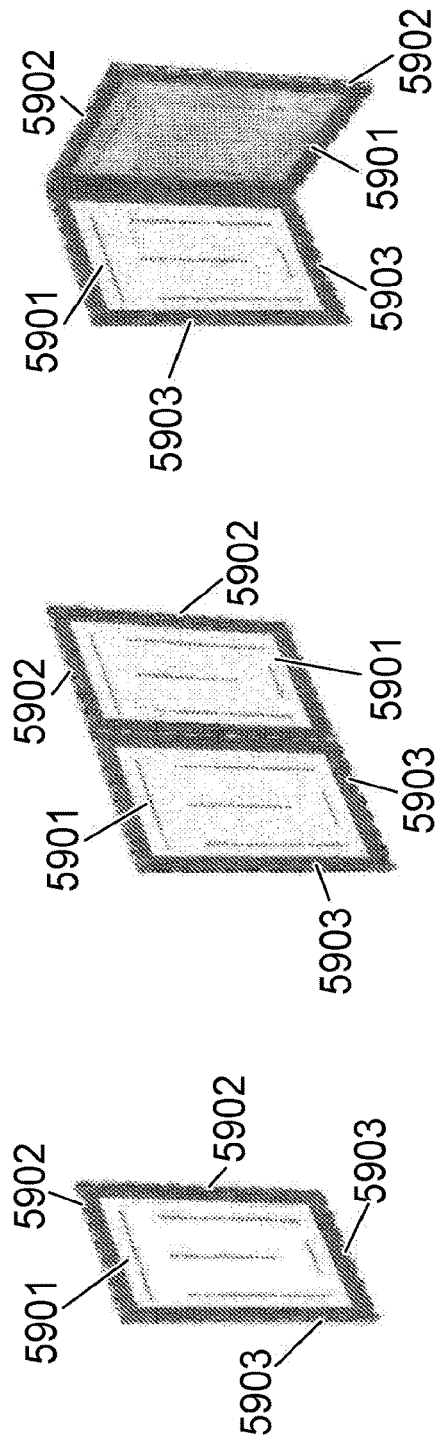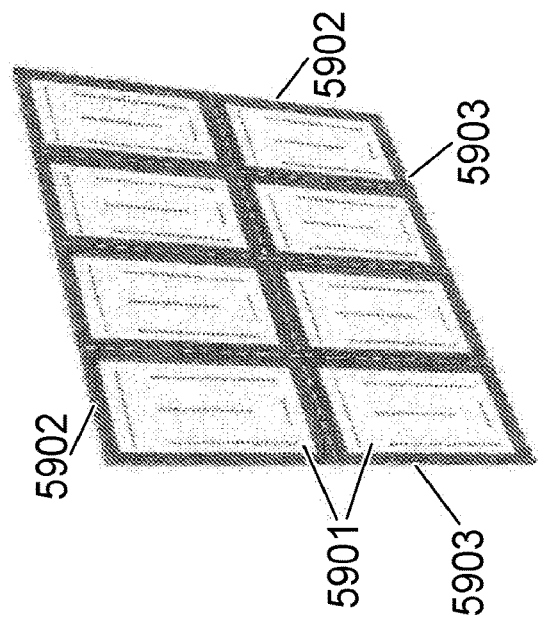
FIG. 59A  FIG. 59B  FIG. 59C  FIG. 59D

ADAPTIVE MULTIVECTOR ILLUMINATION DELIVERY SYSTEM

CROSS-REFERENCE TO RELATED APPLICATIONS

This patent application is a continuation of U.S. Nonprovisional application Ser. No. 16/962,466, filed on Jul. 15, 2020, now allowed, which is a U.S. National Stage Entry of International Application No. PCT/US2019/013817, filed on Jan. 16, 2019, which claims priority to and the benefit of U.S. Provisional Patent Application No. 62/617,755, entitled "ADAPTIVE MULTIVECTOR ILLUMINATION DELIVERY SYSTEM, NETWORK AND VOLUME DISINFECTION MATRIX," filed on Jan. 16, 2018, each of which is hereby incorporated by reference herein in its entirety.

BACKGROUND OF THE INVENTION

The present application generally relates to medical systems, devices and methods, and more particularly relates to the sanitization, disinfection, and sterilization of medical systems, medical devices, and areas of medical facilities and other areas where the control and prevention of disease is desired. Sanitization is a general term often used in relation to ultraviolet light systems and that formally describes agents that reduce bacterial contaminants to safe levels. Disinfection is a more commonly used and appropriate term for ultraviolet light systems and it describes a process that eliminates many or all pathogenic microorganisms, on inanimate objects. Sterilization is formally defined as a validated process used to render a product free of all forms of viable microorganisms. A surface is defined as sterile if it is free from all living microorganism, but the verification of sterility is subject to limitations of test sensitivity and practicality.

Microbial contamination is a global concern within many industries, especially in the healthcare industry. It can cost countries up to billions of dollars in expenses per year, and, more importantly, the contaminant pathogens plague private and public (e.g. healthcare) settings and surroundings. These contaminated surroundings can lead to infections and may ultimately cause deaths. Furthermore, many communicable diseases are transmitted through contact with contaminated areas and surfaces. The types and seriousness of communicable diseases transmitted in this manner are varied. For example, viral and bacterial diseases alike can be communicated by physical contact with surfaces upon which the infectious agents may reside or settle. Further, there is an increasing awareness and concern worldwide of the possibility of widespread outbreaks, or even pandemics, of communicable disease; these concerns stem in part from possible spontaneous mutations of influenza and other viruses, and emergence of new diseases as well as the increasing resistance of bacterial strains to conventional and even to newly-developed and powerful antibiotics.

Existing disinfection devices and systems for health care facilities may be deficient in terms of providing adequate levels of disinfection and reduced disinfection need. For example, liquid chemical technologies have been utilized for the purpose of anti-microbial and disinfection treatment. However, liquid technologies have, in some cases, failed to perform, resulting in patient infections and spread of antibiotic resistant organisms. Moreover, there is a concurrent need for augmentation or even replacement of existing disinfection methods that employ chemicals due to the resistance of certain pathogens like *Clostridium difficile* to traditional chemical disinfectants.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 9A-9D illustrate how the ultraviolet light emits from devices discussed herein, in accordance with at least one example of the present disclosure.

FIGS. 25A-25J illustrate controllably driven bases with program logic, in accordance with at least one example of the present disclosure.

FIGS. 26A-26I illustrate detachable and attachable rails containing ultraviolet sources with coupling mechanisms of a disinfection device, in accordance with at least one example of the present disclosure.

FIGS. 27A-27F illustrate a disinfection device with an expandable ring structure, in accordance with at least one example of the present disclosure.

FIGS. 31A-31D illustrate a disinfection device with a perimeter geometry multi base mechanism, in accordance with at least one example of the present disclosure.

FIGS. 32A-32C illustrate a disinfection device with a perimeter geometry mechanism, in accordance with at least one example of the present disclosure.

FIGS. 40A-40D illustrate disinfection data of the systems discussed herein, in accordance with at least one example of the present disclosure.

FIGS. 41A-41E illustrate irradiance data of the systems discussed herein, in accordance with at least one example of the present disclosure.

FIGS. 59A-59D show examples of self-contained cassettes and the coupling hinges that would be employed in connecting and stacking arrays of cassettes.

DETAILED DESCRIPTION OF THE INVENTION

Figure 1:
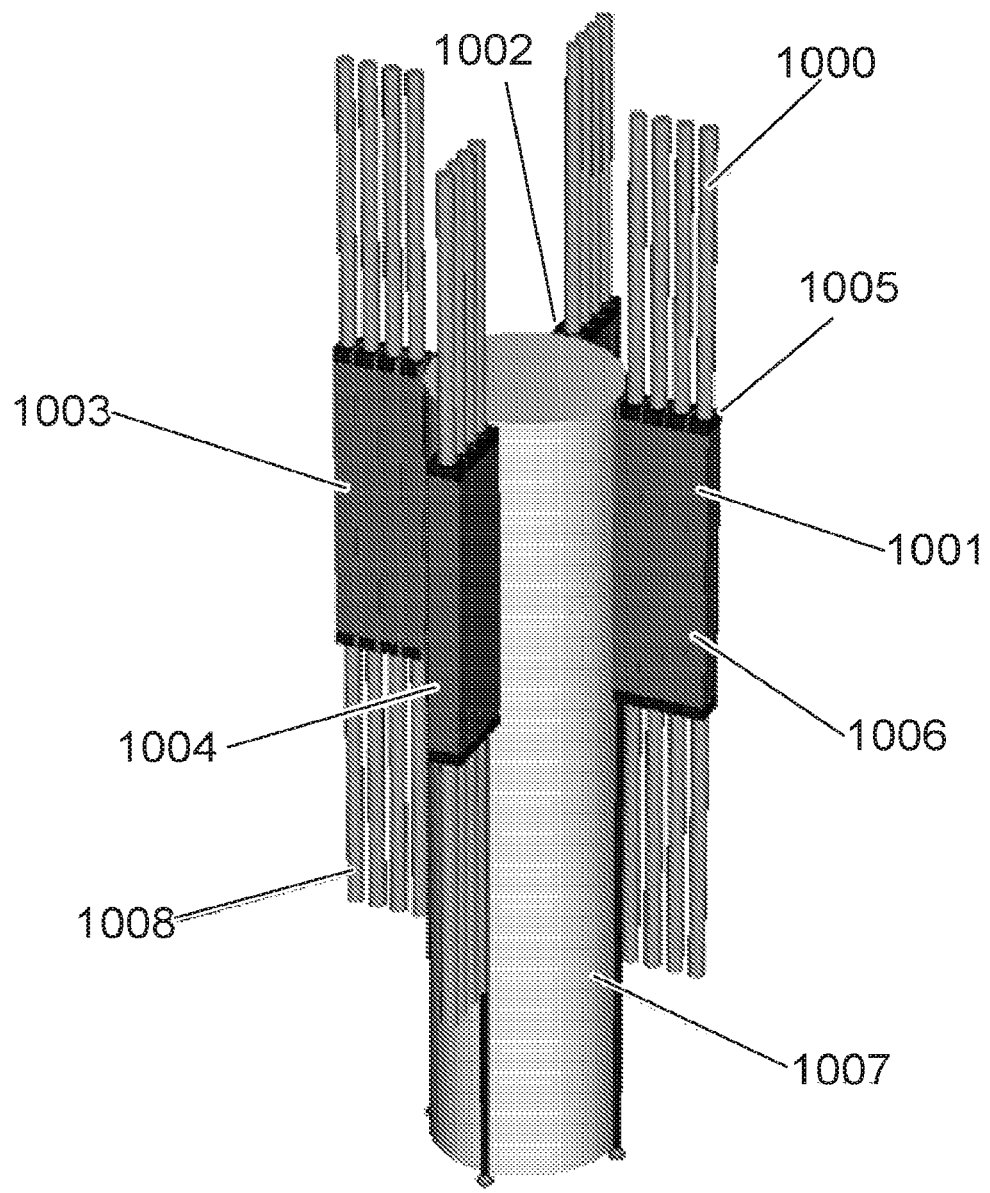
FIG. 1 illustrates a perspective view of a disinfection device in a collapsed compact configuration, in accordance with at least one example of the present disclosure.

Notably, current disinfection technologies that utilize ultraviolet technologies or area ultraviolet disinfection units may not achieve the performance levels nor the proper coverage and exposure to all surfaces necessary to eradicate surface-borne pathogens in medical facilities such that they are competitive with traditional chemical disinfection methods and may not be able to provide complete exposure to every shadowed niche where microbes might reside and escape disinfection. Furthermore, the area ultraviolet disinfection units currently in use often require operating times that negatively impact the schedules and operations of the hospitals in which they are applied. Traditional point source area disinfection systems that have heretofore been used for disinfecting hospital areas often suffer from the performance limitation that the irradiance levels drop off with distance from the ultraviolet source in approximate accordance with the Inverse Square Law (ISL). One example of a point source ultraviolet radiation or light are a single light source or bulb within a target volume or room. Another example is multiple light sources connected to each other in close proximity to each other. Such multiple light sources may be attached to a fixed frame or structure, for example. Examples of these existing disinfection devices, systems, and methods include those disclosed in U.S. Pat. App. Pub. Nos. 2012/0305787, 201710049915, 2008/0213128 and U.S. Pat. Nos. 9,165,756; 8,575,567; 6,656,424; 6,911,177, 6,911,178; 6,911,179; 5,891,399; 9,345,798; and D684671. Other patents and publications which may be related to disinfection devices include U.S. Pat. Nos. 8,907,304; 9,044,521; TW381489Y; TW556556Y; U.S. Pat. No. 7,459,964; CN206063449; WO2010115183; US20150284206; KR101767055: WO2015012592; and KR20150028153.

Thus, a need for improved disinfection devices, systems, and methods for disinfection which may assist in providing disinfected spaces, surfaces, and/or structures, and in combating the spread of diseases that may be communicated via physical contact with contaminated areas. In order for the world to move and adopt alternative light-based technologies, disinfection performance needs to be reliable, consistent and sustainable in a working environment. At least some of these challenges are addressed by the exemplary embodiments disclosed herein.

The above-discussed examples may suffer from variable energy, variable germicidal performance, variable shadowing, variable distances and in combination ultimately errors in performance which is my not produce acceptable results. The parameters listed in the prior art may suffer from a main deficiency pertaining to the drop in light intensity over a certain distance is governed by the Inverse Square Law. This deficiency has a major impact to the efficacy and performance of disinfection using ultraviolet light and can cause a full target volume to be disinfected not to achieve adequate exposure. This can allow microbes, which may reside in a shadowed niche or areas farthest away from ultraviolet sources, to escape disinfection. To compensate for this significant performance limitation, some of the prior art, systems, and methods include increased operating times, combining wavelengths, increases to power and light intensity output or multiple rounds of exposure, which can adversely impact the proper disinfection performance to all the surfaces of interest especially a target volume. The combination of variable energy levels, which dissipate with distance, has major impact on germicidal performance of said prior solutions. Reliance placed on systems using such methods have this significant variability in performance.

Combining the list of variable deficiencies of shadowing, intensity, distance, time, energy as well as variable volume are several limitations that the previous solutions lack, which leaves significant room for improvement of disinfection devices. Volume is the primary variable in the equation of performance with ultraviolet germicidal light in consideration of the Inverse Square Law. Hospitals, doctors' offices, laboratories, classrooms, restrooms, treatment rooms, procedure rooms, operating rooms, scanning rooms, and emergency rooms are all examples of target volumes. All these rooms are essentially target volumes, cube like in nature and of variable volume.

The inventors have recognized that, in order to fundamentally shift toward adoption of alternative non-chemical technologies for the purposes of disinfecting target volumes, all these variables need to be overcome. To address these issues, this disclosure presents solutions including ultraviolet disinfection devices, systems, and methods that specifically intend to create a three-dimensional matrix of distributed ultraviolet energy for which create precise energy via ultraviolet sources disposed on one or more expandable and contractible arms to disinfect a target volume. The one or more expandable and contractible arms allows for portability while easily providing for a customizable disinfection exposure matrix, including large open areas (e.g., large rooms) or smaller constrained areas (e.g., corners, areas with interferences, etc.). The arms may also conveniently allow for only one setup to disinfect an entire room (e.g., emergency room, ICU room, etc.) in a rapid single light exposure cycle, reducing operating time. The matrix of distributed ultraviolet energy also provides a more effective way of efficiently disinfecting all room surfaces and fixed equipment within the room or target volume by directing the ultraviolet energy from multiple angles and directions so as to minimize or reduce shadowing effects and maximizing energy distribution, thereby reducing or eliminating niches wherein microbial combination might otherwise survive the disinfection process. These devices and methods are further easily integrated within, for example, healthcare logistics and allow for effective and efficient disinfection.

In embodiments of the present subject matter, devices, systems, and methods related to disinfecting a room, equipment, and other similar surfaces and items are provided. Specific embodiments of the disclosed device, delivery system, and method will now be described with reference to the drawings. Nothing in this detailed description is intended to imply that any particular component, feature, or step is essential to the invention.

This overview is intended to provide an overview of subject matter of the present patent application. It is not intended to provide an exclusive or exhaustive explanation of the invention. The detailed description is included to provide further information about the present patent application.

FIG. 1 illustrates a perspective view of an exemplary embodiment of a disinfection device in a collapsed or compact configuration. In the present embodiment, the device comprises a base structure 1007 in the form of a cylindrical central column. Optionally, in this and other embodiments, the base structure may have a plurality of shapes (e.g., cylindrical, square, rectangular, hexagonal, triangular, spherical, or irregular) in combination with a plurality of varying circumference throughout the base structure. Optionally, in this and other embodiments, the base of the base structure is configured to rest on the floor and provide a stable frame for the device. Optionally, in this and other embodiments, a plurality of casters may be disposed on the base of the base structure. Optionally, in this and other embodiments, one or more ultraviolet emitting sources can be disposed on the base structure.

FIG. 1 further depicts the ends of four arms 1001, 1002, 1003, and 1004 are operably coupled to the base structure 1007. Optionally, in this and other embodiments, the device possesses one or more arms. Non-limiting examples include one arm, two arms, three arms, four arms, five arms, six arms, seven arms, eight arms, nine arms, ten arms, eleven arms, or twelve arms. Additionally, the four arms 1001, 1002, 1003, and 1004 in FIG. 1 are circumferentially disposed in lamp segments 1005 around the top portion of the base structure 1007. Optionally, in this and other embodiments, the one or more arms are operably coupled to the base structure at a variety of positions. Non-limiting examples include one end of the one or more arms attaching to the center, top, or bottom portion of the base. In FIG. 1, the four arms 1001, 1002, 1003, and 1004 are positioned on the same level on the base structure. Optionally, in this and other embodiments, the one or more arms may be positioned on the same level on the base structure, different level on the base structure, or a combination thereof. Moreover, the four arms 1001, 1002, 1003, and 1004 in FIG. 1 comprises four lamp array segments 1006. Optionally, in this or other embodiments, an arm may possess one or more lamp array segments. Non-limiting examples include one segment, two segments, three segments, four segments, five segments, six segments, seven segments, eight segments, nine segments, ten segments, eleven segments, or twelve segments. In the present embodiment, each lamp array segment 1006 comprises one cylindrical-shaped set of upper ultraviolet emitting lamps 1000 extending up from the segment 1006 and pass from the top of the base structure 1007 and a second cylindrical-shaped set of lower ultraviolet emitting lamps 1008 extending down from the segment 1006. Optionally, in this or other embodiments, a segment may comprise one or more ultraviolet emitting sources. Non limiting examples include one source, two sources, three sources, four sources, five sources, six sources, seven sources, eight sources, nine sources, ten sources, eleven sources, or twelve sources. Optionally, in this or other embodiments, a segment may comprise one or more kinds of ultraviolet emitting sources. Non-limiting examples include ultraviolet Low Pressure or Medium Pressure lamps, or LED ultraviolet sources producing ultraviolet light of any ultraviolet wavelength between 180-400 nm. Optionally, in this or other embodiments, an ultraviolet emitting source may be a plurality of shapes. Non-limiting examples include cylindrical lamps, bulb lamps, U-tube lamps, biaxial lamps, or point-source LEDs. Optionally, in this or other embodiments, an ultraviolet emitting source may comprise a variety of sizes and lengths. Non limiting examples include ultraviolet emitting sources lengths as short as LEDs or as long as typical high output ultraviolet lamps. Optionally, in this or other embodiments, the one or more ultraviolet emitting sources may comprise a plurality of ultraviolet emitting elements. In the present exemplary embodiment, the lower set of emitters 1008 does not extend all the way to the bottom of the base to provide clearance with the floor for transportation of the device.

Optionally, in this and other embodiments, the upper ultraviolet emitting lamps may be at the same level or below the top of the base structure. In the present embodiment, the ultraviolet emitting lamps 1000 and 1008 are configured on the lamp array segment 1006 to be disposed parallel to the base structure. Optionally, in this or other embodiments, one or more ultraviolet emitting sources may be disposed in a plurality of locations on the segment. Non-limiting examples include on the top of the extendable arm, or on the bottom, on any side, or any combination thereof. Optionally, in this or other embodiments, an ultraviolet emitting source may be fixed in length or be configured to extend and contract radially outward from the arm.

Optionally, in this or other embodiments, an ultraviolet emitting source may be disposed at a variety of angles relative to the segment. Non-limiting examples include the one or more ultraviolet emitting source disposed orthogonally to the segment, transverse to the segment, or at any acute or obtuse angle relative to the segment.

Optionally, in this or other embodiments, one or more arms, one or more segments, or one or more ultraviolet emitting sources may be configured to rotate or swivel. Optionally, in this or other embodiments, the arms, segments, and ultraviolet emitting sources are modular. Optionally, in this or other embodiments, additional segments may be added onto or taken away to provide additional configuration options and extend or decrease the reach of the arm. Optionally, in this or other embodiments, additional ultraviolet emitting sources may be added or taken away to provide additional configuration and disinfection options depending on the set up of the target area or room to be disinfected.

Figure 2:
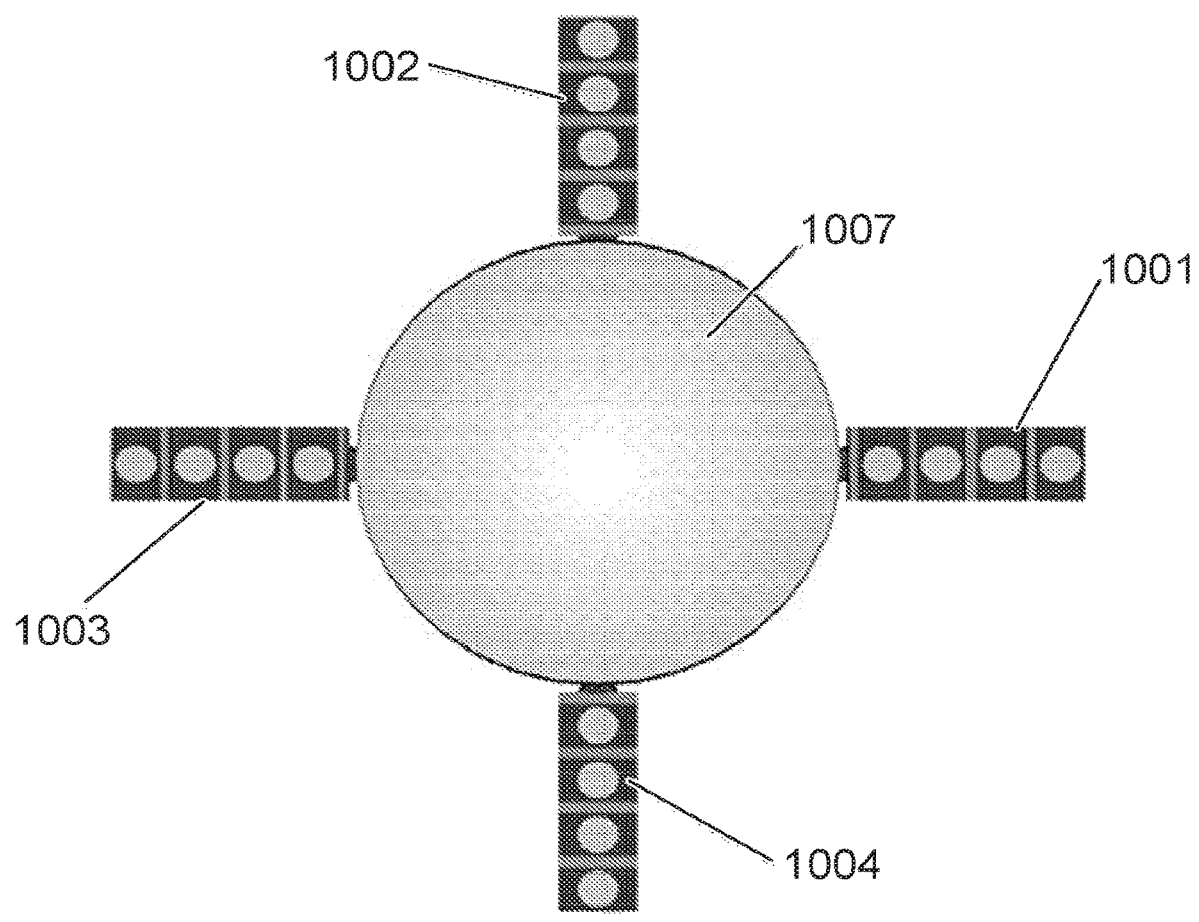
FIG. 2 illustrates an overhead view of the disinfection device of FIG. 1, in accordance with at least one example of the present disclosure.

FIG. 2 illustrates an overhead view of the disinfection device of FIG. 1. The four arms 1001, 1002, 1003, and 1004 on the base structure 1007 are positioned orthogonally and equidistant to one another. Optionally, in this and other embodiments, the one or more arms may be disposed at a variety of positions relative to one another. Non-limiting examples include: the one or more arms evenly spaced from one another, the one or more arms unevenly spaced from one another, or a combination of the one or more arms evenly spaced and unevenly spaced from one another, or the one or more arms separated from one another by 180 degrees, 120 degrees, 90 degrees, 72 degrees, 60 degrees, 45 degrees, 40 degrees, 36 degrees, or 30 degrees on a cylindrical-shaped base structure. Optionally, in this and other embodiments, the arm angular spacing can be adjustable around the central column to adjust to different dimensions of target volumes of spaces. Optionally, in this or other embodiments, the one or more arms may be configured to be expandable radially away from and contractible back in a linear fashion relative to the base structure.

Figure 3:
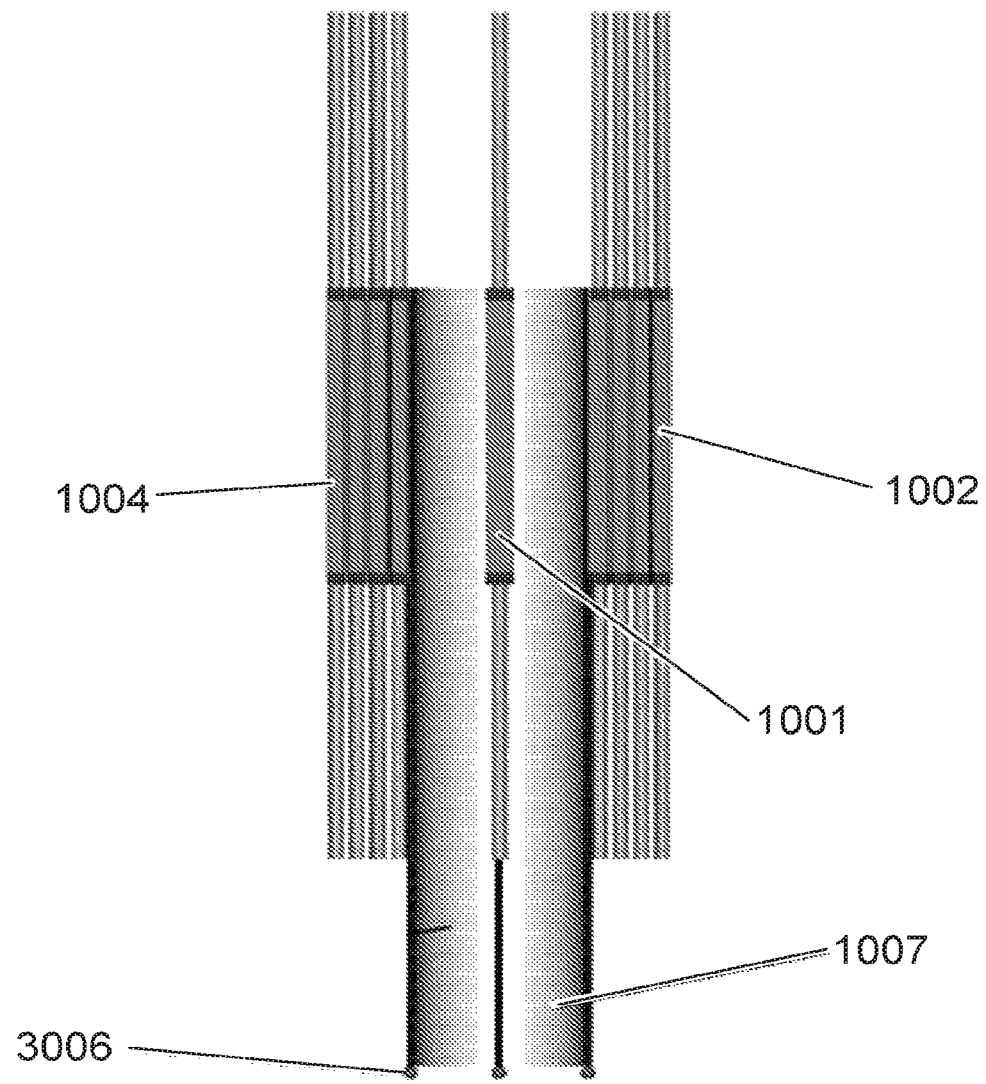
FIG. 3 illustrates a side view of the disinfection device of FIG. 1, in accordance with at least one example of the present disclosure.

FIG. 3 illustrates a side view of an exemplary embodiment of FIG. 1. FIG. 3 depicts the disinfection device that includes column support wheels or casters 3006 attached to the bottom of the base structure 1007 to facilitate transport and to allow the arms 1001, 1002, and 1004 to be rolled out in multiple configurations to adapt to the target volume surfaces and dimensions. Optionally, in this or other embodiments, the device may or may not include casters 3006 attached to the bottom of the base structure. Optionally, in this or other embodiments, the device may include one or more vertical tracks to enable the extendable arms to translate up or down relative to the base structure Optionally, in this or other embodiments, the device may include one or more tracks running horizontally along the circumference of the base structure and is configured to attach to the one or more arms and allow the one or more arms to translate around the base structure. Optionally, in this or other embodiments, the one or more arms may further comprise a pivot axis on the end that operably couples to the base structure, wherein the pivot axis is configured to allow an arm to be adjusted at a variety of angles relative to the base structure. Non-limiting examples include arms arranged vertically, horizontally, or any angle in-between horizontal and vertical. Optionally, in this or other embodiments, a pivot axis may include a releasable locking mechanism to lock the angle of rotation of an arm. Optionally, in this or other embodiments, a minimum pivot angle could be 10, 20, 30, 40, 50, 60, 70, 80 or 90 degrees from the vertical and a maximum angle could allow up to a full 360 degrees of rotation. Optionally, in this and other embodiments, the pivot axis may include a releasable locking mechanism to lock the angle of rotation of the arm as well as release the arm entirely from the central column to enable replacement or adaptation to specific applications.

Figure 4:
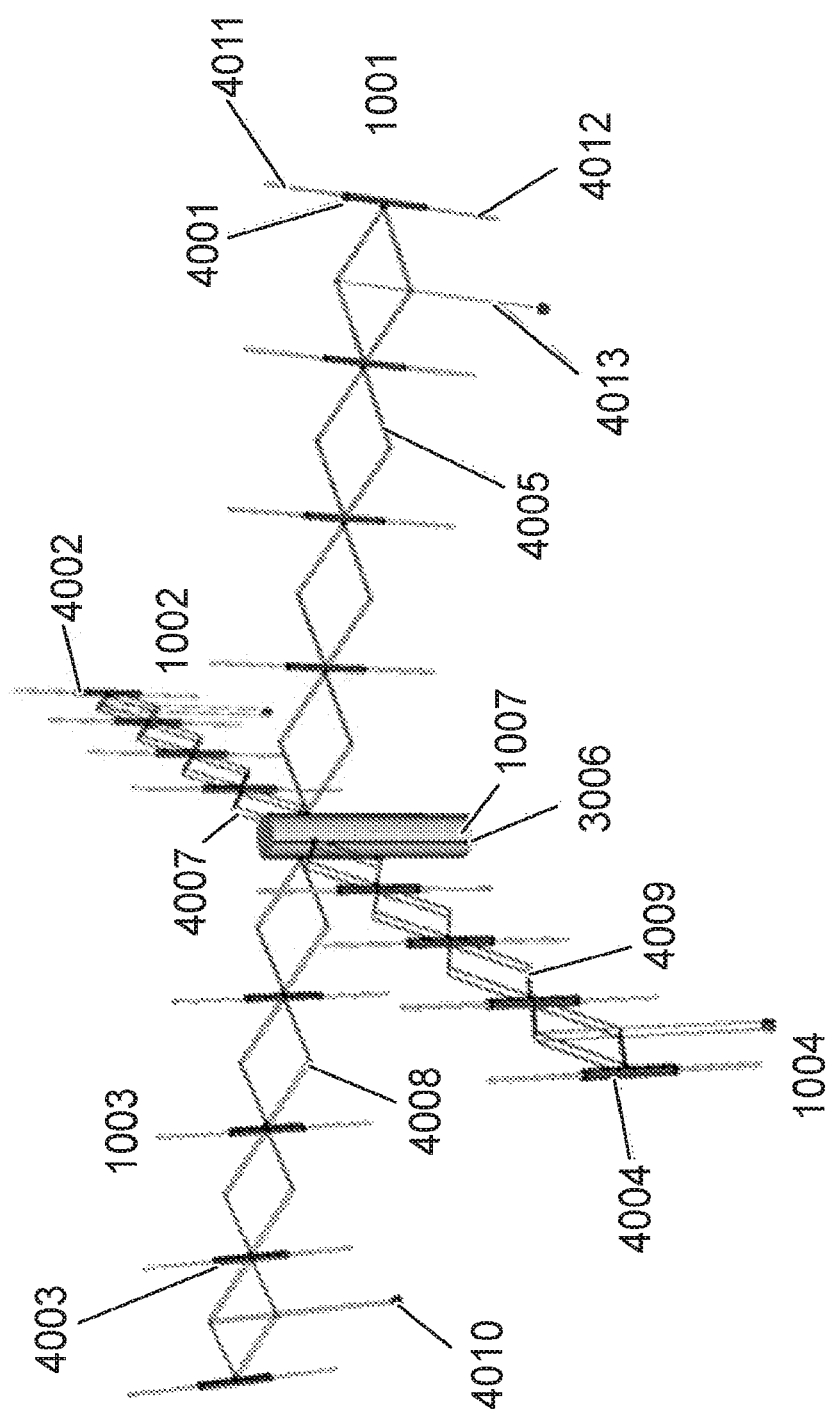
FIG. 4 illustrates a perspective view of the disinfection device of FIG. 3 in an expanded configuration, in accordance with at least one example of the present disclosure.

FIG. 4 illustrates a perspective view of the disinfection device in FIG. 3 in an expanded configuration. FIG. 4 illustrates four arms 1001, 1002, 1003, and 1004, the ends of each arm operably coupled to the base structure 1007. Optionally, in this or other embodiments, the base structure may comprise one or more ultraviolet emitters. Optionally, in this and other embodiments, an ultraviolet emitter may comprise a plurality of shapes and sizes. Non-limiting examples include cylindrical lamps, u-tube lamps, biaxial lamps, bulb shaped lamps, LEDs, etc. In the present embodiment, the base structure is approximately 3 feet. However, in this and other embodiments, the height of the base structure is not limited by any factor except for the limiting height of any ceiling or door way entrance in which it was placed, which might be 4, 5, 6, 7, 8, 9, 10, 11 or 12 feet normally or higher for very large enclosed spaces. Optionally, in this or other embodiments, the device may comprise one or more arms. Each arm, e.g., 1001, is extended radially away from the base structure 1007 which rides on casters 3006. Optionally, in this or other embodiments, each arm may extend out to make contact with the walls or corners of the room or the outer perimeter of the target area. The maximum length of the fully extended arm is limited only by the number of segments and the number of segments is unlimited but practically would remain within some finite number such as 4, 8, 16, 36, or 64. Each arm comprises four lamp array segments, e.g., 4001, 4002, 4003, and 4004, that each includes two ultraviolet emitting sources 4011 and 4012, and four support frame segments, e.g., 4013. Optionally, in this or other embodiments, each arm comprises one or more lamp segments. Non-limiting examples include one, two, three, four, five, six, seven, eight, or more ultraviolet lamps. Lamp array segments 4001, 4002, 4003 and 4004 are disposed where the length of the segment runs vertically. Optionally, in this or other embodiments, a segment may comprise a plurality of shapes and sizes. Non-limiting examples include cubes, rectangles, hexagonal shapes, spheres, etc. The center of each segment is connected by a folding-type support frame, e.g., 4005, 4007, 4008 and 4009. Optionally, in this or other embodiments, each arm comprises an accordion shape, comprising a plurality of linkages that are pivotably coupled together to form folding segments along the arm to allow the arm to accordion into an expanded configuration or collapsed configuration. Folding mechanisms are just one example of translating the ultraviolet sources from a contracted to an expanded configuration. Optionally, in this or other embodiments, a frame may comprise a plurality of shapes and sizes. Non-limiting examples include rectangles, triangles, trapezoids, etc. Optionally, in this and other embodiments, a connection point between the segment and frame may be configured to rotate at a variety of degrees along the horizontal axis. Non-limiting examples of degrees include, inter alia, from 90 degrees to 360 degrees Optionally, in this and other embodiments, a connection point between the segment and frame may be configured to rotate at a variety of degrees along the vertical axis. Non-limiting examples of degrees include, inter alia, from 90 degrees to 360 degrees. Optionally, in this or other embodiments, the support frame is comprised of segments made of steel or aluminum but may also be comprised of other suitable materials including, but not limited to, plastic, wood, metal and other natural or synthetic materials. Each ultraviolet emitting source, e.g., 4011, has a cylindrical shape. Optionally, in this and other embodiments, the ultraviolet emitting source may be any shape, including lamp bulb shape, cylindrical shape, u-tube lamp shape, biaxial shape, bulb shaped lamps, LEDs, laser etc. Optionally, in this or other embodiments, a ultraviolet emitter may be disposed at a variety of positions on the frame or segment or combination thereof. Non-limiting examples include the top, bottom, sides, or anywhere in-between of the frame or segment or combination thereof. One set of ultraviolet emitting source extends radially upward away from the support frame while another set of ultraviolet emitting source extends radially downward away from the support frame. Further, the support wheels or casters, e.g., 4010, on the four extended arms are connected to a support structure which is connected to an upper or lower portion of the support frame. The support casters 4010 are connected to the support frames further away from the base structure 1007 to prevent the device from tipping over in the expanded configuration. Optionally, in this or other embodiments, each arm may comprise a plurality of support wheels connected to the superior portion of a plurality of segments. Optionally, in this or other embodiments, a support wheel may connect to an inferior portion of a segment or frame Optionally, in this or other embodiments, an arm may comprise one or more segments, one or more frames, and one or more ultraviolet emitters.

Figure 5:
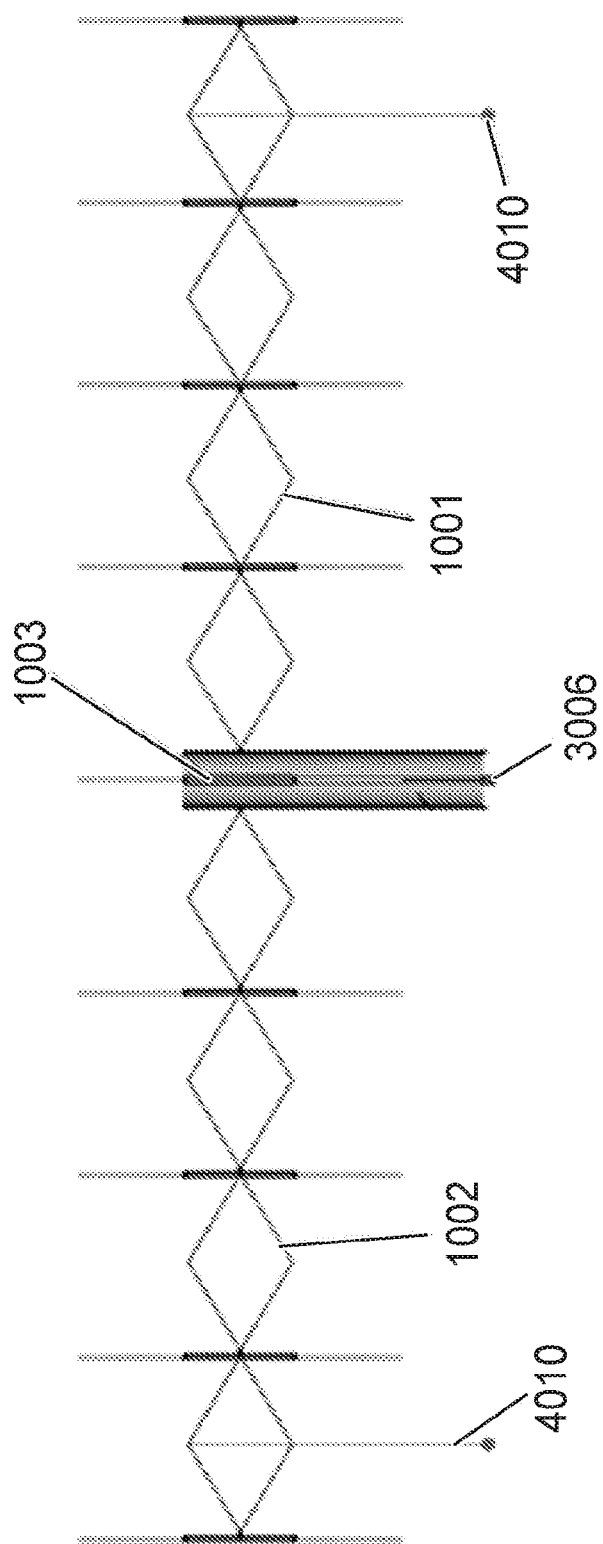
FIG. 5 illustrates a side view of the disinfection device of FIG. 4, in accordance with at least one example of the present disclosure.

FIG. 5 illustrates a side view of the disinfection device of FIG. 4 and shows the base structure 1007, the extendable arms 1001 and 1003 (in profile) and one of the extendable arms 1003 (in edge view), and the support frame casters 4010 and base structure casters 3006.

Figure 6:
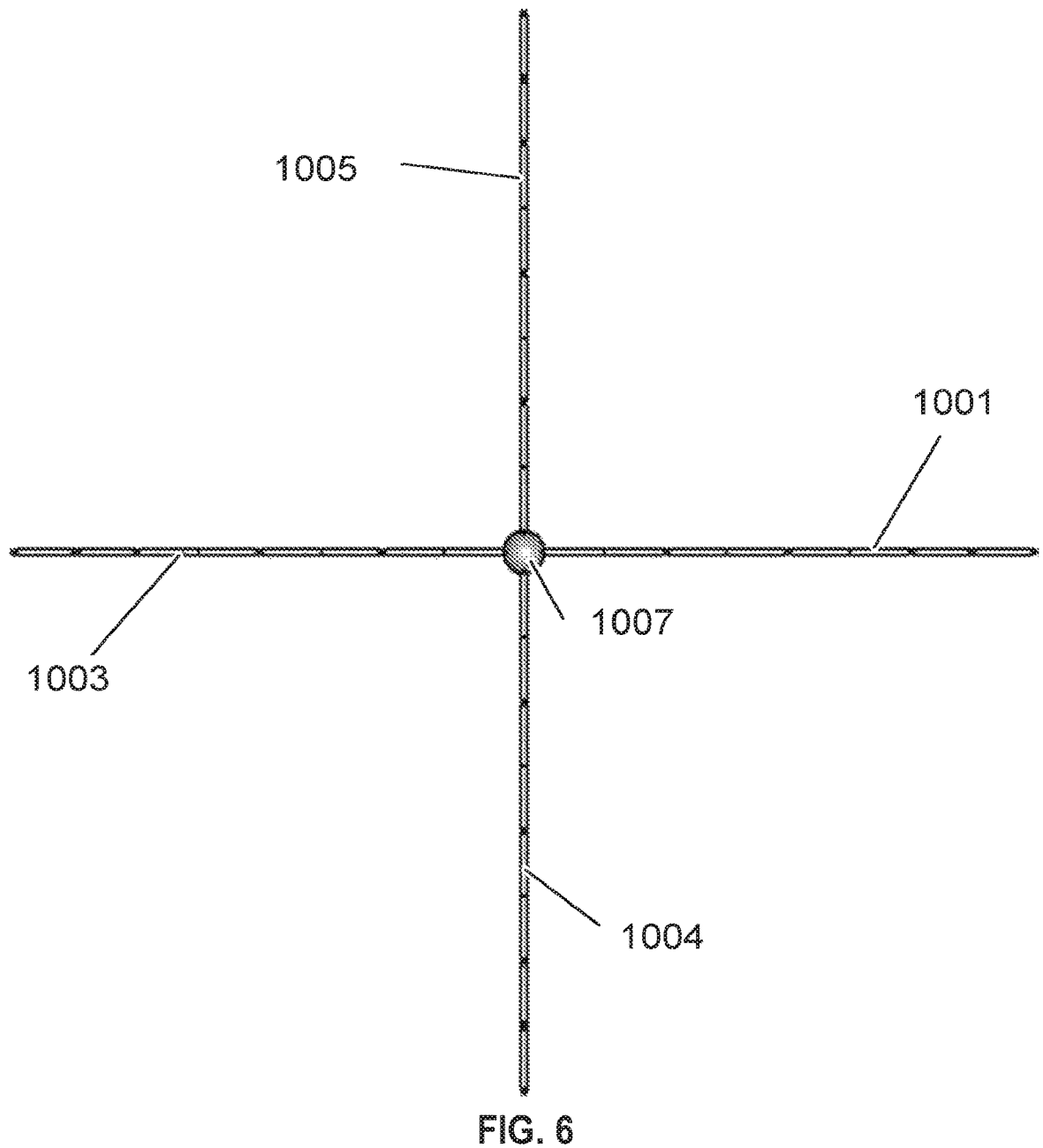
FIG. 6 illustrates an overhead view of the disinfection device of FIG. 4, in accordance with at least one example of the present disclosure.

FIG. 6 illustrates an overhead view of the disinfection device of FIG. 1 in a fully extended configuration. In this preferred embodiment the extendable arms 1001, 1002, 1003, and 1004 are arranged at right angles to each other and are connected to the base structure 1007. The one or more arms, e.g., 1001 can each be reconfigured to adapt to a plurality of room shapes including rectangular rooms, square rooms, round rooms, trapezoidal rooms, etc.

Figure 7:
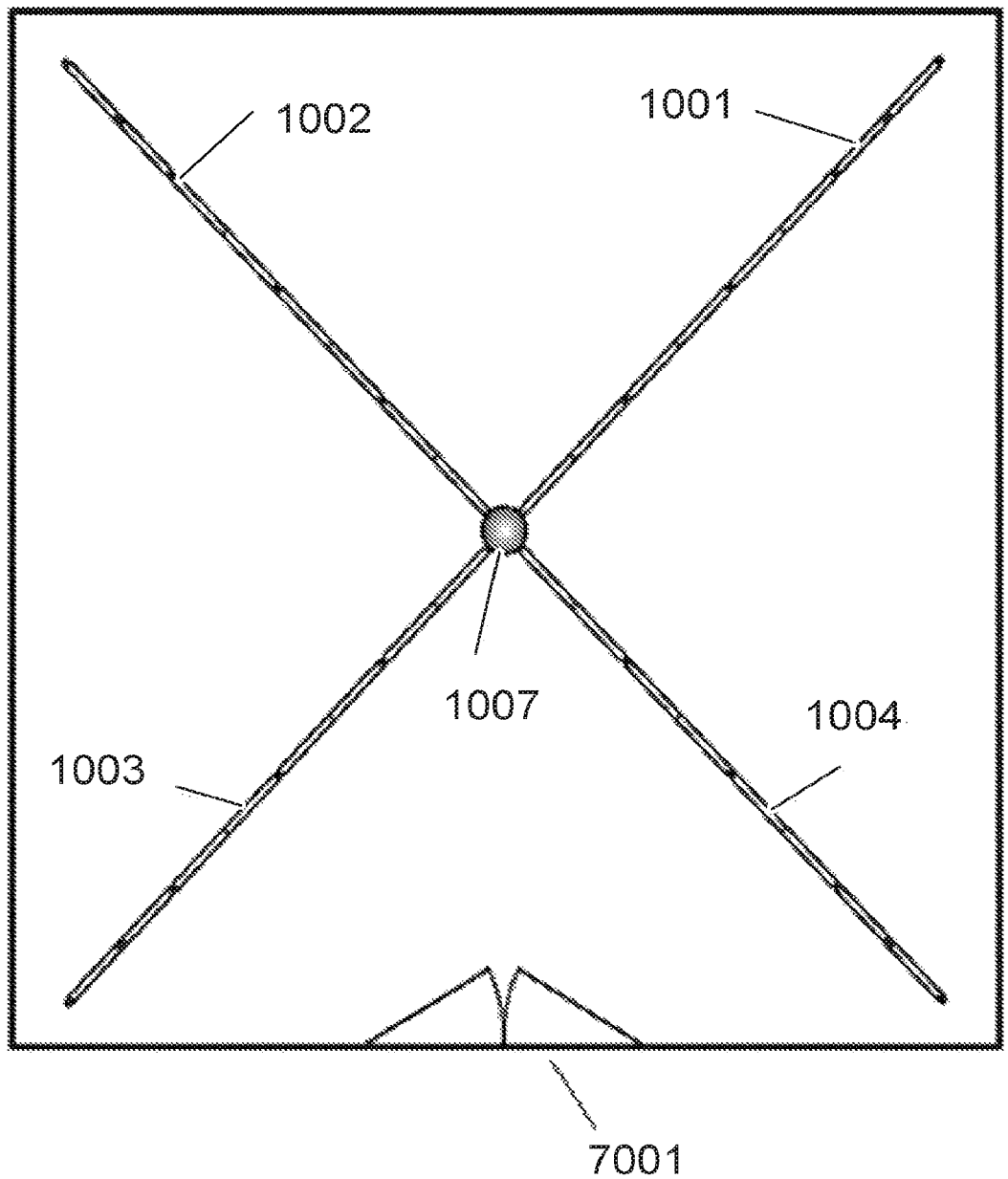
FIG. 7 illustrates an overhead view of the disinfection device of FIG. 1 deployed in a room, in accordance with at least one example of the present disclosure.

FIG. 7 illustrates an overhead view of the disinfection device of FIG. 1 in a square room in the fully extended configuration. The device is situated inside a room with a door through which the disinfection device is transported. In the present embodiment, each arm 1001, 1002, 1003, and 1004 is extended towards the four corners of the room to achieve maximum coverage. In other embodiments, the arms may be extended towards the four walls of a room, the entrance of a room, or other portions along the perimeter of the room or target area.

Figure 8:
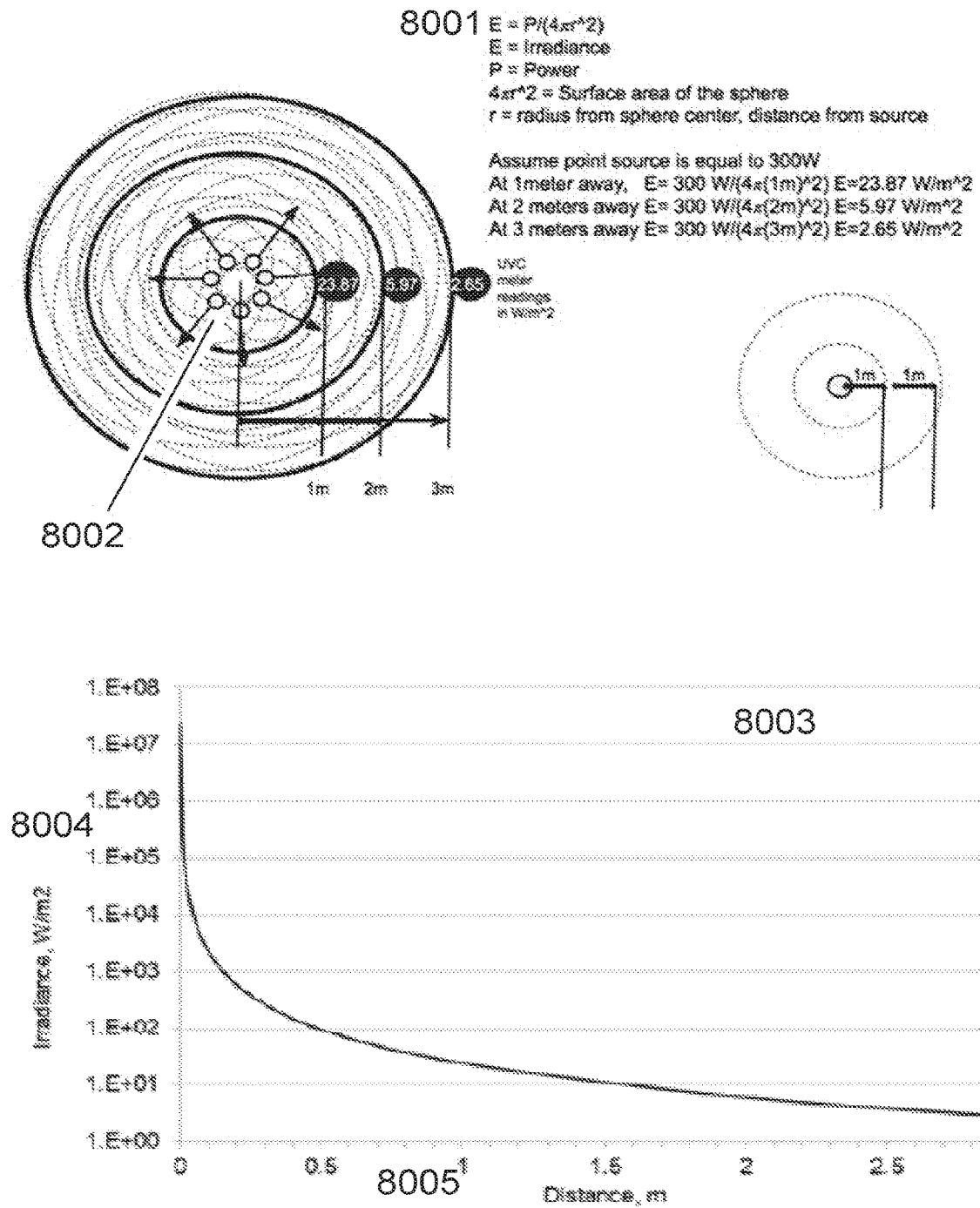
FIG. 8 illustrates the classic Inverse Square Law and a representative point source disinfection device in the prior art, in accordance with at least one example of the present disclosure.

FIG. 8 illustrates the classic Inverse Square Law and the manner in which light intensity diminishes from a representative point source disinfection device in the prior art. The Inverse Square Law is represented by the formula $E=P/(4\pi r^2)$ 8001. Irradiance is represented by "E" with units $W/m^2$, power is represented by "P" with units W, and the surface area of a sphere is "$4\pi r$" in units $m^2$, where r is the radius or distance from the point source in m. A representation of a prior art point source disinfection device with a plurality of light sources disposed in a circular shape 8002 is also provided. Assume the distances from the center of the plurality of light sources to the smallest ring, middle ring, and largest ring, are measured at 1 meter, 2 meters, and 3 meters, respectively. Under the present example utilizing a point source disinfection device, assuming a uniform power distribution of 300 W at every distance from the point source device, the amount of irradiance at the smallest ring, at 1 m, would be approximately 23.87 $W/m^2$; the amount of irradiance at the middle ring, at 2 m, would be approximately 5.97 $W/m^2$; and the amount of irradiance at the largest ring, at 3 m, would be approximately 2.65 $W/m^2$. In sum, the amount of ultraviolet light irradiance greatly diminishes with distance from the plurality of light sources disposed in the center or closely together. As an example, the graph 8003 further depicts the amount of light irradiance E (Watts/meter$^2$) 8004 from a point source of 300 Watts diminishing with distance (m) 8005. This significant diminution of light from a point source, e.g., a cylindrical lamp, or disinfection device utilizing a point source model which is comprised of several lamps in a centralized region exemplifies one of the major problems with prior art disinfection units that are configured to utilize a point source. The highest ultraviolet light intensity occurs only in close proximity to the ultraviolet lamp surface. However, at farther distances that may exist in any normal size room the intensity of ultraviolet light at these distances is often so diminished that it is insufficient to produce significant levels of disinfection without arduous and extended exposure times. Furthermore, most point source area disinfection units currently available that either use a single lamp or a cluster of lamps located close together which act much like a single light source and as a result there are often many surfaces within a room that will not be directly exposed to ultraviolet light but will be subject to shadows and variable levels or bacteria or pathogens remaining. Both of the aforementioned problems with current point source area disinfection systems and the prior art referenced are overcome by the distributed matrix of ultraviolet lamps in the current embodiment of the adaptive multivector matrix device which physically constructs and adapts to form a distributed grid that creates a multivector field of ultraviolet light.

Figure 9A:
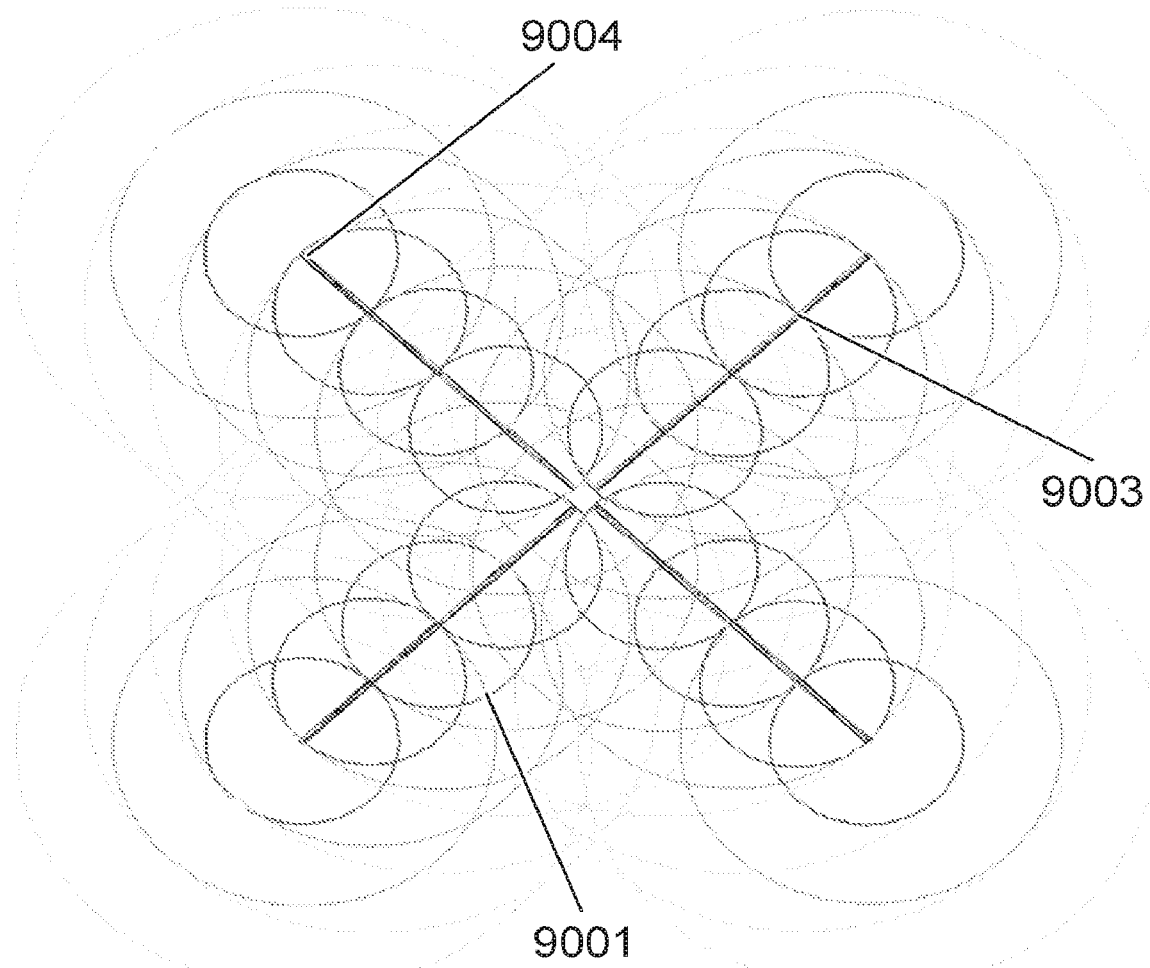

FIGS. 9A-9D illustrate exemplary embodiments of how the ultraviolet light intensity emits from exemplary embodiments of the present disclosure. Instead of following a traditional point source device with inverse square law model, the plurality of light sources, e.g., 9003 in the present embodiment are disposed along the length of the plurality of arms, e.g., 9004. Doing so, the areas of high intensity are distributed more uniformly by the extended arms, e.g., 9004. Optionally, in this and other embodiments, the areas of high intensity of ultraviolet energy are distributed more uniformly in a room or target volume. Optionally, in this and other embodiments, the areas of high intensity of ultraviolet energy are distributed uniformly in a room or target volume. In this and other embodiments, the net effect of the distributed light sources provides a more even distribution of multivectored light and simultaneously avoids the problems of shadowing. Optionally, in this and other embodiments, the computation of the actual intensity in the room at any point depends on the contribution and multivector summation from each of the distributed light sources. Additionally because the lamps are more precisely distributed throughout the room in this and other embodiments, the intensity levels throughout the room will be more homogenous than in the point source models, compared at a minimum on the basis of equivalent total lamp wattage, and will not suffer from the drastic drop-off in intensity after 0.5 meters, 1, 2, 3, and 4 meters, which is seen with a prior art central point source models. Optionally, in this and other embodiments, the degree to which the intensity is homogenized across the room or target volume depends on the number, types, strength, or positioning of the light sources. Optionally, in some embodiments, with up to a theoretically infinite number of ultraviolet sources, the intensity profile in the room or target volume would be precisely distributed and constant at the average value of intensity in the room. This approach, which overcomes the deficiencies associated with point source models of light, does not depend on having an infinite number of lamps and there will be in some embodiments some finite number of lamps that will provide a superior intensity distribution and that will also provide multivectored light coming from a sufficient number of directions that the problem of shadowing will be overcome. FIG. 9A which shows how optionally, in this and other embodiments, the concentric circular contours 9001 of ultraviolet intensity overlap and thereby produce better coverage and intensity across varying distances throughout the volume of space or room or target area in comparison to a point source model concentrated at the center of the room. Optionally, in some embodiments, the measurement of the irradiance utilizing this exemplary adaptive matrix could demonstrate 1-20 $W/m^2$, 1 meter away with only approximately 1-100 W of power from the center of the embodiment and show higher intensities farther away from the exemplary embodiment providing better coverage, higher intensity and therefore more adequate and faster disinfection of all surfaces in a volume of space in comparison to a point source model.

In other exemplary embodiments, lamps are illustrated in FIG. 9B of embodiment 9010, which has four extendable arms. The smaller circles, e.g., 9111, around each lamp, e.g., 9112, represent an irradiance contour. It can be seen that overlapping smaller circles form a field of multivector light that is outlined by the dark straight lines that form an X-shape 9113. The larger fainter circles, e.g., 9114, which represent a lower irradiance level, also overlap to form diamond-shaped areas, e.g., 9115, in-between the extended arms, e.g., 9116, where the multivector light field is lower than the area within the dark straight lines that form the X-shape 9113. Optionally, in this and other embodiments, these areas of reduced irradiance would be, in a square or rectangular shaped room occupied by the device, areas near the center area of each wall.

FIG. 9C illustrates an exemplary embodiment of what happens when a fifth arm 9020 with a lamp 9021 is inserted between any other two extended arms 9022 and 9023 in the area of reduced irradiance, and this lamp is represented by the small circle and circular area which is expanded into FIG. 9D. Optionally, in this and other embodiments, one or more arms may be added or removed onto the device Optionally, in this and other embodiments, the fifth extended arm may comprise a plurality of ultraviolet emitting sources, which may comprise lamps. In the instant embodiment, when this fifth lamp 9021 on the fifth arm 9020 is placed in the area of lowest irradiance within the multivector light field, the irradiance level is increased and the multivector light field is furthermore evenly distributed. That is, a more homogenous level of multivector light, or more flat irradiance contours, can be achieved by inserting lamps anywhere the irradiance field is demonstrates a potential lowering of energy.

FIG. 9D illustrates a magnified image of the region once the fifth lamp 9020 and a fifth extended arm 9021 is added to the device. A circular area of increased irradiance 9030 is created in the spot between two other extended arms 9022 and 9023 (which might be adjacent to a room wall, for example). This method can be repeated for the other three areas of reduced irradiance between the arms to render the overall multivector contour more homogenous. Optionally, in this and other embodiments, adding arms with additional sources to the device to areas of lesser irradiance could be repeated ad infinitum until complete homogeneity of the multivector irradiance field was achieved. Optionally, in other embodiments, only a few additional lamps are added until the multivector irradiance field became sufficiently homogenous or evenly distributed to achieve high levels of disinfection at every point within the room or enclosed space or target area. Optionally, in this and other embodiments, additional point sources may be added onto the device. The method of incrementally adding arms with additional ultraviolet emitting sources to create a well-distributed field of multivector light to render the irradiance contours more homogenous. Optionally, in this and other embodiments, this effective method of disinfecting a target area is done in a single exposure cycle. Optionally, in this and other embodiments, a single exposure cycle can last 10 seconds, 20 seconds, 30 seconds, 40 seconds, 50 seconds, 60 seconds, 70 seconds, 80 seconds, 90 seconds, 100 seconds, 110 seconds, 120 seconds, 130 seconds, 140 seconds, 150 seconds, 160 seconds, 170 seconds, 180 seconds, 190 seconds, or 200 seconds. Optionally, in this and other embodiments, a single exposure cycle can last up to 20 minutes.

In this and other embodiments, the level of ultraviolet light intensity is more widely distributed in the available space and creates a more uniform field or distributed matrix of ultraviolet light in which rays of ultraviolet light from multiple directions can reach every surface and thereby provide much more effective and efficient disinfection of these surfaces in less time than traditional point source area disinfection units, the latter advantage being critical to health care facilities and operating rooms which operate on tight schedules and which have limited time for disinfection processes. Optionally, in this and other embodiments, the distributed matrix of ultraviolet light can be adaptive through the adaptive arms or the ultraviolet sources on the arms or the base structure. Optionally, in this and other embodiments, the distributed matrix of ultraviolet light can be adaptive by adjusting the amount of irradiance coming from the one or more ultraviolet sources on the one or more arms. Optionally, in this and other embodiments, the arms are collapsible and extendable. In this and other embodiments, the design can be engineered to perform a unique function, the function of efficient, effective and rapid disinfection of nosocomial pathogens, which is of great value to health care facilities who are in a constant struggle against pathogens that constantly adapt to antibiotics as well as chemical disinfectants and who have been facing the limitations of the aforementioned point source models which, unlike the current disclosure, have been found to be of limited effectiveness within the time constraints of normal hospital cleaning procedures and which incompletely disinfect room or surfaces due to the problem of shadowing and Inverse Square Law.

Figure 10:
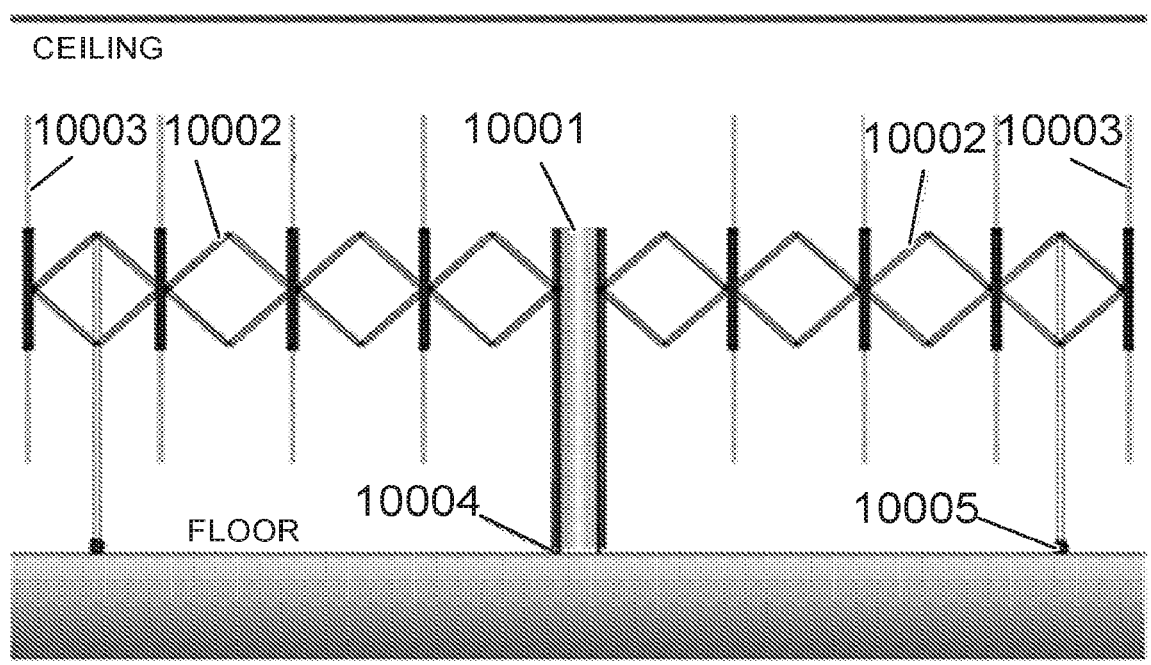
FIG. 10 illustrates a side view of the disinfection device of FIG. 4 deployed in a room with the floor and ceiling depicted, in accordance with at least one example of the present disclosure.

FIG. 10 illustrates a side view of a disinfection device deployed in a room in which the floor and ceiling are also illustrated. The base structure 10001 supports the extended arms, e.g., 10002 which support the ultraviolet lamps, e.g., 10003. The base structure is supported on casters 10004 while the extended arms are supported on casters 10005. In this illustration the folding mechanism is only partly extended and in full extension the folding arms will fold flat against each other. In this and other embodiments the extendable arms can be removable through a simple latching mechanism disposed on the end of the extendable arms operably coupled to the base structure that will facilitate replacement of parts and that will allow simple configurations (e.g., three arms only or two arms only) to be implemented as the application may require.

Figure 11A:
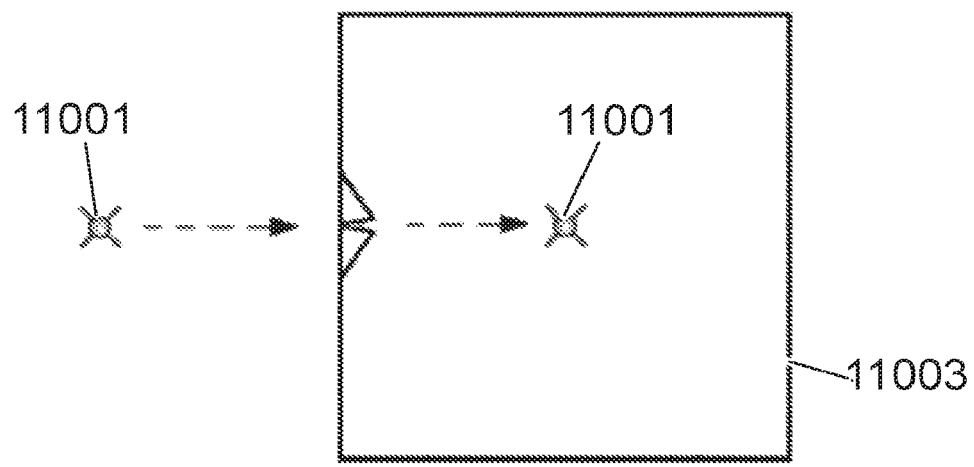
FIGS. 11A-11C illustrate stages of deployment of a disinfection device, in accordance with at least one example of the present disclosure.
Figure 11B:
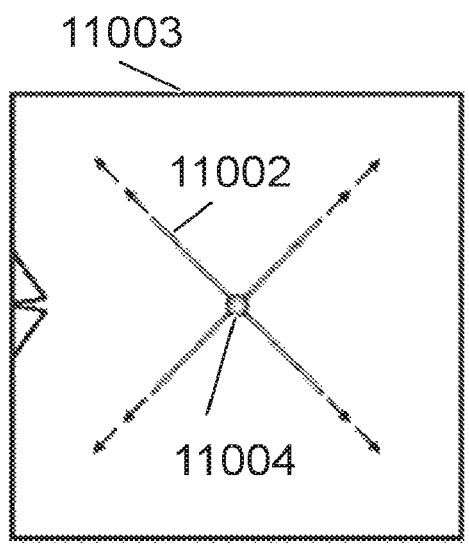
Figure 11C:
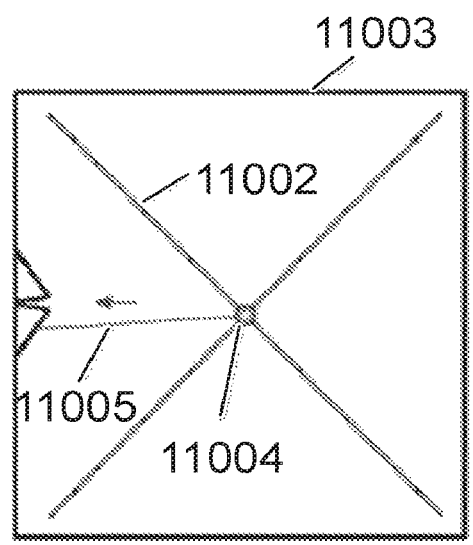

FIGS. 11A-11C illustrate exemplary stages of deployment of a disinfection device. FIG. 11 A illustrates the device 11001 in its portable configuration being moved through a doorway to a desired resting position within a square like room 11003 in which surfaces are to be disinfected. Optionally, in this or any embodiment, the device may be disposed in any location in a target area or room. FIG. 11B illustrates each of the four arms, e.g., 11002 of the device expanding from the base structure 11004 to fill the available volume of space in the room 11003. Optionally, in this or any embodiment, the arms may be simultaneously expanding towards the four corners or walls of the room. Optionally, in this or other embodiments, the arms may expand manually or automatically. In other embodiments, the one or more arms may expand at different times and at different lengths. In FIG. 11C, each of the four arms, e.g., 11002 have completed expansion from the base structure 11004 and the device is ready for the disinfection process. Optionally, in this or any embodiment, the device provides for eradication of microorganism ranges between 80%, 90%, 99%, 99.9%, 99.99%, 99.999%, 99.9999% or greater of pathogenic microorganisms. The device may optionally in any embodiment be configurable to function in a large open area (e.g., large rooms or hospital wards), or smaller constrained areas (e.g., corners, areas with interferences, etc.). The device may additionally be configurable to require only one setup for an entire room with one light cycle (e.g., emergency rooms, ICU rooms, etc.). The room to be disinfected may be part of a hospital room or may further include a hospital bed. The device may also be optionally in any embodiment be configured to be part of a mobile unit to disinfect temporary medical field operations remote from a hospital. Additionally, FIG. 11C illustrates a tether mechanism 11005 gets pulled from the system and attaches to entry and exit points within a volume of space such that when any change in position is detected from entry or exit points it shuts down the lights on the system to prevent accidental exposure of a user upon attempt to enter the volume of space receiving disinfection. The tether can be made of string material, plastic or metallic wire that is expandable and retractable from the device and there can be multiple tethers for multiple exit and entry points. Additionally, a timer located outside of the room which communicates wirelessly with the base 11004 and a control system within the base the nm time of the device and indicating to the user that an ultraviolet light cycle is in process. Additionally, a screen located outside of the room 11003 can display the timer or the duration of the ultraviolet cycle as well as an image of the light cycle in progress via a video recording device incorporated in one of the arms of said device.

Figure 12:
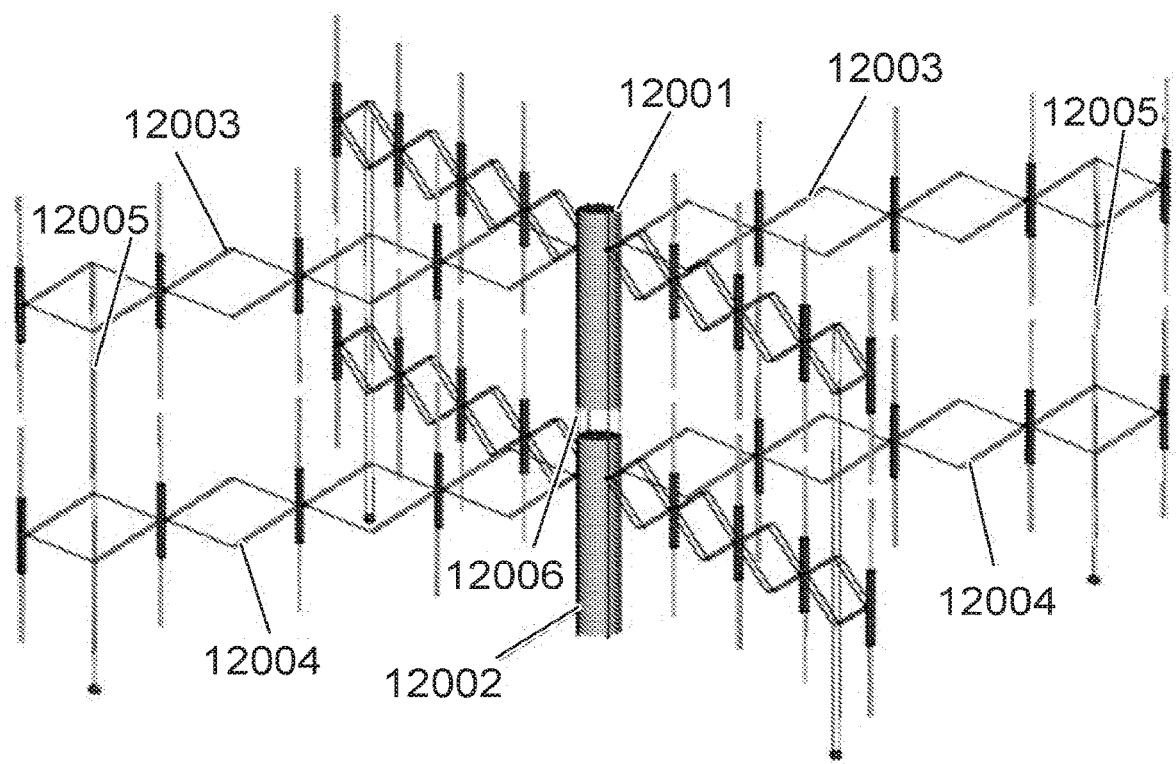
FIG. 12 illustrates a stackable disinfection device, in accordance with at least one example of the present disclosure.

FIG. 12 illustrates an exemplary embodiment as a stackable feature for disinfection. In this embodiment the disclosure can be stacked via attachments 12006 on top of the lower central column 12002 connected to the upper central column 12001, and at attachments of the supports 12005 of the extended arms 12003. The extendable arms 12003 can extend in this stacked arrangement. Stacking permits upwards expansion of the disinfection system where it may be desired to disinfect surfaces at higher levels. Stacking is not limited to a pair of disinfection devices and more than two devices could be stacked for areas with very high ceilings.

Figure 13:
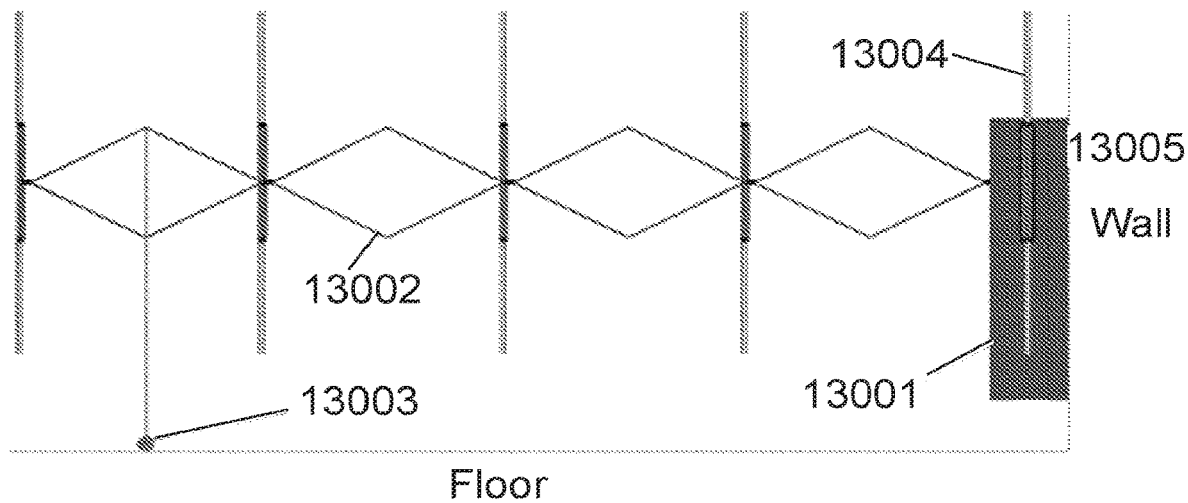
FIG. 13 illustrates a disinfection device configured to hang from a wall structure, in accordance with at least one example of the present disclosure.

FIG. 13 illustrates an exemplary embodiment of a disinfection device configured to hang from a wall structure 13005. In this embodiment the central column 13001 may be rectangular in form and may be coupled with a permanent wall attachment (not shown) to facilitate attachment and removal. The extendable arms 13002 would provide extension of the array of ultraviolet lights 13004 away from, and alongside the wall 13005 and additional support would be provided by the vertical arm support with rolling casters 13003. Alternatively, in other embodiments, the attachment of the central column to the wall 13005 may be permanent.

Figure 14:
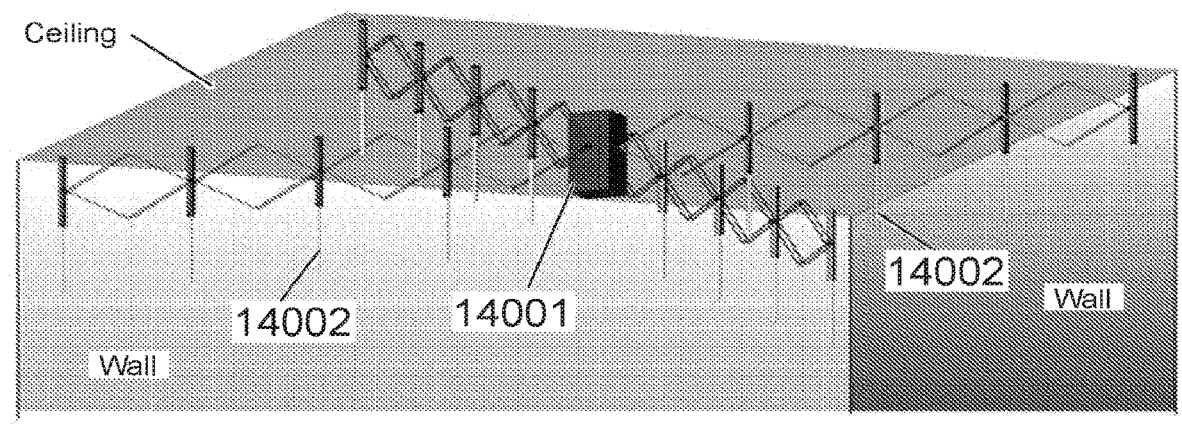
FIG. 14 illustrates a disinfection device configured to hang from a ceiling, in accordance with at least one example of the present disclosure.

FIG. 14 illustrates an exemplary embodiment of the disclosure configured to hang from a ceiling. In this embodiment a rectangular central column 14001 is attached permanently or temporarily to the ceiling. In the example shown the lamps 14002 are attached from the bottom of the extendable arms but other embodiments may include lamps on the topside of the extendable arms as well. In this embodiment additional supports such as ceiling hooks may be employed to provide structural support to the extended arms. In other embodiments the ceilings hooks may be foregone and the extendable arms may extend downwards at some angle, e.g. 45 degrees and require no additional support.

Figure 15:
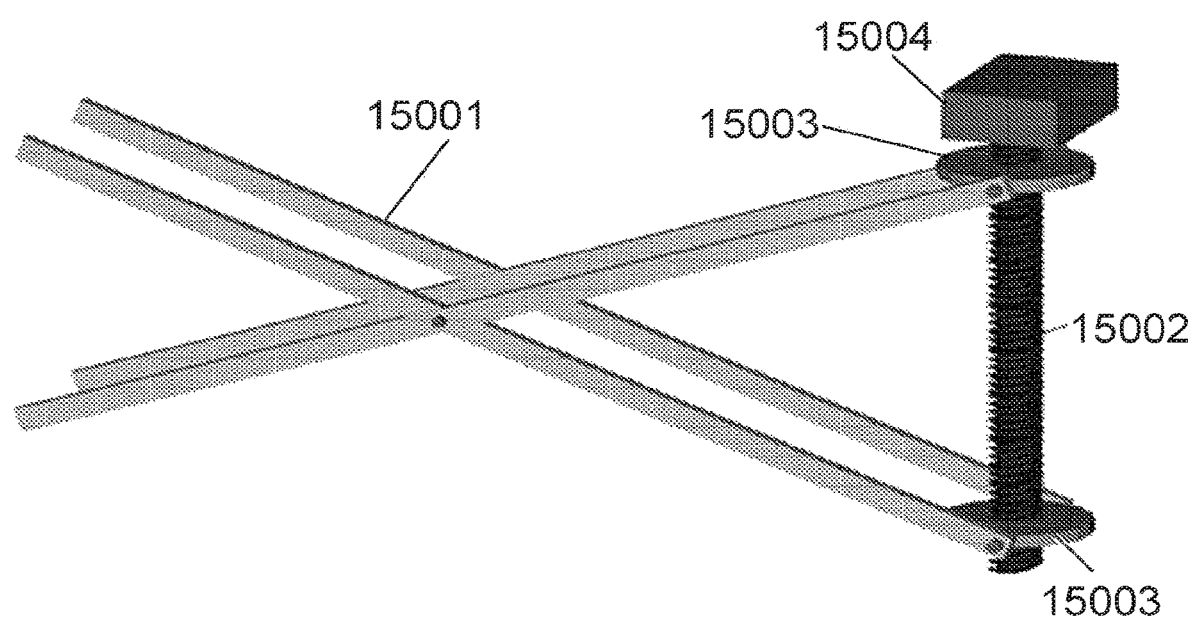
FIG. 15 illustrates a locking mechanism on the disinfection device of FIG. 1, in accordance with at least one example of the present disclosure.

FIG. 15 illustrates an exemplary embodiment of a locking mechanism and arm extension mechanism on the system of FIG. 1. The mechanism in this embodiment depends on a screw mechanism 15002 that expands or contracts the folding mechanism that extends or contracts the arms 15001. The screw mechanism 15002 is driven by a motor 15004 that will compress oppositely threaded nuts 15003. The motor-driven folding mechanism can be locked in place via a controller (not shown) or via digital controls (not shown) or manually (not shown). Alternate locking mechanisms, including manual locking, can be utilized. The folding mechanisms with the locking mechanism illustrated in FIG. 14 where utilized for figurative and description purposes only and the arm extension and locking can be accomplished through normal mechanoelectrical means readily know in the art.

Figure 16A:
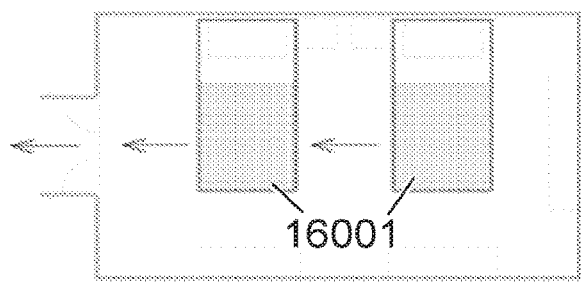
FIGS. 16A-16D illustrate how hospital beds would be removed from a patient room and separately disinfected while the present disinfection device is moved into the room to disinfect the room surfaces, in accordance with at least one example of the present disclosure.
Figure 16B:
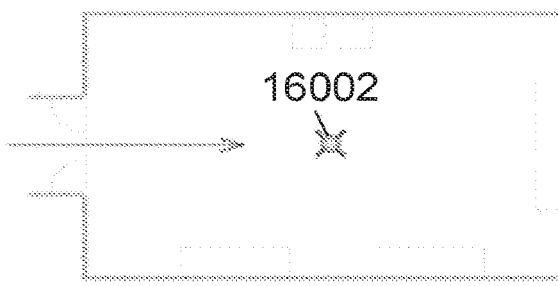
Figure 16C:
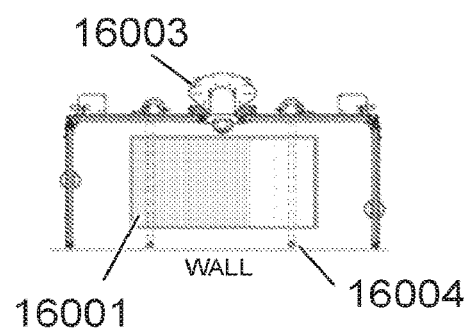
Figure 16D:
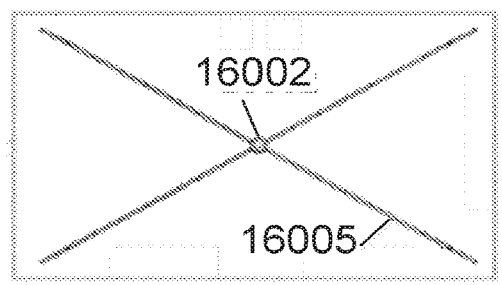

FIGS. 16A-16D illustrate exemplary embodiments of how hospital beds or surgical table would be removed from a patient room and separately disinfected while the present system is moved into the room to disinfect the room surfaces. FIG. 16A shows a hospital patient room with two beds or one bed 16001 that are moved out of the room while the room is disinfected by the device. FIG. 16B shows an exemplary embodiment of the current disclosure 16002 being moved into the patient room through the open doors and positioned for deployment. FIG. 16C shows the patient bed 16001 being separately disinfected by the disinfection system described in U.S. Pat. No. 9,675,720, 16003 placed around the bed and enclosing using a wall 16004 for the fourth side of the enclosed space. FIG. 15D shows the rectangular patient room with the exemplary embodiment of current disclosure 16002 deployed to suit the rectangular dimensions of the room, with the doors now closed. In this example the extendable arms 16005 of the disinfection unit 16002 are set at a non-orthogonal angle to suit the rectangular dimensions of the room and obtain maximum coverage. In some instances or embodiments, the patient bed or surgical table can remain within the volume of space of a healthcare environment and disinfected with the current disclosure during the single cycle of disinfection of the volume of space. In this example, the device would have the appropriate central column design to accept a surgical or patient bed and provide adequate matrix exposure to all reachable sides of the table or bed while simultaneously disinfecting the volume and surfaces within the room including walls and counters.

Figure 17:
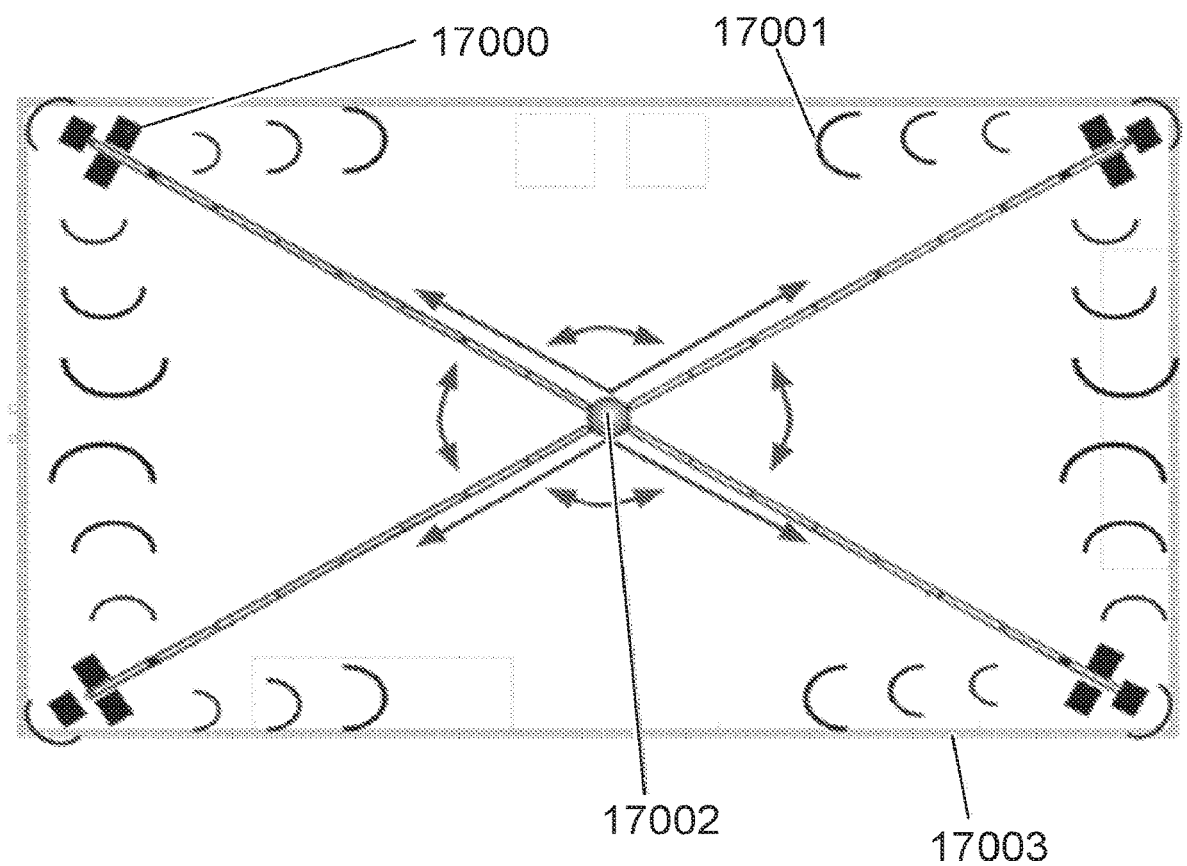
FIG. 17 illustrates how proximity sensors of a disinfection device measure the distance and positioning via communication waves of the plurality of arms, in accordance with at least one example of the present disclosure.

FIG. 17 illustrates how proximity sensors 17000 measure the distance and positioning via communication waves 17001 of the different arms to construct the matrix in varying volumes of spaces. Where the sensors are designed, programmed, and configured to construct a uniform geometric matrix which translates to an evenly distributed light matrix from the device 17002. The sensors measure geometric distance between each arm and between the walls and corners of a volume of space 17003 to manually or robotically adjust the current device's physical geometry and positioning within the room either radially and angularly or both to provide the best suitable matrix for the desired volume of space targeted for disinfection. This is a major differentiating factor between the current disclosure and the prior art.

Figure 18A:
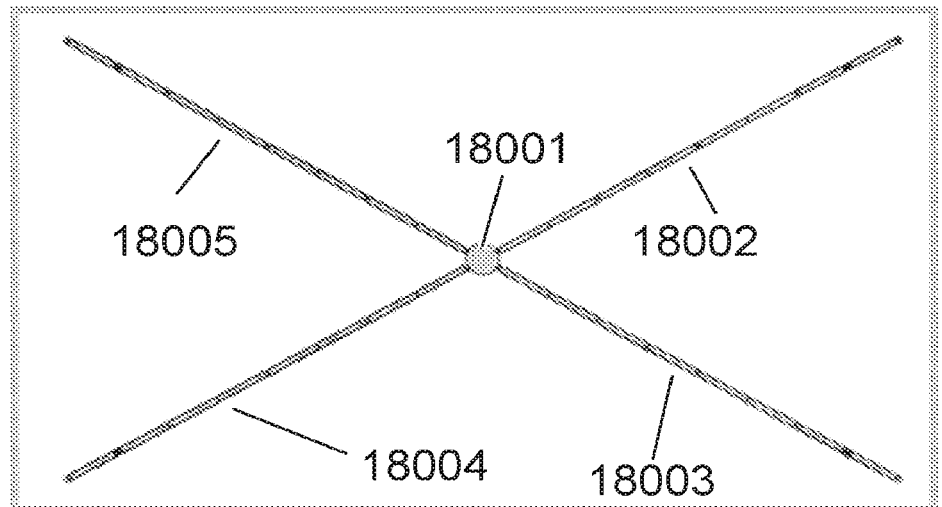
FIGS. 18A-18C illustrate the disinfection device placed in different room shapes, in accordance with at least one example of the present disclosure.
Figure 18B:
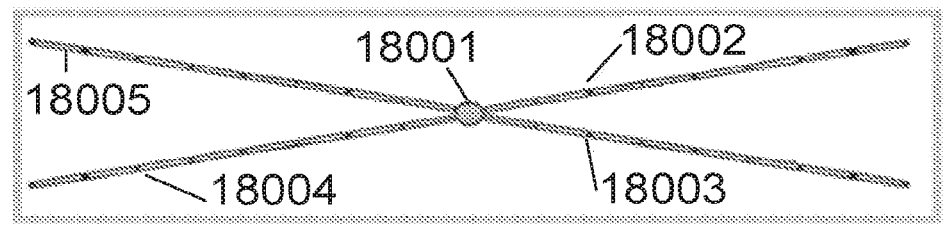
Figure 18C:
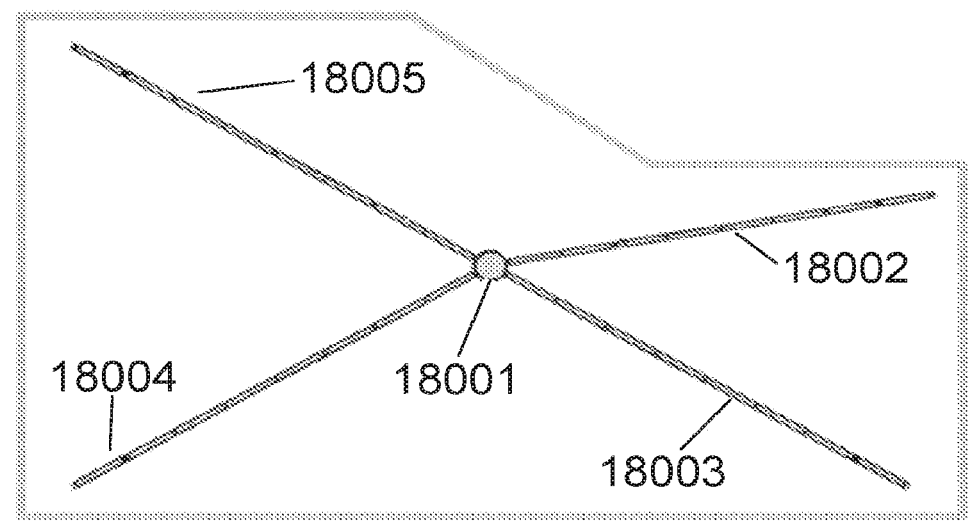

FIG. 18A-18C illustrates how exemplary embodiments of a disinfection device can be adapted to rooms of various shapes by the rotation of the extendable arms as well as the extension of the arms. FIG. 18A shows a typical rectangular room within which an exemplary embodiment of a disinfection device 18001 is placed for a disinfection cycle and for which the two extendable arms at the top 18005 and 18002 and bottom 18003 and 18004 are at an obtuse angle relative to each other while the two extendable arms on the left 18005 and 18004 and the two extendable arms on the right 18002 and 18003 of FIG. 18A are at an acute angle relative to each other. FIG. 18B shows an example of how the extendable arms of the device 18001 is rotated severely to match a long and narrow room or hallway. FIG. 18C illustrates a figurative example of how the extendable arms is rotated in a non-symmetrical manner relative to each other to match the dimensions of rooms with odd or irregular shapes.

Optionally, in this and other embodiments of the device described in any of the figures above may further include an electronic control system including a computer processor configured to execute computer-readably instructions to perform at least one disinfection operation and robotic commands for positioning. In further embodiments, the disinfection operation may utilize some or all of the ultraviolet emitters. Optionally, in this or any embodiment, the control system may be physically configured as part of the extendable frame. Further, the control system may include a transceiver configured to send and receive information over a communication network. Moreover, the control system may be configured to transmit information providing the identity of at least of (a) an item in the target area and (b) the location of one or more target areas. In some embodiments, the information transmission may indicate that the item or target area location has been disinfected by the disinfection device. Any embodiment of the processor may optionally be configured to selectively control the ultraviolet intensity and duration of the ultraviolet source for the disinfection operation. Any embodiment of the processor may further be configured to adjust power supplied to the ultraviolet source, based on age-based degradation of the ultraviolet source in order to provide consistency of ultraviolet light intensity from the radiation source. All embodiments of the processor may also be configured to selectively control the plurality of ultraviolet radiation emitting devices dependent upon which of the plurality of shapes in which the extendable arms and arrays are configured. All embodiments of the processor may optionally be configured to power on a subset of the ultraviolet emitting devices while one or more of the other ultraviolet emitting devices is powered off, or to receive a signal from one or more sensors configured to measure ultraviolet light exposure in the target areas, or to receive at least one signal from a sensor configured to identify at least one of (a) an item in the target area, and (b) a physical location of the target area, or any combination therein. The processor may further employ at least one signal generated based on at least one RFID tag or decals, indicators or markers utilizing Bluetooth or wireless communication which will be disposed on the item in the target area and/or at the physical location of the target area or volume. In further embodiments, the processor may include multiple underlying processors.

FIGS. 19A-19G illustrate an ultraviolet emitting device 1900 with expandable and collapsible arms, in accordance with at least one example of the present disclosure. FIGS. 19A-19G are discussed below concurrently. The ultraviolet emitting device 1900 can include a structure 1902 that can include light sources 1904, a base 1906, wheels 1908a-1908d (only wheels 1908a-190c are visible), also referred to as wheels 1908, and arms 1910a-1910d The structure 1902 can also include a first rail 1912a-1912d and a second rail 1914a-1914d. Each of the arms 1910a-1910d can include a bracket 1916 having rollers 1918a-1918d (only the top rollers 1918a-1918b are visible, the bottom rollers 1918c-1918d can be under the top rollers 1918a-1918b). Each of the brackets 1916 can include a hinge 1920. The arms 1910a-1910d can each include links 1922a-1922d and links 1924a-1924d, respectively. The arms 1910a-1910d can further include a second bracket 1926a-1926d, respectively, and a cross-member 1928a-1928d, respectively. Also shown in FIGS. 19A-19G is a central axis A.

The structure 1902 can be a rigid or semi-rigid structure positionable within a target space and movable between a collapsed position and an expanded position within the target volume. The light sources 1904 can be ultraviolet light sources such as bulbs or other devices configured to emit ultraviolet radiation. The light sources 1904 can be connected to the structure 1902 to emit ultraviolet light in a substantially homogenous irradiance within the target volume in any position between the collapsed position and the expanded position, as discussed in detail further below.

The base 1906 can be a rigid or semi-rigid member comprised of materials such as one or more of metals, fibrous materials, composites, plastics, combinations thereof, or the like. The base 1906 can be configured to support the structure 1902 and the light sources 1904 within the target volume. The base 1906 can have a height relatively larger than its width and length. In some examples, the base 1906 can have a geometric shape substantially of a rectangular prism. The wheels 1908 can be wheels, casters, or the like configured to enable the ultraviolet emitting device 1900 to roll within the target volume.

The arms 1910a-1910d, the first rail 1912a-1912d, the second rail 1914a-1914d, the bracket 1916, the hinge 1920, the links 1922a-1922d, the links 1924a-1924d, the second bracket 1926a-1926d, respectively, and the cross-member 1928a-1928d can each be a rigid or semi-rigid body comprised of materials such as one or more of metals, plastics, foams, elastomers, ceramics, composites, combinations thereof, or the like.

The arms 1910a-1910d can be movable arms or supports releasably securable to the first rail 1912a-1912d and the second rail 1914a-1914d, respectively. The arms 1910a-1910d can be movable along the first rail 1912a-1912d and the second rail 1914a-1914d, respectively, substantially transverse to the central axis A. The arms 1910a-1910d can be movable between an expanded position (away from the base 1906) and a collapsed position (adjacent to the base 1906).

The first rail 1912a-1912d and the second rail 1914a-1914d can each be long and relatively thin members securable to the base 1906 and can be configured to support the arms 1910a-1910d thereon. The first rail 1912a-1912d and the second rail 1914a-1914d can be releasably securable to the base 1906 and can extend around a periphery of the base 1906 substantially transverse to the central axis. That is, each component of the first rail (1912a, 1912b, 1912c, and 1912d) can be secured to one side of the base 1906 to extend entirely around the base 1906. In other examples, the first rail 1912 can include fewer portions and may not extend entirely around the base 1906. The second rail 1914a-1914d can be similarly configured but can be spaced away from the first rail 1912a-1912d substantially parallel thereto. In some examples, the structure 1902 can include only the first rail 1912a-1912d or the second rail 1914a-1914d or portions of each.

The bracket 1916 can be a coupling member connectable to the first arm 1910a, though each arm 1910a-1910d can include a bracket. The bracket 1916 can be hingeably coupled to the arm 1910 via the hinge 1920, which can allow the first arm 1910a to rotate about the hinge 1920 and therefore the first rail 1912a and the support 1906. The rollers 1918a-1918d can be wheels or other rolling members optionally including bearings connected to the bracket 1916 and engage with the first rail 1912a such that the rollers 1918a-1918d can support transfer of the weight (forces) of the first arm 1910a to the first rail 1912a. The rollers 1918a-1918d can also rotate with respect to the bracket 1916 to allow the bracket to translate in a low friction manner with respect to the first rail 1912a to allow the first arm 1910a to translate with respect to the first rail 1912a and with respect to the support 1906. The brackets 1916 can thereby allow the arms 1910a-1910d to be translated to any position on their respective first rails 1912a-1912d. Though the bracket is discussed as having four rollers, the bracket can include fewer or more rollers, such as 1, 2, 3, 5, 6, 7, 8, 9, 10, or the like rollers. The second brackets 1926a-1926d can be similarly configured but connectable to the second rail 1914a-1914d, respectively. In some examples, the brackets 1916 and the second brackets 1926 can be interchangeable.

The links 1922a-1922d and the links 1924a-1924d can be parallel sets of linkages connectable to the brackets 1916a-1916d and the brackets 1926a-1926d, respectively. Each of the links 1922a-1922d and the links 1924a-1924d can be hingeably coupled to each other to enable the arms 1910a-1910d to move between their expanded positions and collapsed positions independently of each other. In some examples, the links 1922 can be connected to each other in one of a scissor linkage arrangement. FIG. 19E shows inside links 1930*a*-1930*n* and outside links 1932*a*-1932*n* coupled together to enable movement of the arm 1910*b*. The number of links 1930*a*-1930*n* and 1932*a*-1932*n* can be any number to create an arm having a desired range of motion, such as 1, 2, 3, 4, 5, 6, 7, 8, 9, 10, 15, 20, or the like. Other straight-line linkage arrangements can be used in other examples. In other examples, non-linear linkages can be used. The cross-member 1928*a*-1928*d*, respectively can be bars rods, or other rigid members connecting the first brackets 1916*a*-1916*d* to the brackets 1926*a*-1926*d*, respectively.

The ultraviolet emitting device 1900 can also include a user interface 1925, which can be a screen connected to a controller and one or more other components within the base or housing 1906, such as sensors, and/or an actuator or motor. The user interface 1925 can include any or all of the components of the computer system 4400 of FIG. 44, especially the display device 4410, the input device 4412, and the navigation device 4414. In operation, a user can use the user interface 1925 to control operation of the ultraviolet emitting device 1900.

Figure 19A:
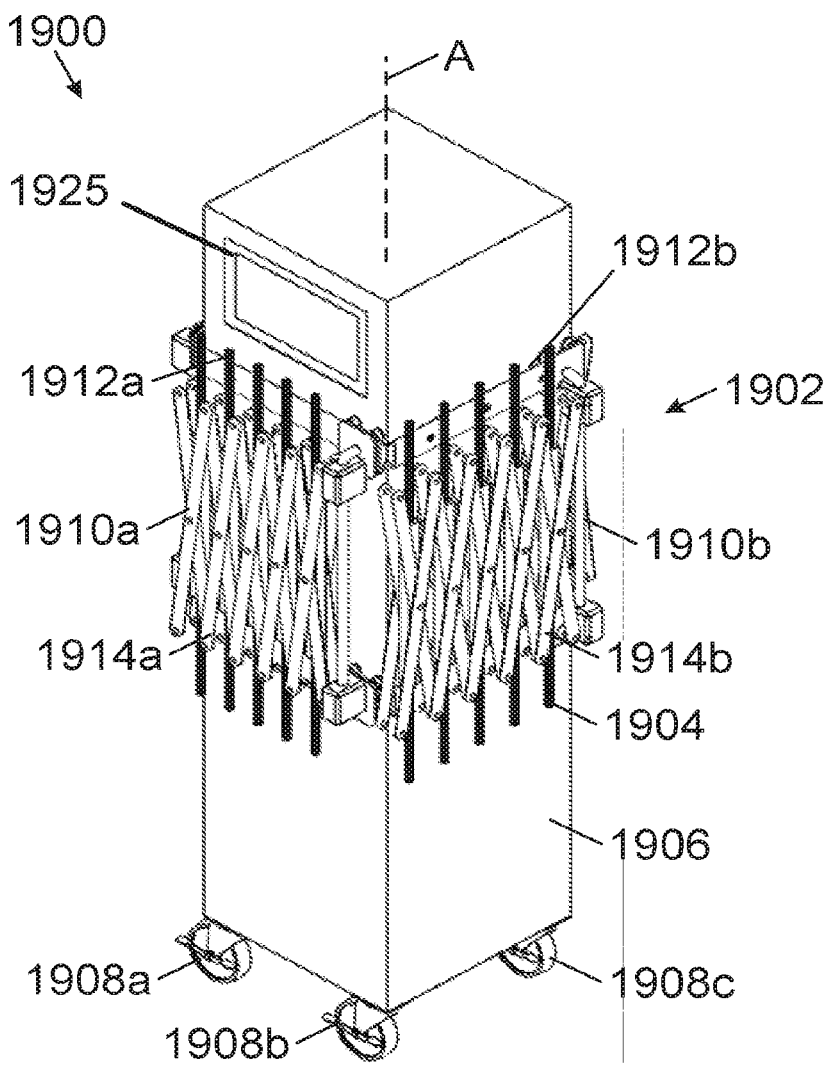
FIGS. 19A-19G illustrate a disinfection device with expandable and collapsible arms, in accordance with at least one example of the present disclosure.
Figure 19B:
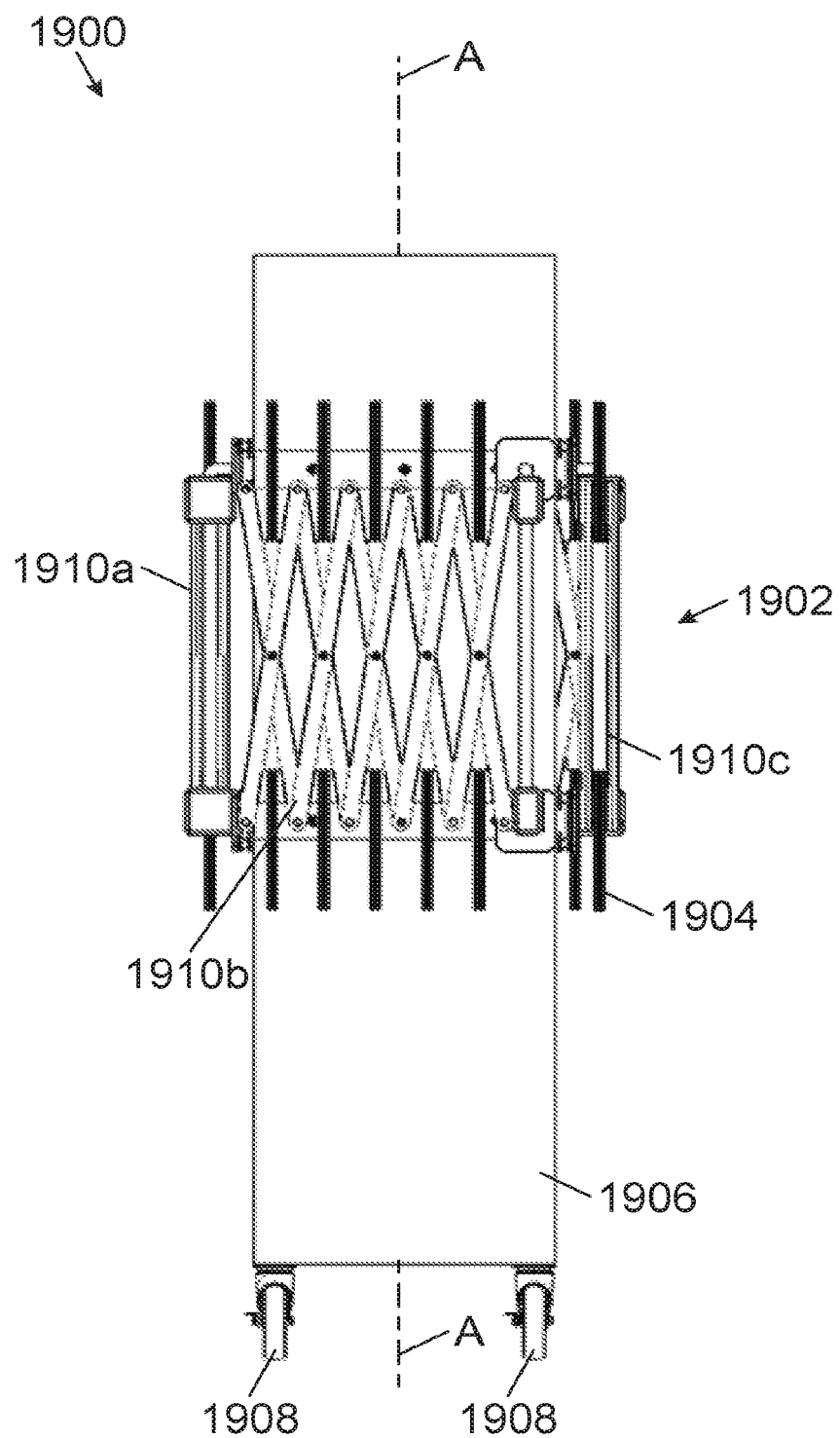
Figure 19C:
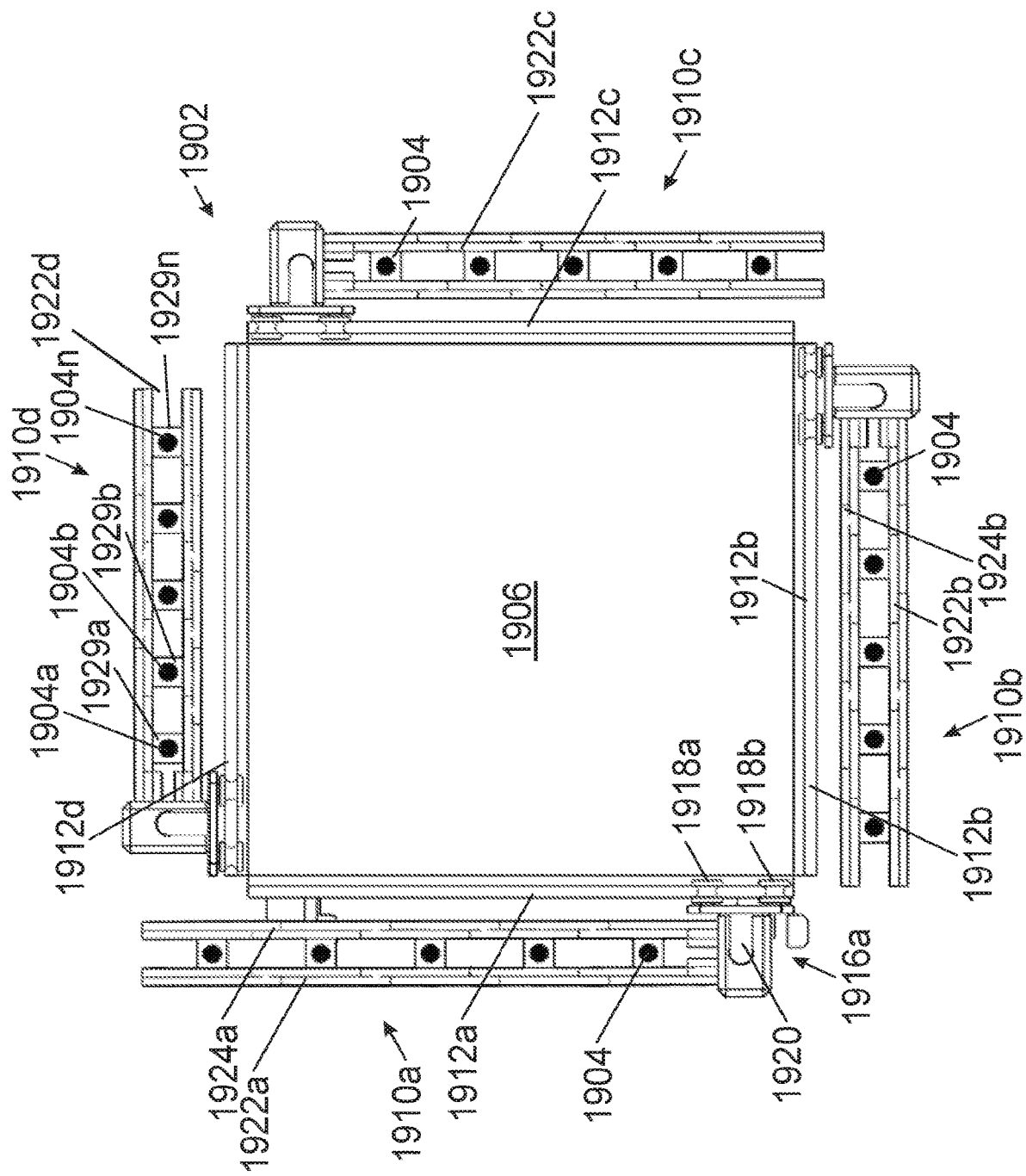

FIG. 19C shows a top view of the ultraviolet emitting device 1900, which shows that the arms 1910 can each include light source holders 1929*a*-1929*h*, each configured to hold one or more the light sources 1904*a*-1904*h* therein. The light source holders 1929 can each be connected to and supported by the links 1922 and 1924, such that the light source holders 1929 and therefore the light sources 1904 move with the links 1922 and 1924. The light source holders 1929 can be positioned on each arm 1910 such that the light sources 1904 are connected to each arm 1910 such that each of the light sources 1904 of, for example a plurality of light sources for arm 1910*d*, is proportionally spaced with respect to each of the light sources 1904*a*-1904*h* as the arm 1910*d* is moved between the collapsed position and the expanded position. The first plurality of light sources of the arm 1910*d*, for example, can also be proportionally spaced so as to emit ultraviolet light in a substantially homogenous irradiance within the target volume in any position between the collapsed position and the expanded position. That is, each of the light sources 1904*a*-1904*h* of the arm 1910*a* can be proportionally spaced from each adjacent light source of the arm 1910*a*. The light sources 1904*a*-1904*h* can maintain their proportional spacing at any position between the collapsed position and the expanded position of the arm 1910*a*. Each of the arms 1910 can have such an ability to proportionally space the light sources 1904 of that arm.

The light sources between arms 1910 may not be proportionally spaced, depending on the size and shape of the target volume, as the arms 1910 can extend as far as required (as long as the arm is sufficiently long) to position the arms 1910 to achieve homogenous irradiation within the target volume. In several examples, the distance between light sources 1904 between arms (for example 1904*a* and 1904*b*) can be symmetrically spaced and in some examples, the lights sources 1904 can be asymmetrically spaced.

Figure 19D:
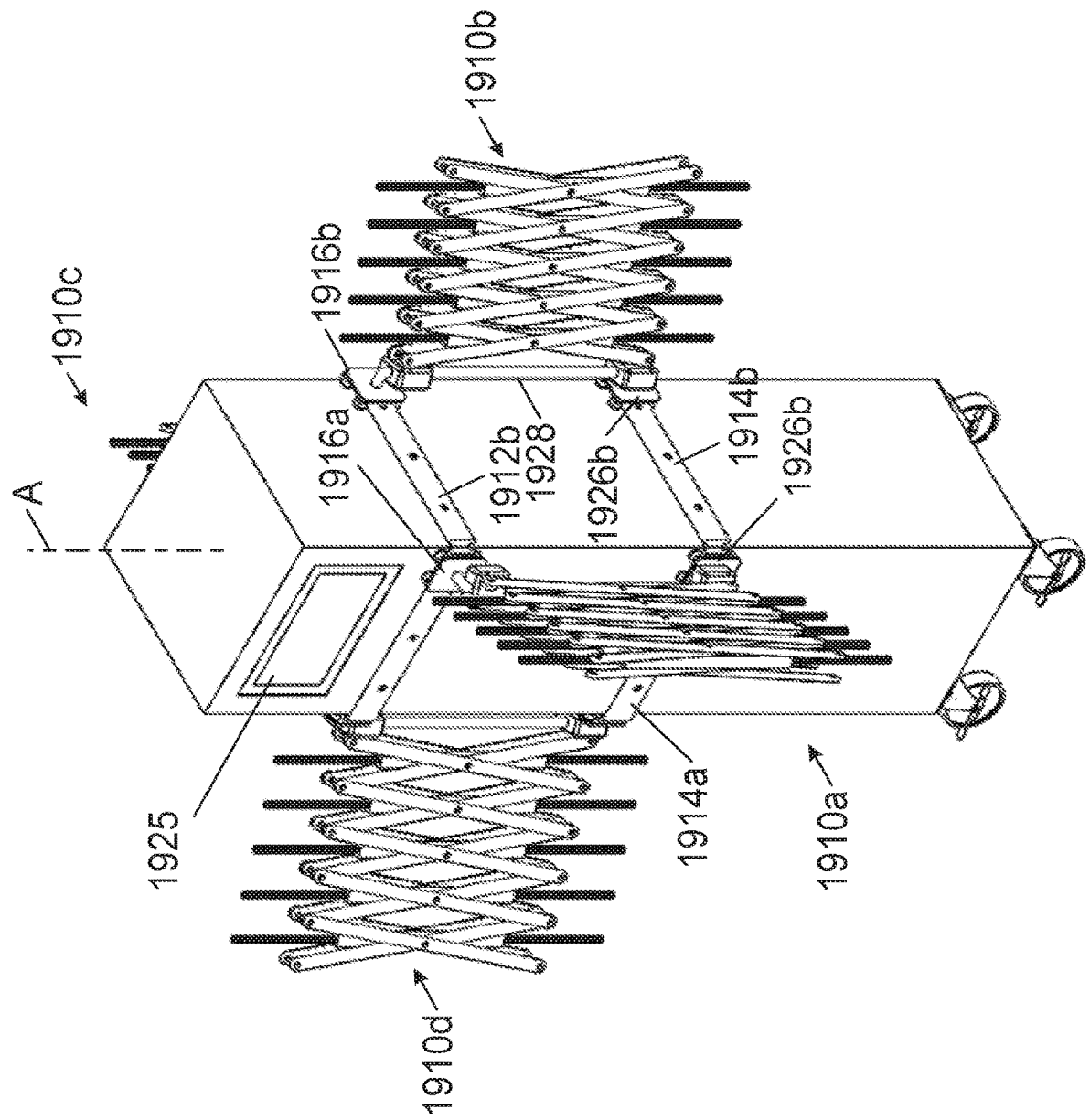
Figure 19E:
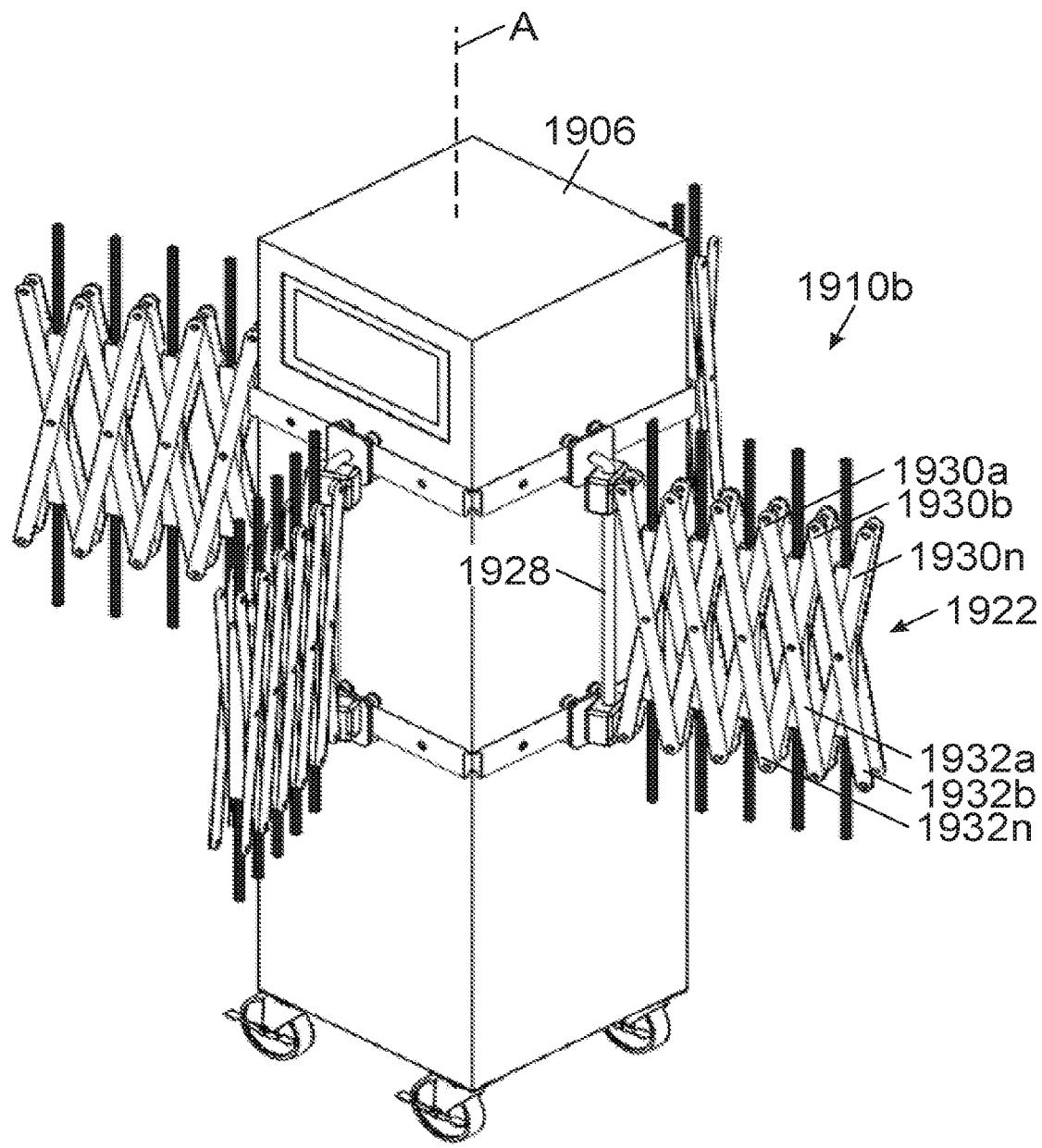
Figure 19F:
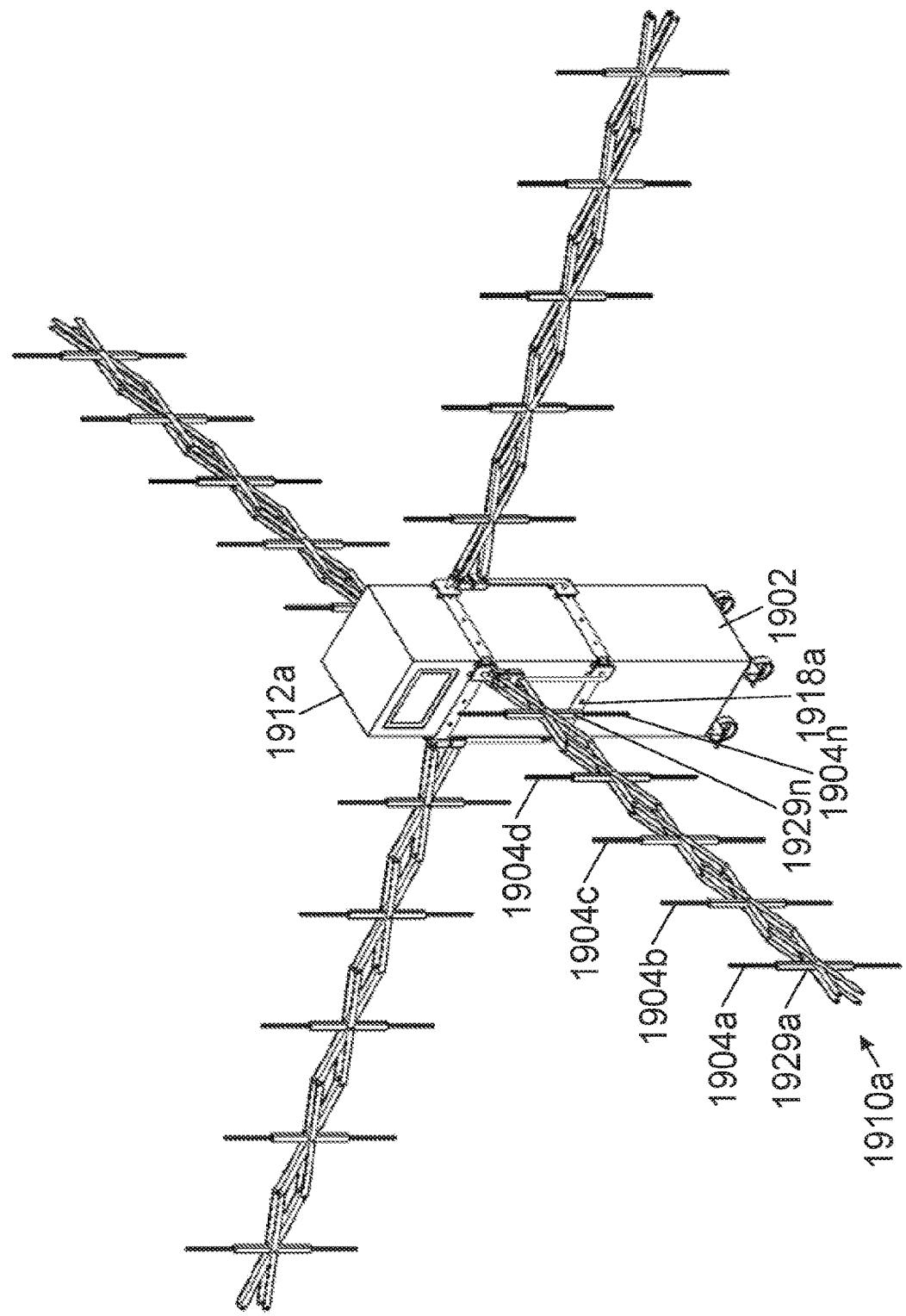
Figure 19G:
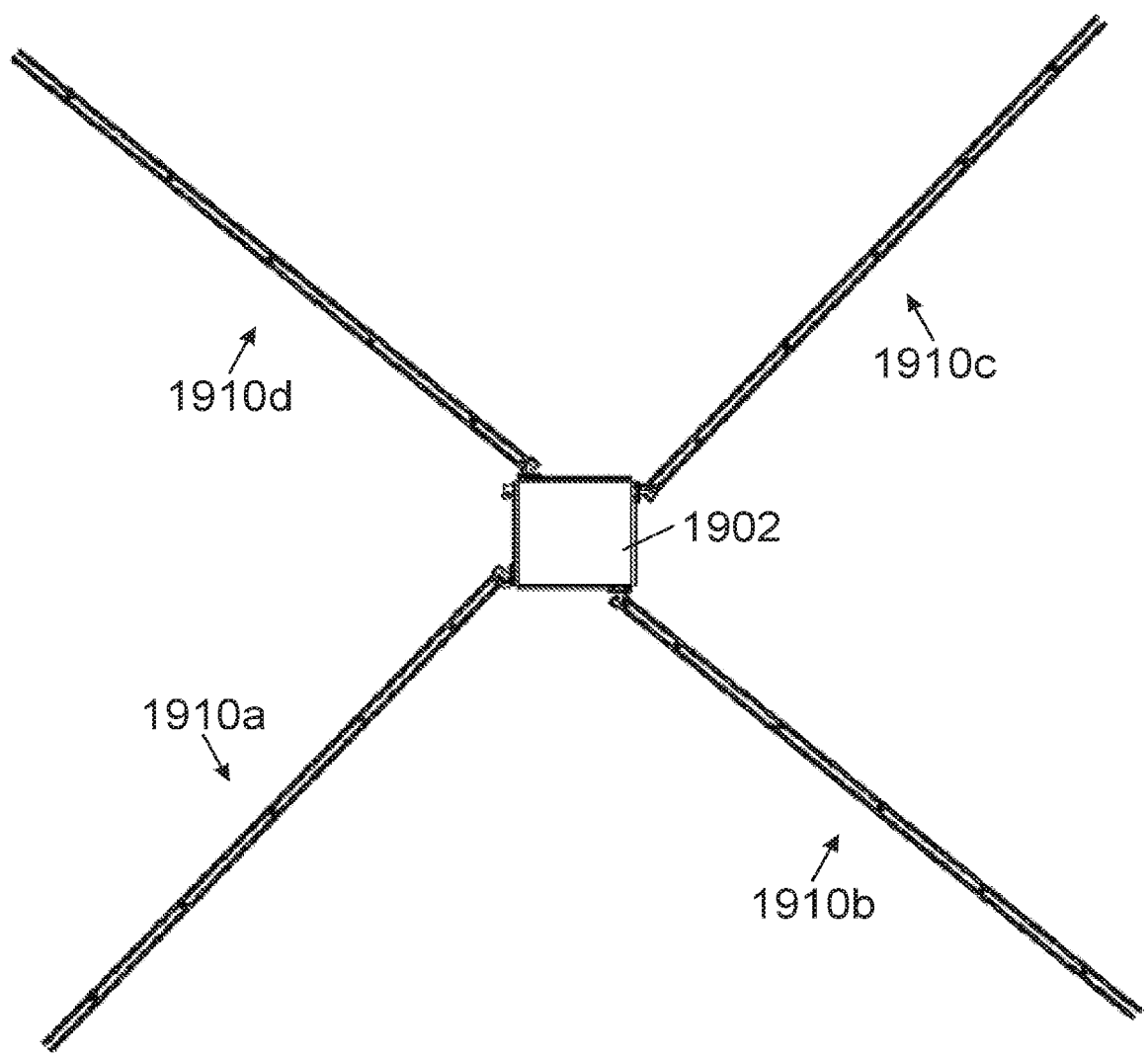

In operation, after the first rails 1912 and second rails 1914 are secured to the base 1906 and the arms 1910 are each connected to the rails 1912 and 1914, the arms can be pivoted at the brackets 1916 and 1926 to extend radially outward from the base 1906, as shown in FIG. 19D. Each of the arms 1910 can be translated along the rails 1912 and 1914 to a desired position. FIG. 19D shows each of the arms 1910 at a right side of the rails 1912 and 1914 and FIG. 19E shows each of the arms 1910 approximately at a middle of the rails 1912 and 1914. Before or after translating the arms 1910 along the rails 1912 and 1914, one or more of the arms 1910 can be positioned between a collapsed position. FIGS. 19A-19E show the arms in a substantially collapsed position and FIGS. 19F-19G show the arms 1910 in a substantially expanded position. The arms 1910 can be positioned at any position between the collapsed and expanded positions.

FIG. 19F also shows how the light sources 1904*a*-1904*h* can be spaced evenly (or proportionally) with respect to each other in the expanded position as related to the dimensionality of the target volume. As discussed above, the light source brackets 1929 can be connected to the links 1922 and 1924 to move therewith. As shown in FIG. 19F, the brackets 1929 can translate radially outward from the base 1906 as the arms 1910 move from the collapsed position to the extended position while maintaining the light sources 1904 in even or proportional spacing with respect to each light source 1904 of each arm 1910. That is, as shown in FIG. 19F, the light sources 1904*a*-1904*h* can be evenly spaced on the (first) arm 1910*a*.

Similarly, the second arm 1910*b* can be releasably securable to the first rail 1912 and the second rail 1914 and can be movable along the first rail 1912 substantially transverse to the central axis A and substantially orthogonally to the first arm 1910*a*, and the second arm 1910*b* can be movable between an expanded position and a collapsed position. The second arm 1910*b* can have a second plurality of light sources 1904 connected thereto such that each of the light sources 1904 can be proportionally spaced with respect to each of the light sources 1904 as the second arm is moved between the collapsed position and the expanded position.

The third arm 1904*c* and the fourth arm 1910*d* can be similarly configured. For example, the third arm 1910*c* can be releasably securable to the first rail 1912 and the second rail 1914 and can be movable along the first rail 1912 substantially transverse to the central axis A, substantially parallel to the first arm 1910*a*, and substantially orthogonally to the second arm 1910*b*, and the third arm 1910*c* can be movable between an expanded position and a collapsed position. The third arm 1910*c* can have a third plurality of light sources 1904 connected to the third arm 1910*c* such that each of the light sources 1904 can be proportionally spaced with respect to each of the light sources 1904 as the third arm is moved between the collapsed position and the expanded position. The fourth arm 1910*d* can be releasably securable to the first rail 1912 and the second rail 1914 and movable along the first rail 1912 substantially transverse to the central axis A, substantially orthogonally to the first arm 1910*a* and the third arm 1910*c* and substantially parallel to the second arm 1910*b*, and the fourth arm 1910*d* can be movable between an expanded position and a collapsed position. The fourth arm 1910*d* can have a fourth plurality of light sources 1904 connected to the fourth arm 1910*d* such that each of the light sources 1904 can be proportionally spaced with respect to each of the light sources 1904 as the fourth arm 1910*d* is moved between the collapsed position and the expanded position.

Figure 20A:
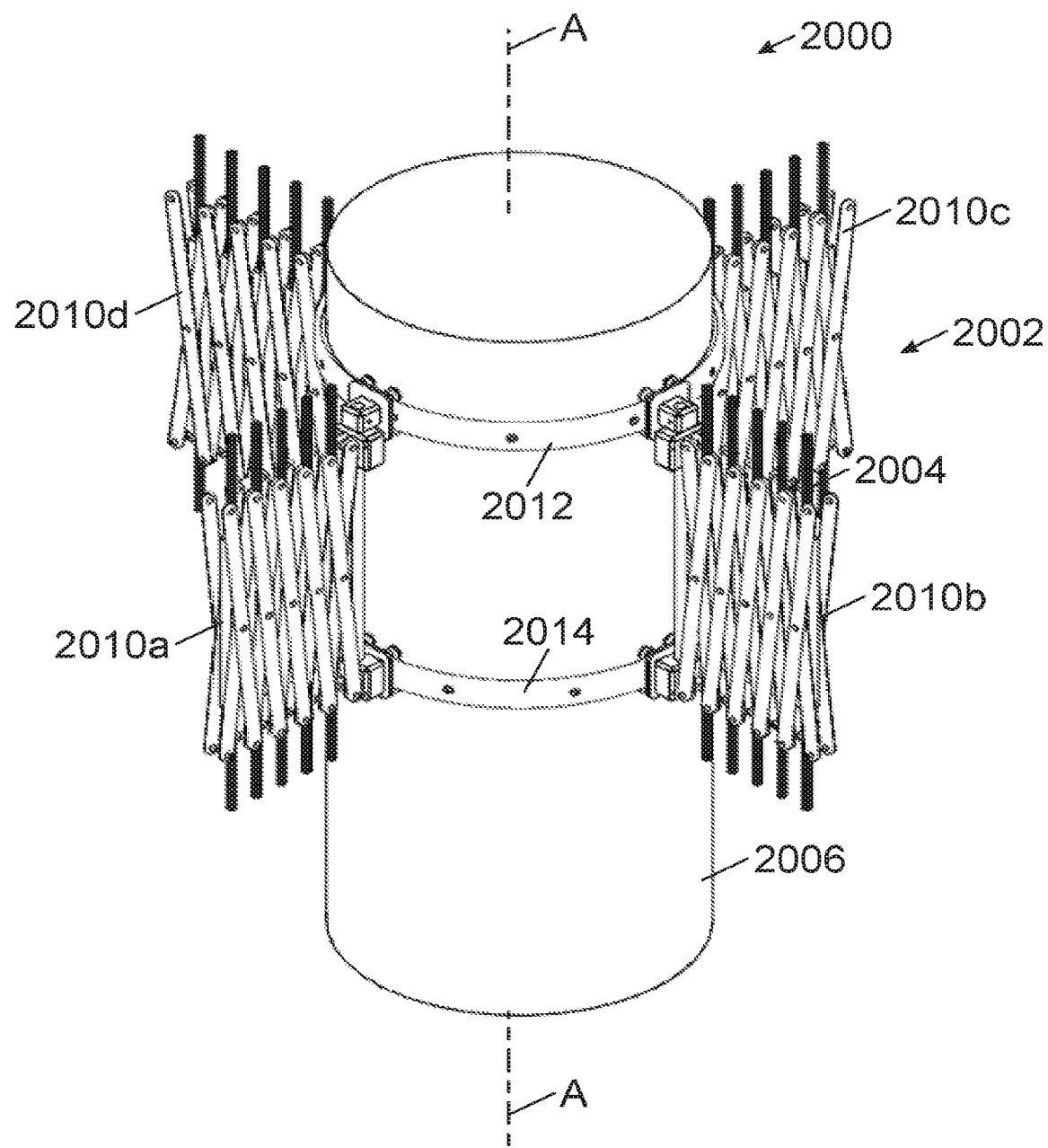
FIGS. 20A-20G illustrate a disinfection device with expandable and collapsible arms, in accordance with at least one example of the present disclosure.
Figure 20B:
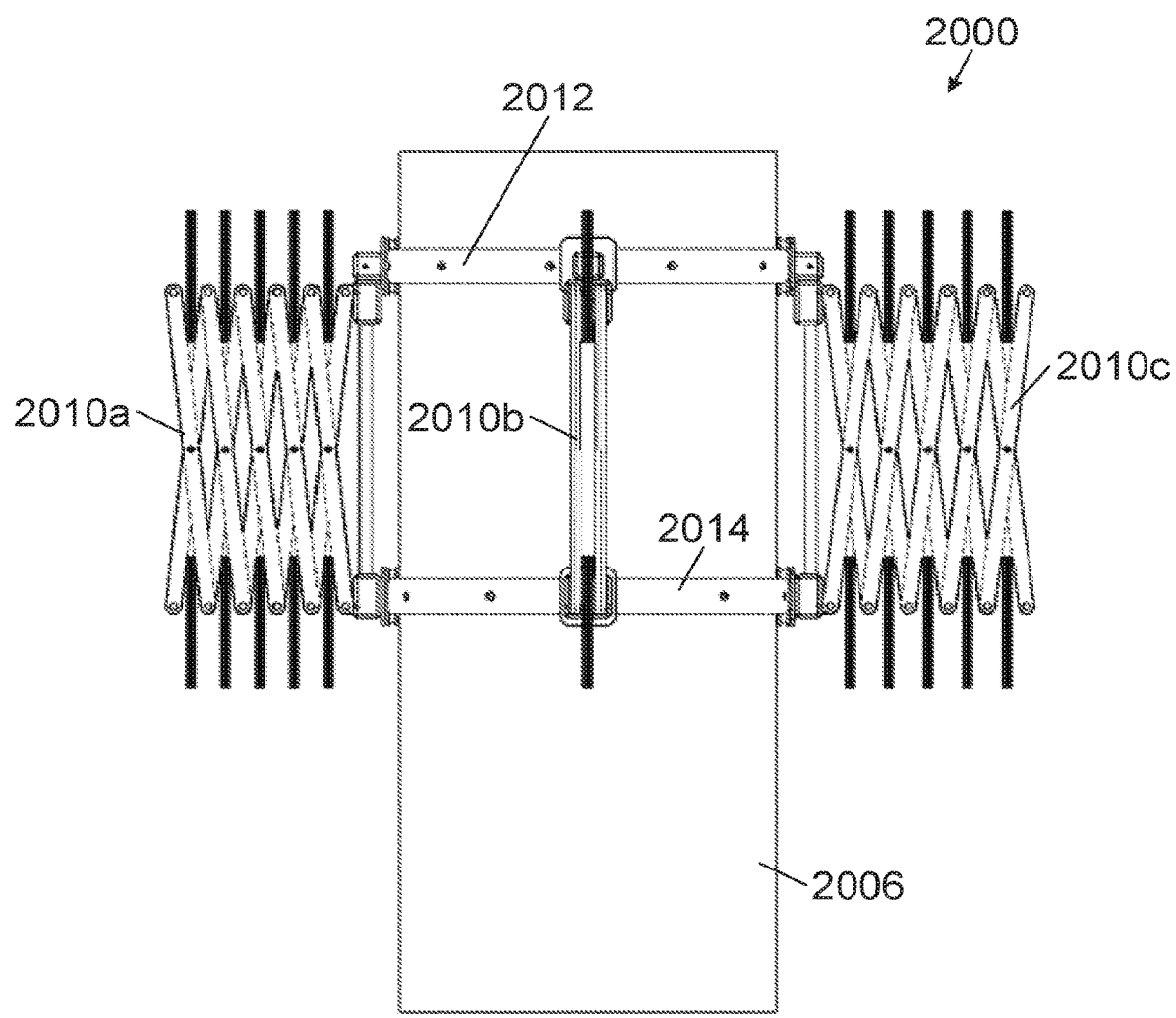
Figure 20C:
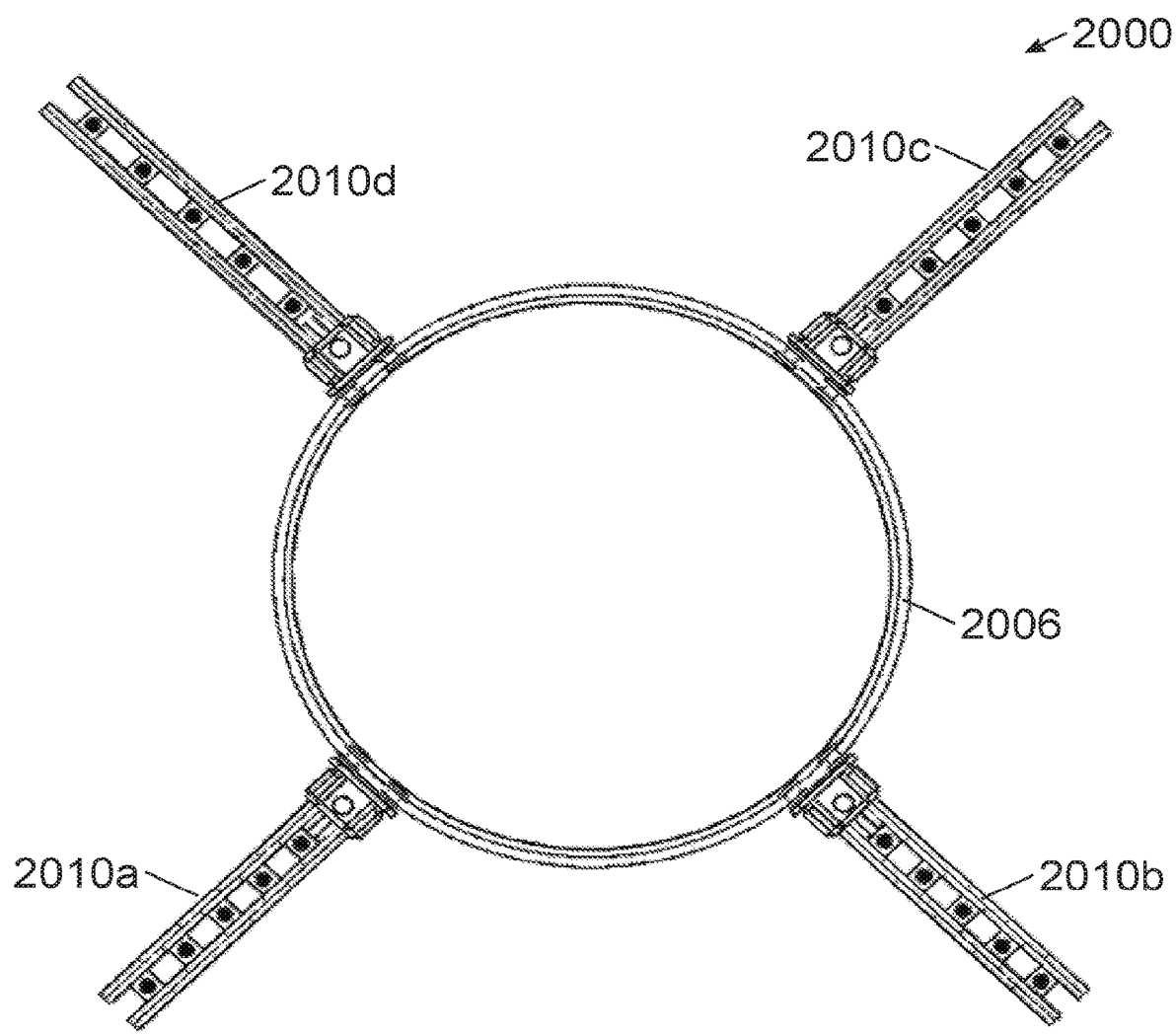
Figure 20D:
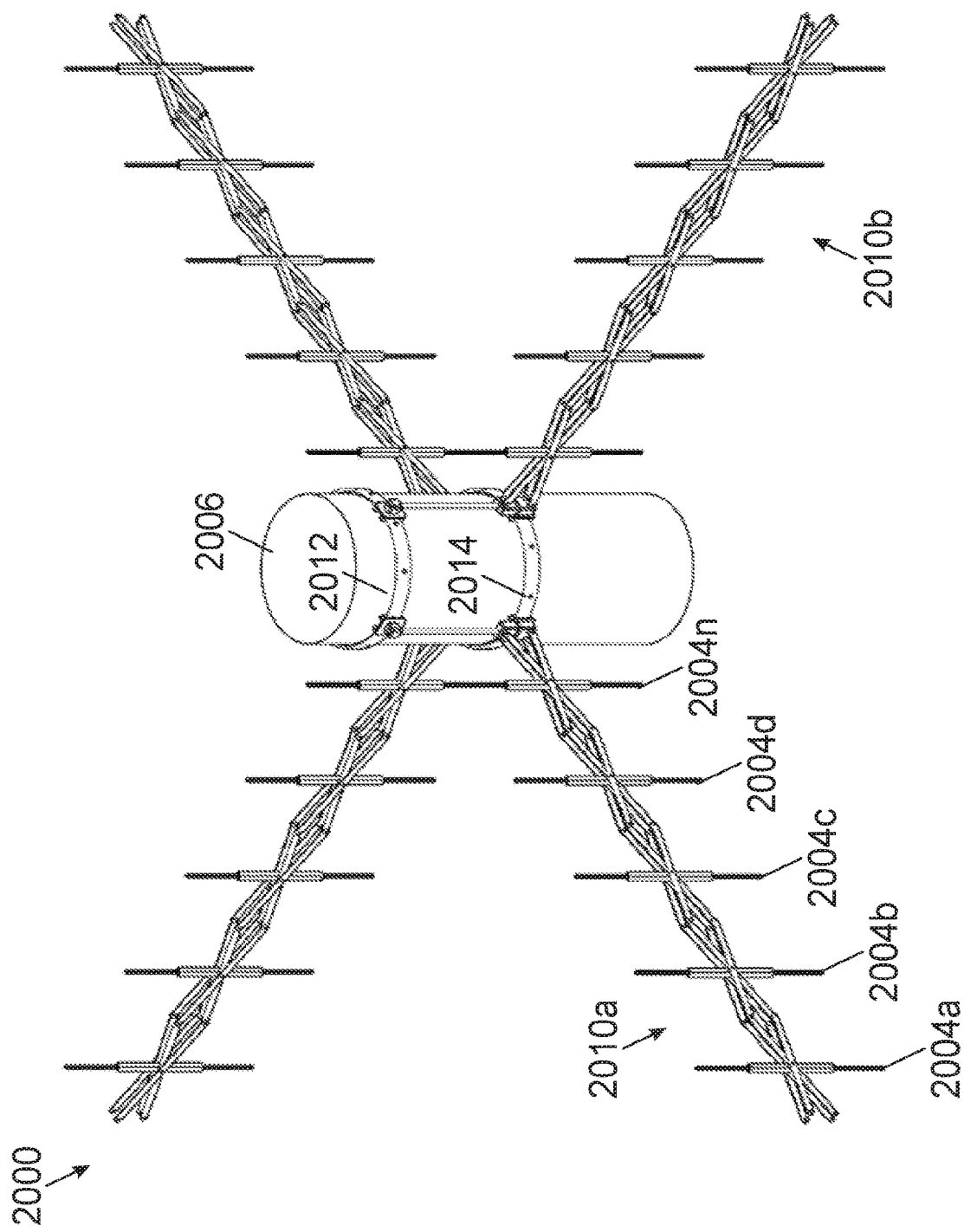
Figure 20E:
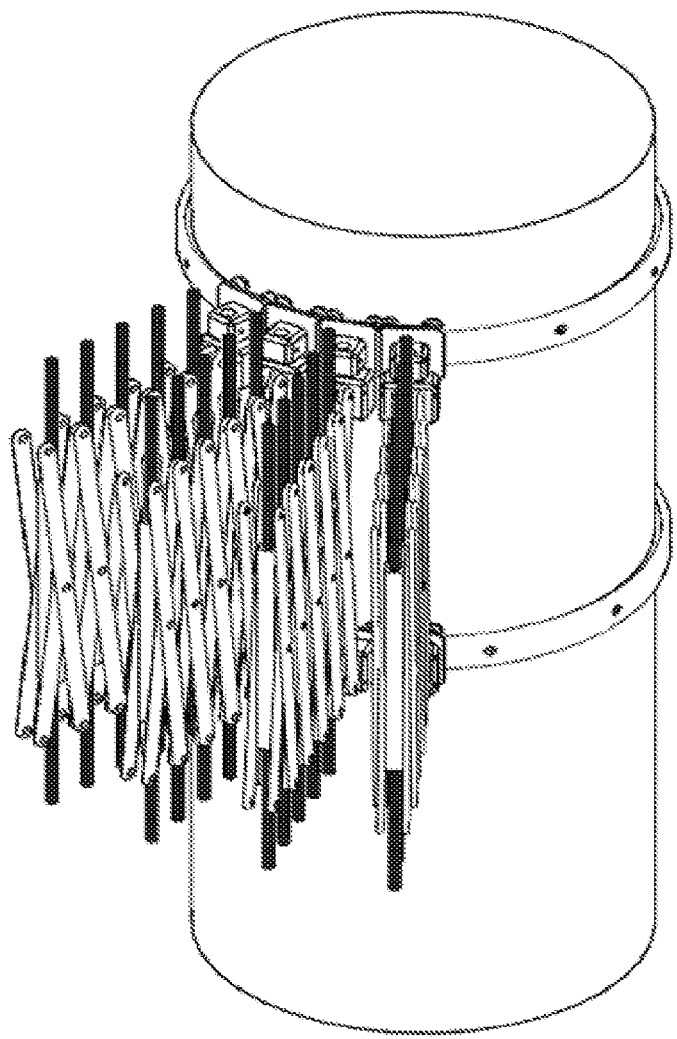
Figure 20F:
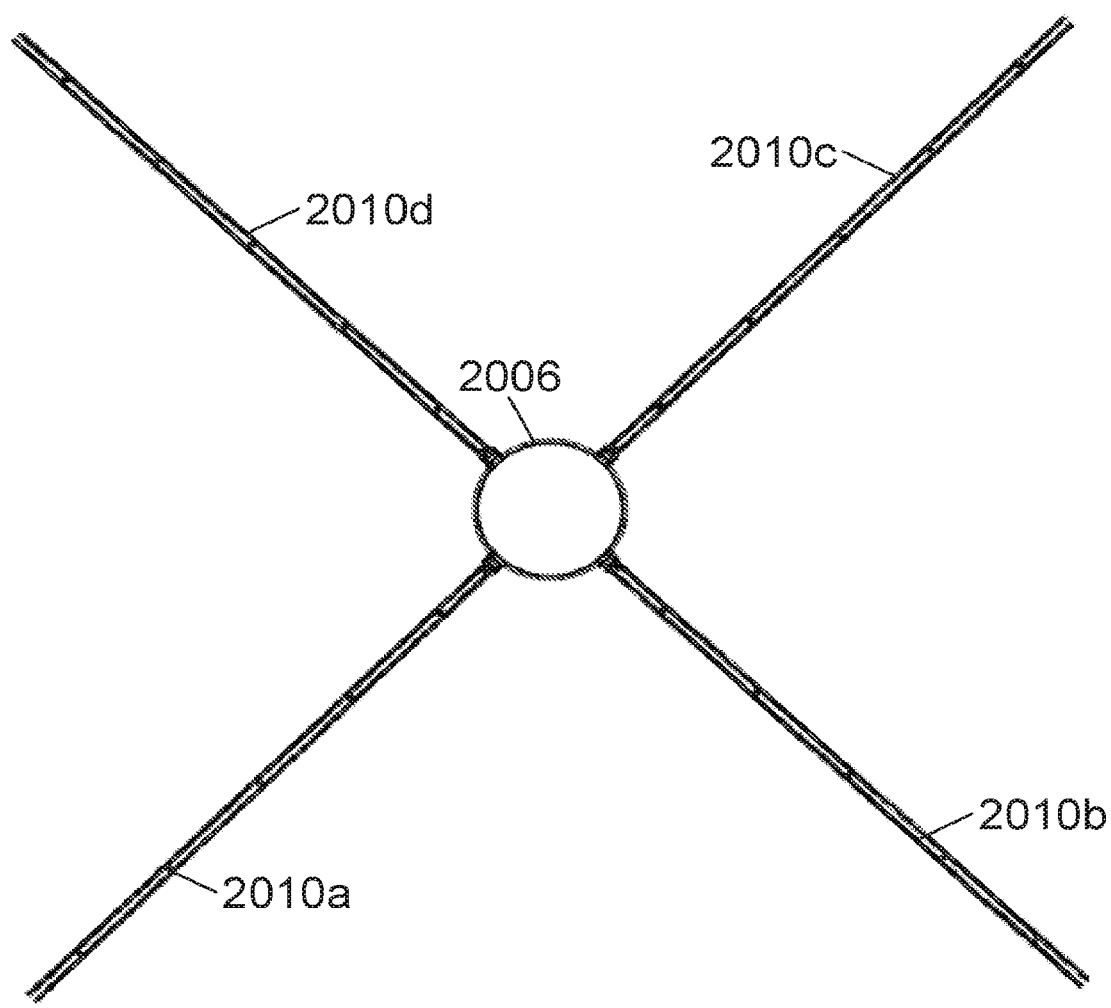
Figure 20G:
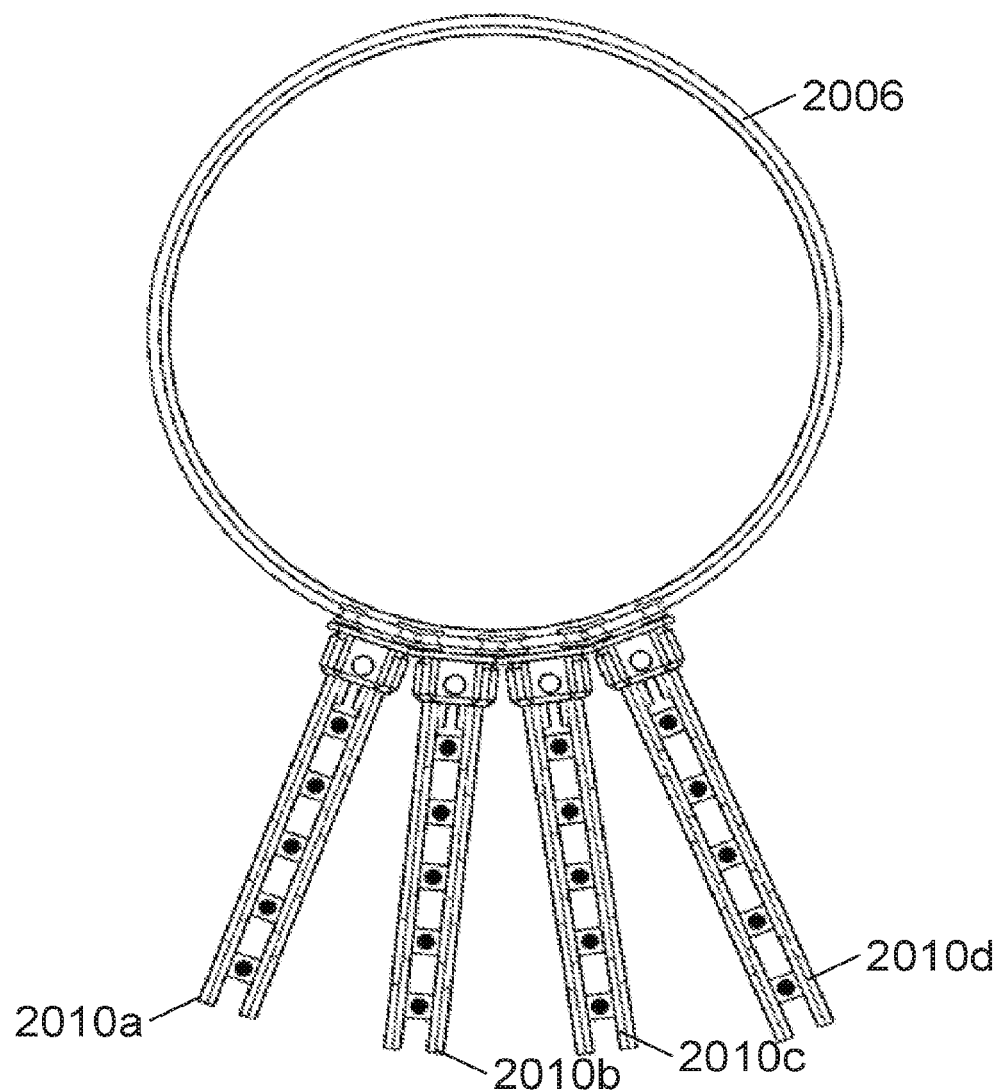

FIGS. 20A-20G illustrate a disinfection device 2000 with expandable and collapsible arms, in accordance with at least one example of the present disclosure. The disinfection device 2000 can be similar to the disinfection device 1900 of FIG. 19 in that the structure 2002 of the disinfection device 2000 can be similar in design and operation to the disinfection device 1900, discussed above, except that the base 2006 can be substantially cylindrical, where the rails 1912 and 1914 can extend around the circumference of the base 1906 cylindrically. Such a configuration can allow for the arms 2010a-2010d to translate in a circular motion be spaced substantially evenly around the base 2006, as shown FIGS. 20A-20D and 20F, or asymmetrically (uneven), as shown in FIGS. 20E and 20G. The disinfection device 2000 can thereby provide an even distribution of light sources 2004a-2004n, as shown in FIG. 20D or an asymmetric distribution, as shown in FIG. 20E, which can help provide a homogenous irradiance within the target volume in any position between the collapsed position and the expanded position in target volumes having atypical or abnormal shapes.

FIGS. 21 A-20G illustrate a disinfection device 2100 with expandable and collapsible arms, in accordance with at least one example of the present disclosure. The disinfection device 2100 can include a circular base structure 2106 with compartments 2105a-2105d, which can allow for storage of arms 2110a-2110d. The arms 2110 can include a cover 2111 and a handle 2113. The handles 2113 can be operable to move the arms 2110 between the expanded and collapsed positions and the covers 2111 can protect the light sources 2104 during storage and transportation of the disinfection device 2100.

Figure 21A:
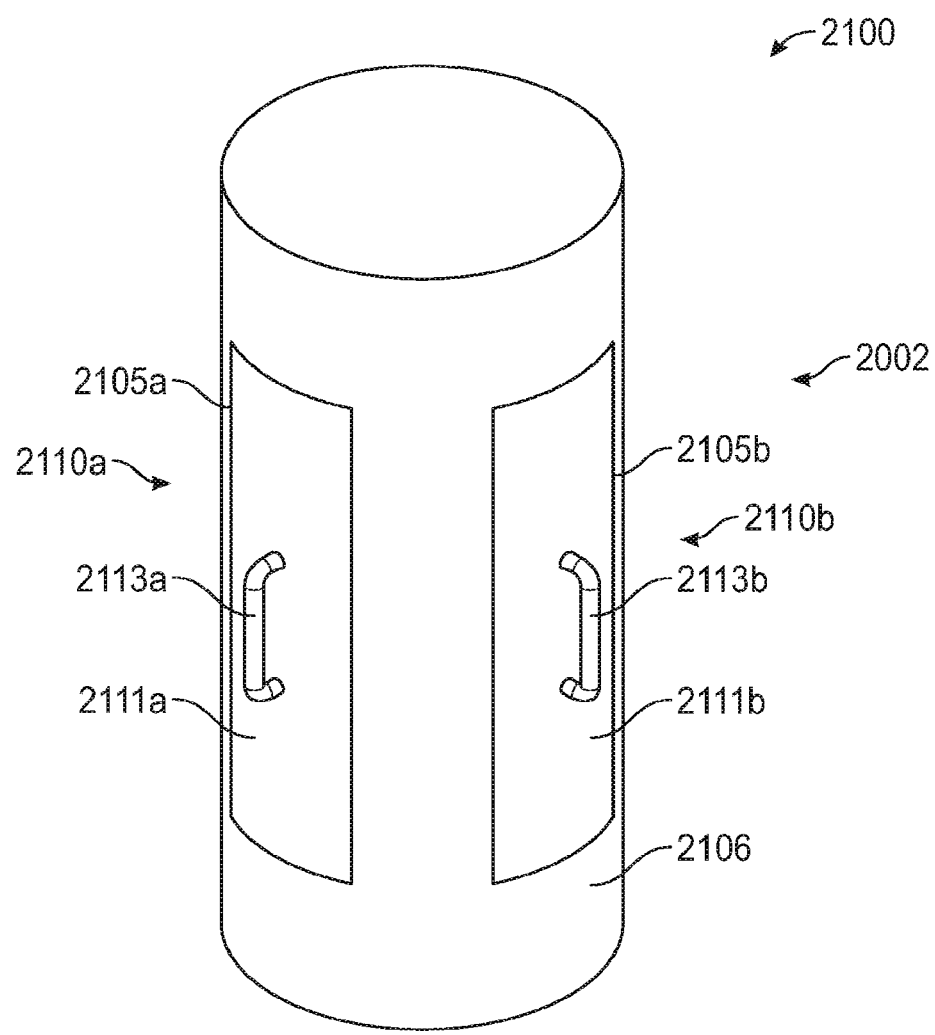
FIGS. 21A-21G illustrate a disinfection device with expandable and collapsible arms, in accordance with at least one example of the present disclosure.
Figure 21B:
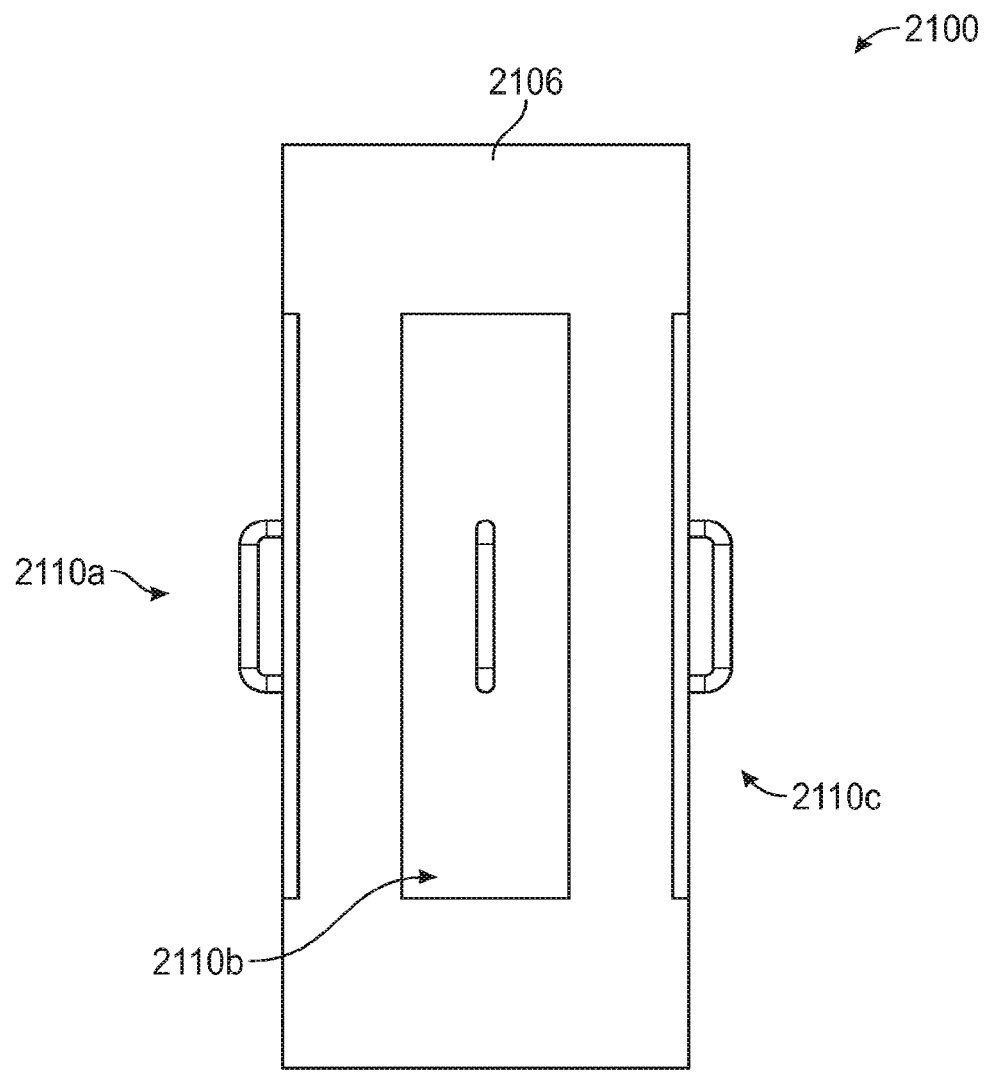
Figure 21C:
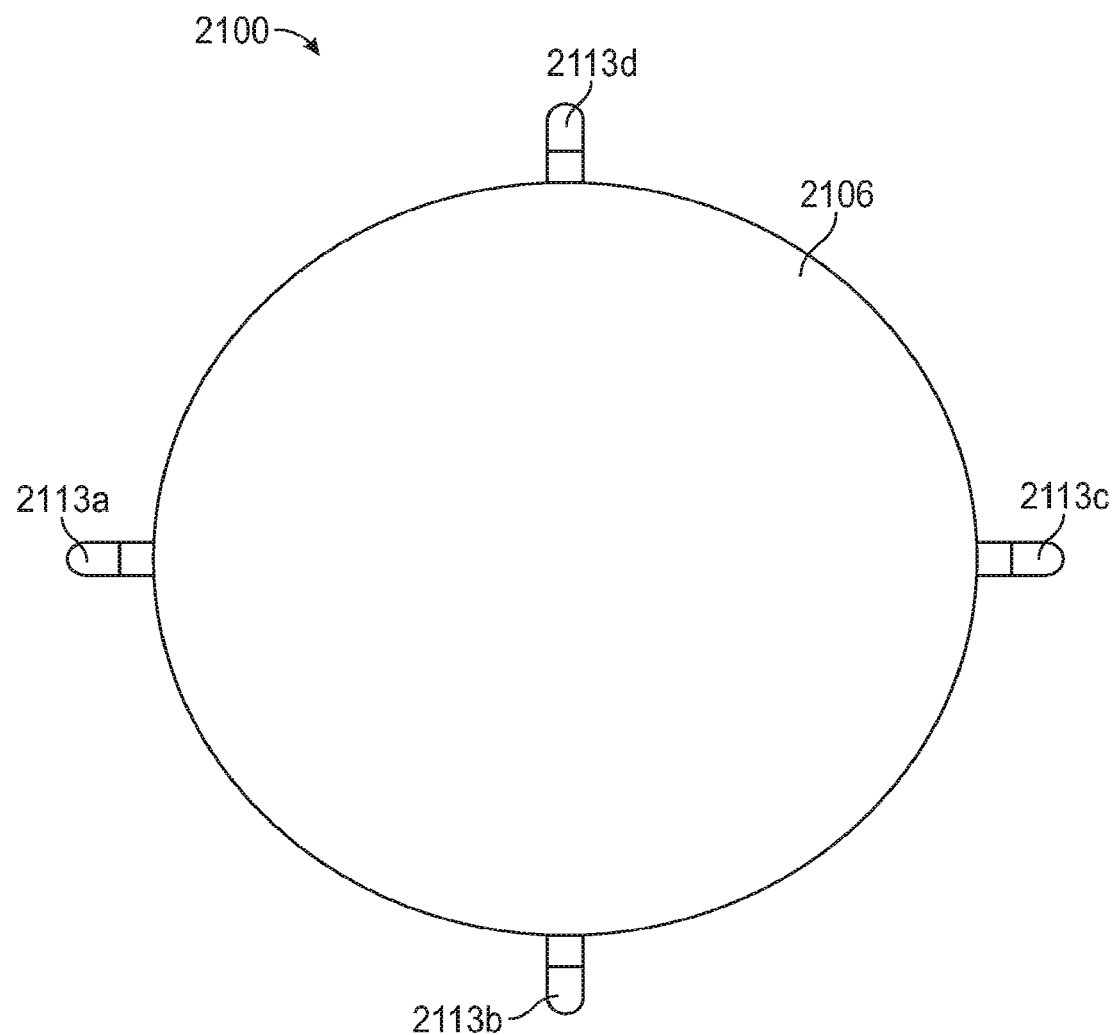
Figure 21D:
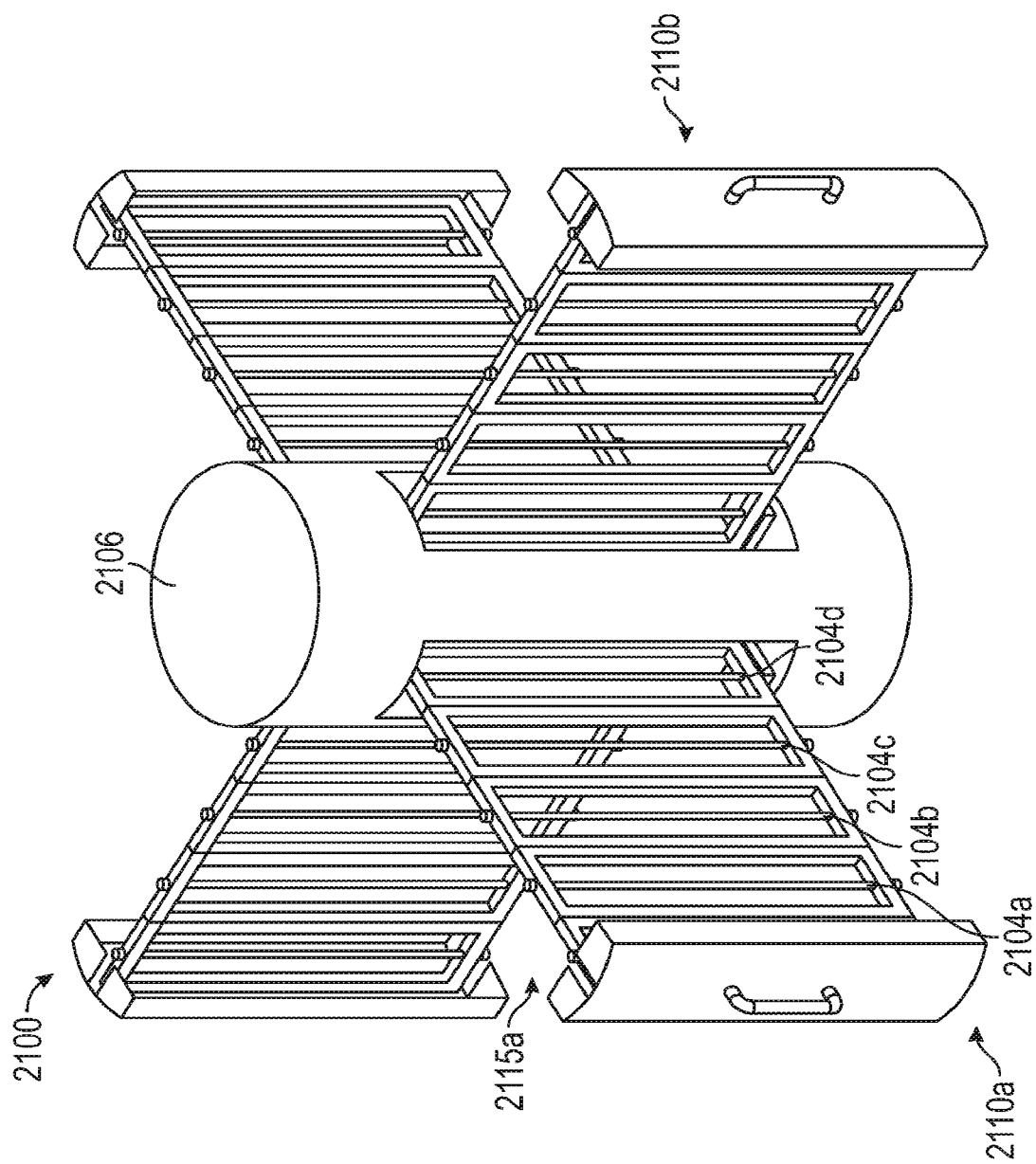

FIG. 21D shows a support frame 2115 of each of the arms 2110 in the expanded position. Each of the support frames 2115 can be comprised of segments 2117a-2117h such that each of the light sources 2104 is spaced substantially proportionally with respect to each of the light sources 2104. The arms 2110 can be spaced evenly around the base 2106 in some examples and unevenly or asymmetrically in other examples. There can be 1, 2, 3, 4, 5, 6, 7, 8, 9, 10, or the like arms 2110.

Figure 21E:
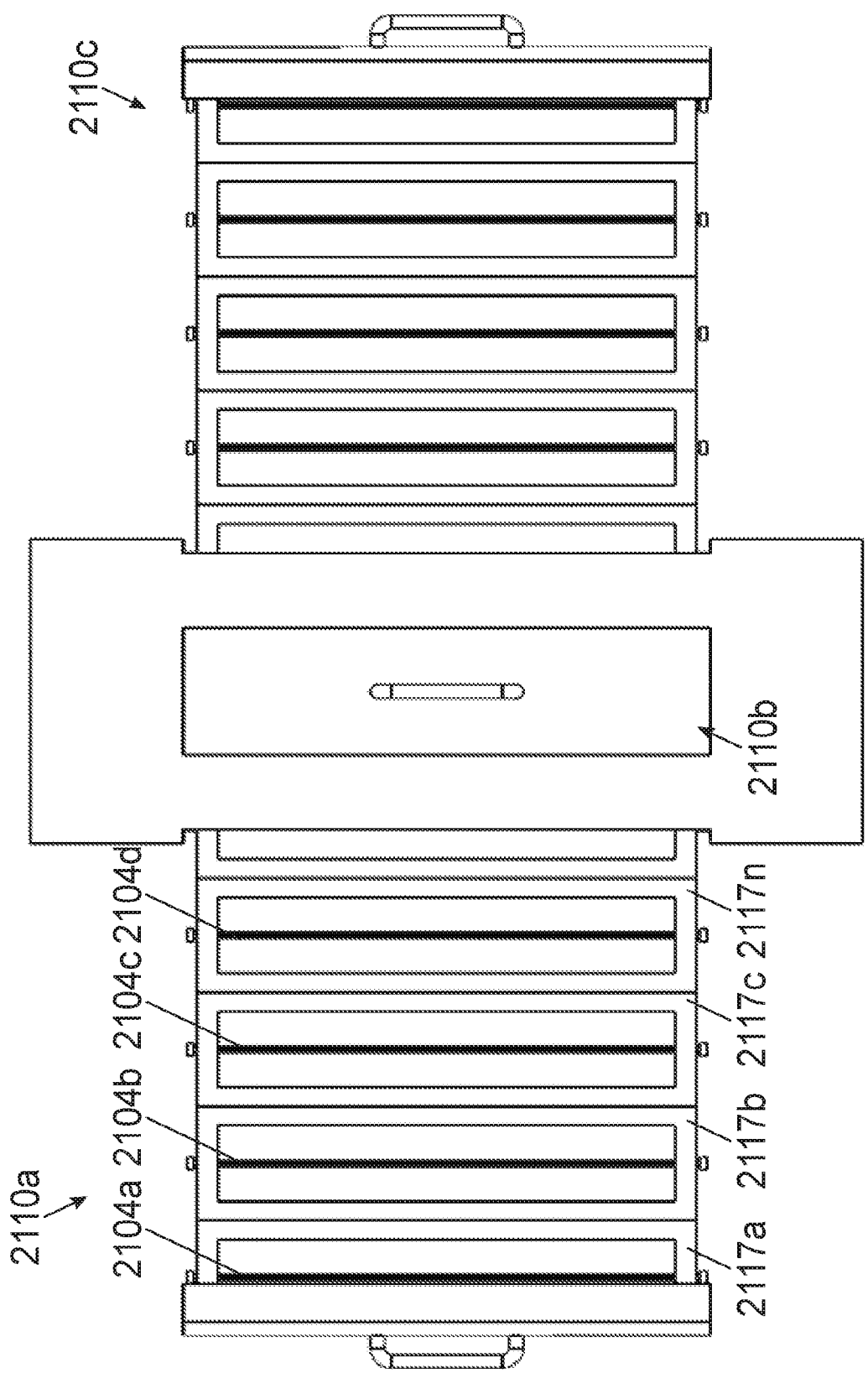

The support frame 2115 segments 2117 can be rectangular in shape, but can be other shapes in other examples FIGS. 21D and 21E show the light sources 2104 being held structurally within the dimensions of each of the segments 2117. The support frame segments 2117 can be hinged together at preset distances so that when the arms 2110 are expanded to accommodate the target volume the energy field created by the light sources 2104 is substantially evenly distributed proportionally based on geometry, ultraviolet light source intensity, and time.

Figure 21F:
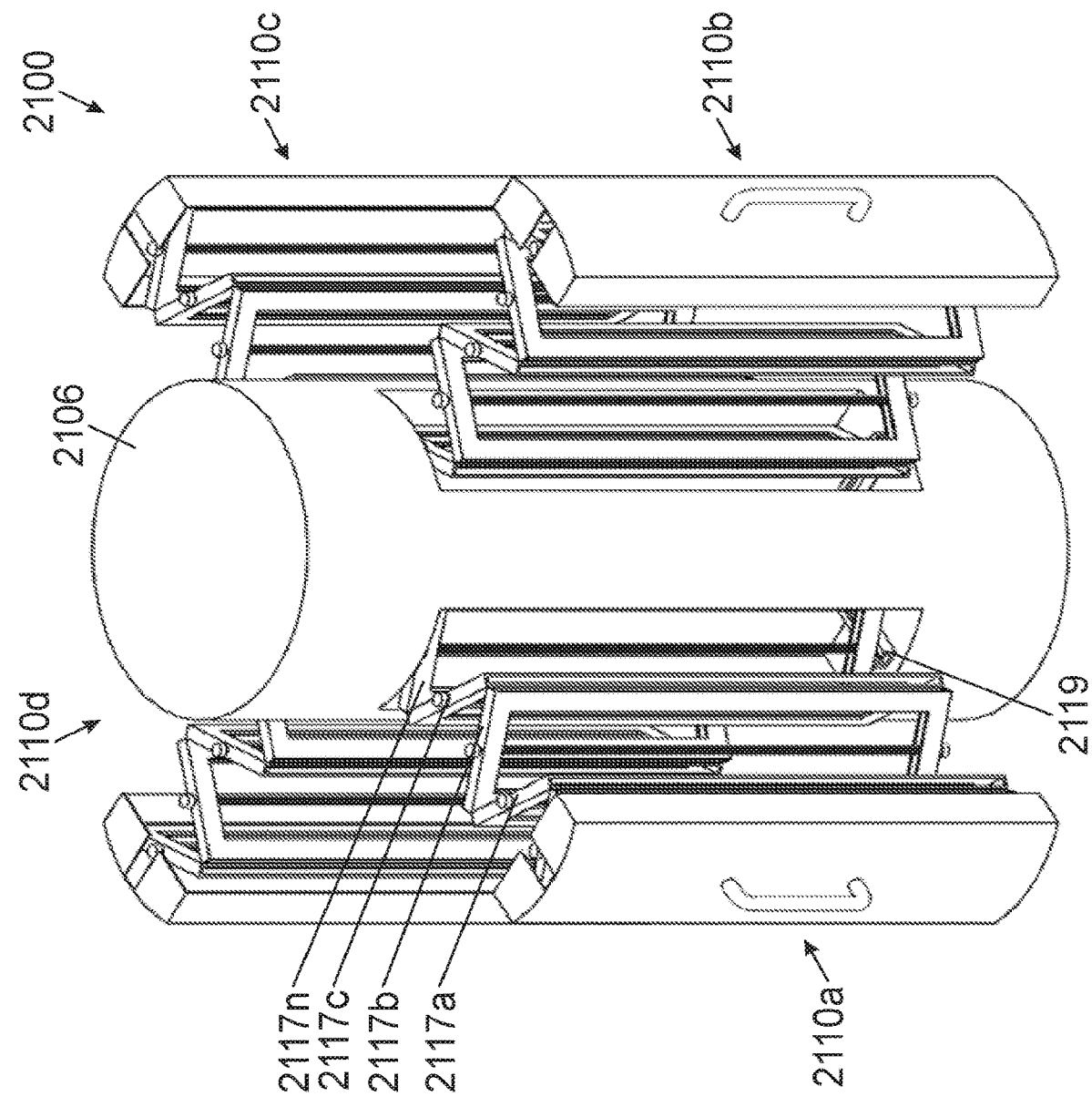
Figure 21G:
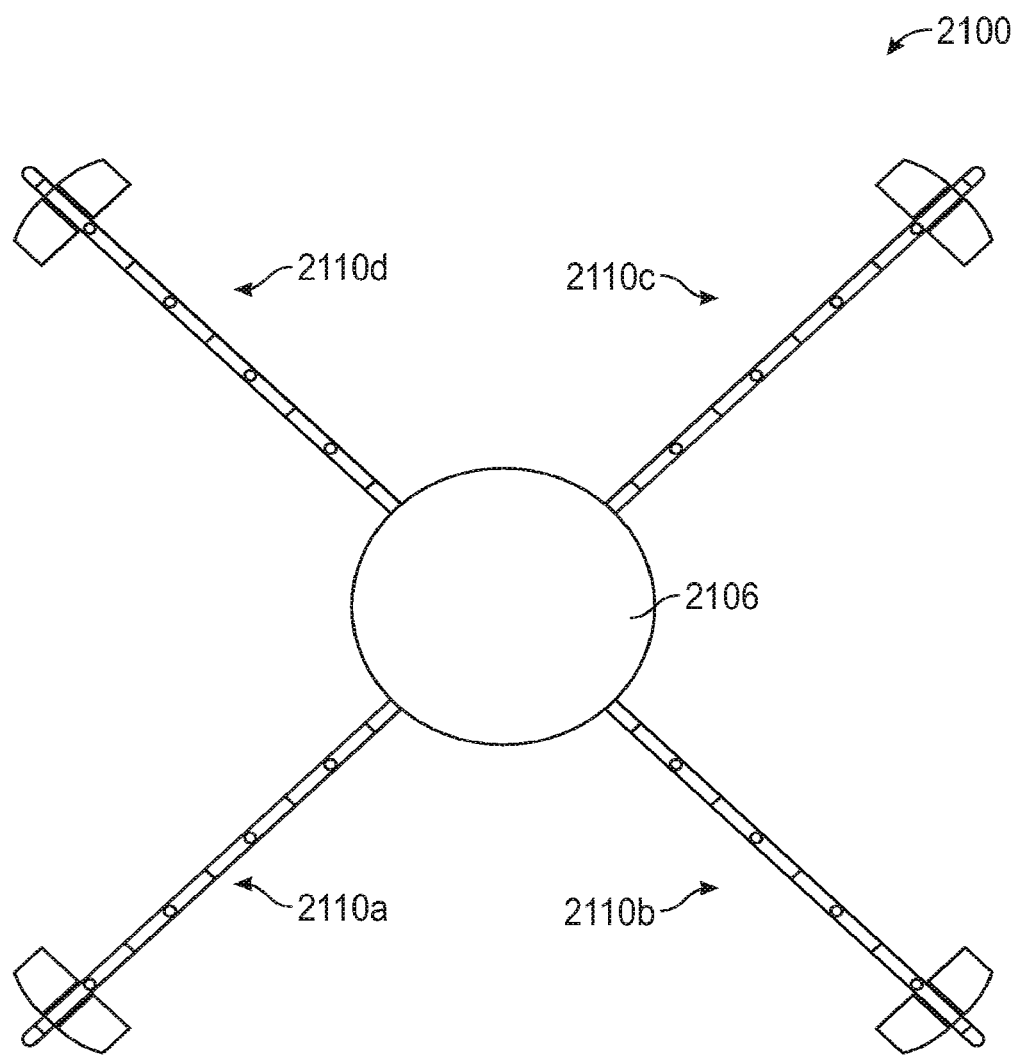

FIG. 21F shows how the segments 2117a-2117h can operate to allow the arms 2110a-2110d to move between the collapsed position and the expanded position using an alternative arm mechanism. That is, the segments 2117a-2117h can be hingeably connected at each end to allow for the arms 2110 to expand and collapse substantially linearly. In some examples, the base 2106 can include rails 2119 to guide movement and support the arms 2110. This functionality allows for the arms 2110 to adapt proportionally to the variable target volumes that it will be applied to in the field. The support frame segments 2117 can fold and swivel around the hinges can provide inward and outward movement of the arms similar of that shown and discussed of the arms of FIG. 11B.

Figure 22A:
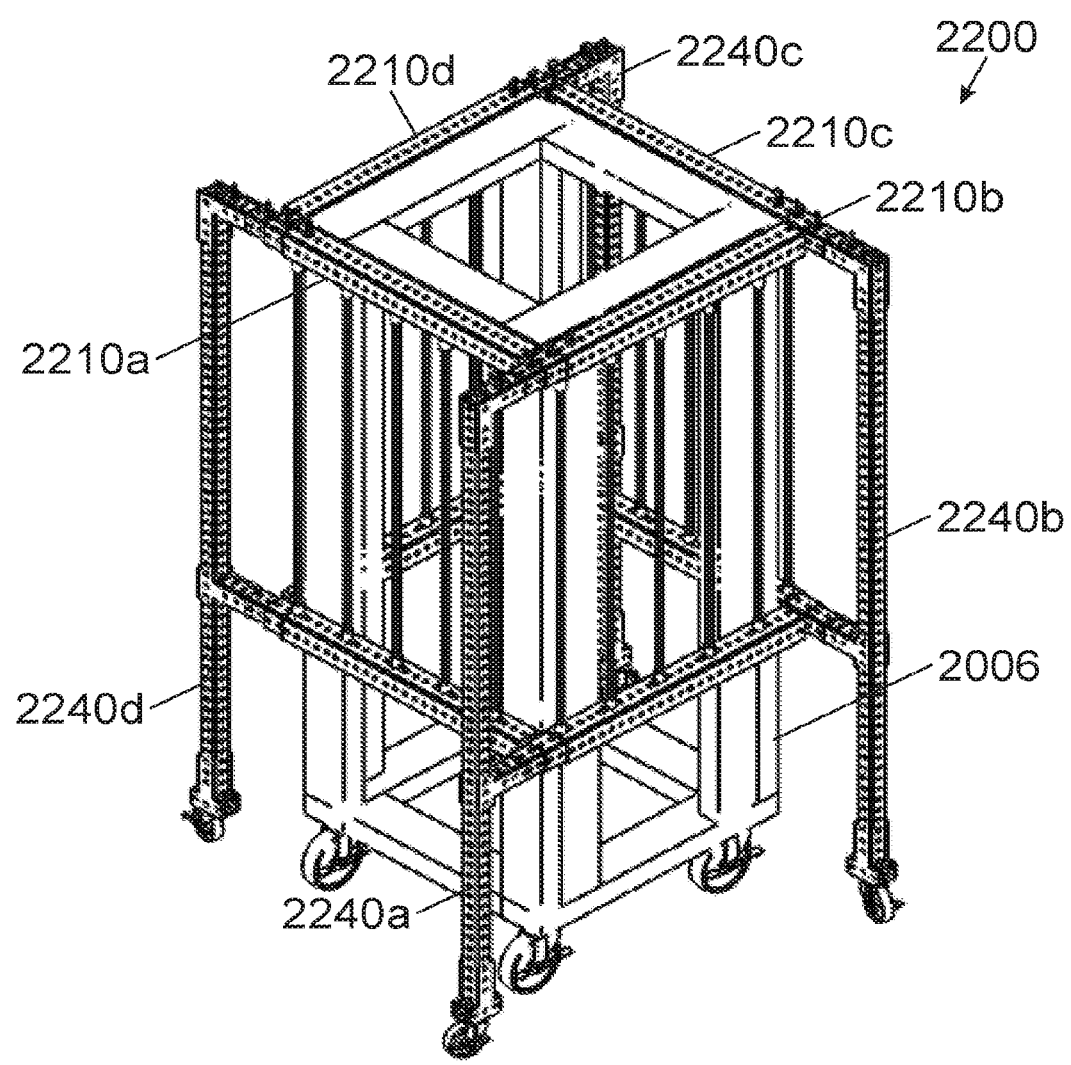
FIGS. 22A-22G illustrate a disinfection device with expandable and collapsible arms, in accordance with at least one example of the present disclosure.
Figure 22B:
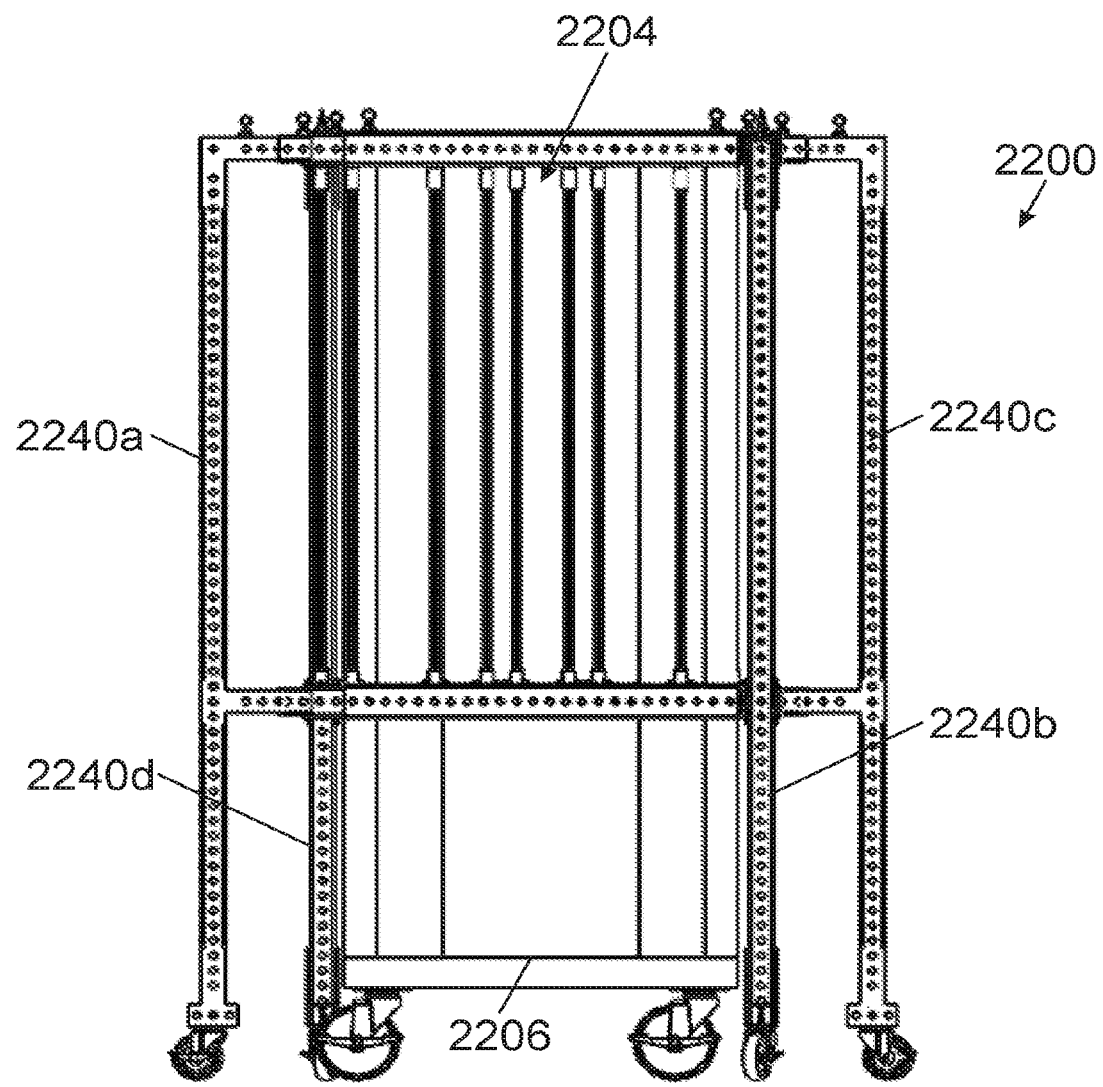
Figure 22C:
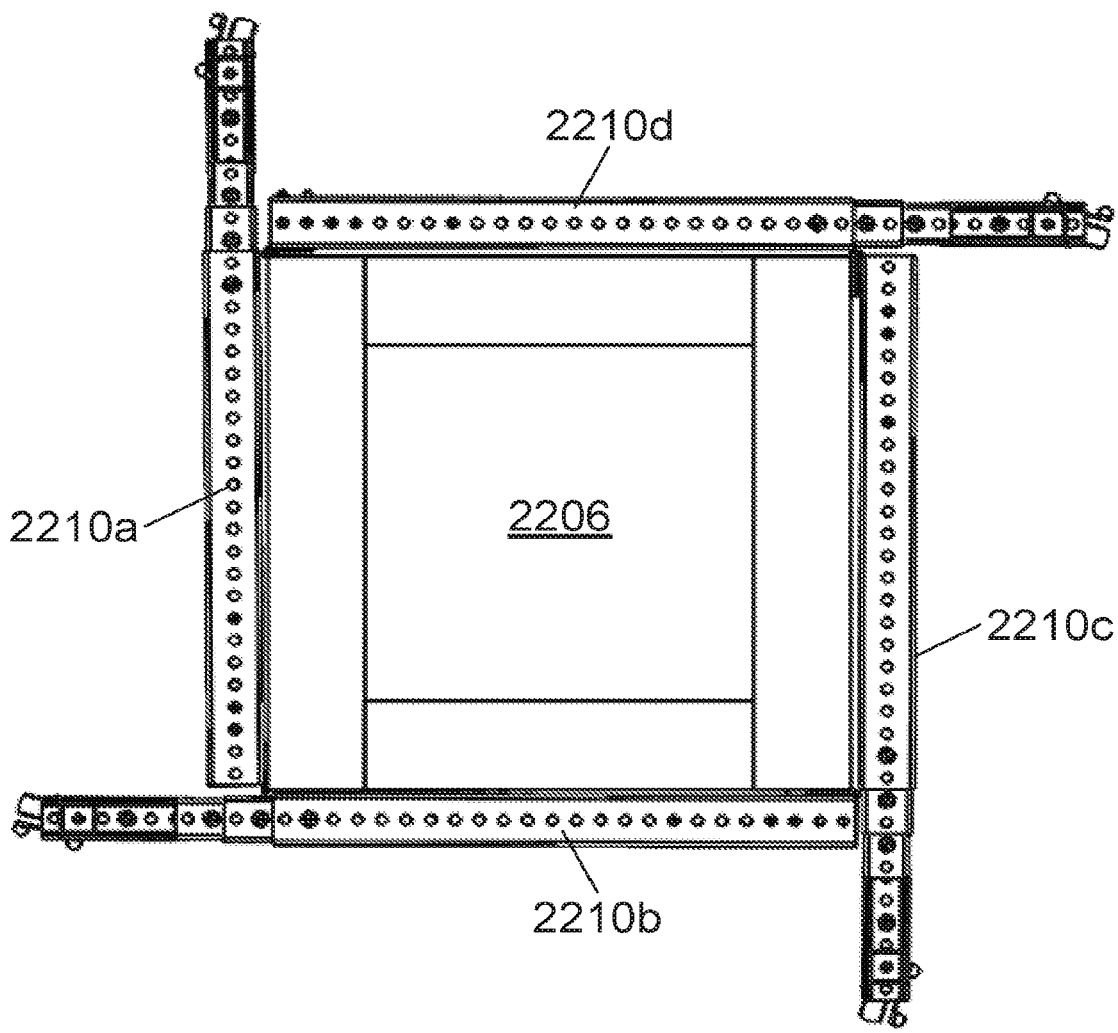
Figure 22D:
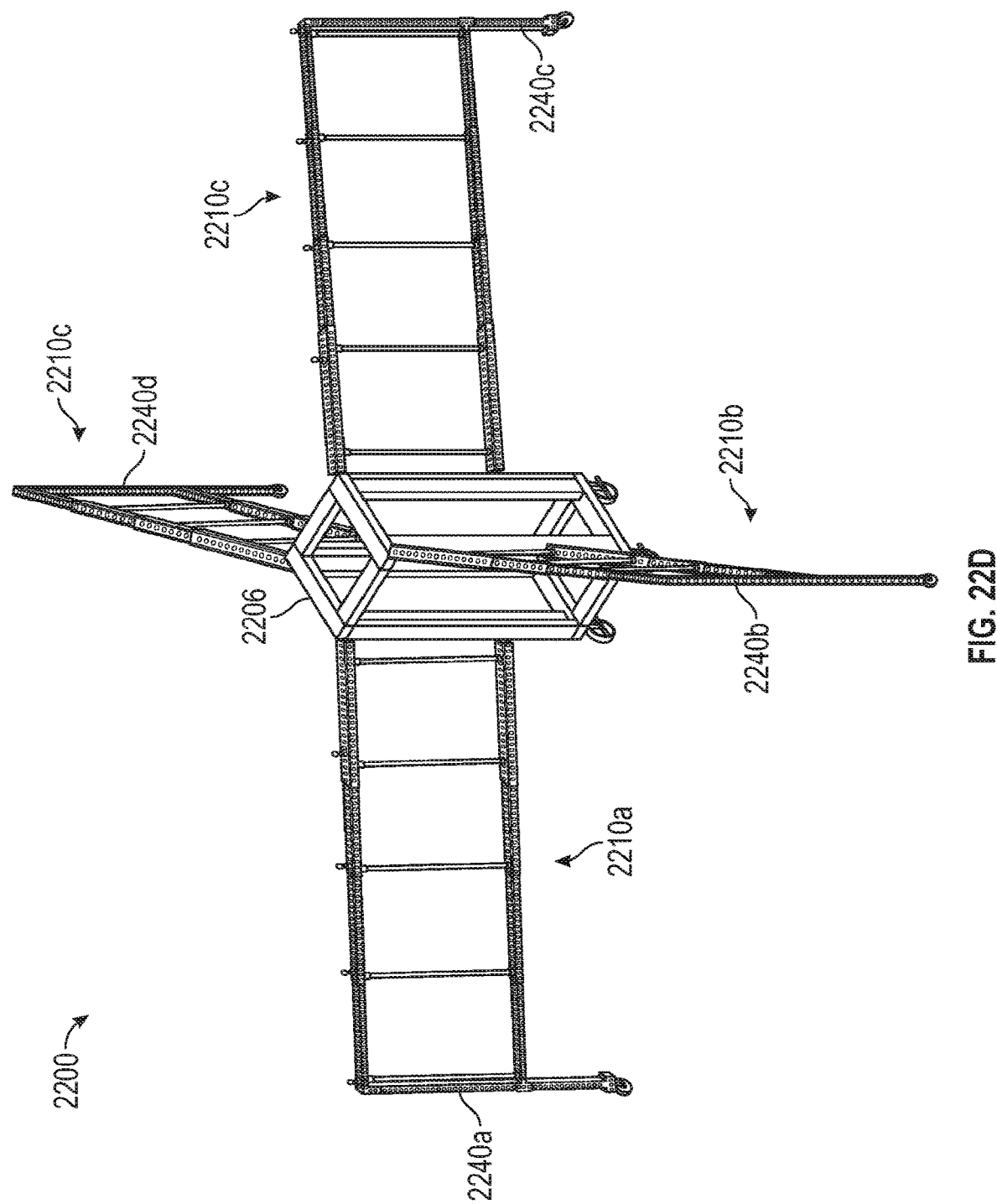
Figure 22E:
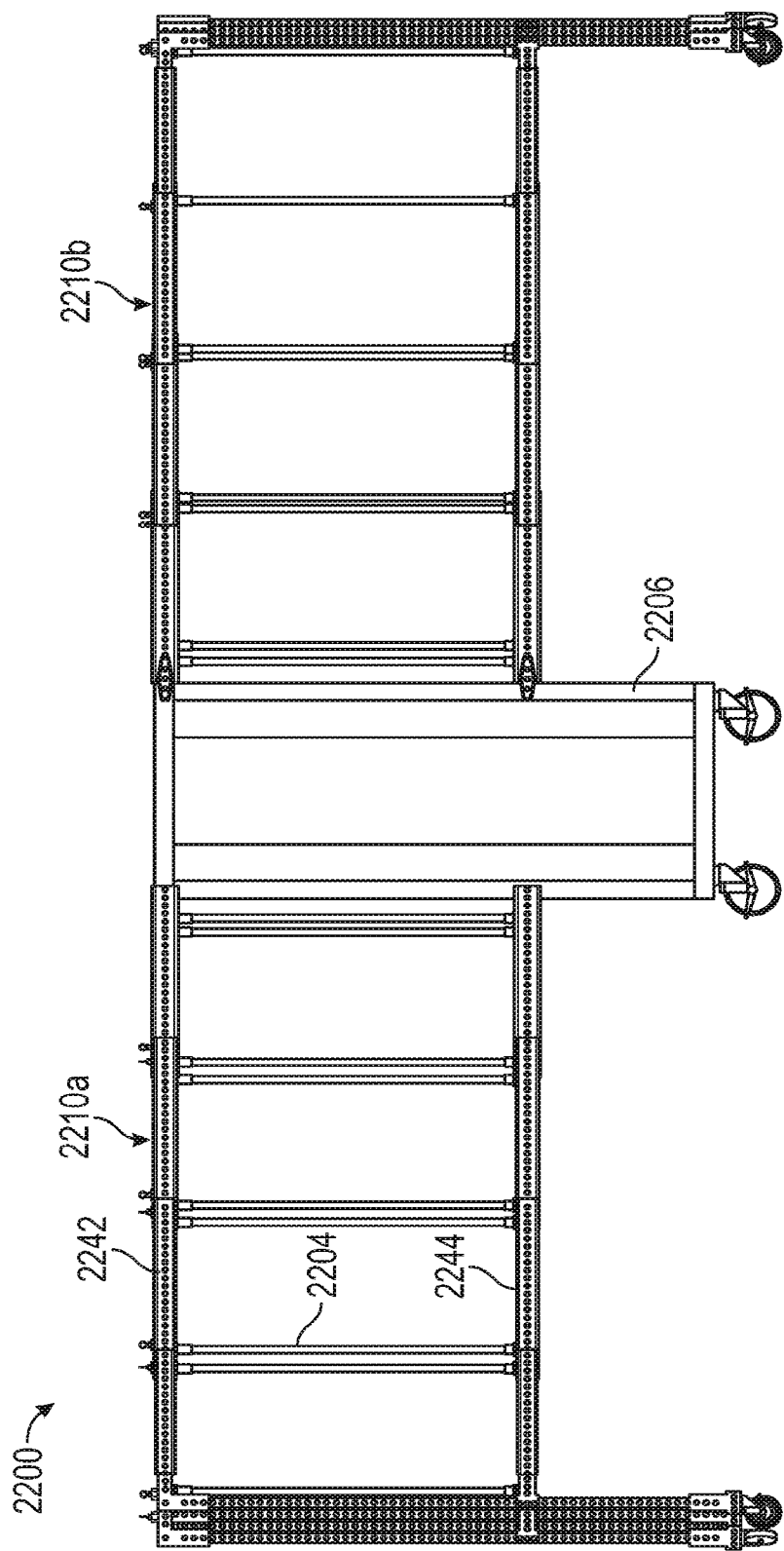
Figure 22F:
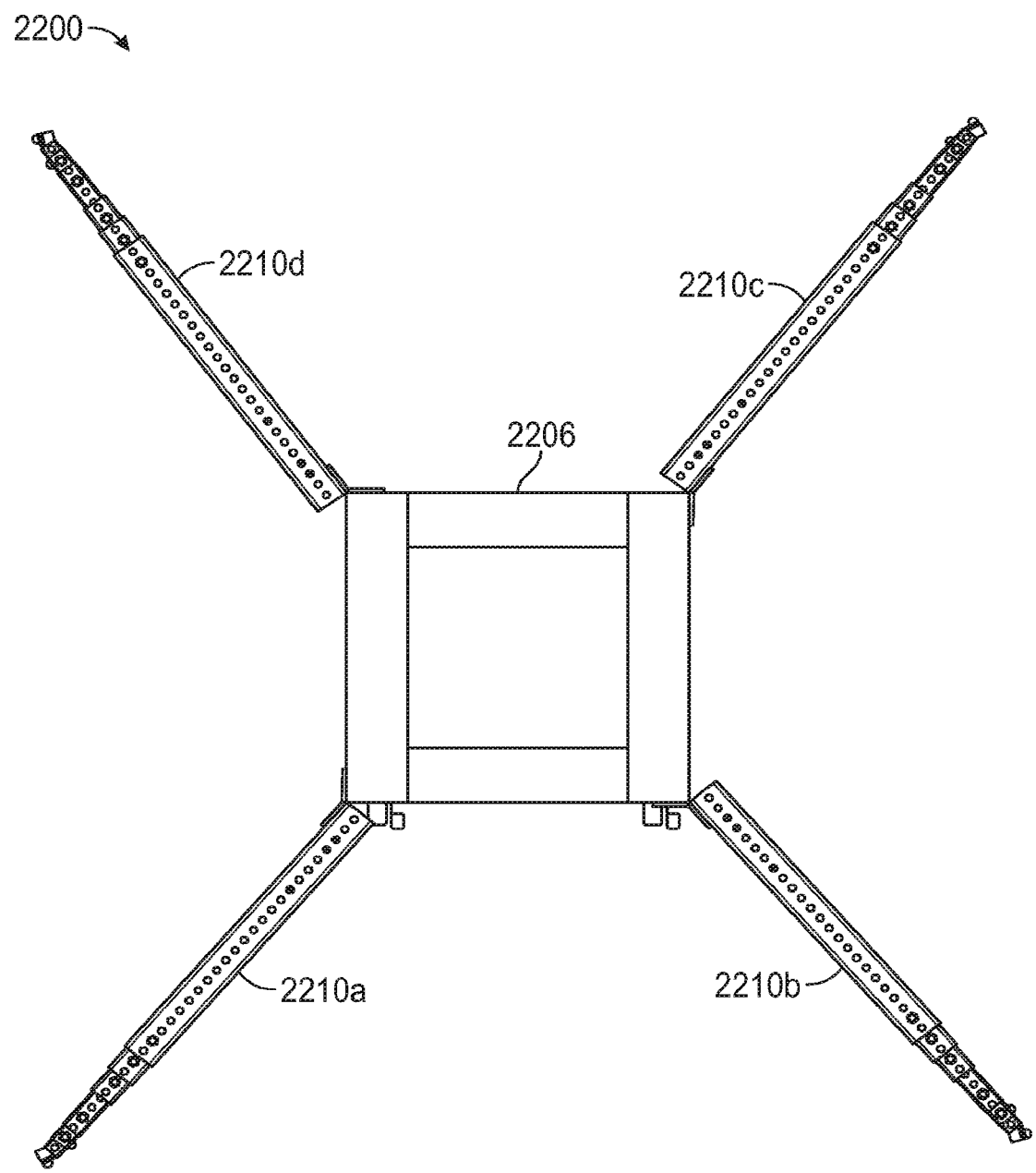
Figure 22G:
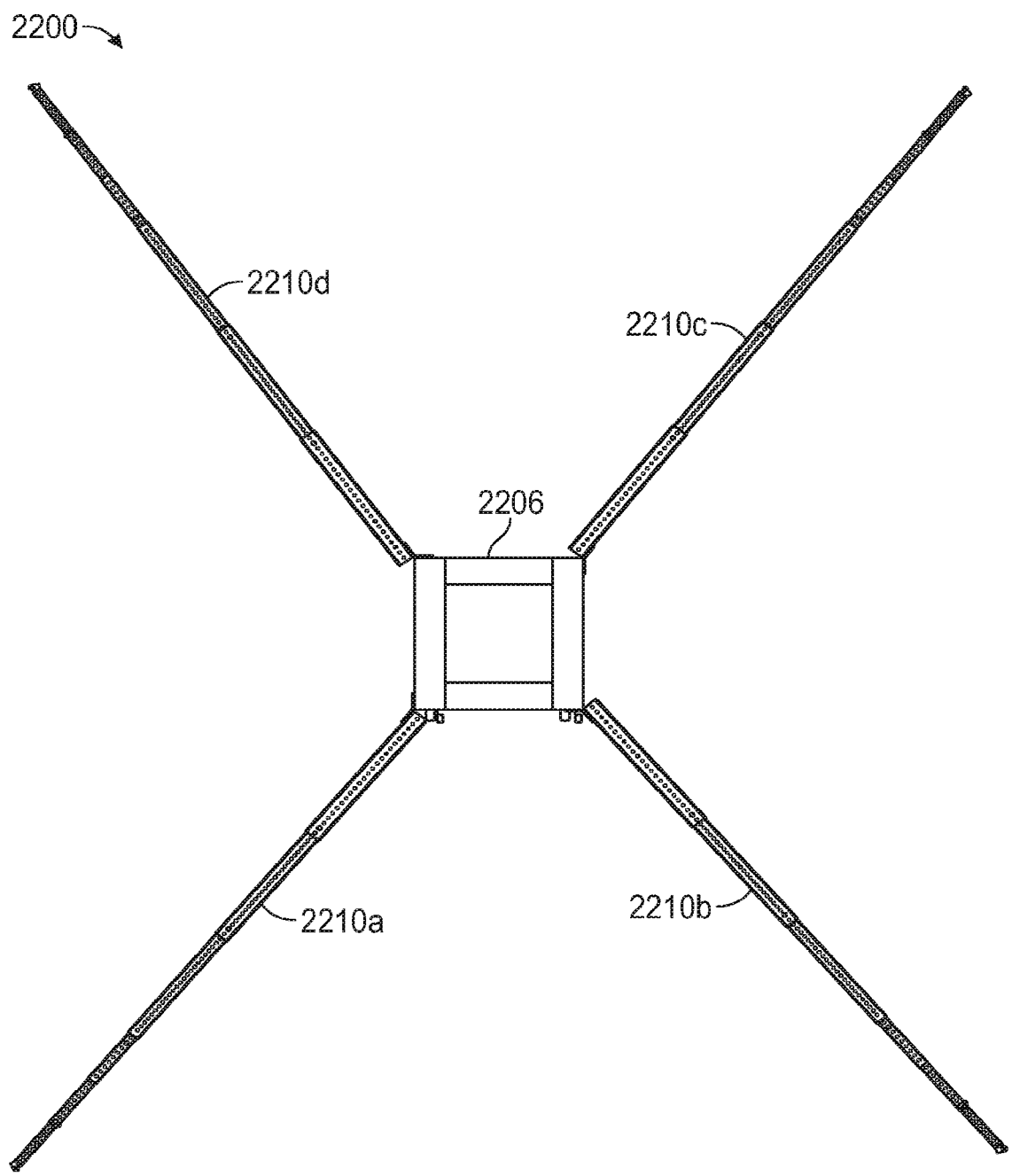

FIGS. 22A-22G illustrate a disinfection device 2200 with expandable and collapsible arms, in accordance with at least one example of the present disclosure. FIG. 22A shows a perspective view of the disinfection device 2200. FIG. 22B shows a side view of the disinfection device 2200, and FIG. 22C shows a top view of the disinfection device 2200, which can include a base structure 2206, similar to others discussed above. The disinfection device 2200 can include arms 2210a-2210d and frame support segments 2240a-2240d. The base 2206 can include wheels or casters as can each of the support segments support segments 2240a-2240d, which can move independently of the base 2206. FIG. 22D shows an isometric view and FIG. 22E shows an elevation or side view of the disinfection device 2200 where the arms 2210a-2210d are in the deployed position, away from the base 2206. FIG. 22F shows a top view of the disinfection device 2200 with the arms 2210 deployed and rotated away from the base 2206 and in the collapsed or unextended position. FIG. 22G shows a top view of the disinfection device 2200 with the arms 2210 in the extended position.

It is important to note that for small target volumes like small treatment rooms or bathrooms the light cycle for the device would be initiated with the arms not deployed as show in FIG. 19C and FIGS. 22A-22C and for larger target volumes the device's arms and support frame segments would be deployed and expanded as shown in FIGS. 22D-22G. The expansion along the support frame segments would be correlated to the dimensions of the target room and or volume, while simultaneously the ultraviolet light sources would proportionally position themselves via the arm expansion mechanism to construct the light matrix of precise energy for the corresponding target room and or volume.

Figure 23A:
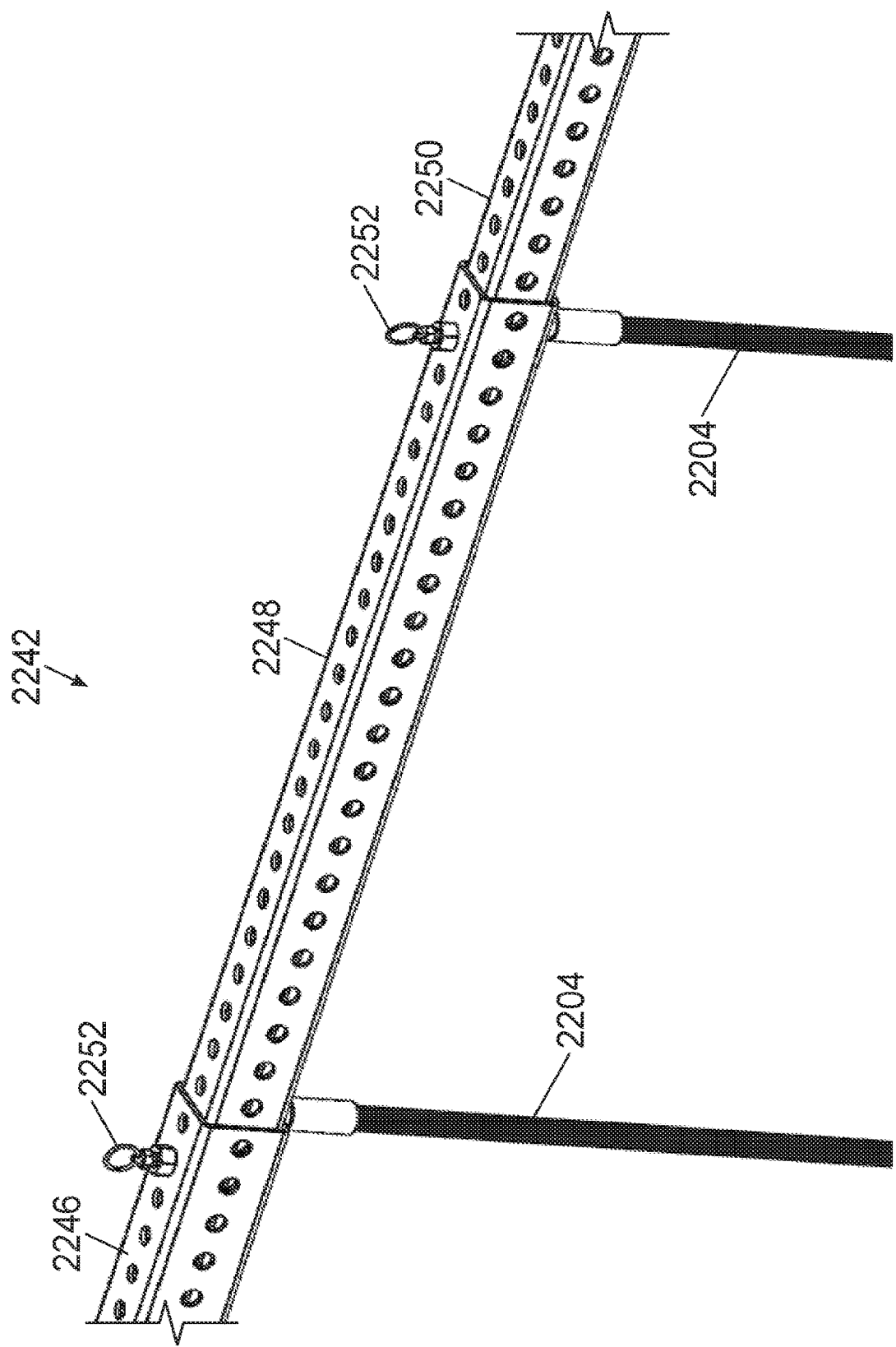
FIGS. 23A-23B illustrate a rail deployment mechanism, in accordance with at least one example of the present disclosure.
Figure 23B:
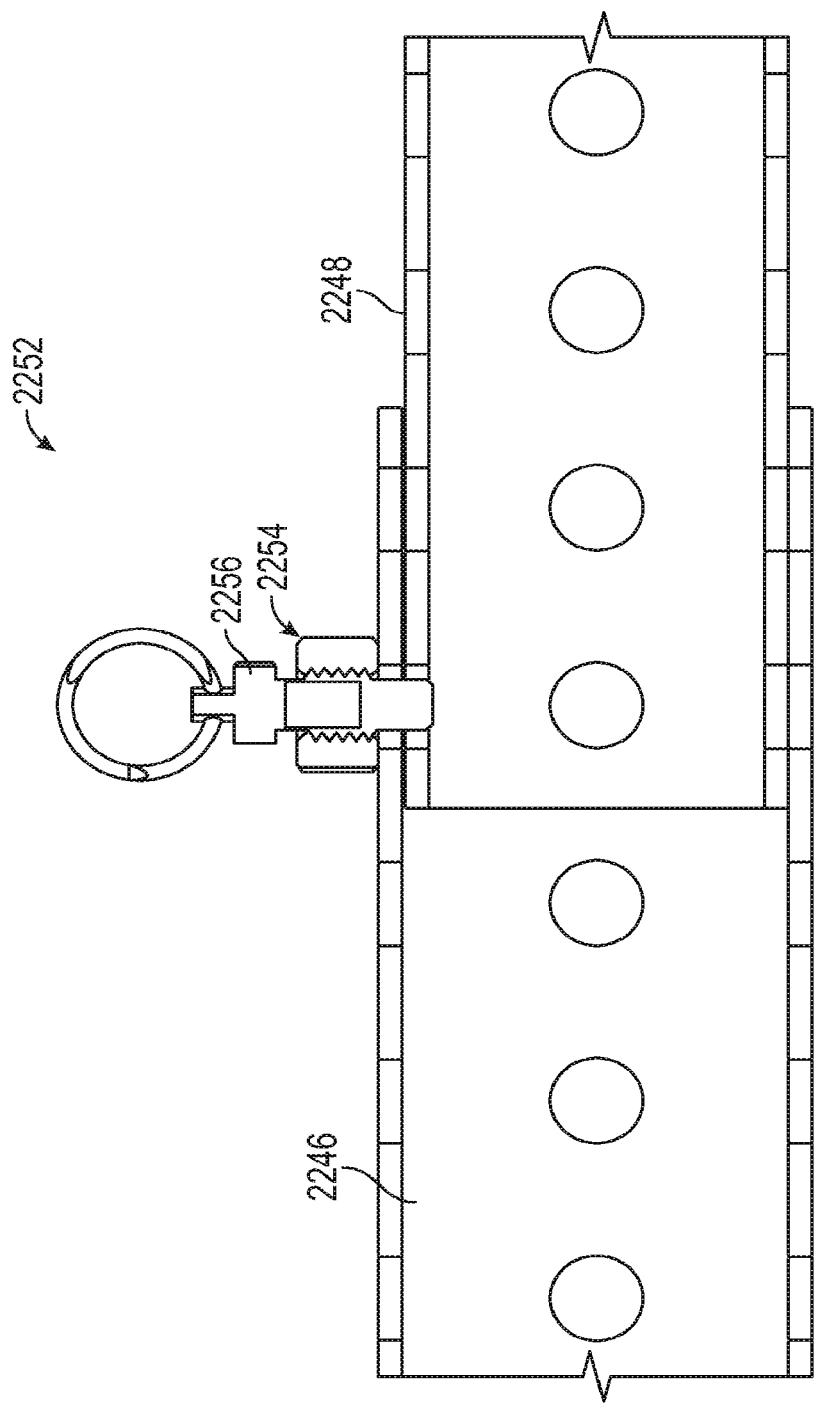

FIGS. 23A-23B illustrate a rail deployment mechanism 2242, in accordance with at least one example of the present disclosure. FIG. 23 A shows the rail deployment mechanism 2242, which can include a first portion 2246, a second portion 2248, and a third portion 2250, where the first portion can receive the second portion 2248 and the third portion 2250 therein, in a telescoping arrangement. The first portion 2246 can be secured to the structure or base 2206. The rail deployment mechanism 2242 can include as many portions as is required to reach a total desired expansion distance needed for the application or model within a target volume.

Additionally, the telescoping members (portions 2246-2250) can include locks 2252. As shown in FIG. 23B, the locks 2252 can each include a nut 2254 and a bolt 2256, which can be threadably secured to each other to secure the portion 2246 to the portion 2248 to prevent relative translation (telescoping) thereof.

FIGS. 24A-24F illustrate a disinfection device 2400 with expandable and collapsible arms, in accordance with at least one example of the present disclosure. The disinfection device 2400 can include light sources 2404a-2404n, a base 2406, and arms 2410a-2410d. The base 2406 of the disinfection device 2400 is shown as being substantially cylindrical, but can be other shapes in other examples, such as a cuboid, rectangular prism, triangular prism, or the like.

Figure 24A:
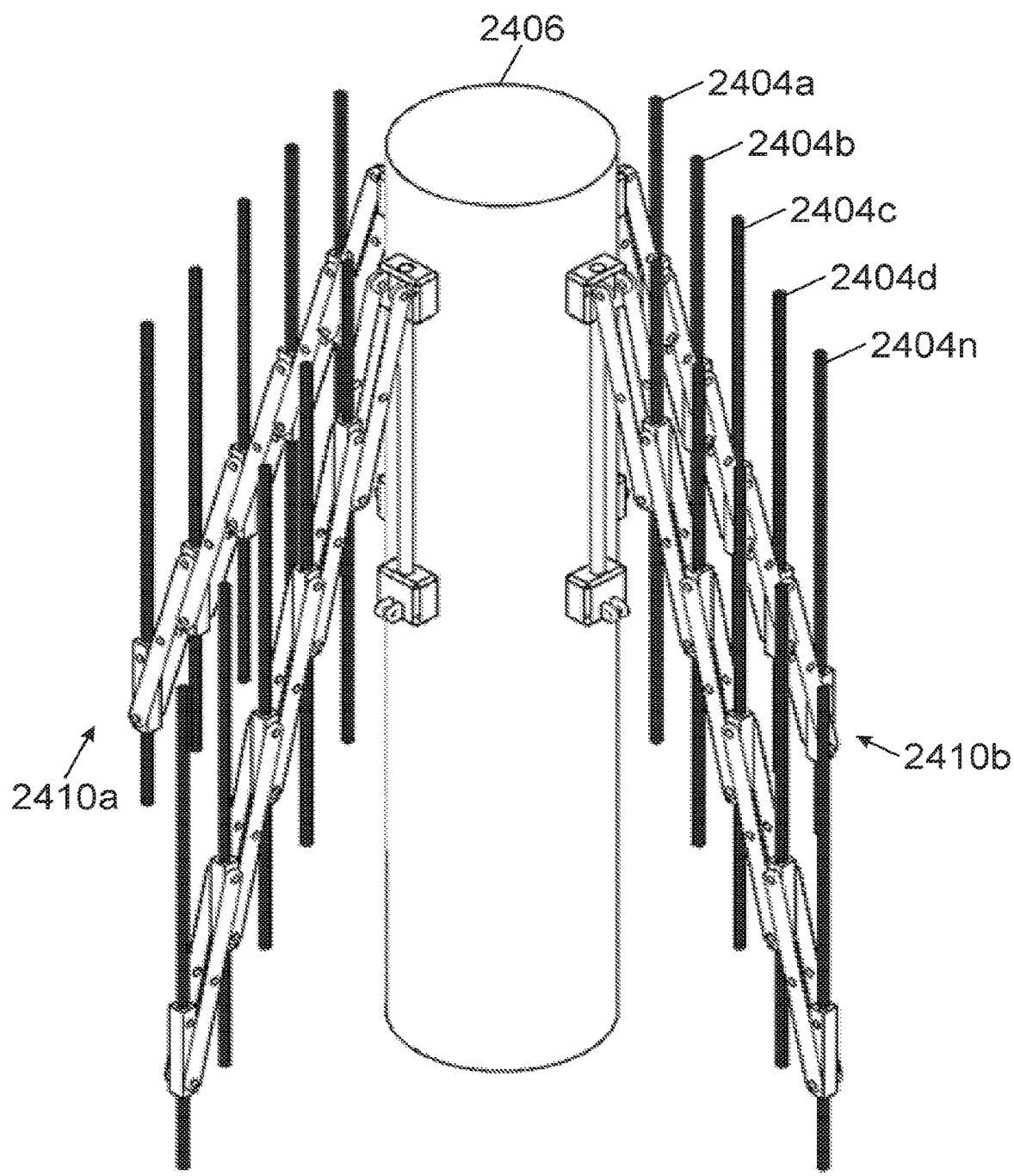
FIGS. 24A-24F illustrate a disinfection device with expandable and collapsible arms, in accordance with at least one example of the present disclosure.
Figure 24B:
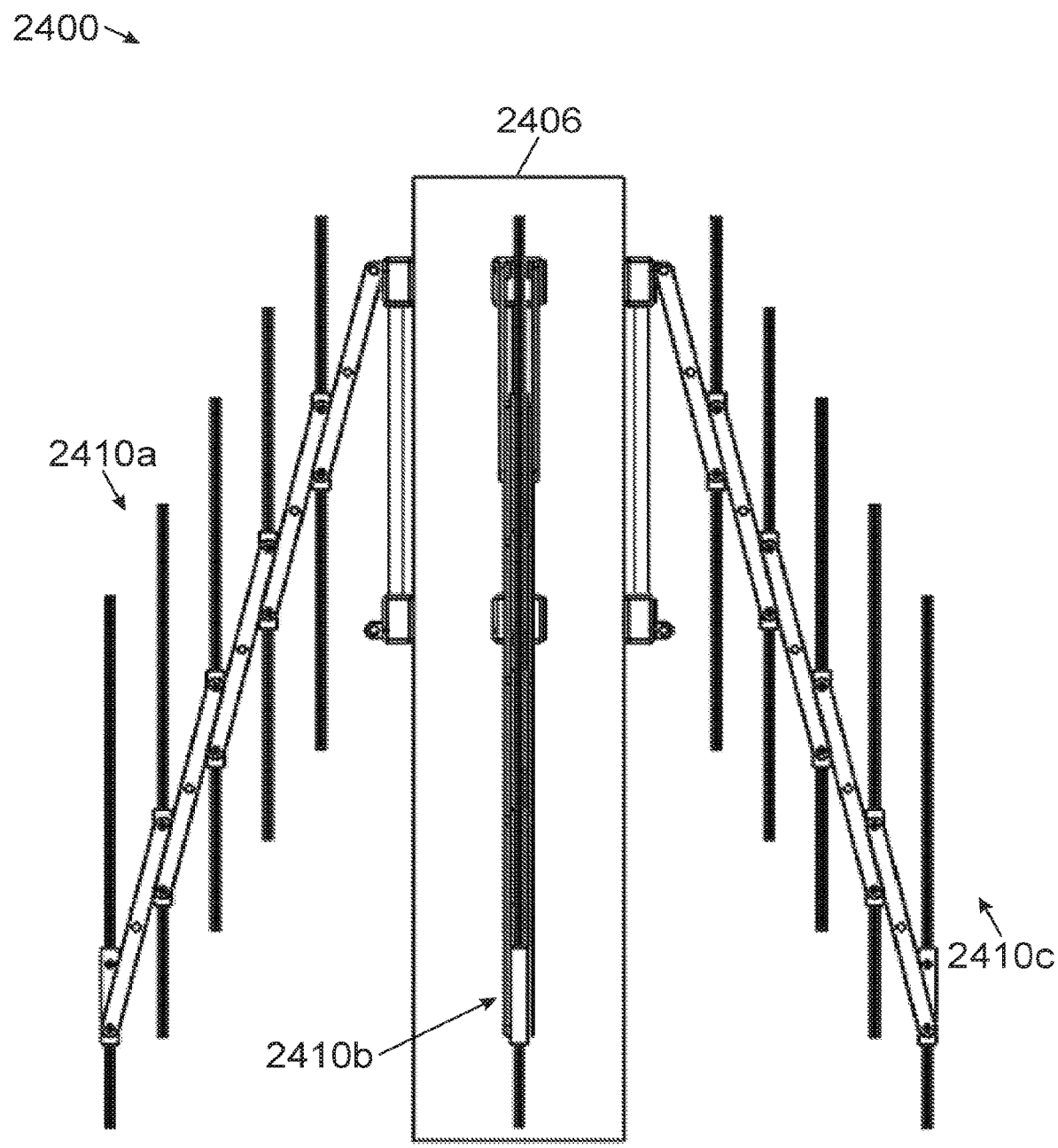
Figure 24C:
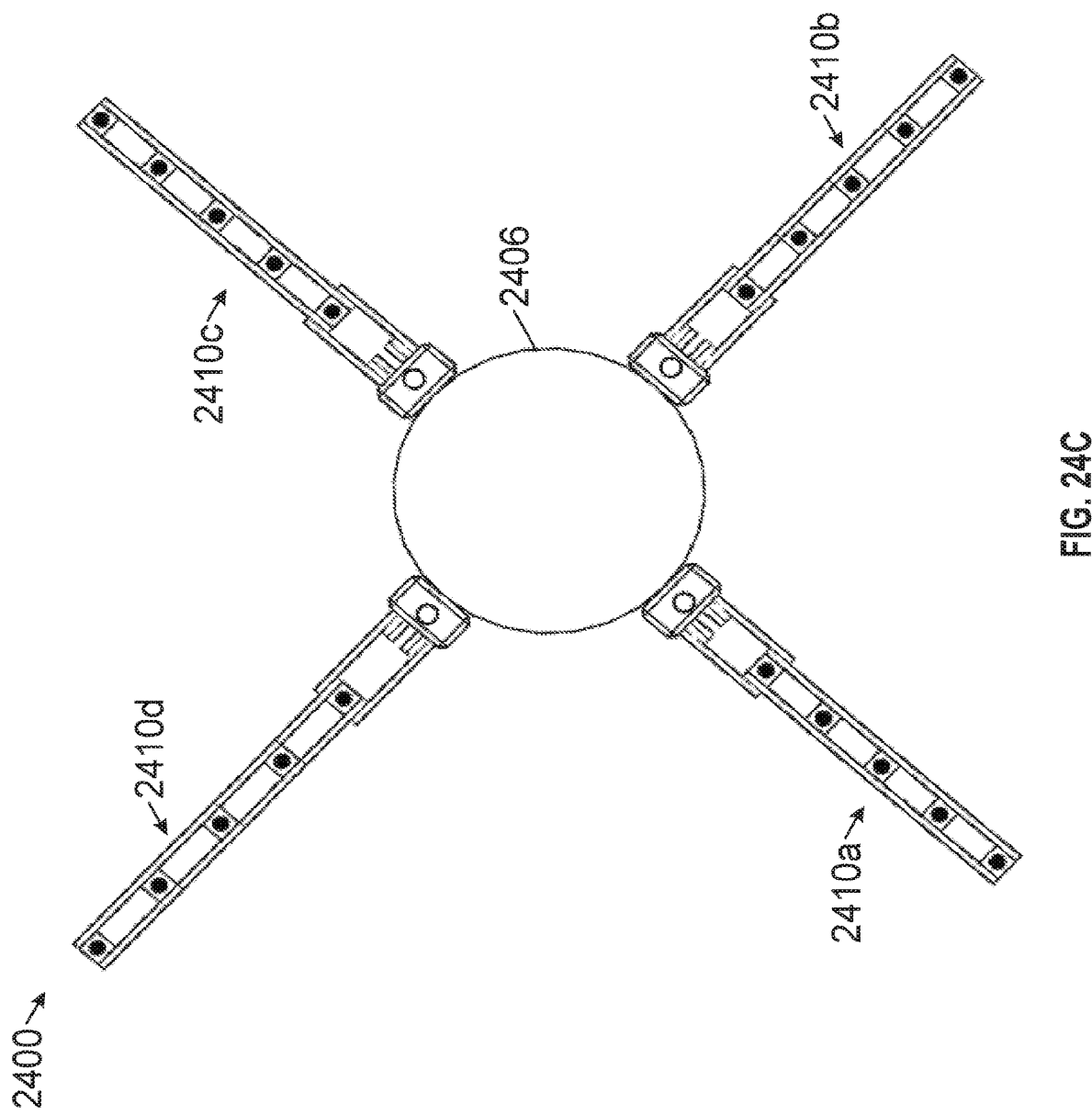
Figure 24D:
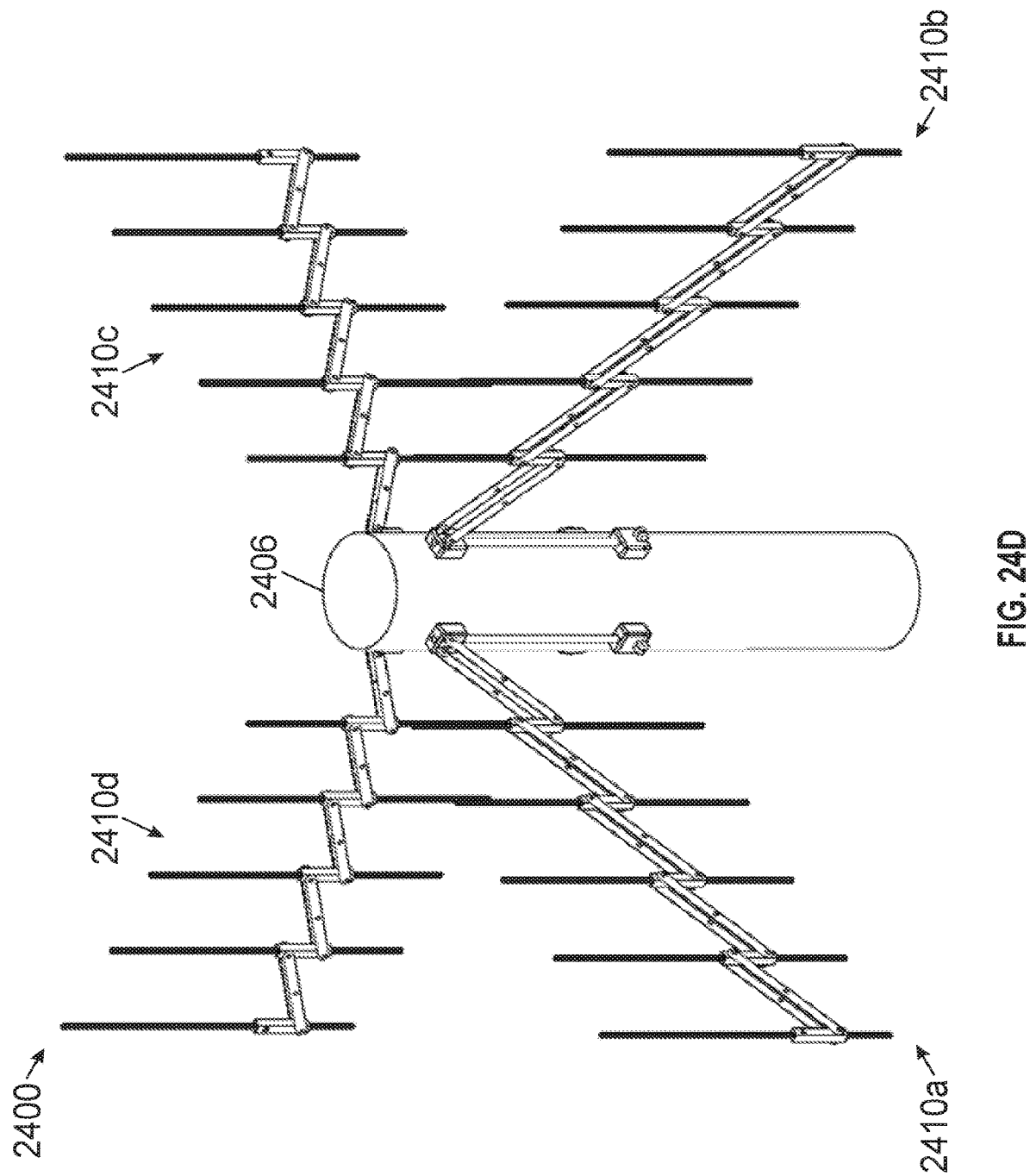
Figure 24E:
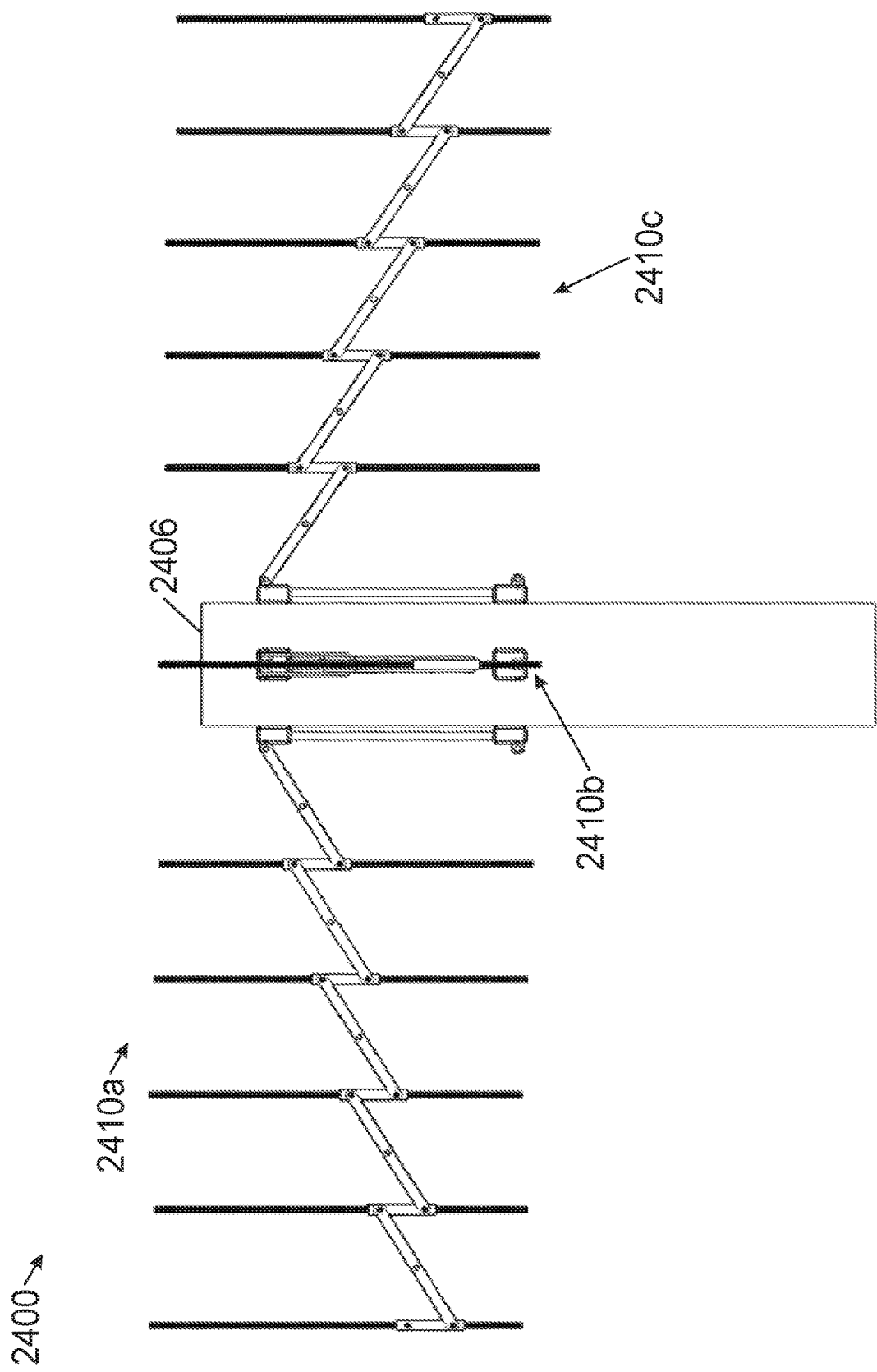

FIG. 24A shows an isometric view, FIG. 24B shows an elevation or side view, and FIG. 24C shows a top view of the disinfection device 2400 with the arms 2410a-2410d in a collapsed position or a near-collapsed position. FIG. 24D shows an isometric view and 24E shows an elevation or side view of the arms 2410 in the extended position. FIG. 24A-24C show the disinfection device in a collapsed position or a near collapsed positions and FIG. 24D-24E show an expanded position.

Figure 24F:
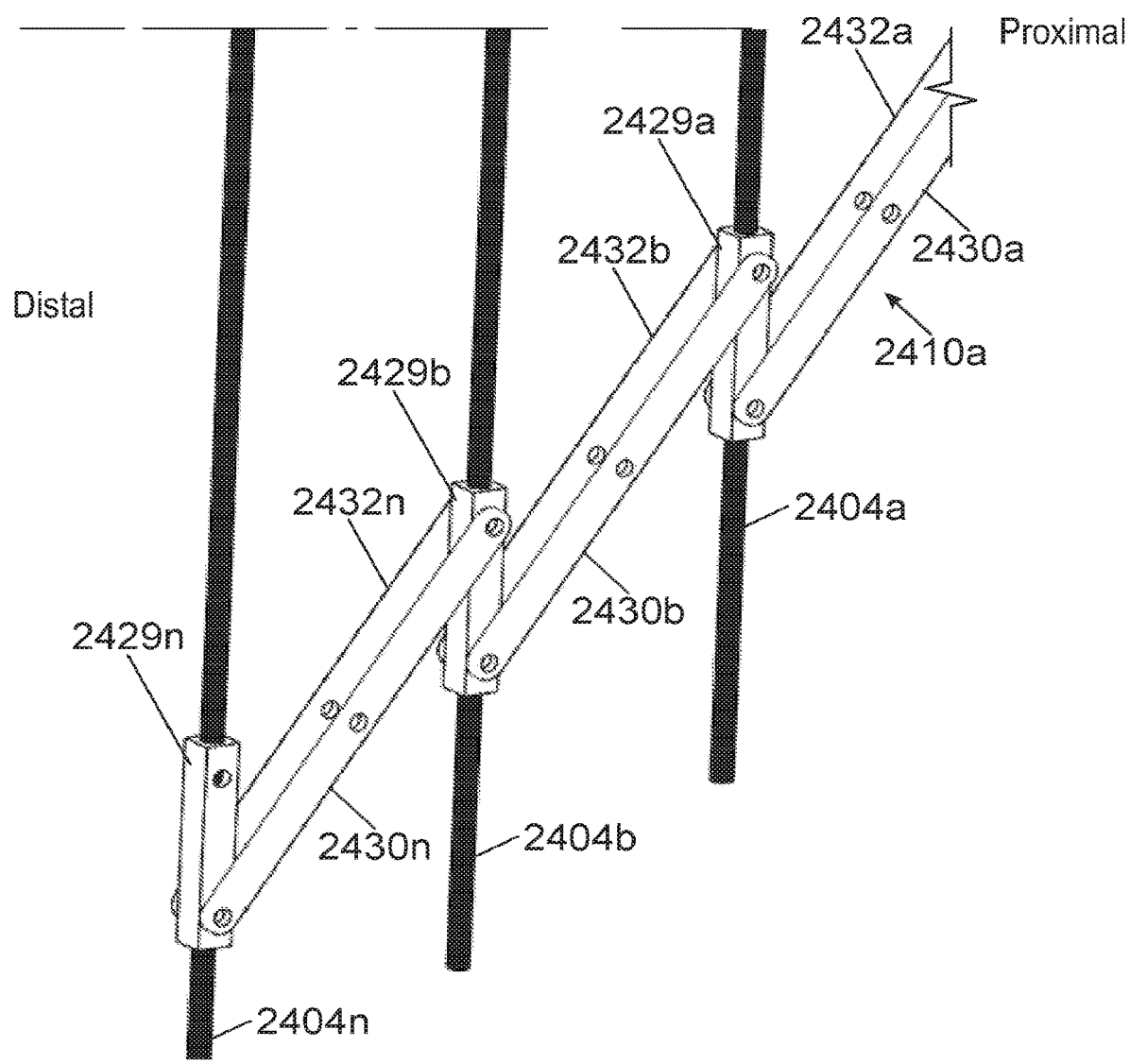

FIG. 24F shows a focused view of the arm 2410a, which can include brackets 2429a-2429n, first links 2430a-2430n, and second links 2432a-2432n. Also shown in FIG. 24F are light sources 2404a-2404n. The first links 2430 can be hingeably coupled to a first side of brackets 2429 and the second links 2432 can be hingeably coupled to a second side of brackets 2429 to create a linkage that extends radially and vertically when moving from the collapsed position to the expanded position. For example, an distal end of the first link 2430a can be hingeably coupled to a bottom portion of the bracket 2429a and a proximal end of the first link 2430b can be coupled to top portion of the bracket 2429a, a distal end of the second link 2432a can be hingeably coupled to a bottom portion of the bracket 2429a on a second side of the bracket 2429a, and a proximal end of the second link 2432b can be coupled to top portion of the second side of the bracket 2429a Such a configuration allows for the light sources 2404 to proportionally distribute the ultraviolet in correlation to the dimensions and volumes of the target volume when the arms 2410 are positioned within the target volume. The light sources 2404a-2404n can extend through the brackets 2429. In some examples the brackets 2429 can be configured to hold more than one light source. Brackets 2429 can hold the light sources 2404 at different positions as seen in FIGS. 24E and 24F to maintain proportionality between the light sources 2404 in the expansion process.

Figure 25A:
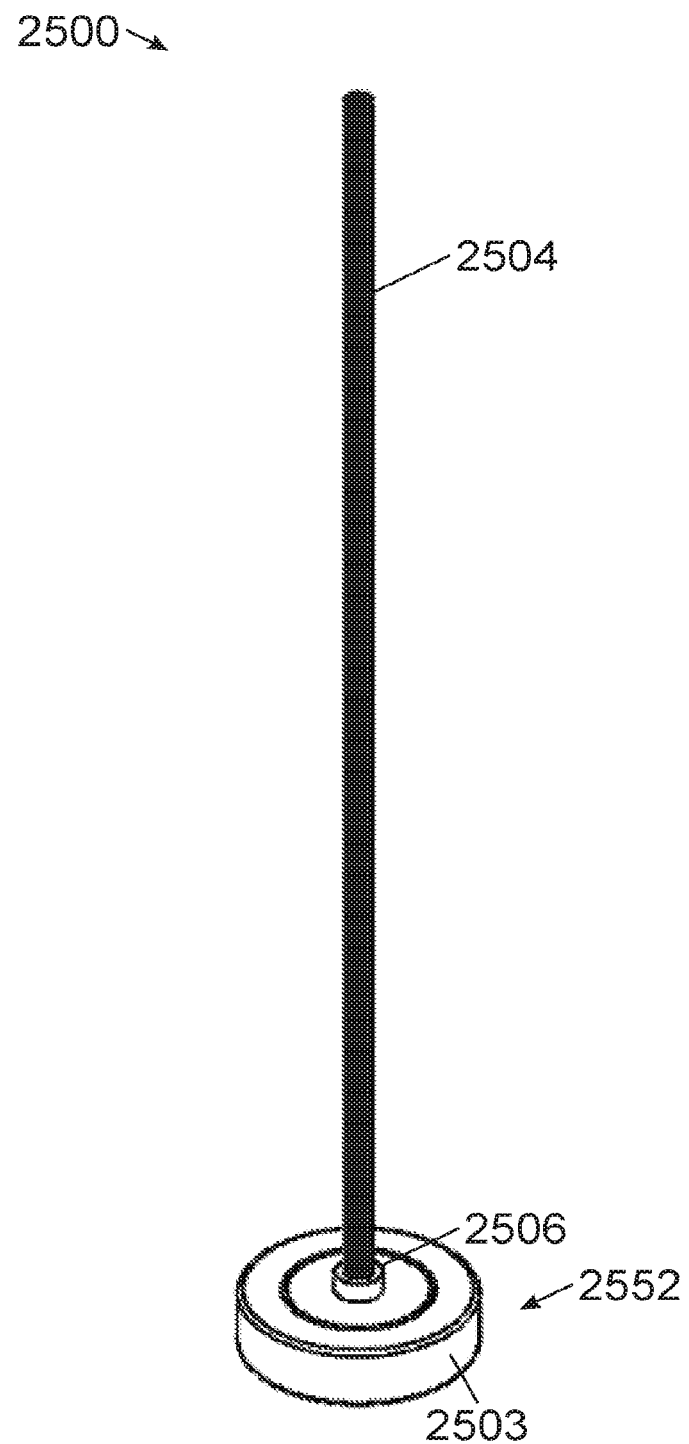
Figure 25B:
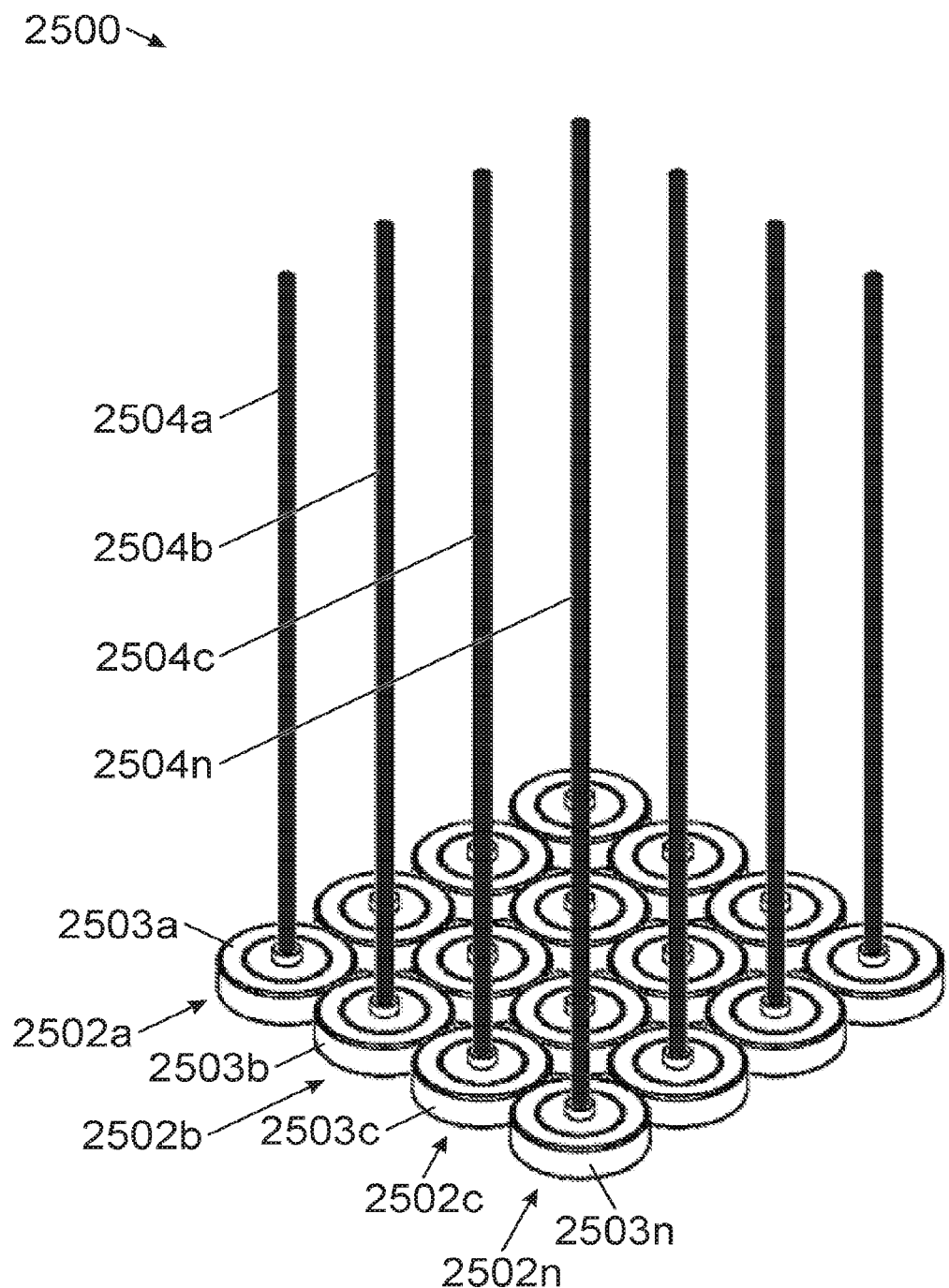
Figure 25C:
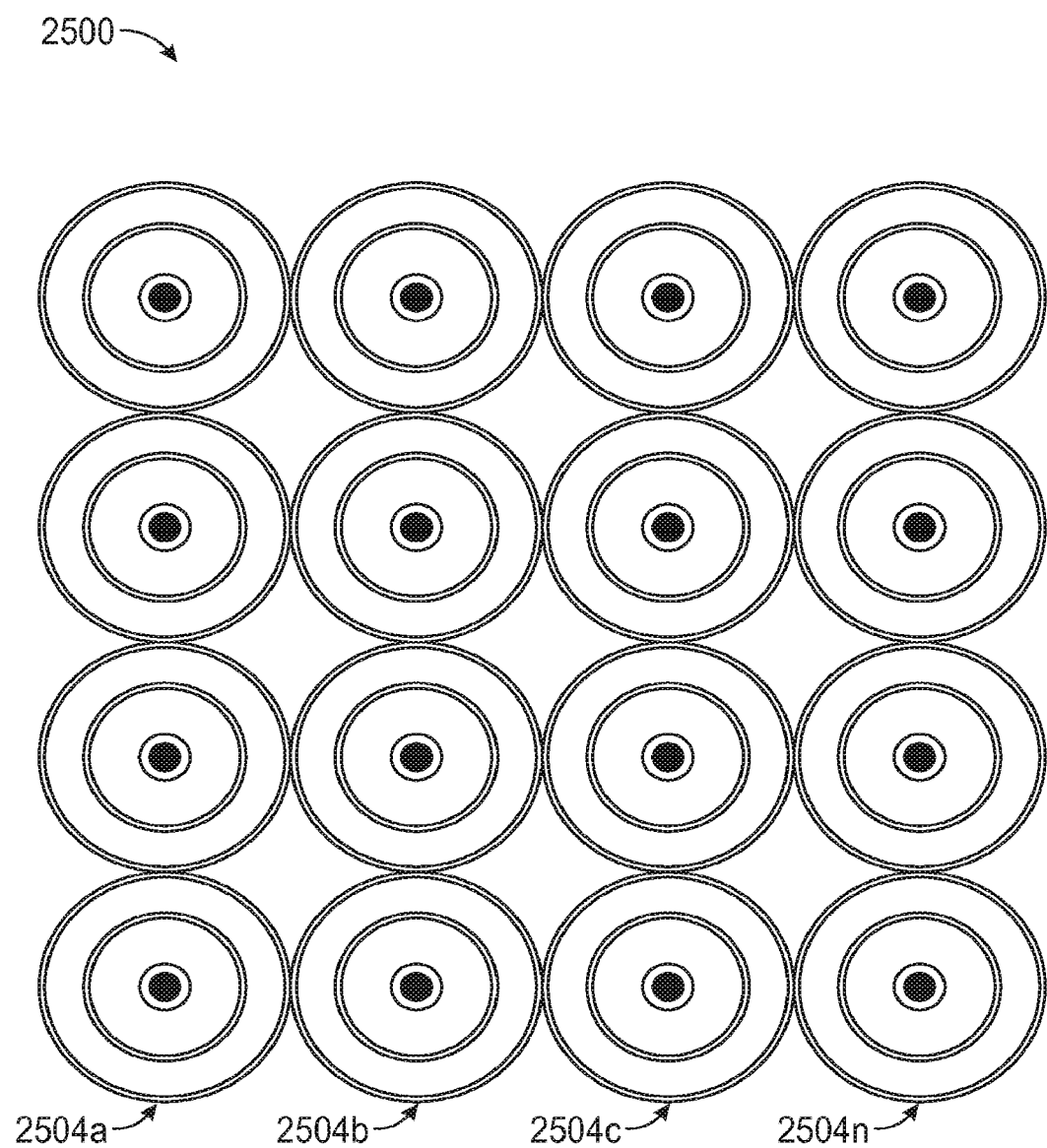

FIGS. 25A-25I illustrate mobile ultraviolet light devices 2502 with program logic, in accordance with at least one example of the present disclosure. FIG. 25A shows an isometric view of a single mobile ultraviolet light device 2502, FIG. 25B shows an isometric view of a system 2500 including a plurality of mobile ultraviolet light devices 2502a-2502n, and FIG. 25C shows a top view of the system 2500 including the plurality of mobile ultraviolet light devices 2502a-2502n. Each of the mobile ultraviolet light devices can include a base 2503, a light source 2504, and a coupler 2506.

The base 2503 can include a housing or shell comprised of rigid or semi-rigid materials, such as one or more of metals, plastics, foams, elastomers, ceramics, composites, combinations thereof, or the like. The base 2503 can be connected to the coupler 2506 where the coupler 2506 can extend through a top portion of the base 2503. The base 2503 can also be sized and shaped to house a driver (such as wheels or tracks) that can be engageable with a surface of the target volume. The base 2503 can further support a motor that can be connected to the driver. The motor can be controllable to operate the driver to cause the base 2503 to move with respect to the surface to move the base within the target volume. The light source 2504 can be consistent with those discussed above and can be supported by the base 2503. The base 2503 can further include a controller therein (such as the system 4400 of FIG. 44), where the controller can be in communication with the motor and the light source (such as through a network interface 4420 of FIG. 44). The controller can also be operable to position the base 2503 within the target volume. In some examples, a plurality of mobile ultraviolet light devices 2502a-2502 can be configured to operate the light sources 2504a-2504n such that the lights of the plurality of mobile ultraviolet light devices, together, emit ultraviolet light in a substantially homogenous irradiance within the target volume Such a system of mobile ultraviolet light devices 2502 does not require arms, support frame segments, rails or a rigid mechanical frame system to expand or deploy the ultraviolet sources 2504a-2504n for a desired construction of a light matrix with precise energy. Instead, this the mobile ultraviolet light devices 2502 can operate using various parameters, communication between the devices and individual movement of the devices within a target volume.

Figure 25E:
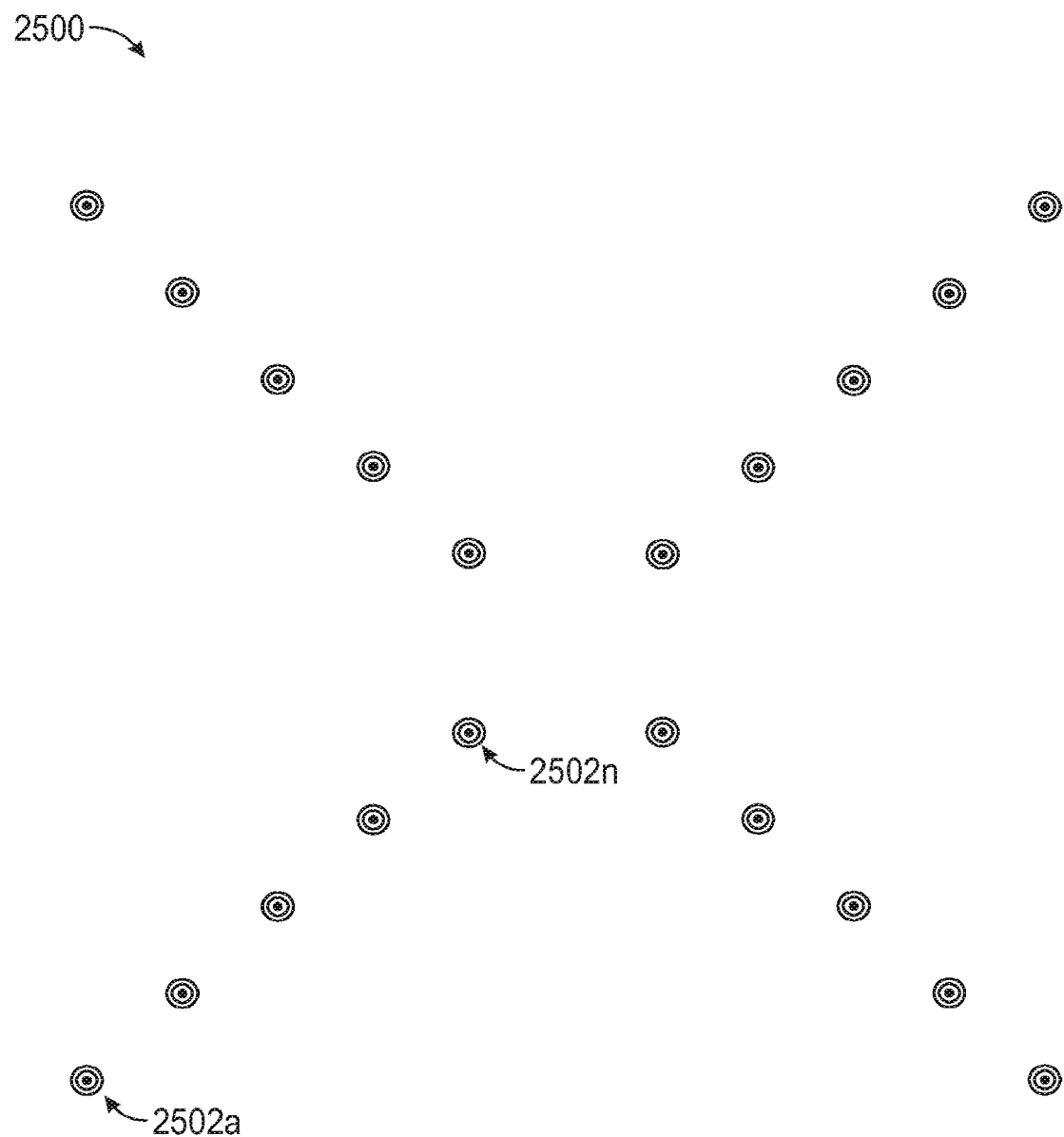

FIG. 25D shows an isometric view of the system 2500 including a plurality of mobile ultraviolet light devices 2502a-2502n and FIG. 25E shows a top view of the system 2500 including a plurality of mobile ultraviolet light devices 2502a-2502n, which can be arranged in any pattern, as desired, within a target volume to achieve a homogenous light energy matrix. The mobile ultraviolet light devices 2502a-2502n are shown in an X or cross configuration in FIG. 25D and FIG. 25E.

The mobile ultraviolet light devices 2502a-2502n can include various sensors (such as input sensors 4418 of FIG. 44), not visible in FIGS. 25, incorporated within the bases 2503 and light source holders that can detect distance, coordinates correlating to other mobile ultraviolet light devices 2502a-2502n, visual recognition of indicators or symbols that aid in the organization and dimensioning of the mobile ultraviolet light devices 2502a-2502n in constructing the light matrix of precise energy with pre-programmed code, and/or dual input and output sensors for artificial intelligence and machine learned parameters when placed in numerous target volume fields when initiated within a targeted room.

The mobile ultraviolet light devices 2502a-2502n can be deployed within a target volume 50, as shown in FIGS. 25F-25J. The target volume 50 can include surfaces 52, 54, and 56, where the surface 52 can be a floor and the surfaces 54 and 56 can be walls. The target volume can include more or less walls, in other examples, such as 3, 4, 5, 6, 7, 8, 9, 10 or the like. The target volume 50 can be of various sizes, such as 1 meter to 20 meters in width by 1 meter to 20 meters in length by 2 meters to 5 meters in height. In some examples, the target volume 50 can be 1.5 meters to 8 meters in width and length. In some examples, the target volume 50 can be 6 meters to 8 meters in width and length.

Figure 25F:
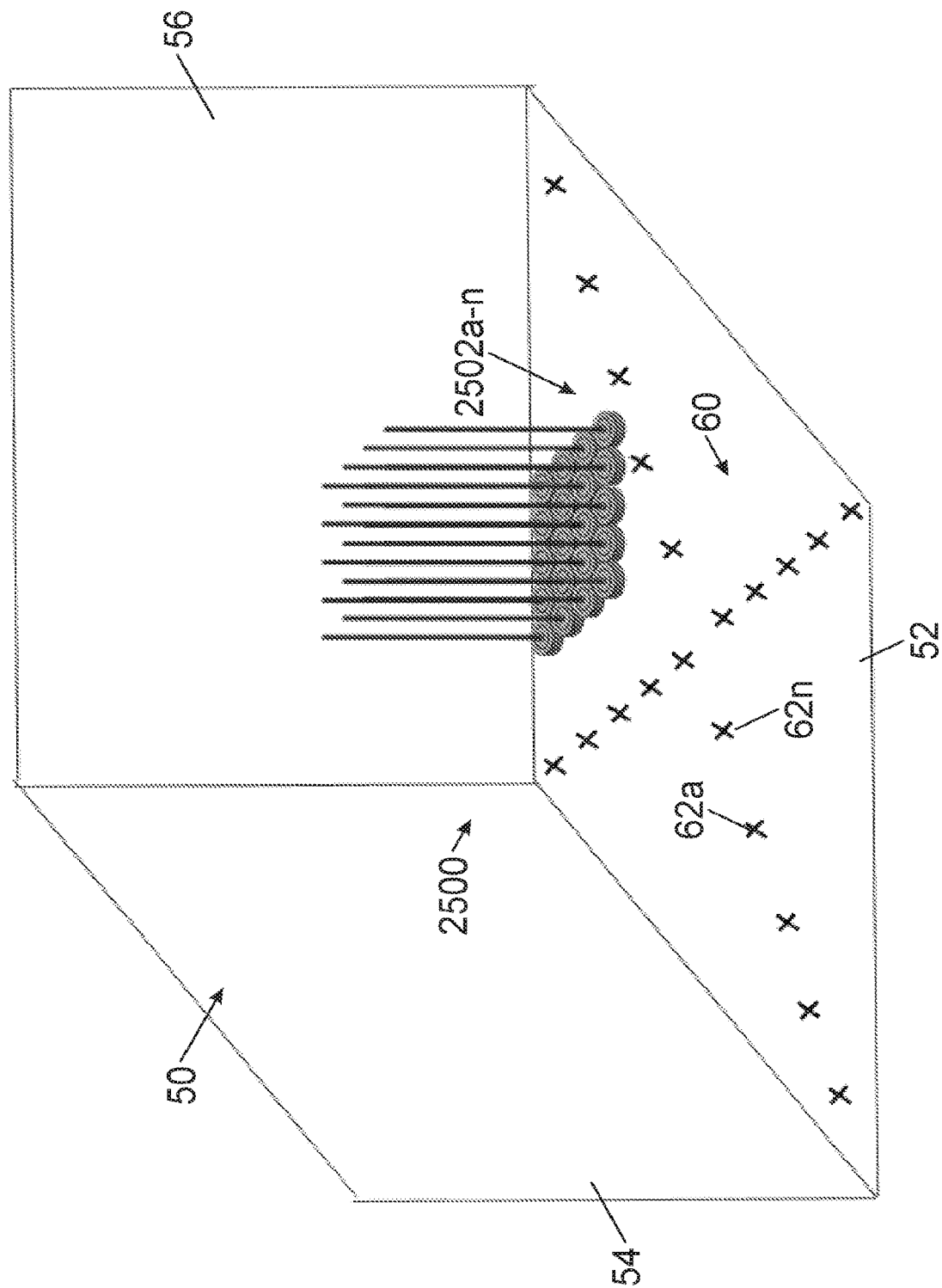
Figure 44:
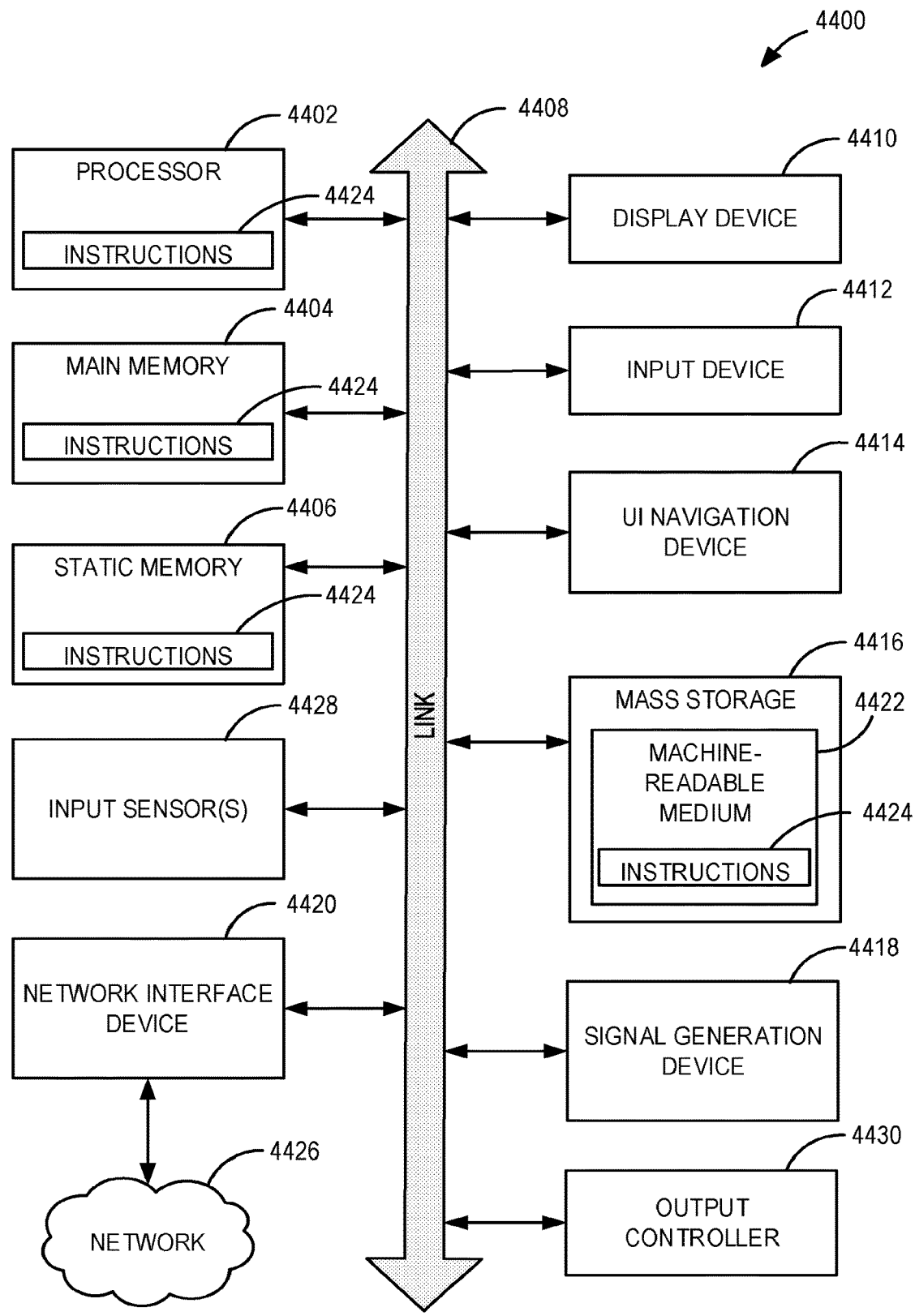
FIG. 44 illustrates a block diagram illustrating an example computer system machine upon which any one or more of the previous techniques may be performed or facilitated by, in accordance with at least one example of the present disclosure.

In operation of some examples, the system 2500 can include a master control device, such as the computer system 4400 of FIG. 44, which can be in contact with each of the mobile ultraviolet light devices 2502a-2502n. In some examples, the mobile ultraviolet light devices 2502a-2502n can communicate with each other to deploy and organize within the target volume 50. In one example of a deployment process, the mobile ultraviolet light devices 2502a-2502n can be deployed into the target volume, whereby the mobile ultraviolet light devices 2502a-2502n are in one general location within a target volume as shown in FIG. 25F.

In this example, the target volume 50 can include a map 60 of indicators developed by one or more of the controllers of the mobile ultraviolet light devices 2502a-2502n or by the master controller. The map 60 can include indicia 62a-62n, denoted by "X" in FIG. 25F, which can be coordinates defined by the controller based on data from one or more sensors, such as one or more of a proximity sensor, a photosensor, an RFID sensor, an NFC sensor, or the like. The controller can be configured to communicate with the controller of each of the plurality of mobile ultraviolet light devices to develop a destination for each of the mobile ultraviolet light devices 2502a-2502n a destination indicia 62a-62n for each of the mobile ultraviolet light devices 2502a-2502h. Each individual controller of the mobile ultraviolet light devices 2502a-2502n can be configured to operate the motor to move the base within the target volume 50 based on the map 60 and the destination 62a-62n for each of the mobile ultraviolet light devices 2502a-2502n. In some examples, the target volume 50 can include indicia 62a-62n that can be physical decals or markers.

Figure 25G:
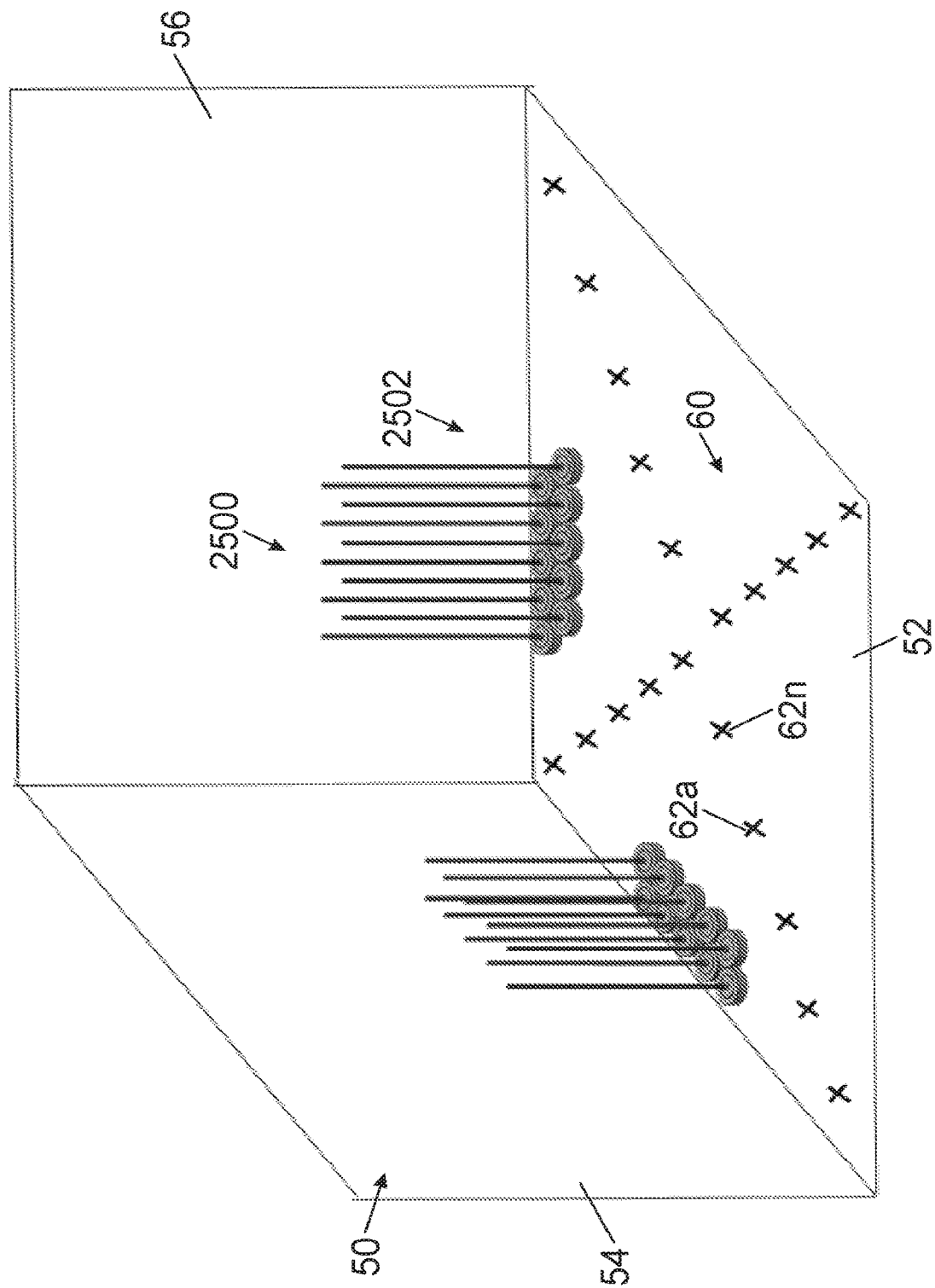
Figure 25H:
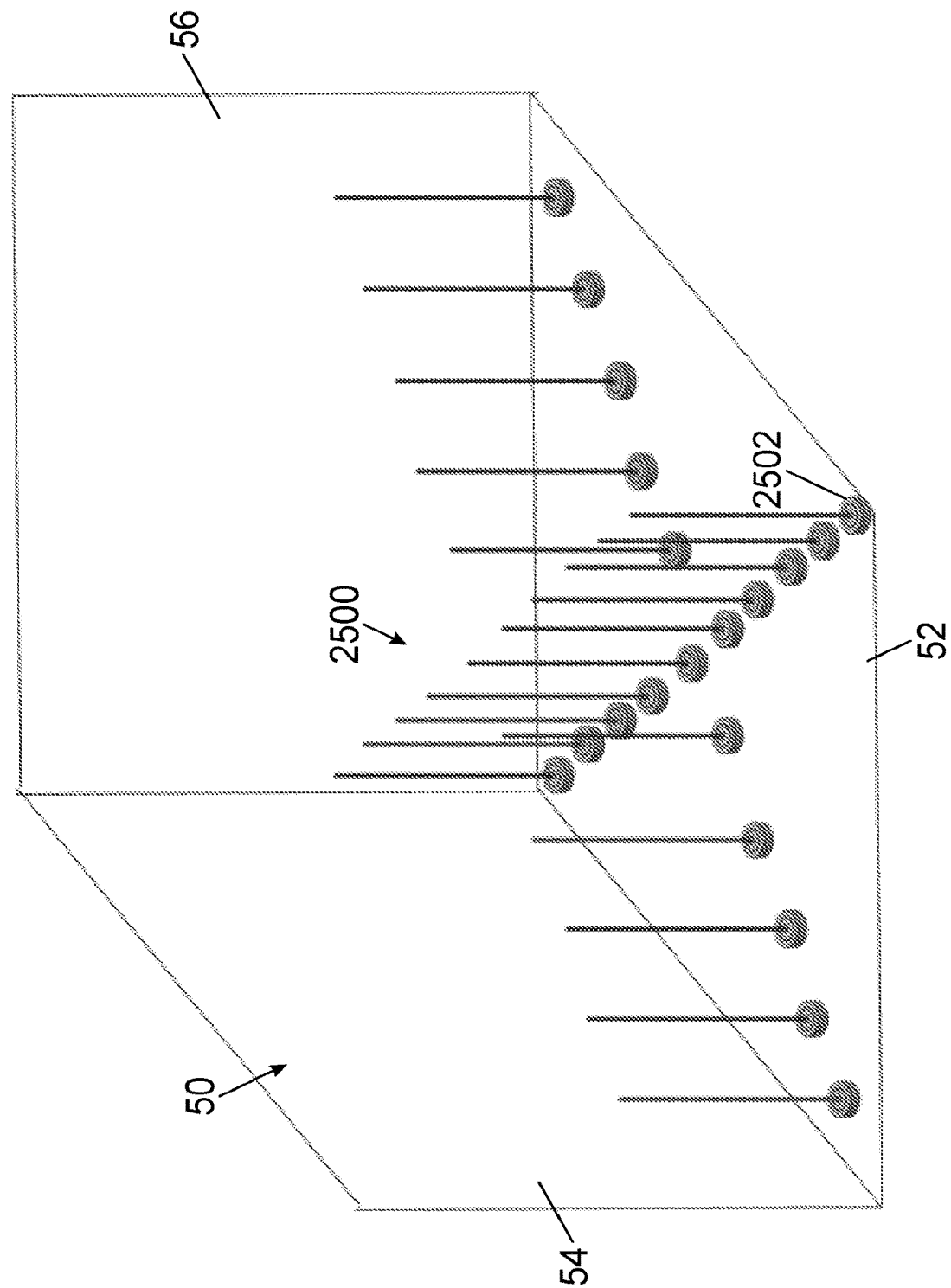

As shown in FIG. 25G, a portion of the mobile ultraviolet light devices 2502a-2502n can move manually or in an automated fashion via programed motors. While moving, sensors of the mobile ultraviolet light devices 2502a-2502n can continue producing dimensions, coordinates, positioning, and identification parameters based on collected sensor data. As shown in FIG. 25H, the mobile ultraviolet light devices 2502a-2502n can move to their corresponding markers within the target volume 50. Once in position, the light sources 2504 can be controlled to emit ultraviolet light within the target volume. For example, the plurality of light sources of the mobile ultraviolet light devices 2502a-2502n can be positioned within the target volume 50 on the indicia 62a-62n, to kill at least 90% of organisms within the target volume within a single cycle of operation of the plurality of light sources. In some examples, the single cycle of operation of the plurality of light sources is less than 20 minutes, the substantially homogenous irradiance of every surface in the target volume can be between 50 and 800 micro Watts per square centimeter, and the target volume 50 is a room having dimensions between 1.5-8 meters in width by 1.5-8 meters in length by 2-5 meters in height. In some examples of operation, the irradiance on some surfaces can be between 400-2000 micro Watts per square centimeter in the homogenous matrix. Once a light cycle has been completed the mobile ultraviolet light devices 2502a-2502n can reorganize in the compact and non-deployed configuration as shown in 25F.

Figure 25I:
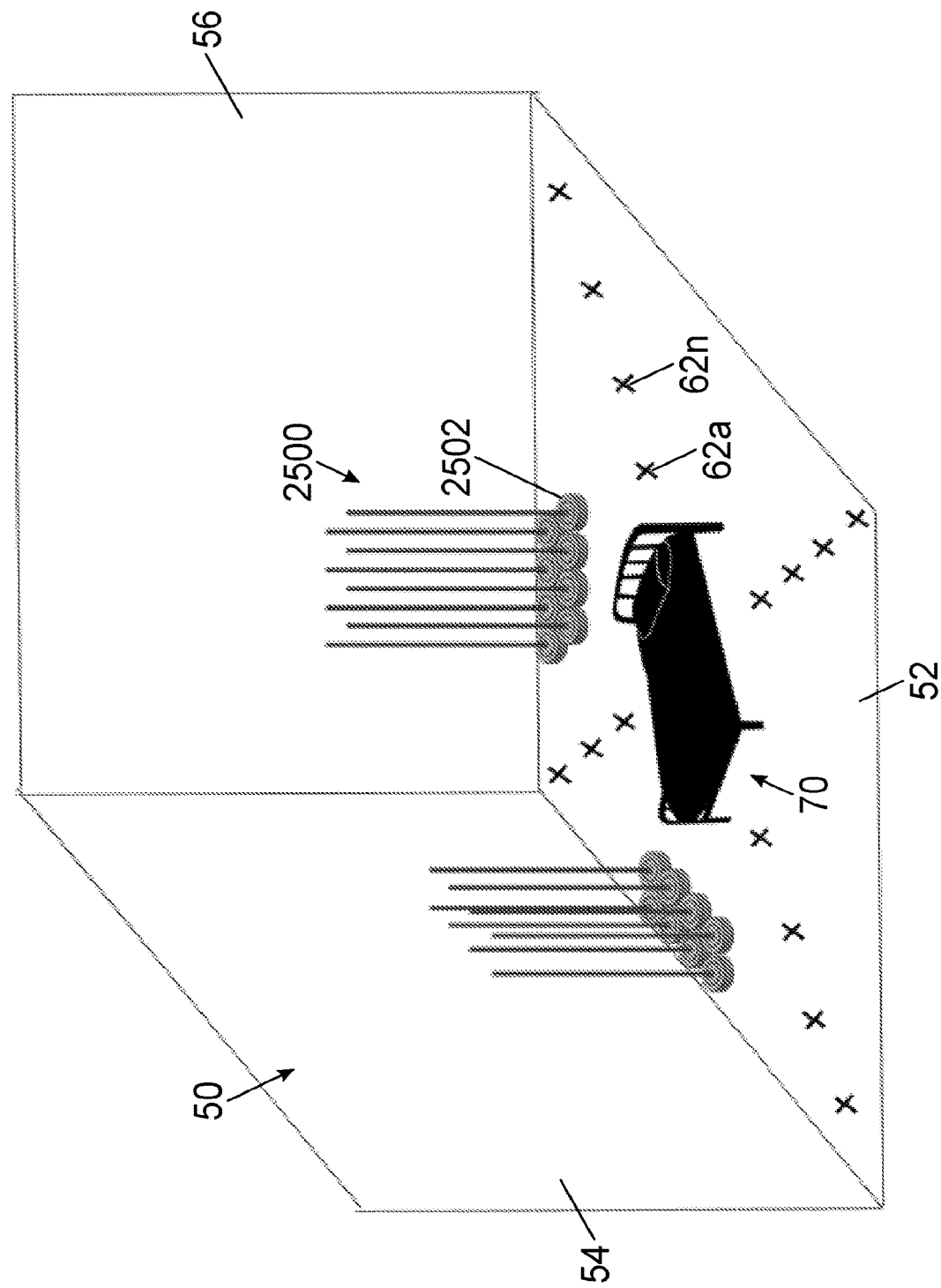
Figure 25J:
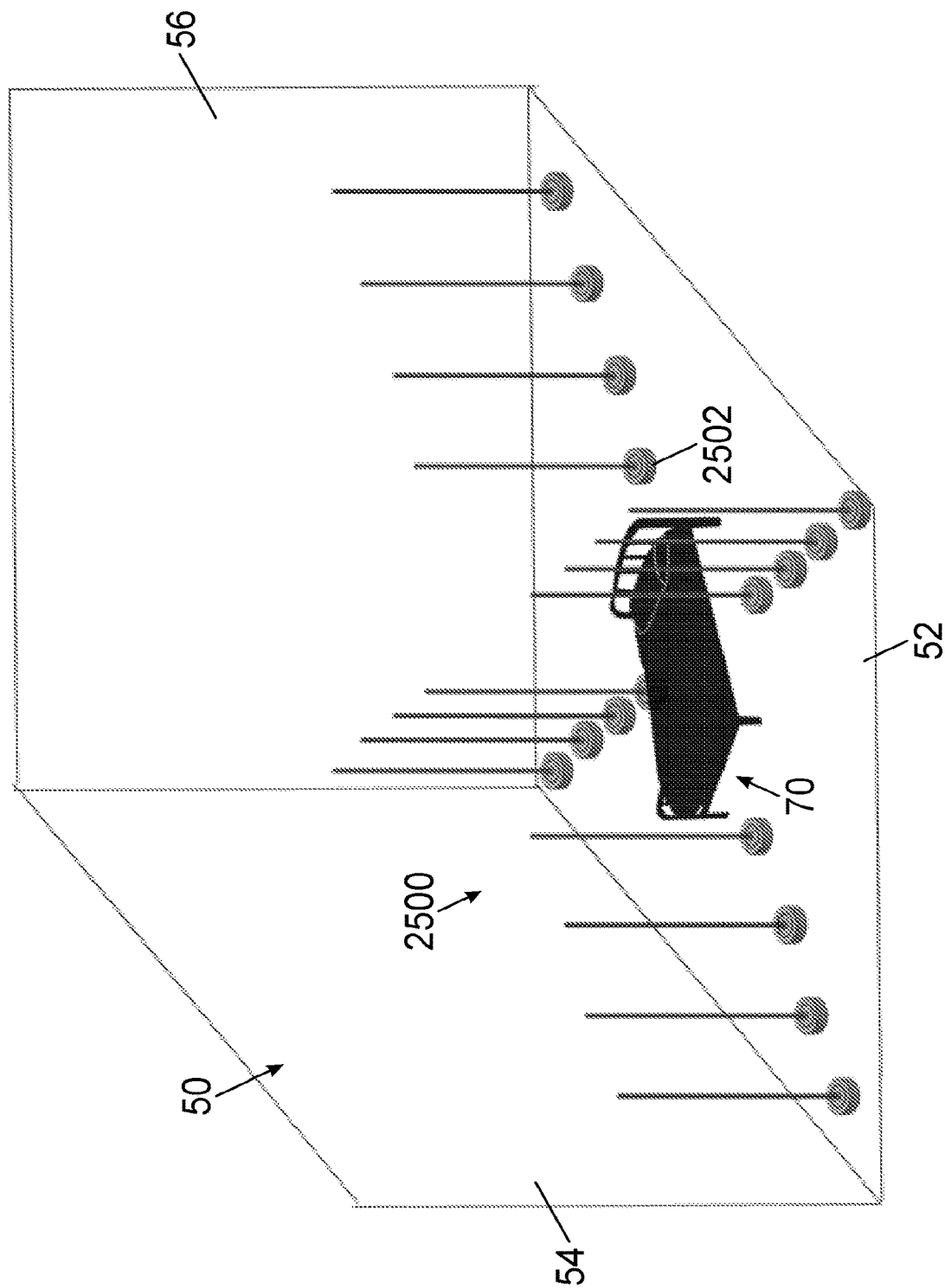

In some examples, the target volume 50 can include one or more inanimate objects, for example a bed 70, as shown in FIGS. 25I and 25J. In such an example, the mobile ultraviolet light devices 2502a-2502n can perform the steps discussed above, where the mobile ultraviolet light devices 2502a-2502n can incorporate a volume and dimension of the inanimate object, such as the bed 70, is taking up within the target volume 50. The mobile ultraviolet light devices 2502a-2502n can position themselves within the target volume 50 while accommodating the spacing and the proportional distance between the bases and ultraviolet sources that would achieve precise energy. This can also be achieved with the disinfection device as shown in FIG. 33.

In some examples, messaging and software parameters can be captured by the multiple proximity, dimension, and coordinate sensors, computed and then established by the controller that is ingesting parameters of interest pertaining to the construction of the light matrix with precise energy by distributing the bulbs on the variable dimensions of the target volume or room.

In some examples, the system 2500 can include a remote controller (such as a computer system 4000), that can be in communication with the controllers of the mobile ultraviolet light devices 2502a-2502n. The remote controller can be operable to selectively move individual mobile ultraviolet light devices within the target volume 50, as desired.

FIGS. 26A-26I illustrate detachable and attachable rails containing ultraviolet sources with coupling mechanisms of a disinfection device, in accordance with at least one example of the present disclosure.

Figure 26A:
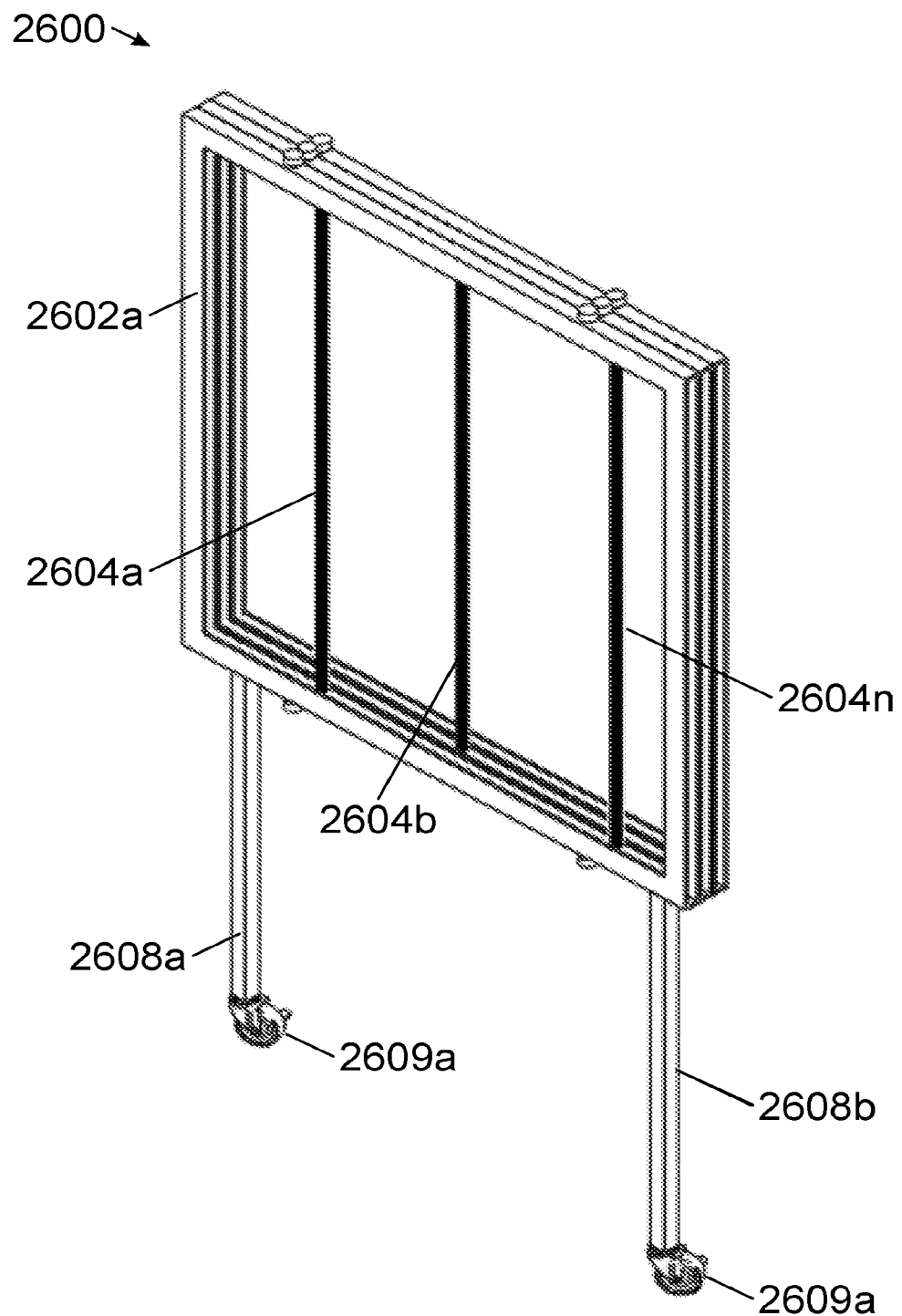
Figure 26C:
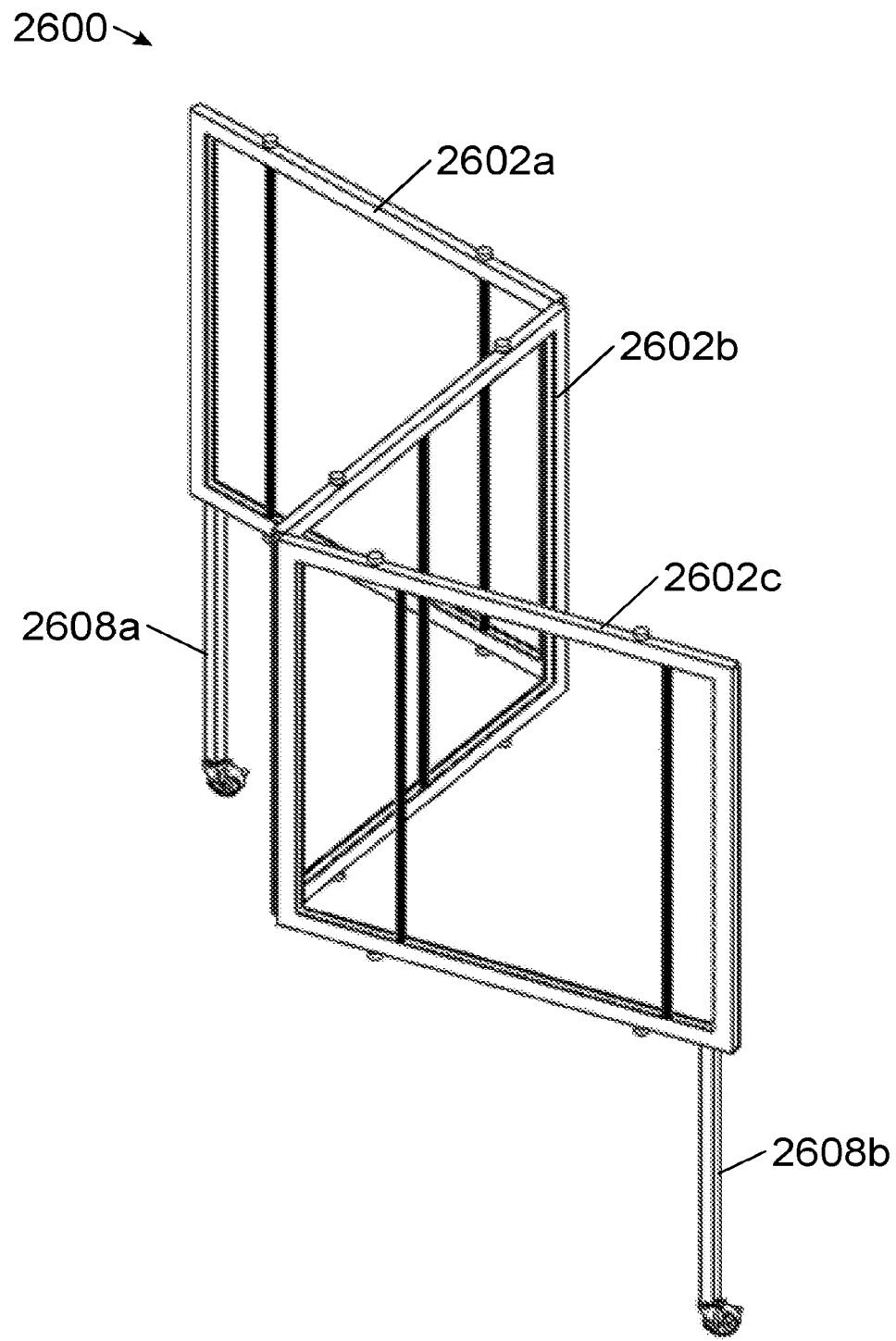
Figure 26D:
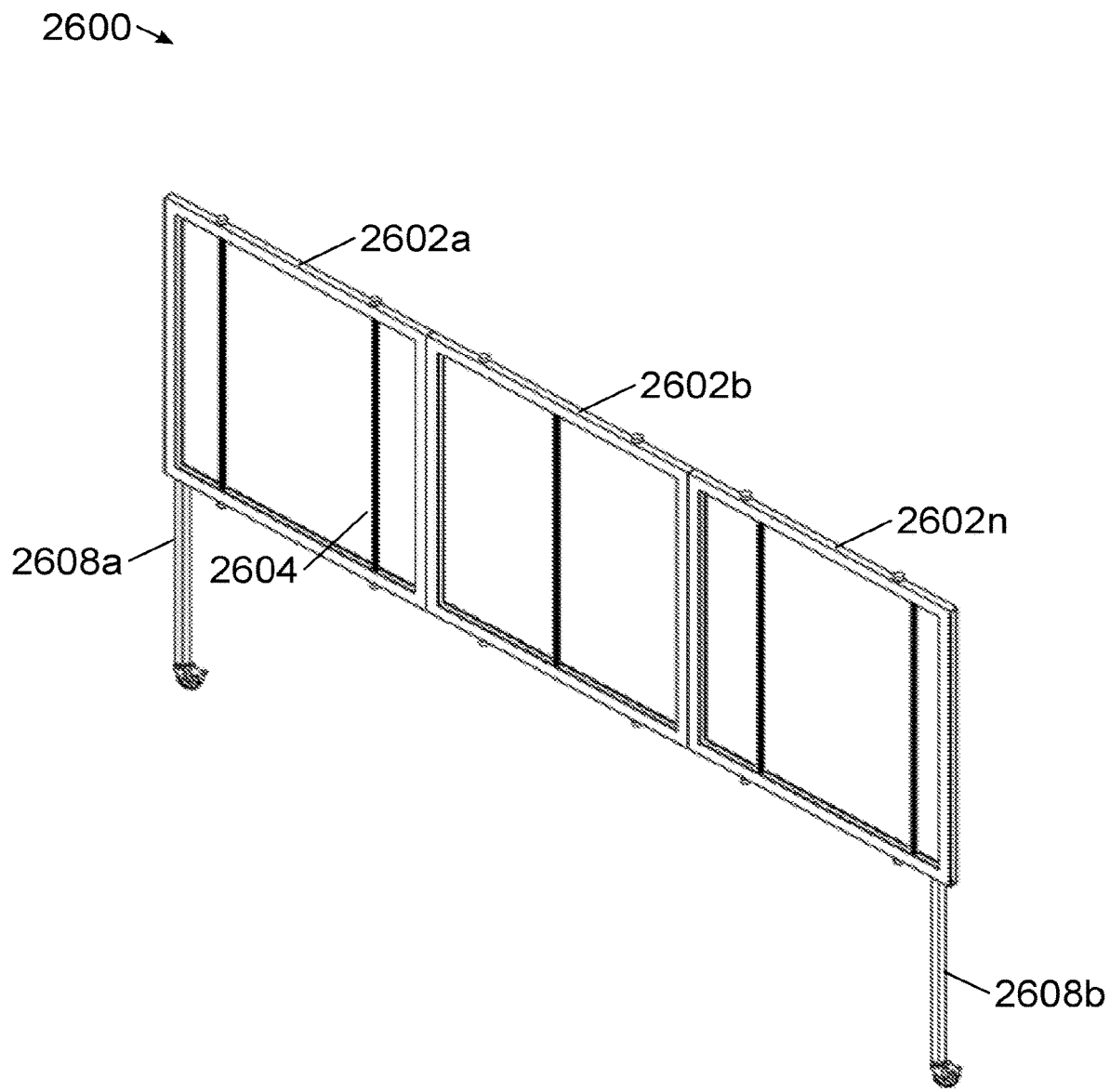
Figure 26E:
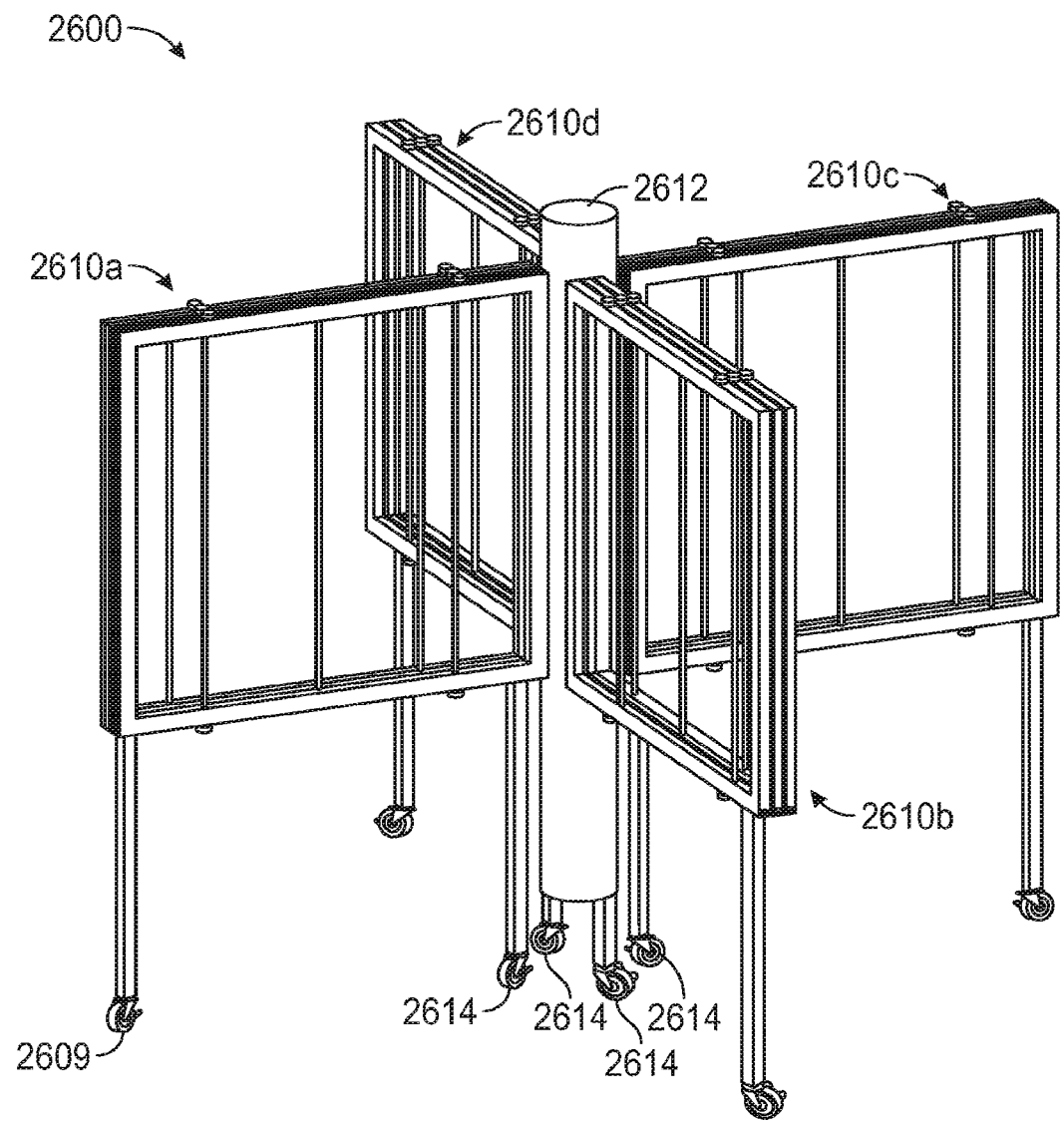
Figure 26F:
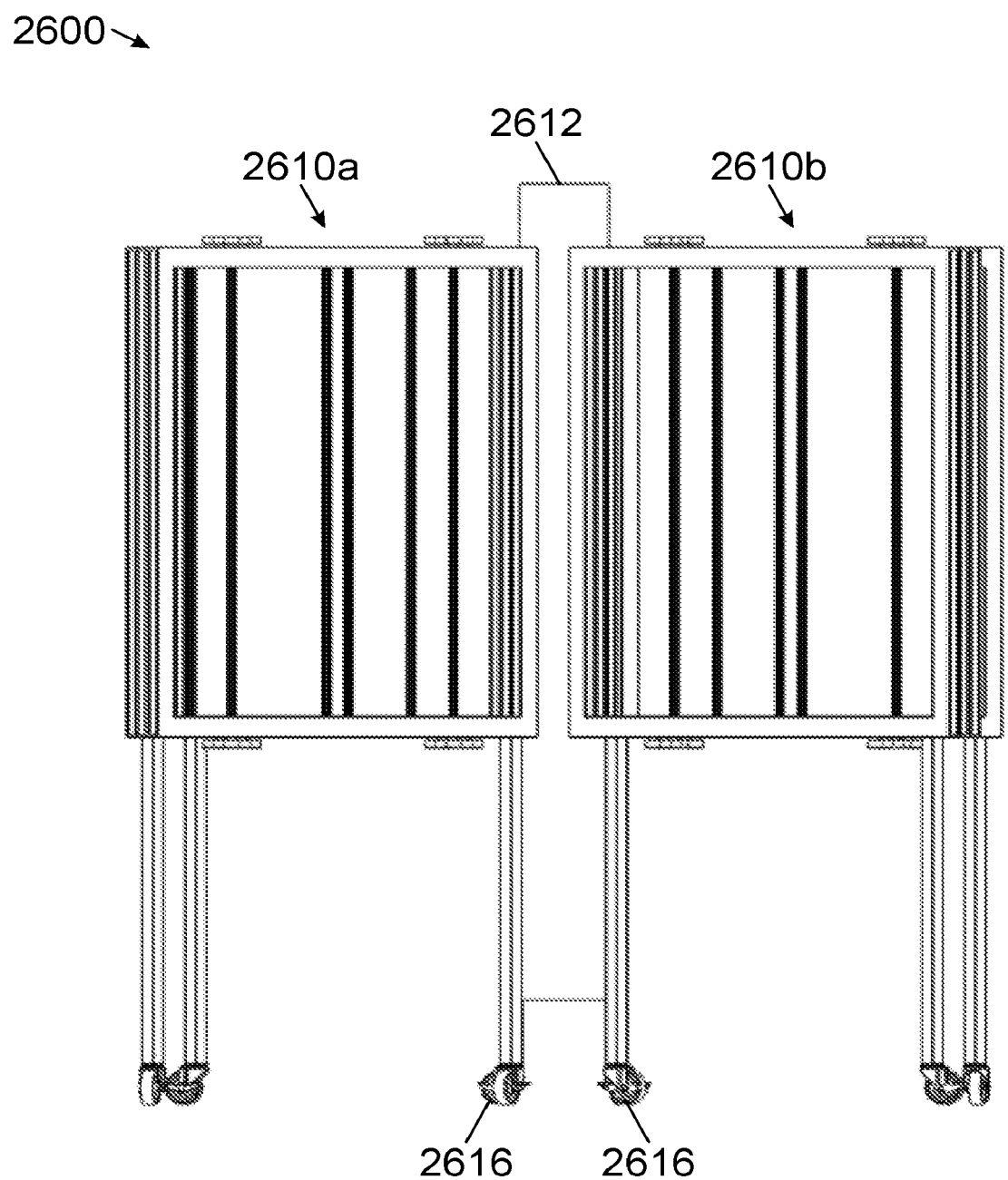
Figure 26G:
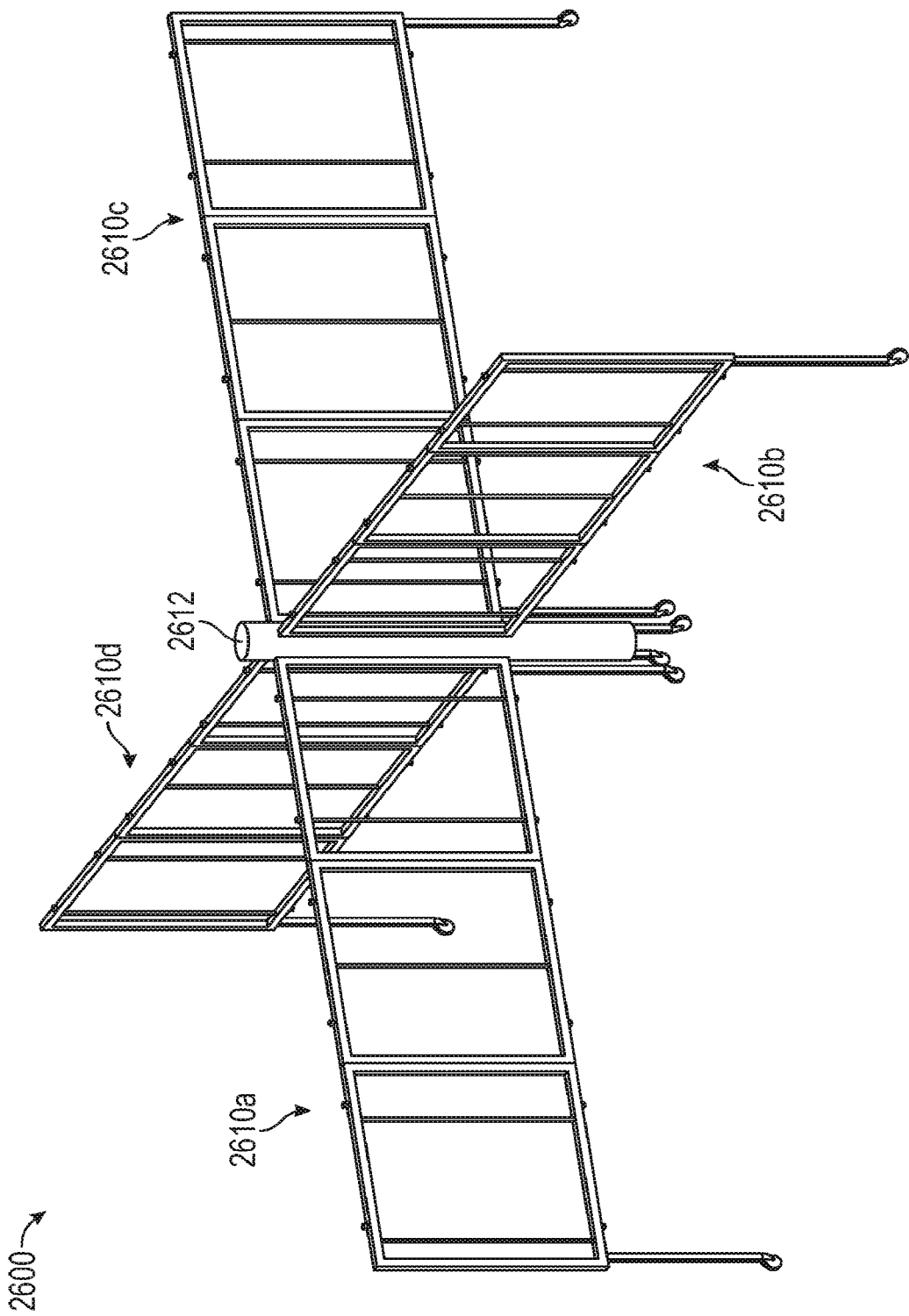
Figure 26H:
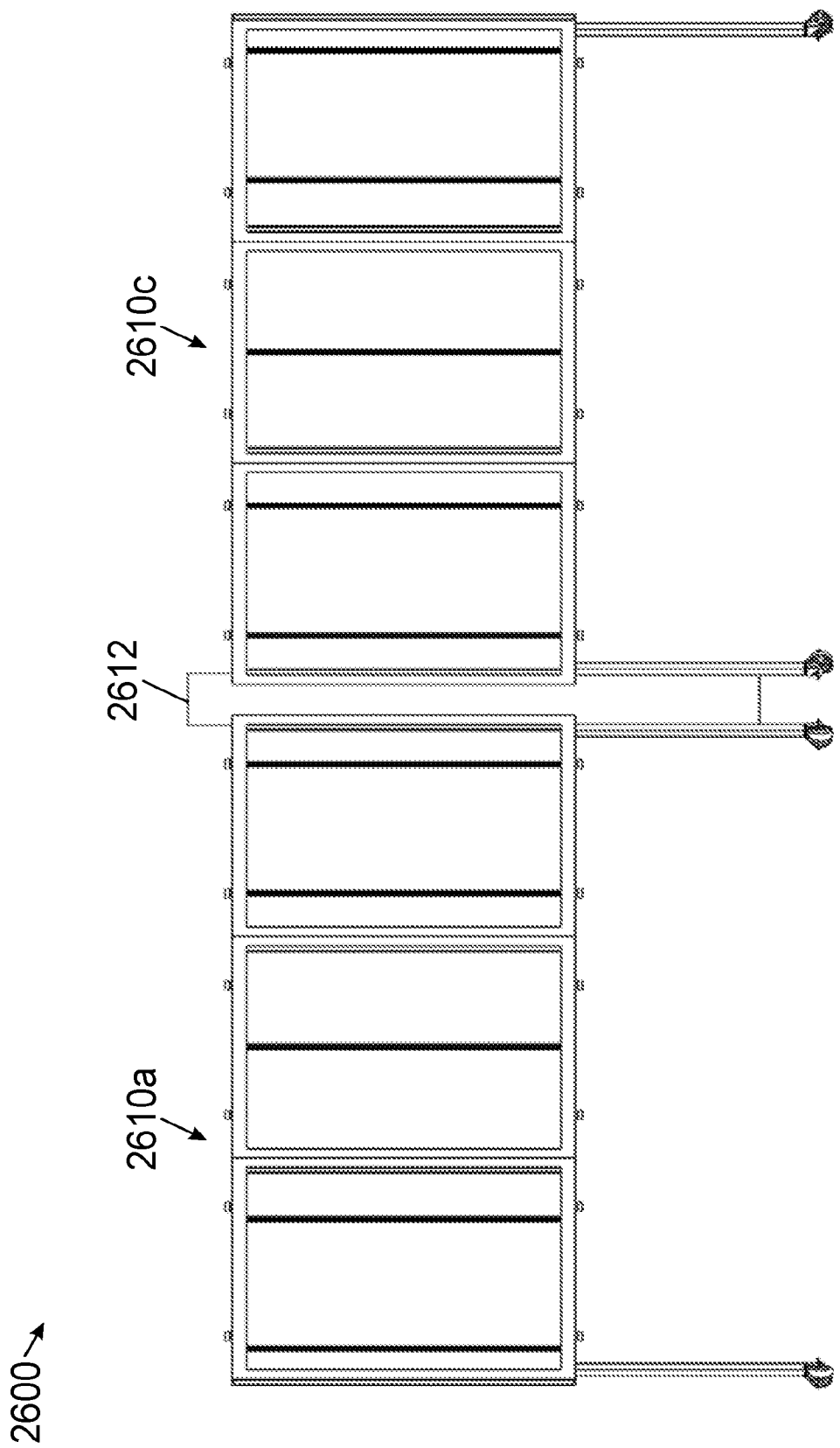
Figure 26I:
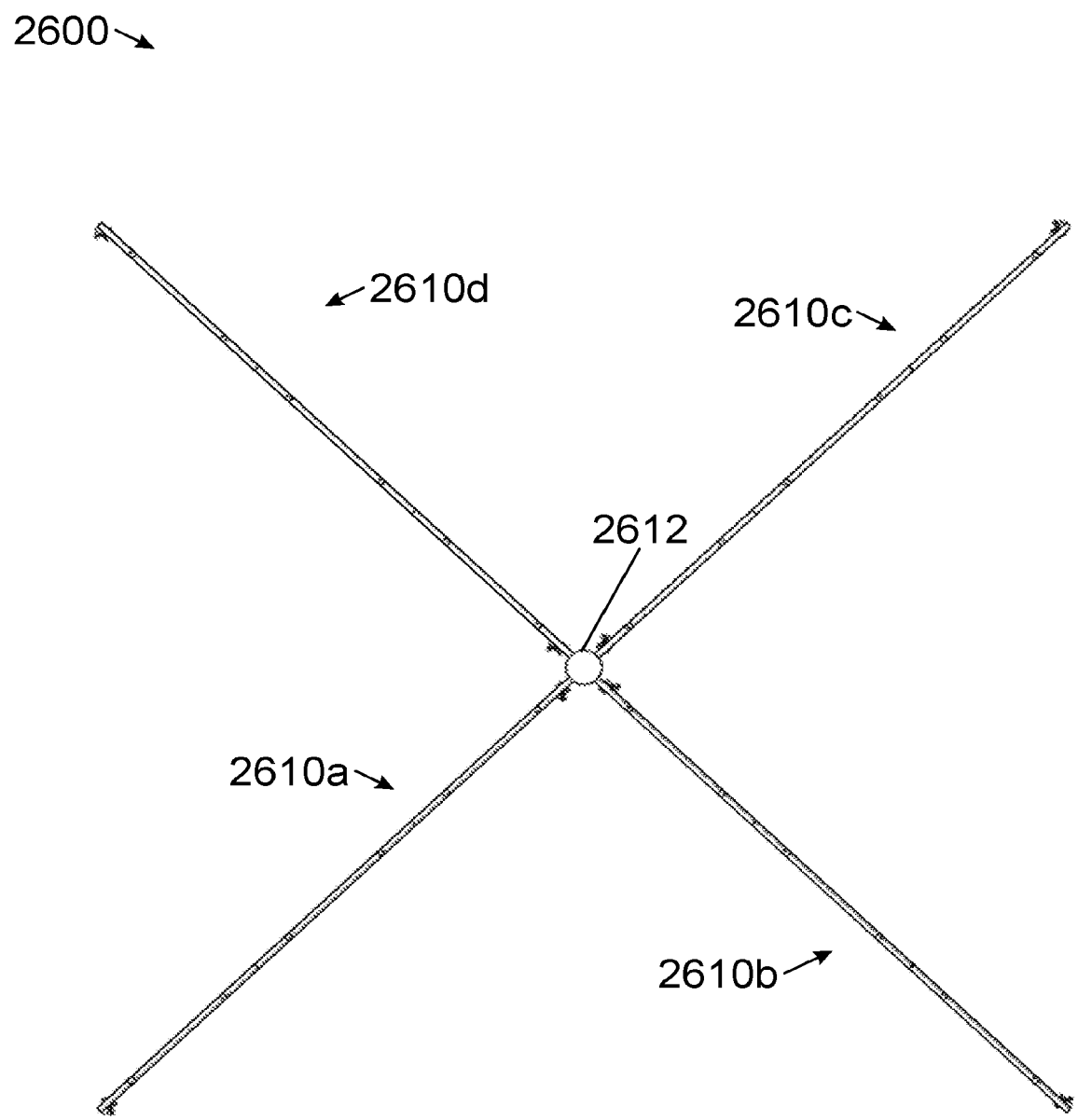

The disinfection device 2600 can include a frame member 2602a which houses ultraviolet sources 2604 within the frame member 2602a, as shown in FIG. 26A-26I. The frame members 2602 can be supported by bases or legs 2608a-2608b, which can include respective casters 2609a-2609b. An arm 2610a, as shown in FIG. 26E, can be constructed independently from the base structure of FIGS. 26A-26D, where the frame members 2602 can be added as needed. The frame members 2602 can be deployed and expanded by coupling frame members together as seen in FIGS. 26C and 26D to create an arm 2610 at a desired length. The arms 2610a-2610d can be coupled together by a base 2612 (which can optionally include casters or wheels 2614), as shown in FIGS. 26E and 26F in a collapsed configuration, and in FIGS. 26G, 26H, and 26I in an expanded configuration.

Figure 27A:
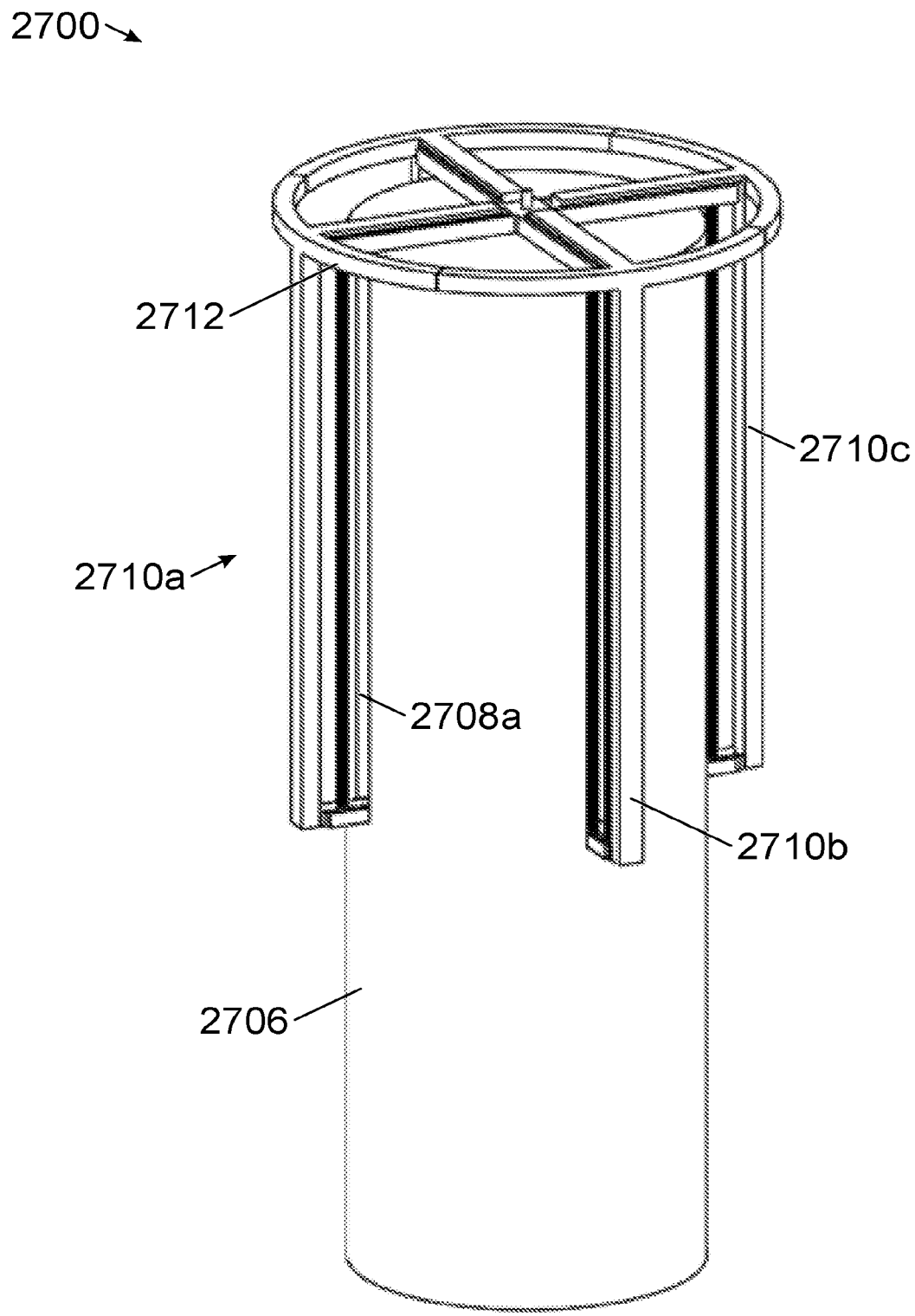
Figure 27B:
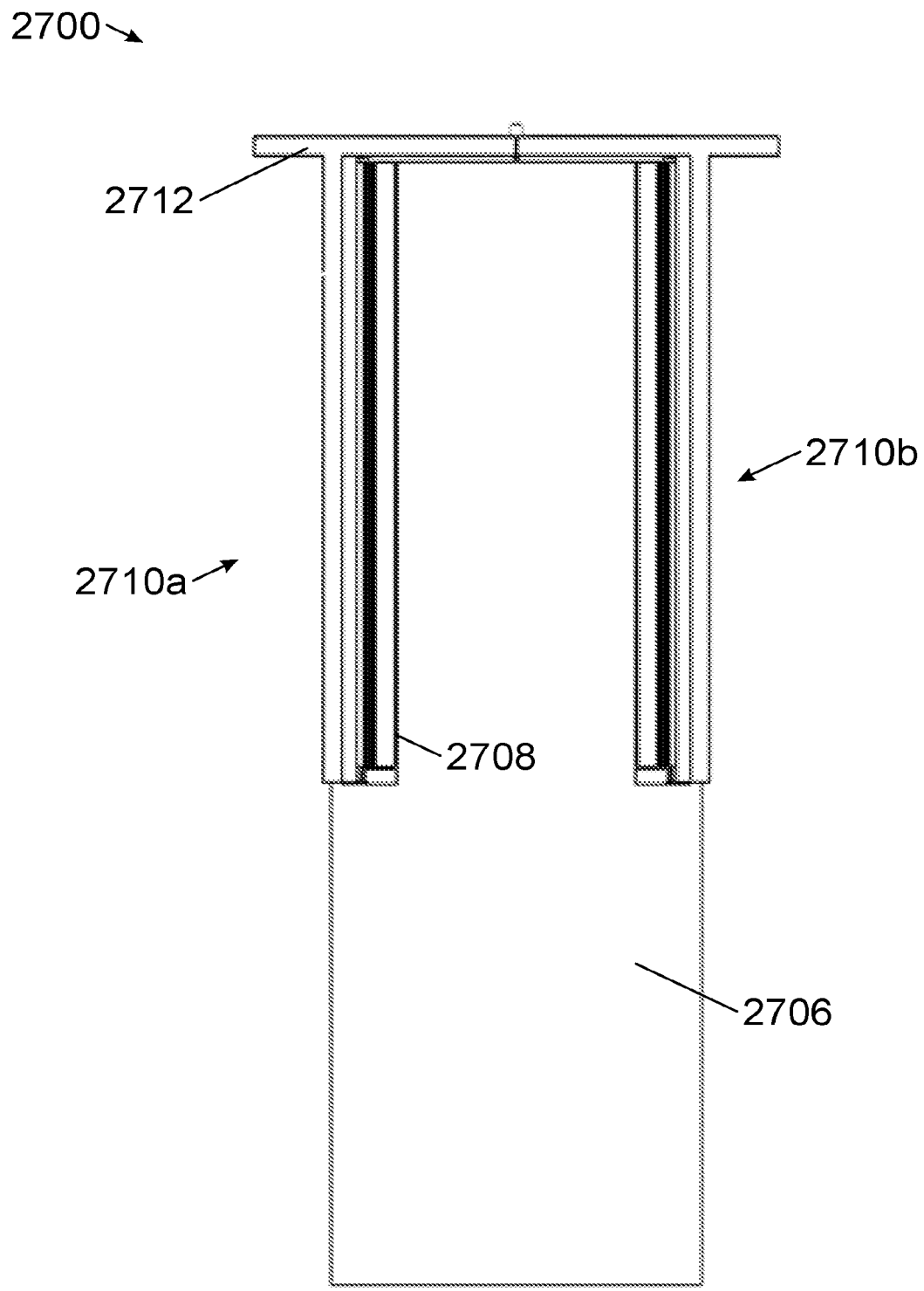
Figure 27C:
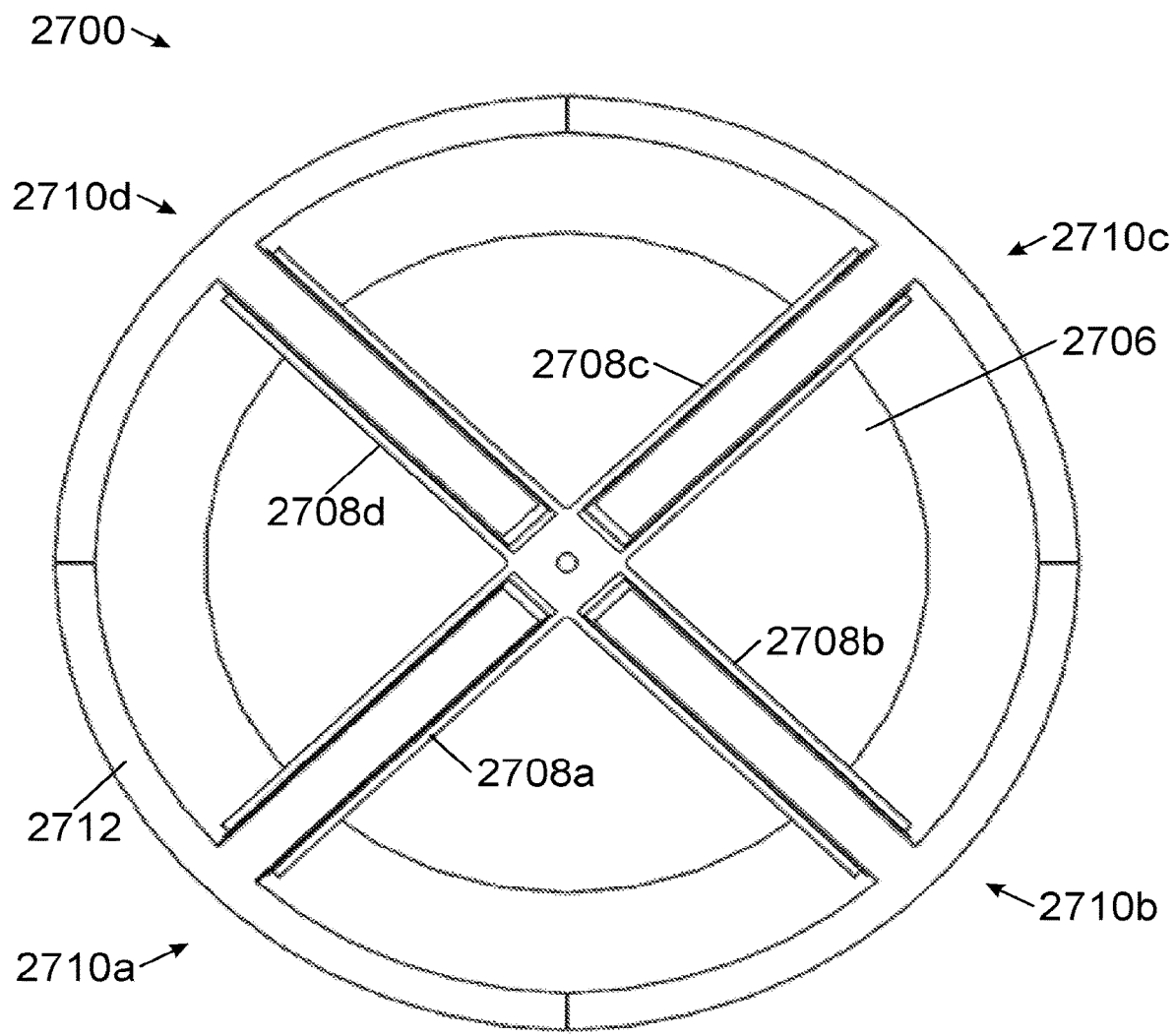
Figure 27D:
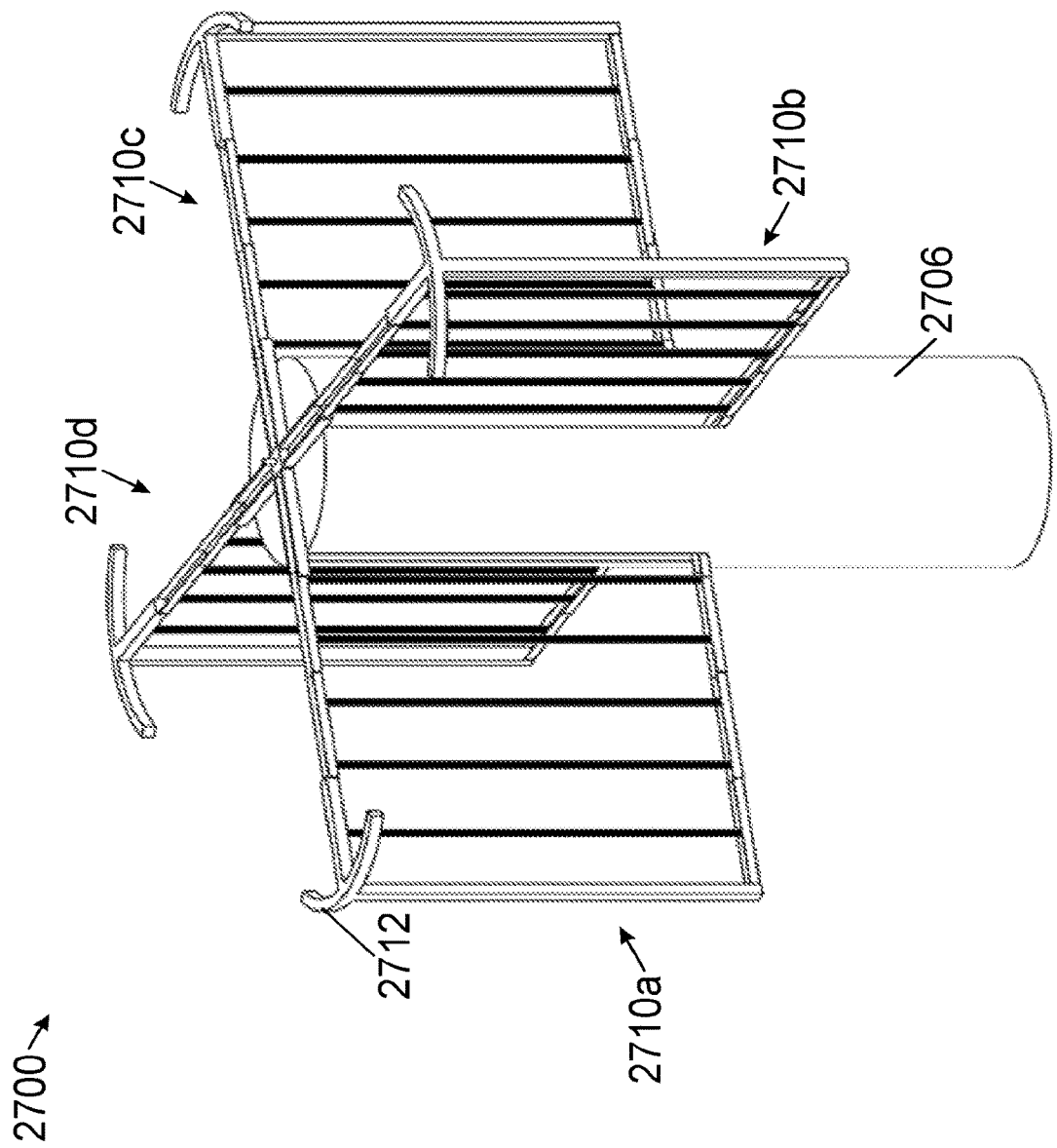
Figure 27F:
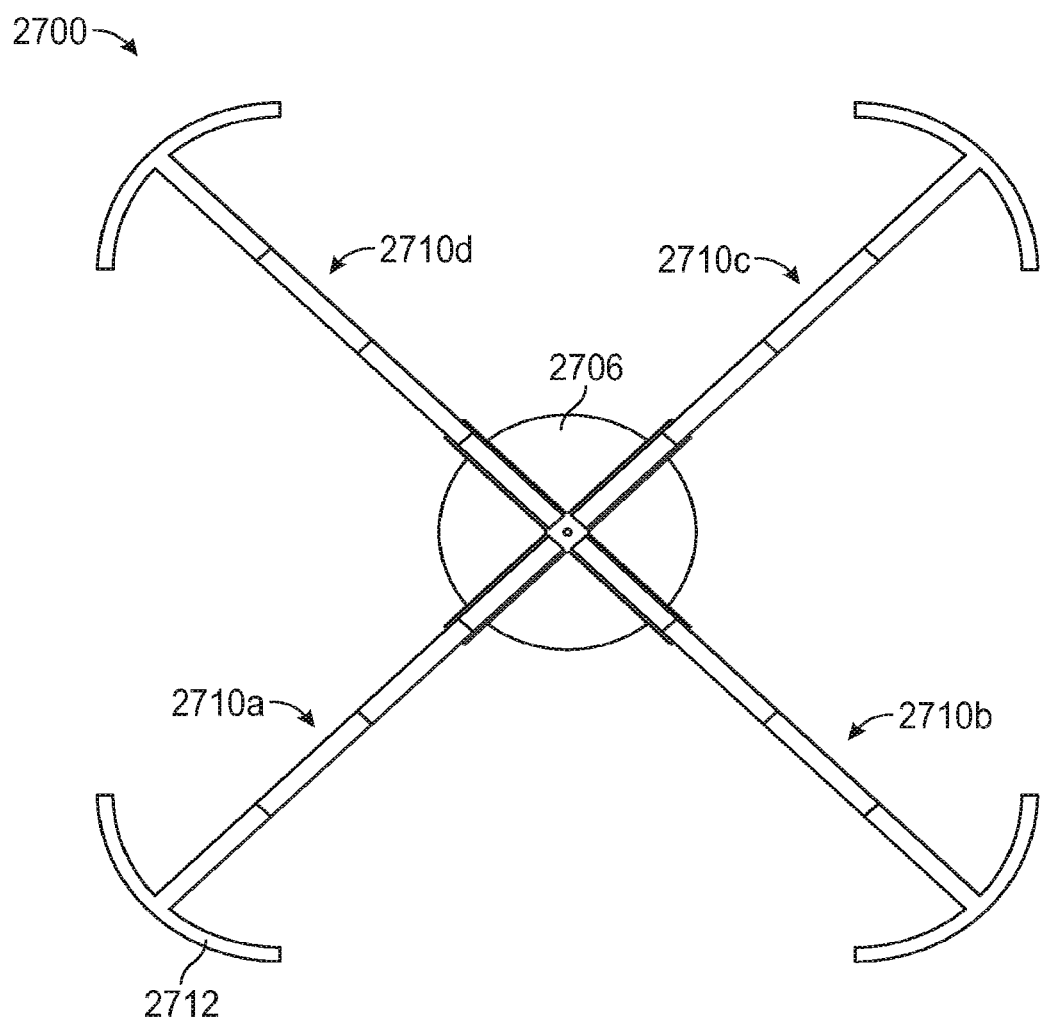

FIGS. 27A-27F illustrate a disinfection device with an expandable ring structure, in accordance with at least one example of the present disclosure. FIG. 27A shows a perspective view, FIG. 27A shows an elevation view, and FIG. 27C shows a top view of a disinfection device 2700 that can include a base 2706 (including channels 2708a-2708d, also referred to as compartments 2708). The disinfection device 2700 can include arms 2710a-2710d collapsible into their respective channels 2708a-2708d and expandable therefrom. Each of the arms 2710a-2710d can include an arcuate handle 2712 sized and shaped to conform to an outer periphery of the base 2706, which can be cylindrical in some examples. In some examples, the arms 2710a-2710d can be mechanically connected such that pulling radially outward on one handle 2712 can cause movement of all of the arms 2710a-2710d radially outward from the channels 2708a-2708d of the base 2706 to the extended configuration, which can help save set-up and pack-up time.

Figure 28:
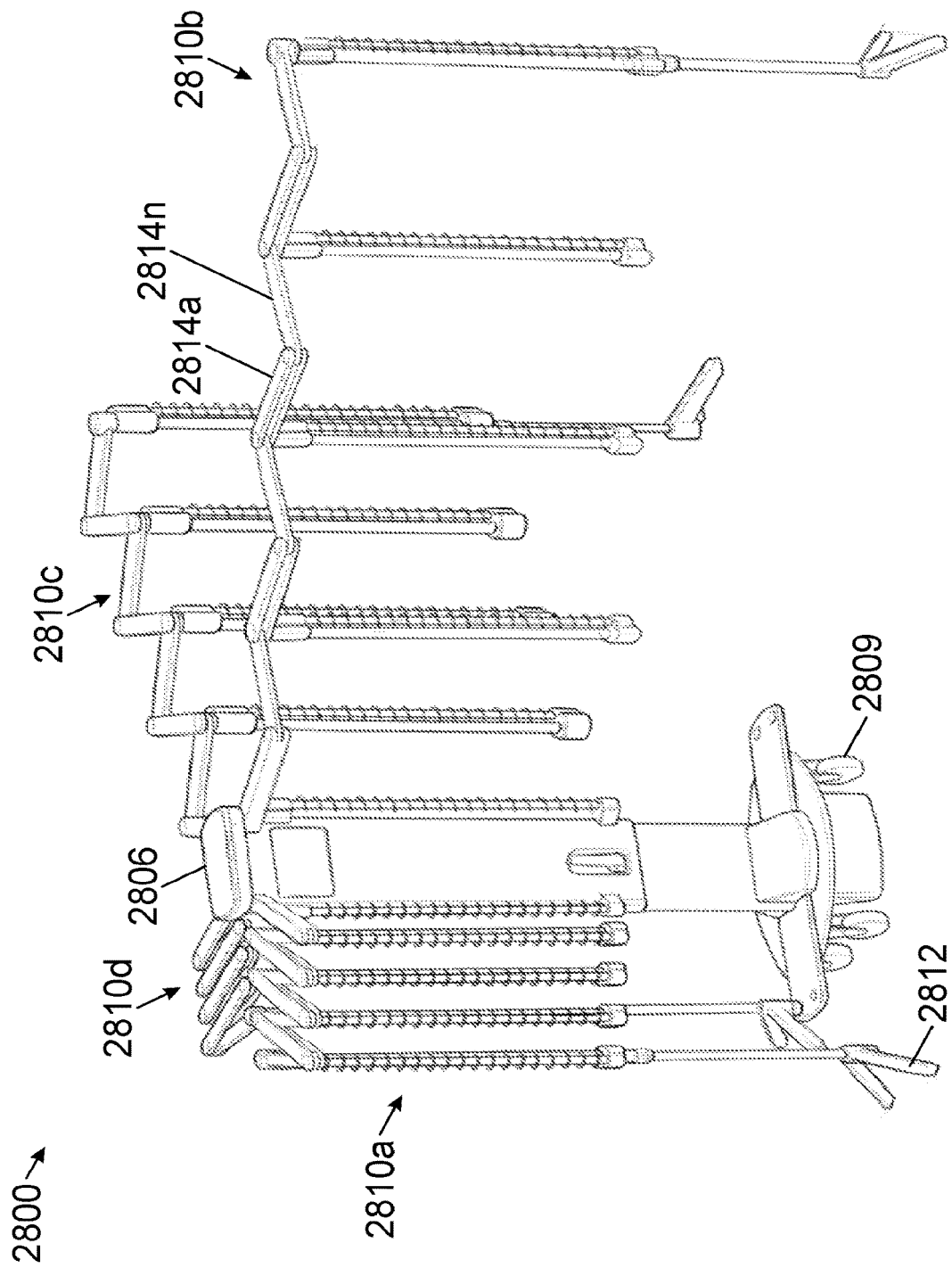
FIG. 28 illustrates a disinfection device with horizontal expandable tracks with telescoping support structures, in accordance with at least one example of the present disclosure.

FIG. 28 illustrates a disinfection device 2800 with horizontal expandable tracks with telescoping support structures, in accordance with at least one example of the present disclosure. The disinfection device 2800 can include a base 2806 having wheels 2809, in some examples. The disinfection device 2800 can include arms 2810a-2810d, which including linkages 2814a-2814h, which can enable a motor or a user to expand and collapse their respective arms 2810a-2810d. Each of the arms 2810a-2810d can include a base 2812 for support of the arms 2810a-2810d in the extended position.

Figure 29:
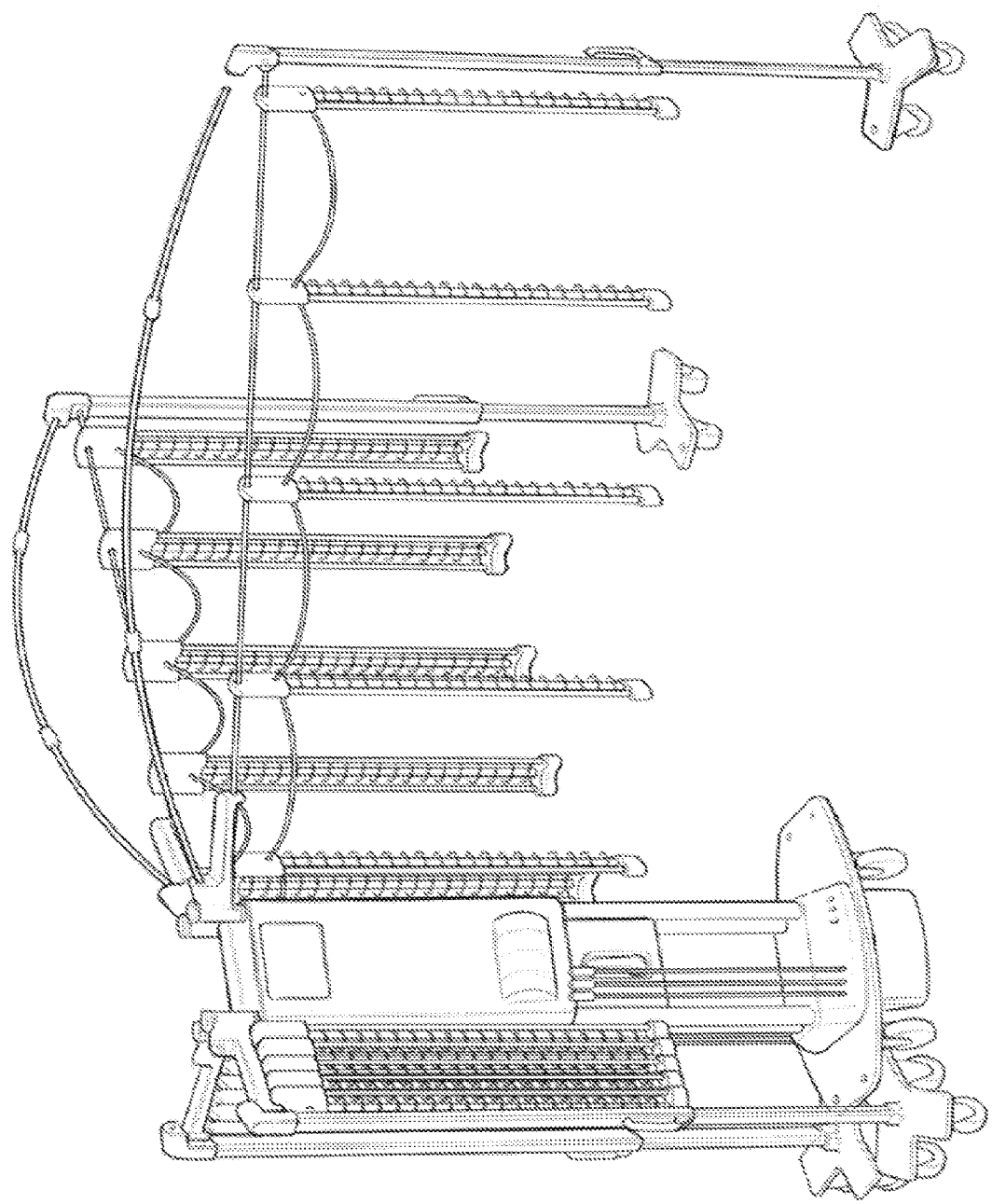
FIG. 29 illustrates a disinfection device with a tension rod extension mechanism, in accordance with at least one example of the present disclosure.

FIG. 29 illustrates a disinfection device 2900 with a tension rod extension mechanism, in accordance with at least one example of the present disclosure.

Figure 30:
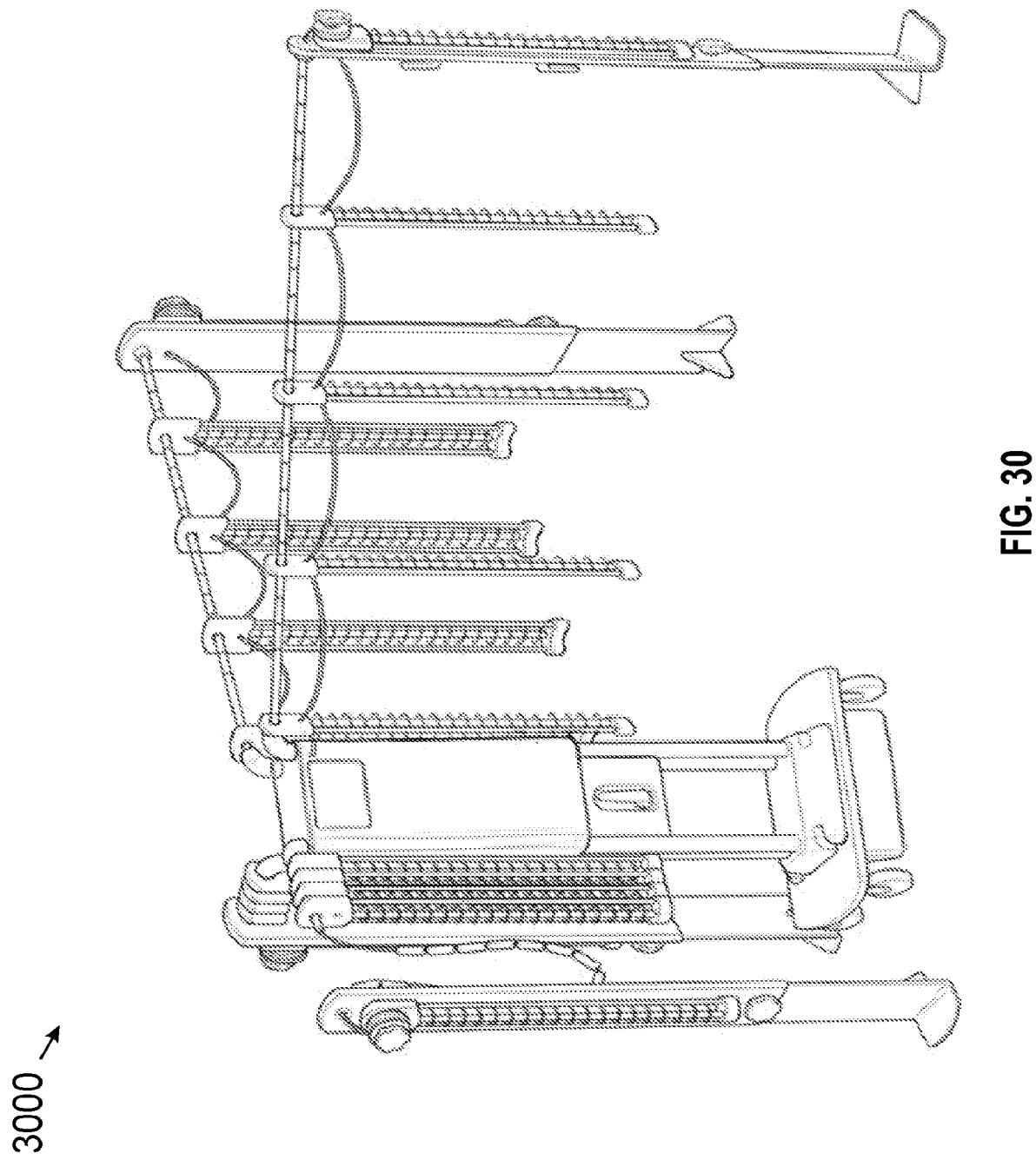
FIG. 30 illustrate a disinfection device with a compression segment rail mechanism, in accordance with at least one example of the present disclosure.

FIG. 30 illustrates a disinfection device 3000 with a compression segment rail mechanism, in accordance with at least one example of the present disclosure. The disinfection device 3000 can be similar to the disinfection device 2800, except that the drapes or lamps can be supported by rods, which can be telescopic, in some examples, and can break down in other examples. Further, the arms of the disinfection device 3000 can include bases having stands, which may be separable from the base and from each other.

Figures 32A, 32B:
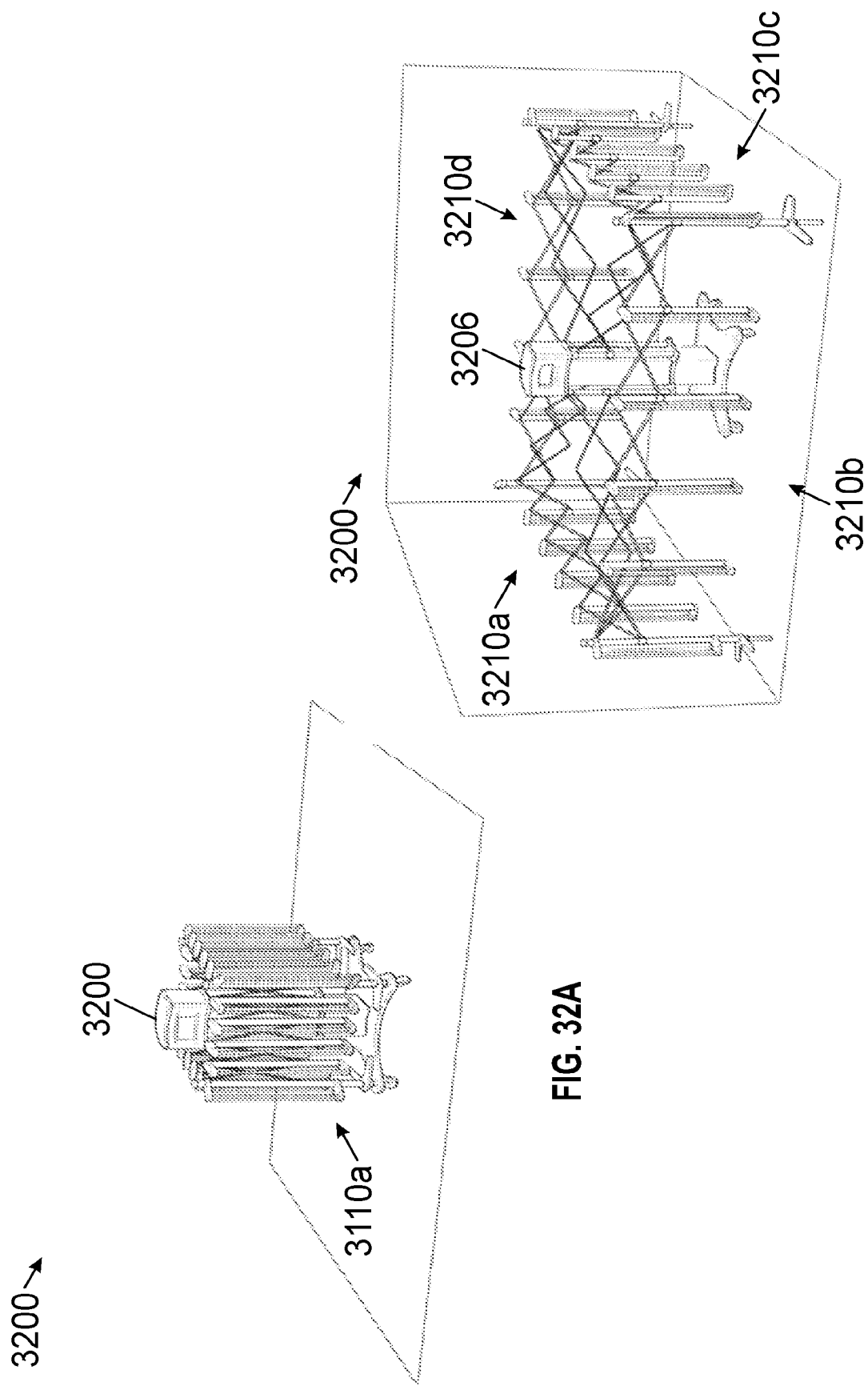
Figure 33A:
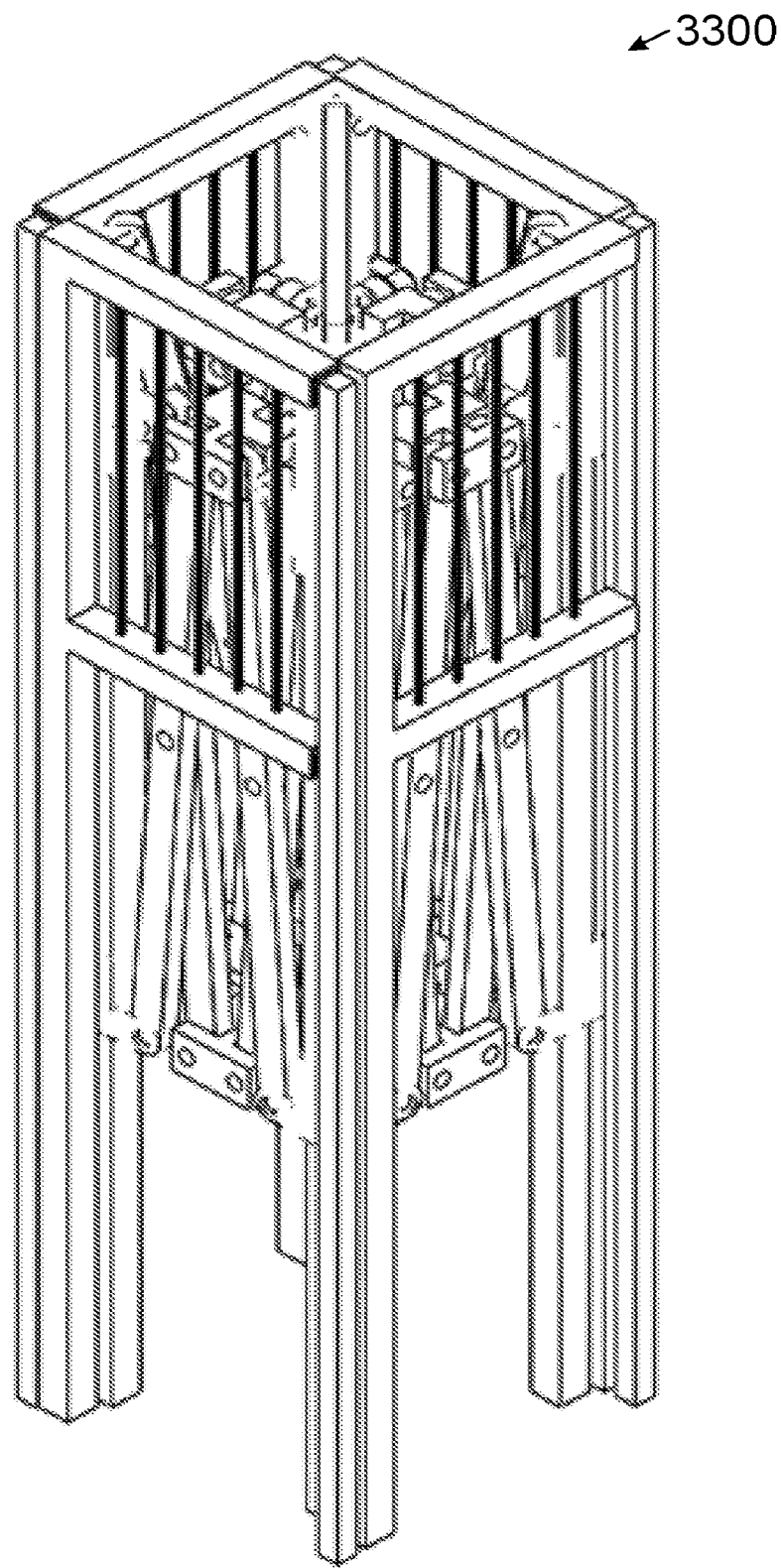
FIGS. 33A-33G illustrate a disinfection device with an expandable base structure with deploying arms, in accordance with at least one example of the present disclosure.
Figure 33B:
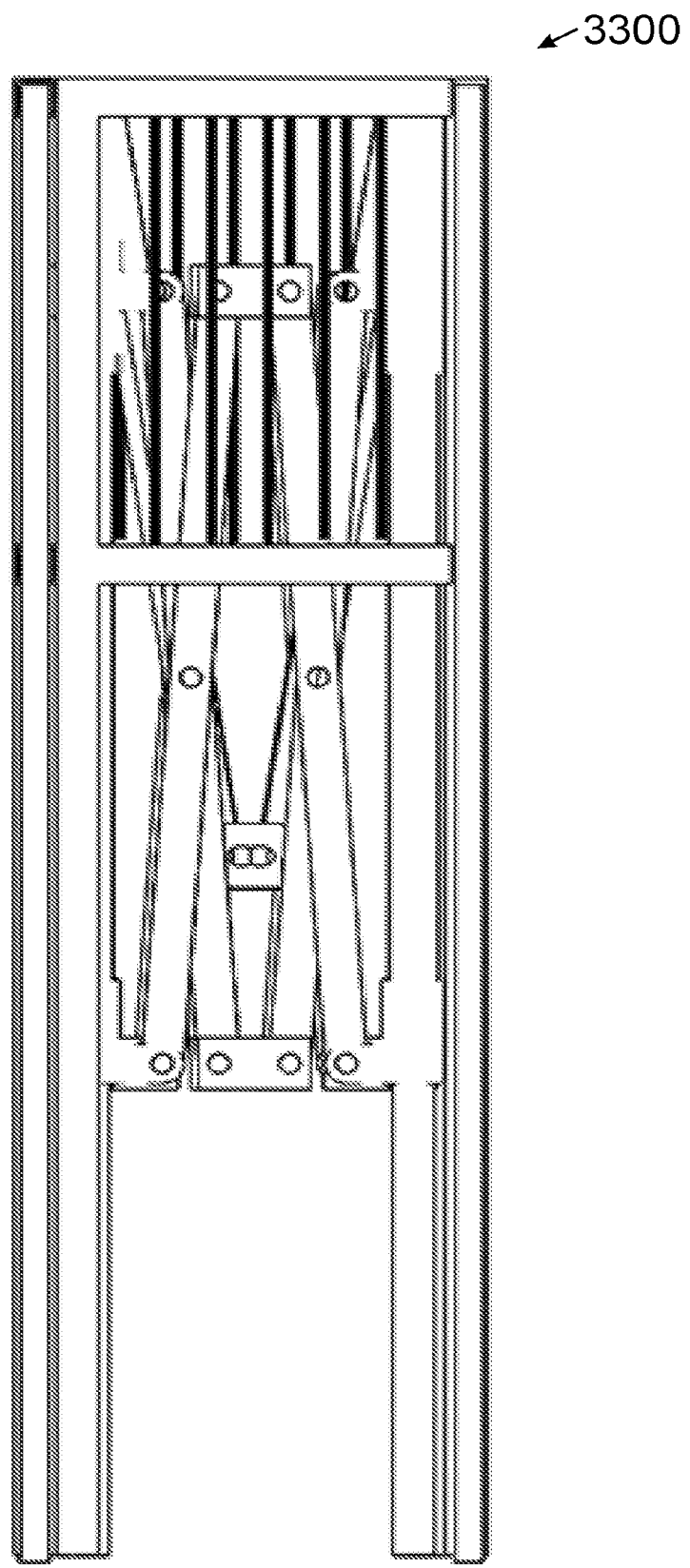
Figure 33C:
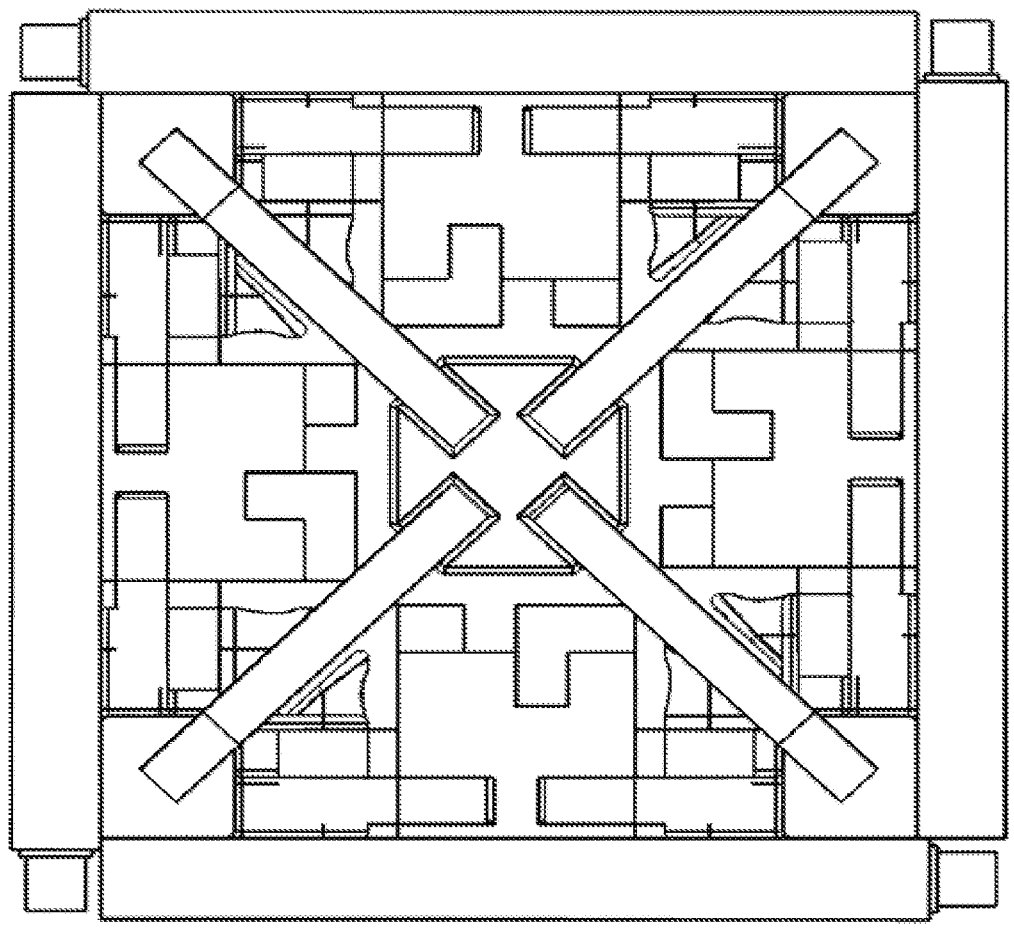
Figure 33D:
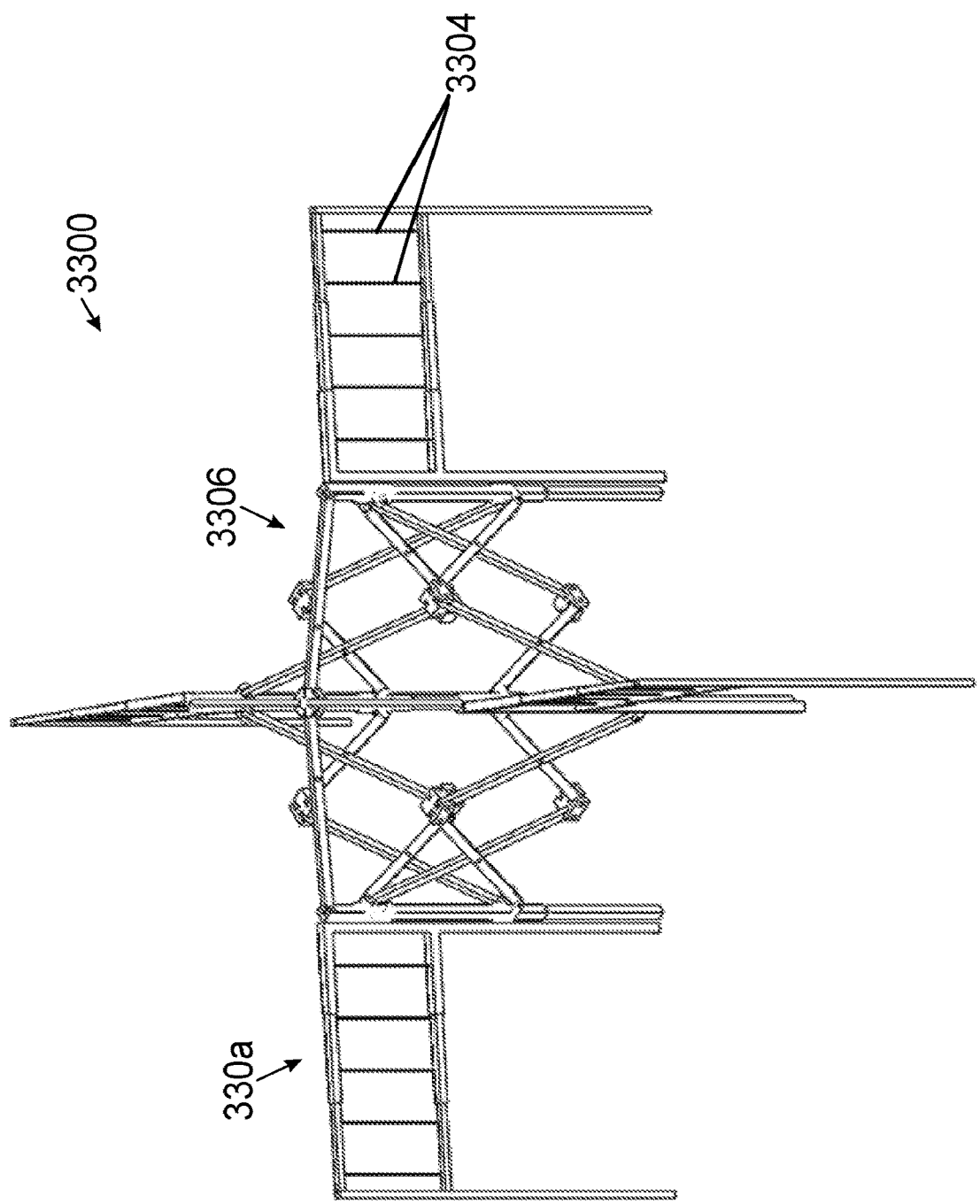
Figure 33E:
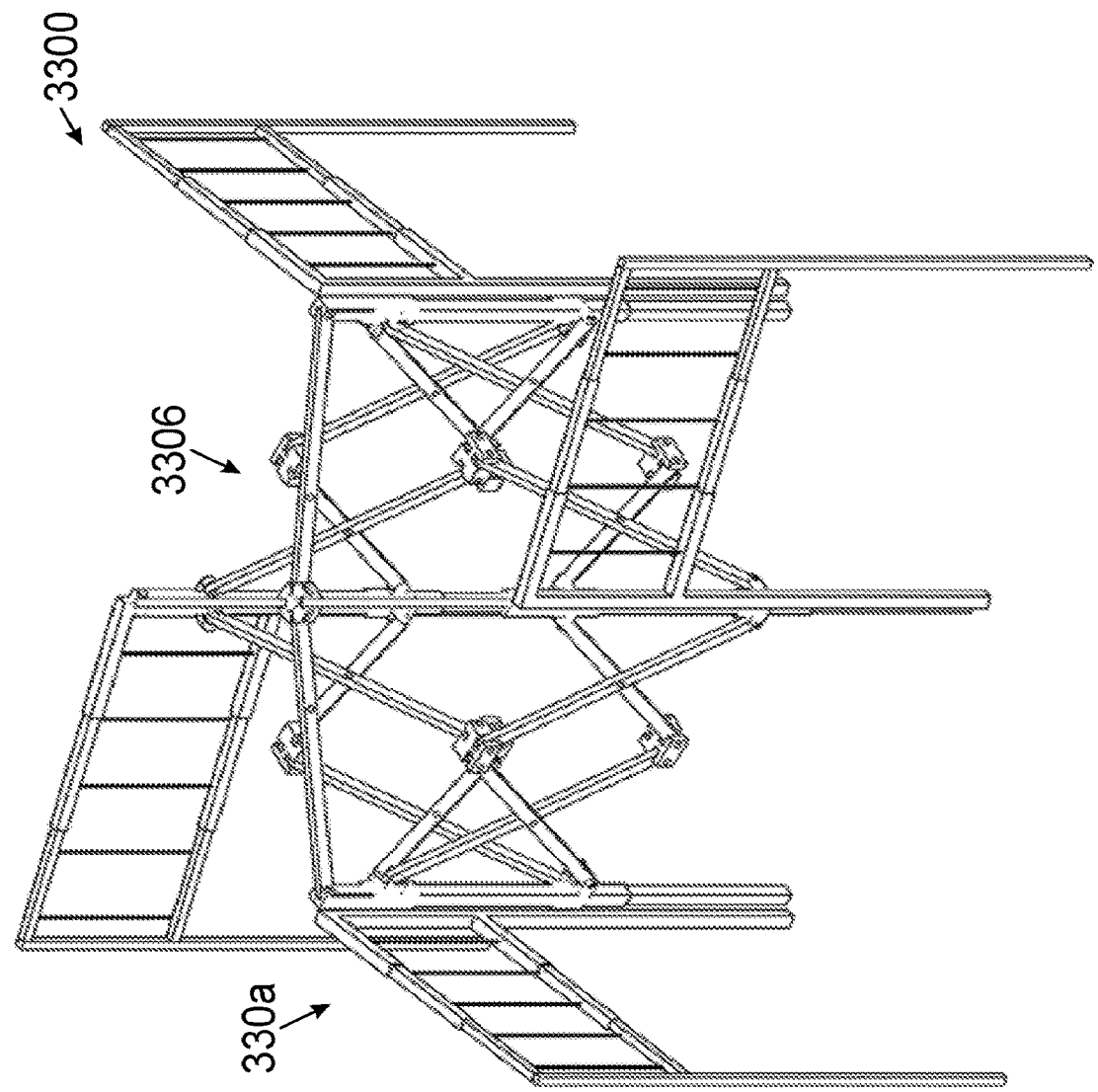
Figure 33F:
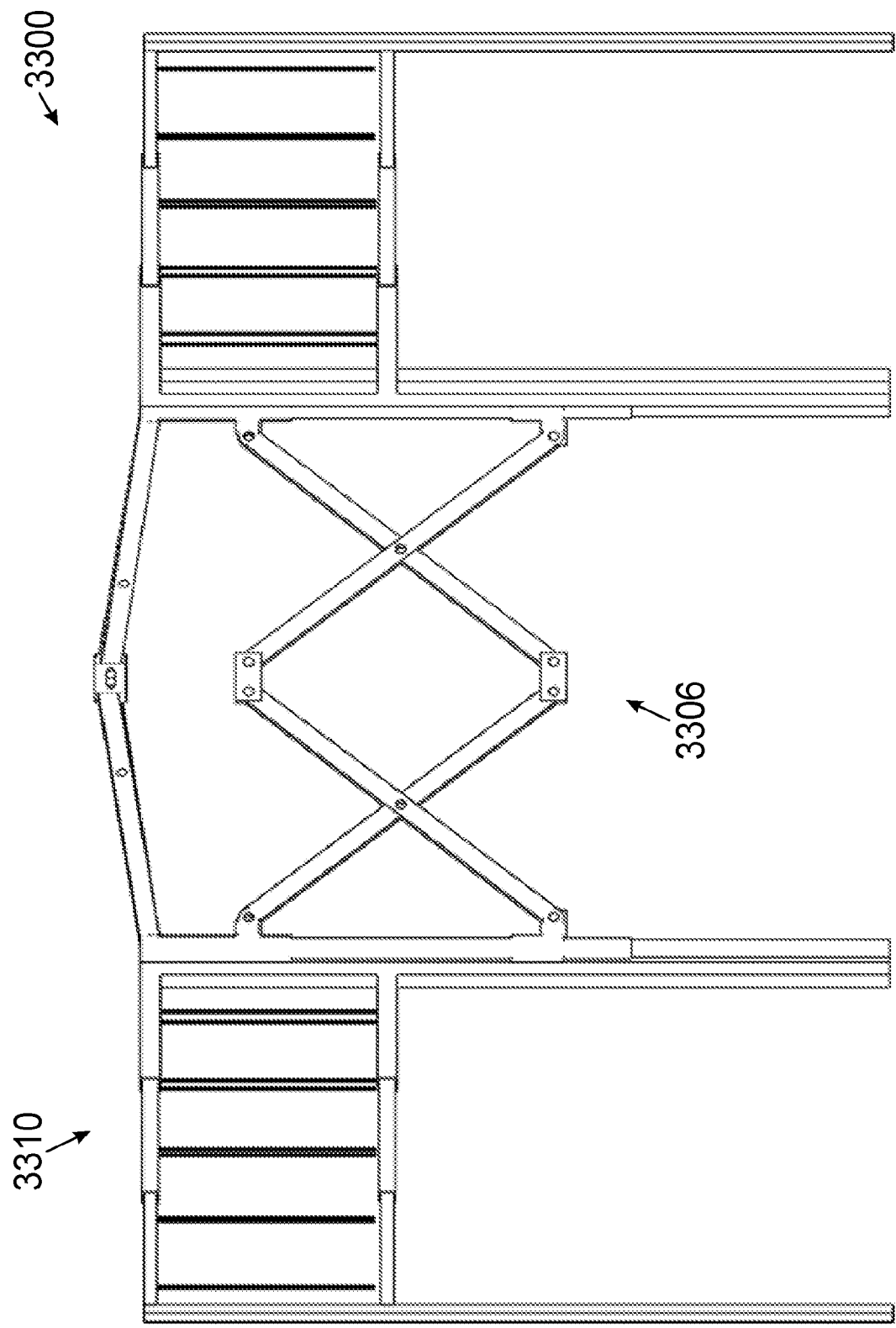
Figure 33G:
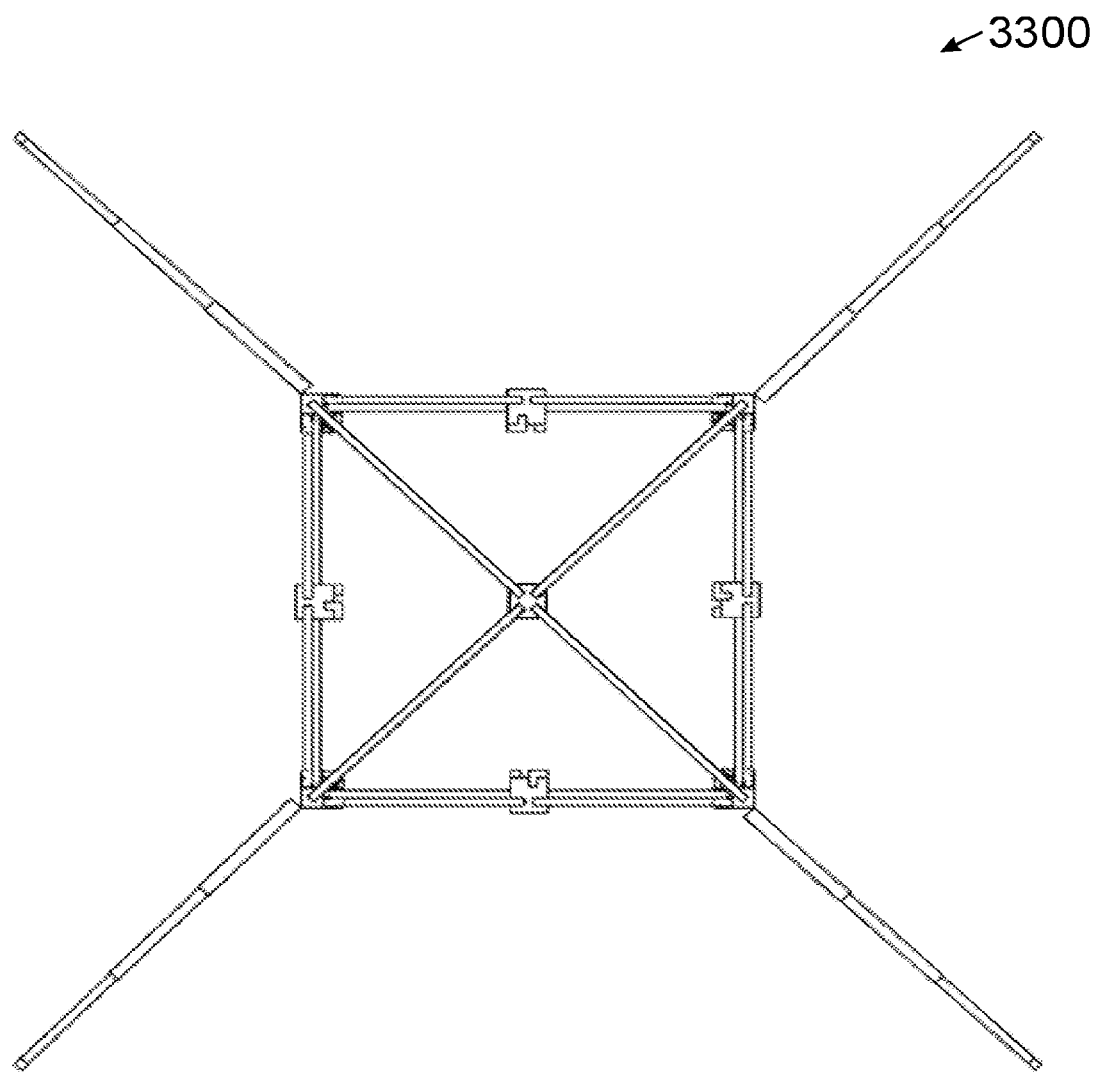

FIG. 31 A illustrate perspective views of a disinfection device 3100 with a perimeter geometry multi base mechanism, in accordance with at least one example of the present disclosure. FIG. 31 A shows the device 3100 in a collapsed position and FIG. 32B shows the device 3100 in an expanded position. The disinfection device 3100 can include bases 3106a and 3106b, which can be separable and movable via wheels or casters 3109 within a target volume 50 having a floor 52 and walls 54 and 56. The disinfection device 3100 can include arms 3110a, which can form a perimeter around the volume 50 for proportional distribution of the light sources 3104 (connected to the arms 3110) within the target volume.

FIG. 31C shows an elevation view of the arm 3110a, which can include links 3120 and 3122, drapes 3124a-3124n, and collars 3126. The Drapes 3124a-3124n can each include light sources 3104. The links 3120 and 3122 can be hingeably coupled to each to fold or collapse relatively to move the arm 3110a between the extended and collapsed position. FIG. 31C shows a side view of the arm 3110a, showing how the collars 3126 can hook onto the link 3122 and can slide or translate thereon to be positioned on the arm 3110a within the target volume to emit a substantially homogenous irradiance within the target volume 50.

FIG. 31D shows an elevation view of the arm 3110a, which can include links 3130-3138 (each including a track) and couplers 3140, which can support the light sources 3104 thereon. The links 3130 can fold and unfold to move between expanded and collapsed positions within the target volume 50. FIG. 31D shows a side view of the arm 3110a, showing how the couplers 3140 can hook onto the rails or tracks for the links 3130-3138 and can slide or translate thereon. FIG. 31E also shows how the links 3130-3138 can fold to stack on top of each other.

FIGS. 32A-32C illustrate a disinfection device 3200 with a perimeter geometry mechanism, in accordance with at least one example of the present disclosure. The disinfection device 3200 can include a base 3206 and arms 3210a positionable within a target volume. FIG. 32A shows a perspective view of the disinfection device 3200 positioned in the target volume in a collapsed position. FIG. 32B shows a perspective view of the disinfection device 3200 with the arms 3210a-3210d in an extended position within the target volume near a perimeter of the target volume (such as walls). In some examples, the base 3206 can include one or more light sources to help emit a substantially homogenous irradiance within the target volume.

FIG. 32C shows a focused view of an arm of the disinfection device 3200, illustrating a bulb distribution mechanism, which can be moved between the collapsed and expanded position by links, such as a scissor linkage arrangement similar to those discussed above.

FIGS. 33 A-33 G illustrate a disinfection device 3300 with an expandable base structure 3306 with deploying arms 3310, in accordance with at least one example of the present disclosure. The arms 3310 can be telescopic, similar to those discussed above, and the structure 3306 can include multiple links or linkages configured to, together with the deploying arms 3310, move the arms 3310 between a collapsed and an expanded position to emit a substantially homogenous irradiance within the target volume from a plurality of light sources 3304 (shown FIG. 33D). As shown in FIG. 33F, a canopy delivery system of the structure 3306, can include a center base structure that can be expanded upward to accommodate a bed or table in the center of the target volume of a room.

Figure 34:
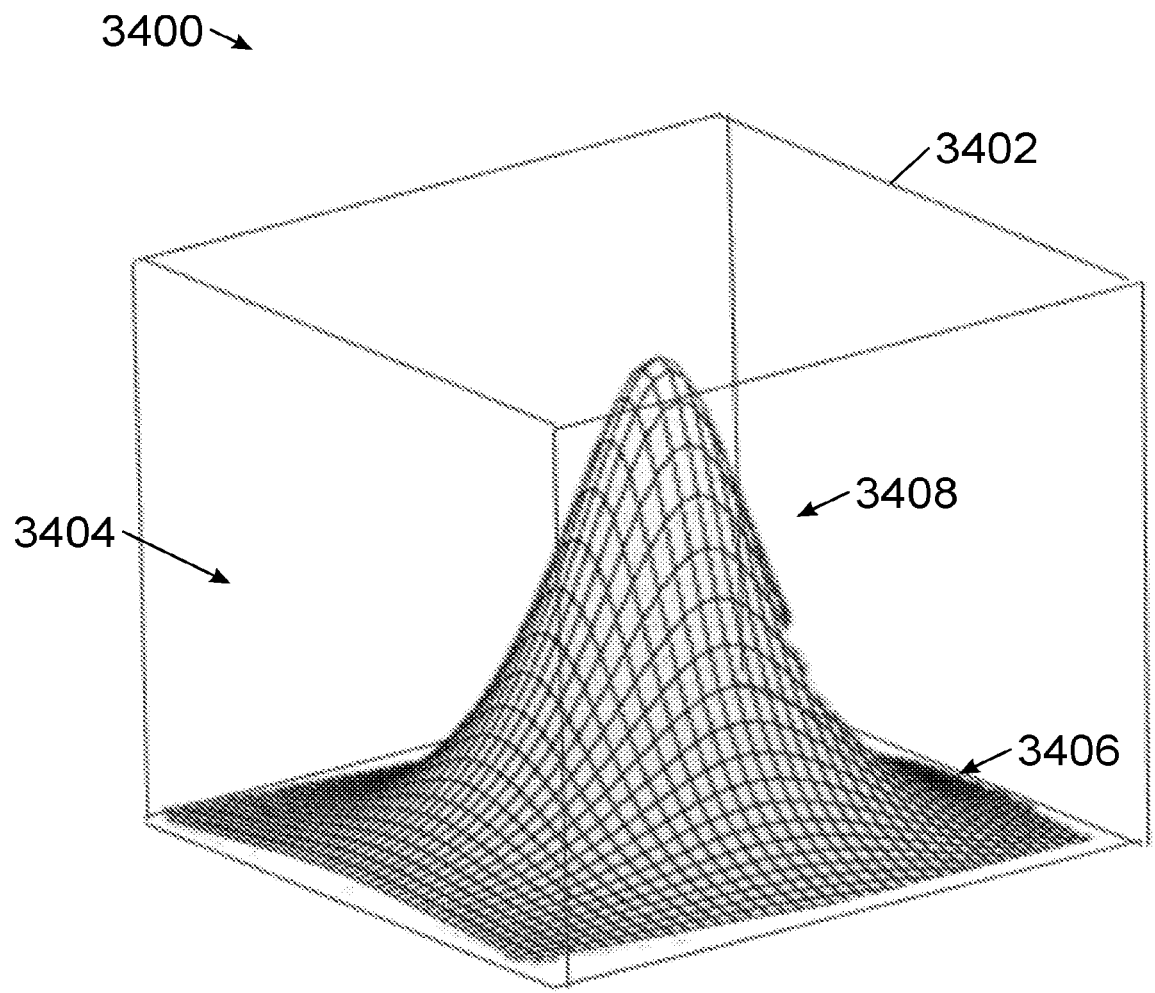
FIG. 34 illustrates a point source energy volume reference within a room, in accordance with at least one example of the present disclosure.

FIG. 34 illustrates a point source energy volume reference within a room, in accordance with at least one example of the present disclosure. The graph 3400 can represent a room 3402 or a target volume 3402 in which a point source (centralized ultraviolet light sources or single ultraviolet source) is positioned substantially in a center of the target volume 3402. An irradiance 3404 of the point sources is represented by a topological mesh, where irradiance increases along a vertical axis of the graph 3400. As shown by the graph 3400, irradiance spikes near a center 3408 and falls to nearly zero near a perimeter 3406, which is described earlier by the inverse square law.

Figure 35:
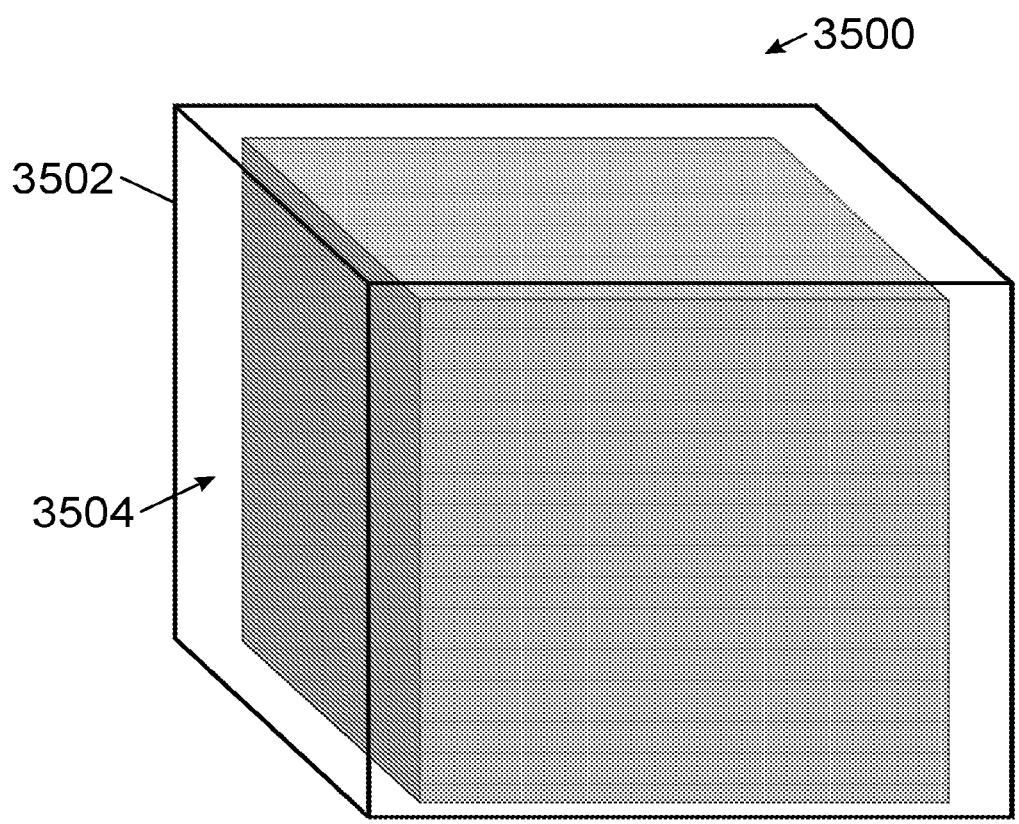
FIG. 35 illustrates a homogenous matrix of energy volume within a room achieved by numerous delivery mechanisms as described previously, in accordance with at least one example of the present disclosure.

FIG. 35 illustrates a graphic representation 3500 of a homogenous matrix 3504 of energy volume within a room 3502 achieved by the various disinfection devices discussed previously, in accordance with at least one example of the present disclosure. FIG. 35 illustrates an abstract example of a distribution of light intensity fora disinfection device configured to emit a homogenous light matrix with a predetermined energy or ultraviolet intensity within a target volume 3502 where the volume 3502 can be a patient room. Such a device can overcome the inverse square law to fill the volume of space 3502 substantially completely as depicted in a perfect abstract perspective as cube in FIG. 35.

Figure 36A:
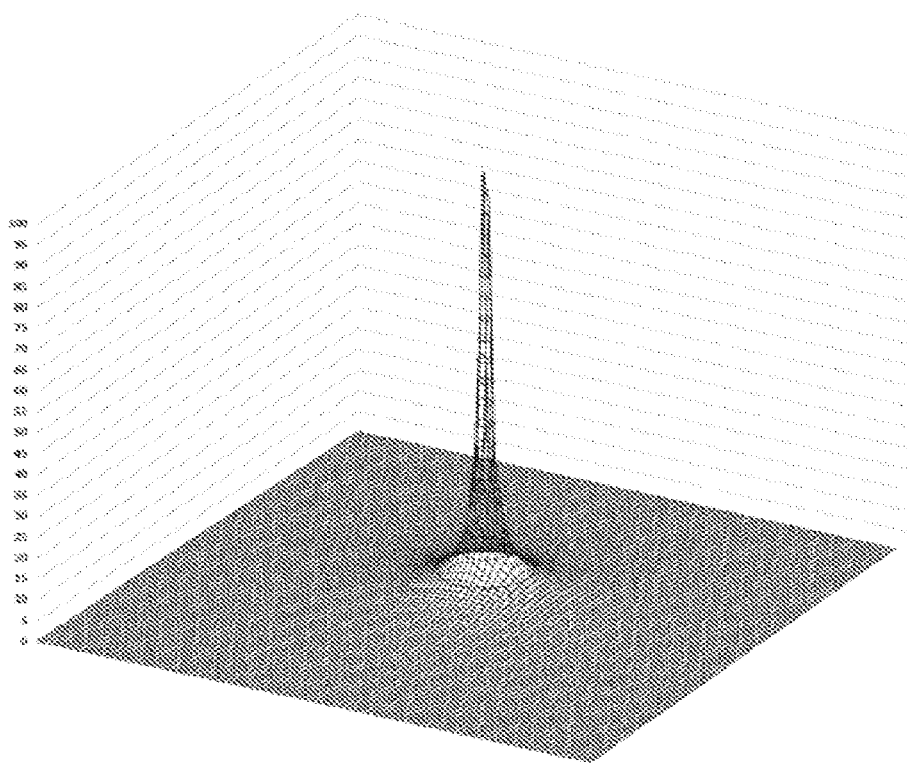
FIGS. 36A-36B illustrate irradiance of a central source in a target volume, in accordance with at least one example of the present disclosure.
Figure 36B:
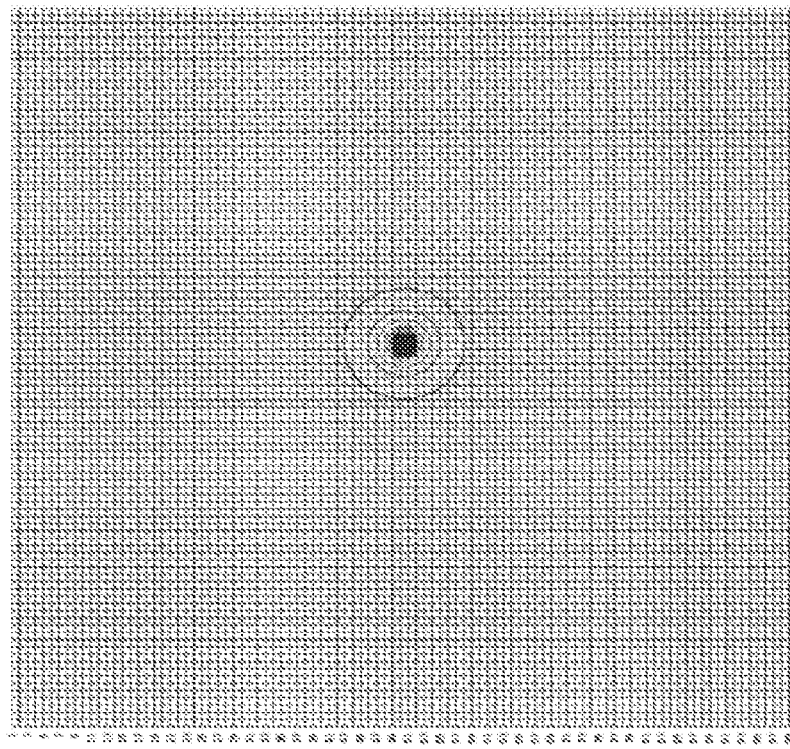
Figure 37A:
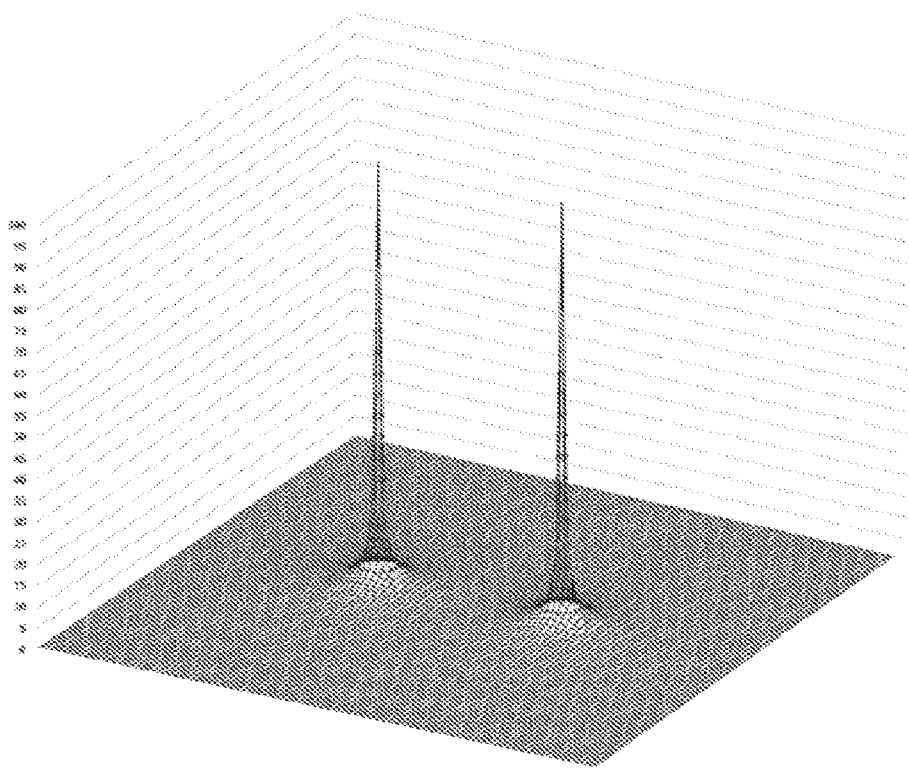
FIG. 37A-37B illustrate irradiance of two sources in a target volume, in accordance with at least one example of the present disclosure.
Figure 37B:
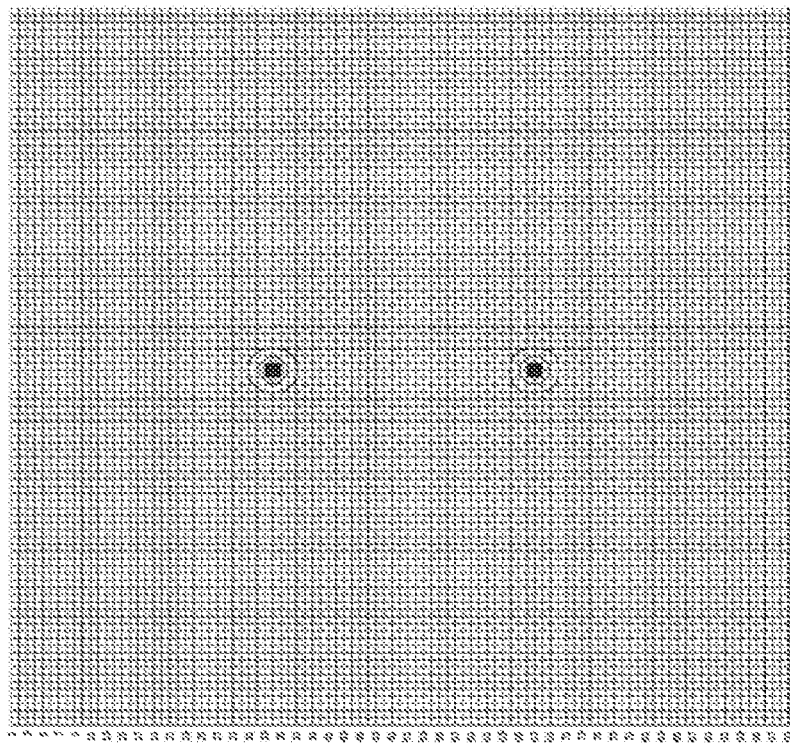
Figure 38A:
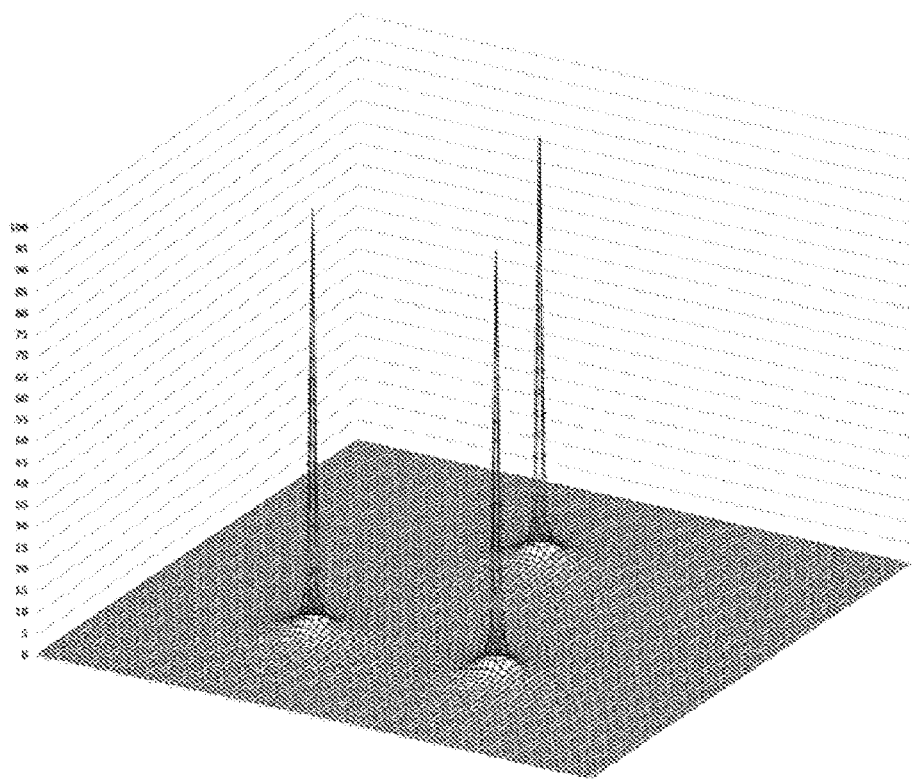
FIG. 38A-38B illustrate irradiance of three sources in a target volume, in accordance with at least one example of the present disclosure.
Figure 38B:
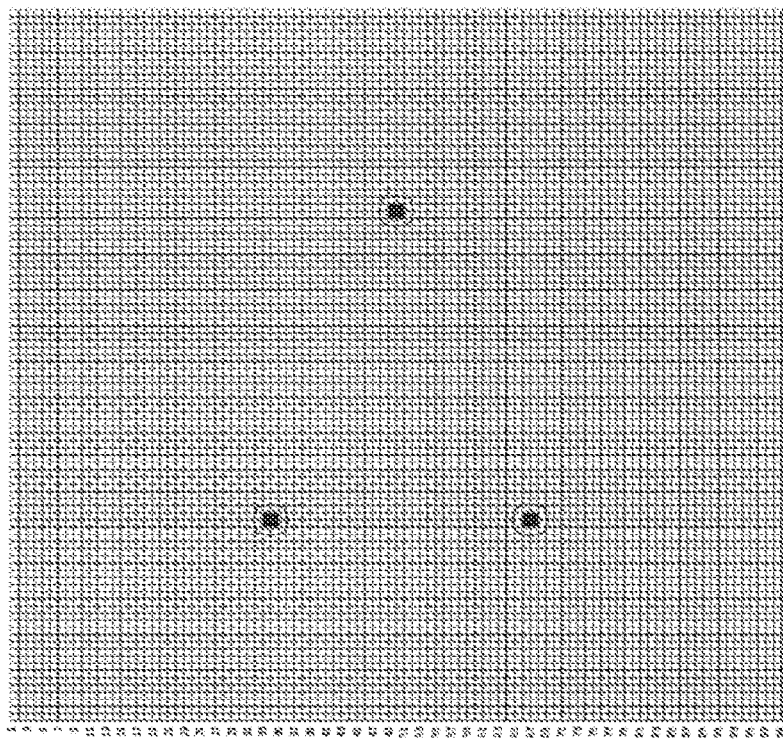

FIGS. 36A-36B illustrate irradiance of a central source in a target volume, in accordance with at least one example of the present disclosure. FIG. 36A shows a perspective view of an irradiance of a point source, represented by a topological mesh, where irradiance increases along a vertical axis of the graph. FIG. 36B shows a top view of the graph. Similarly, FIG. 37A-37B illustrate an irradiance of two sources in a target volume, in accordance with at least one example of the present disclosure, where FIG. 37A shows a perspective view and FIG. 37B shows a top view of an irradiance of two point sources, represented by a topological mesh, where irradiance increases along a vertical axis of the graphs. FIG. 38A-38B illustrate irradiance of three sources in a target volume, in accordance with at least one example of the present disclosure, where FIG. 38A shows a perspective view and FIG. 38B shows a top view of an irradiance of three point sources, represented by a topological mesh, where irradiance increases along a vertical axis of the graphs.

FIGS. 36A-38B represent point source devices of some of the prior art, where single sources (or an aggregate of ultraviolet sources) where the irradiance drops off with distance as discussed above with respect to FIG. 34. Conversely, irradiance of the devices of this disclosure, discussed above, are represented in FIGS. 39A and 39B as a three-dimensional light matrix of a topological mesh where irradiance increases along the vertical axis.

Figure 39A:
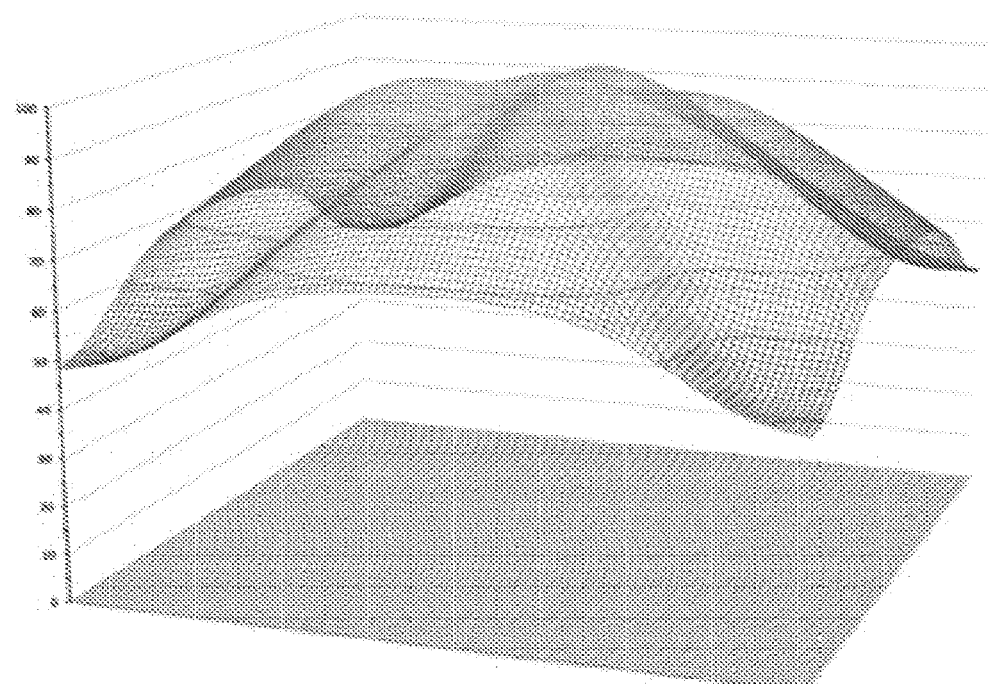
FIG. 39A-39B illustrate irradiance of an energy matrix in a target volume, in accordance with at least one example of the present disclosure.
Figure 39B:
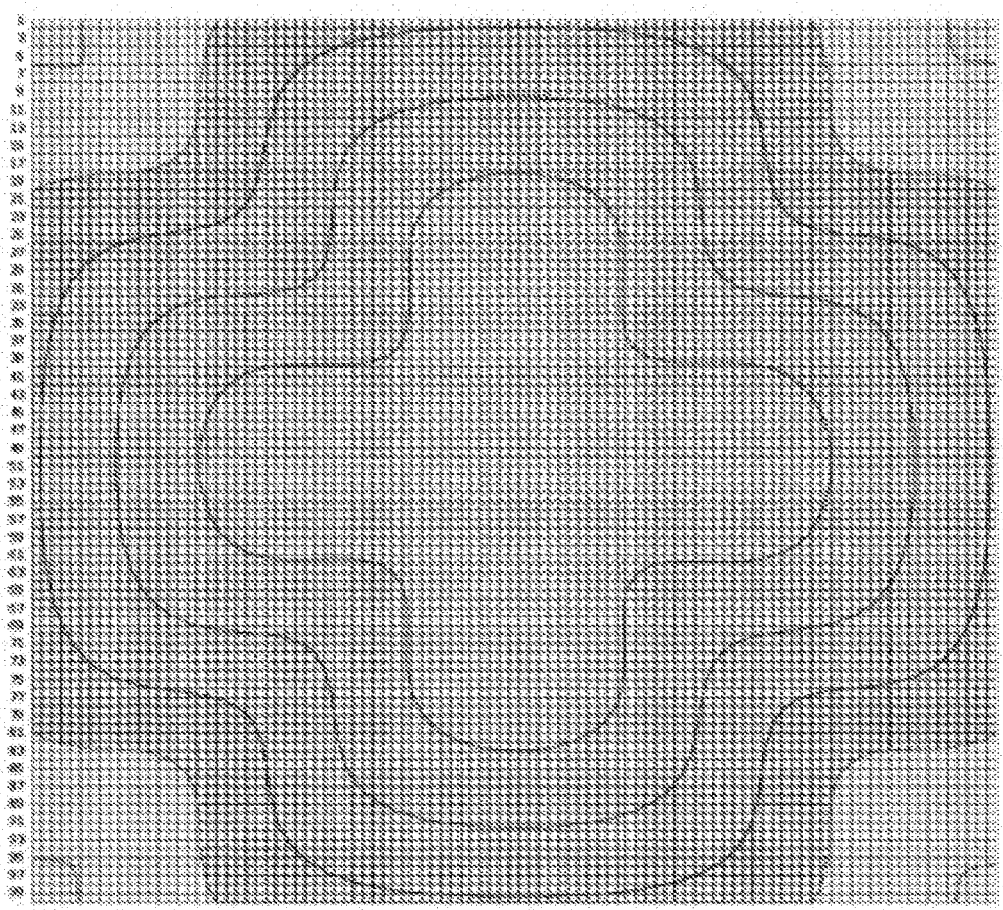

As shown in FIGS. 39A and 39B, a substantially homogenous light energy can be produced throughout the volume. FIG. 39A shows a side view and FIG. 39B shows a top view of irradiance produced by a device as observed, where the device is any one of the different embodiments discussed earlier in FIG. 19A-39G. The irradiance (z axis) has been normalized to 100% of maximum irradiance. The x-axis of FIGS. 39A and 39B shows 100 increments, which represent increments along a wall and the y-axis shows 100 increments along an adjacent wall.

The same wattage was used to create each of irradiances of the graphs of FIGS. 36-39 in the different configurations. For the single point source of FIGS. 36A-36B, a total of 282 watts is represented by one source at the center of the room. For the double point source of FIGS. 37A-37B, two locations of 141 watts each are represented by the two sources located centrally in the room. For the triple point source of FIGS. 38A-38B, three locations of 94 watts each are represented by the three sources located centrally in the room. For FIGS. 39A-39B, which represent embodiments the devices described of the disclosure herein, 20 lamps were expanded to form an "x" formation across a room, where the device included 5 bulbs per arm, each with a wattage of 14.1 watts per bulb or light source. As shown in FIGS. 39A-39B, a substantially homogenous irradiance is achieved in the room as compared to the various point source examples shown in FIGS. 36A-38B.

FIGS. 40A-40D illustrate an experimental setup and disinfection data from experiments performed on the systems discussed herein, in accordance with at least one example of the present disclosure. More specifically, FIGS. 40A-40D illustrate microbiological testing of bacterial survival subject during an 8 point multi-sided evaluation of a homogenous ultraviolet light energy matrix in a 4.57 meter× 4.57 meter room and results therefrom.

Figure 40A:
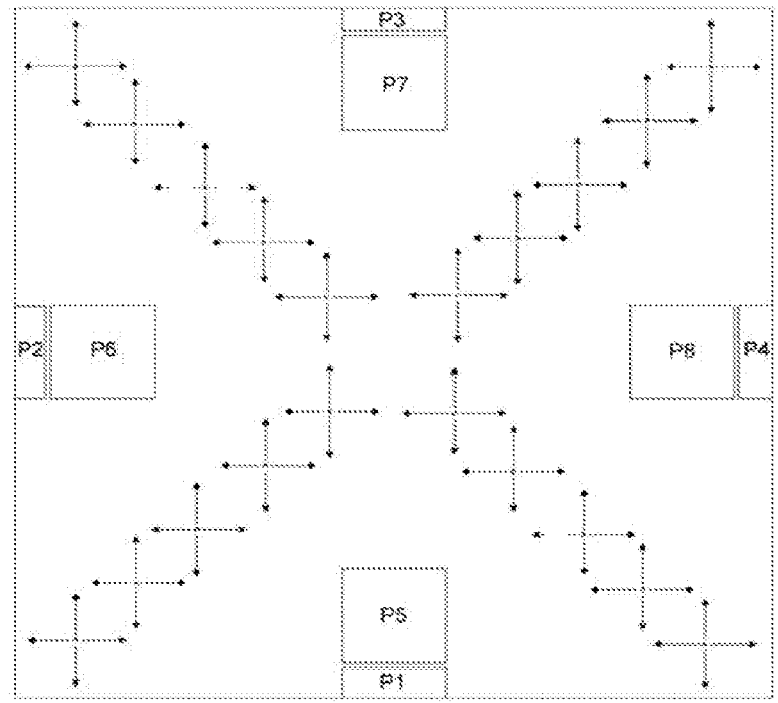
Figure 40B:
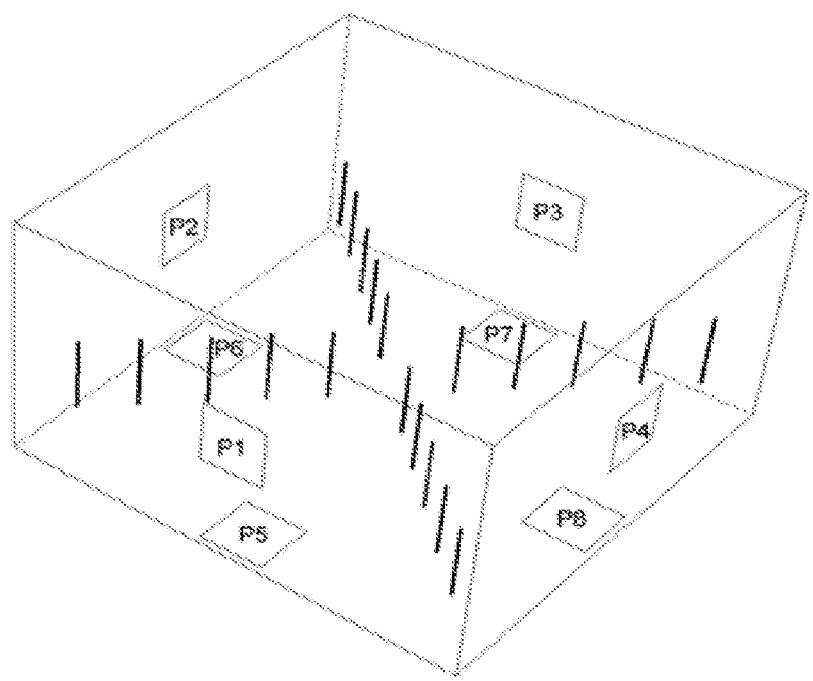

FIG. 40A shows a top view of test setup and FIG. 40B shows a perspective view of the setup. Indicators P1-P4 represent wall test sample locations, indicators P5-P8 indicate floor test sample locations, and arrows represent ultraviolet rays emitted from the multiple light sources. In the experiment of FIGS. 40 A and 40B, contaminated fields with quantitative culture plates of bacteria are placed within each of the boxes marked P1-P8 Each section represents three culture plates (one for each bacteria) per time point exposed to UV energy at time points: 0, 15, 30, 60, 90, & 180 seconds. The zero (0) time point is used as a control. The number of colonies growing on each plate were counted and plotted as a function of time. Isolates of each of the following pathogens were studied:
1) Multidrug-resistant *Pseudomonas aeruginosa*; 2) Carbapenem-resistant *Klebsiella pneumoniae*; and 3) *Candida auris* (*C. auris*).

The inoculum were prepared as follows, the inoculum for the quantitative culture assay was prepared by growing the isolate for 24 h at 37° C. on 5% sheep blood plates for bacteria, and potato dextrose plates for fungus. For bacteria, 4-5 colonies were picked up from fresh culture (sheep blood agar) with a loop and suspended into 3 ml of Normal Saline. Then, the turbidity of the suspension was checked with spectrophotometer at 600 nm and further diluted accordingly to obtain the 0.5 AU stock suspension. For *Pseudomonas aeruginosa*, according to previous calculations 0.5 AU @600 nanometers equals 1×10e9 colony-forming unites/milliliter (CFU/ml). The suspension was then serially diluted (5×1:10) to achieve a 1×10e4 inoculum. For *Klebsiella pneumoniae*, 0.5 AU @600 nm was calculated to be 1×10e8 CFU/ml. In order to obtain the 1×10e4 inoculum, the suspension was serially diluted (4×1:10). The *Candida auris* inoculum was prepared according to standard methods. Some 4-5 colonies of *C. auris* were taken with a loop from a fresh culture and suspended into 3 ml of Normal Saline. The suspension was checked for turbidity at 530 nm using a spectrophotometer. It was then diluted to get the required absorbance unit of 0.119-0.140 (0.5 McFarland standard). This yielded a yeast stock suspension of 1×10e6-5×10e6 CFU/ml. The stock suspension was then further diluted into 1:100 with Normal Saline. This resulted in final inoculum concentration of 1×10e4-5×10e4 CFU/ml. The plates were then labeled, inoculated with 0.1 ml of inocula, placed in the UV energy field, exposed to UV energy for a given labeled time, and then incubated at 37° C. for 24 hours. The number of colonies on a given plate were then counted, recorded, and the mean calculated for each time point and location.

The experiments were run in triplicate for a given species. Values are expressed as means±standard error means (SEMs). All treatment groups were compared against the unexposed control group by analysis of variance (ANOVA). A two-tailed P value of <0.05 is considered to be statistically significant.

The results of the experiment are summarized in FIG. 40C for the wall samples and FIG. 40*d* for the floor samples. Zeroes in FIG. 40C and FIG. 40D represent time of exposure at which organisms are completely cleared from the plates. The data shown in FIGS. 40C-40D represent averages from all samples, one at each symmetrical position. There were six (6) control plates for each bacterium.

Figure 41A:
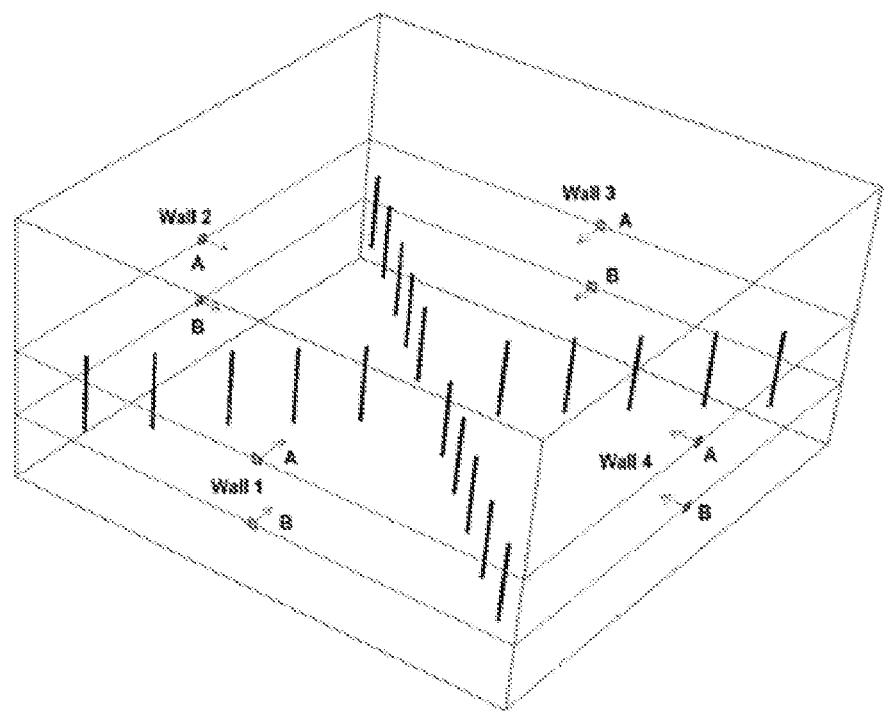
Figure 41B:
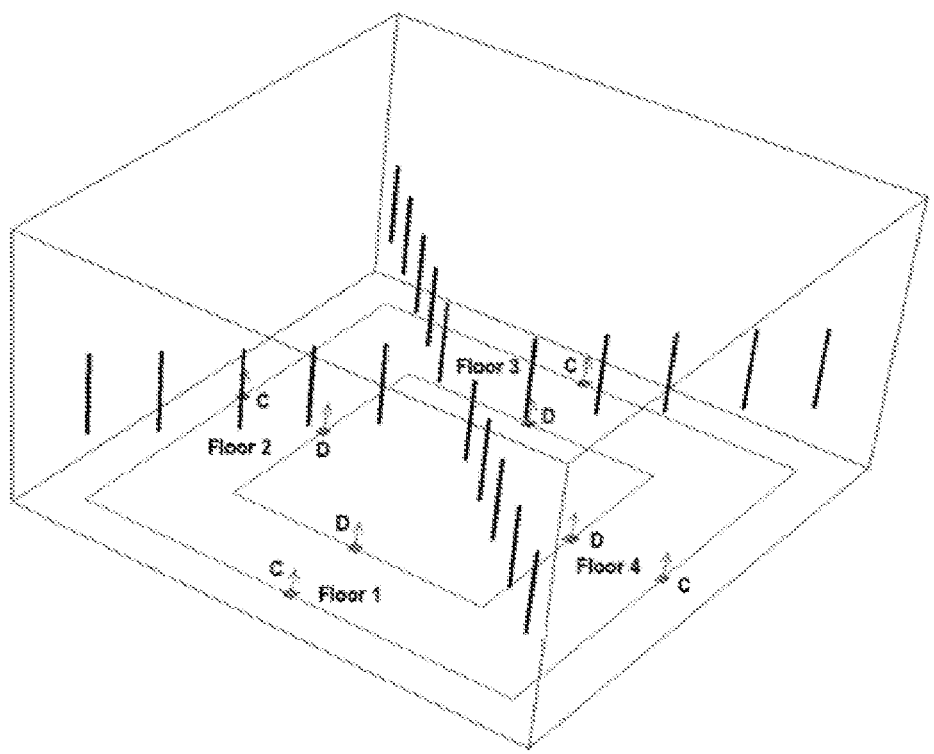

FIGS. 41A-41B illustrate results of irradiance data of an experiment of the systems discussed herein, in accordance with at least one example of the present disclosure More specifically, FIGS. 41 A-41B show results of an experiment where ultraviolet energy was recorded with a photometric sensor at various distances and locations around the example embodiment within a 4.57 meter×4.57 meter room. The readings were recorded in micro watts per centimeter squared (uW/cm$^4$2) over time.

FIGS. 41 A-41B show positions of photosensor readings on walls and a floor, respectively, which are representative of the test setup used to record the measurements below. In these representations, both location and direction of the photometer are shown by the direction of the arrows. Two meters were used to collect data, an ILT 2400 meter which collects data over time every 5 seconds, and a General UV512C meter which takes single readings at a specific position. The positions shown in FIG. 41 A are both at a distance of 228.6 centimeters from a center of the room and are at a height of 64.8 centimeters from the floor (lower sensors, B) and a height of 129.5 cm from the floor (upper sensors, A). One sensor is placed on each of the walls 1-4 at each height, as indicated by A and B. The positions shown in FIG. 41B are both at a height of 0 cm and are at a distance of 150.8 centimeters from a center of the room (inner sensors, D) and a distance of 189.7 centimeters from the center of the room (outer sensors, C). Both FIGS. 41 A-41B show the light sources arranged in the room in an X-configuration.

Figure 41E:
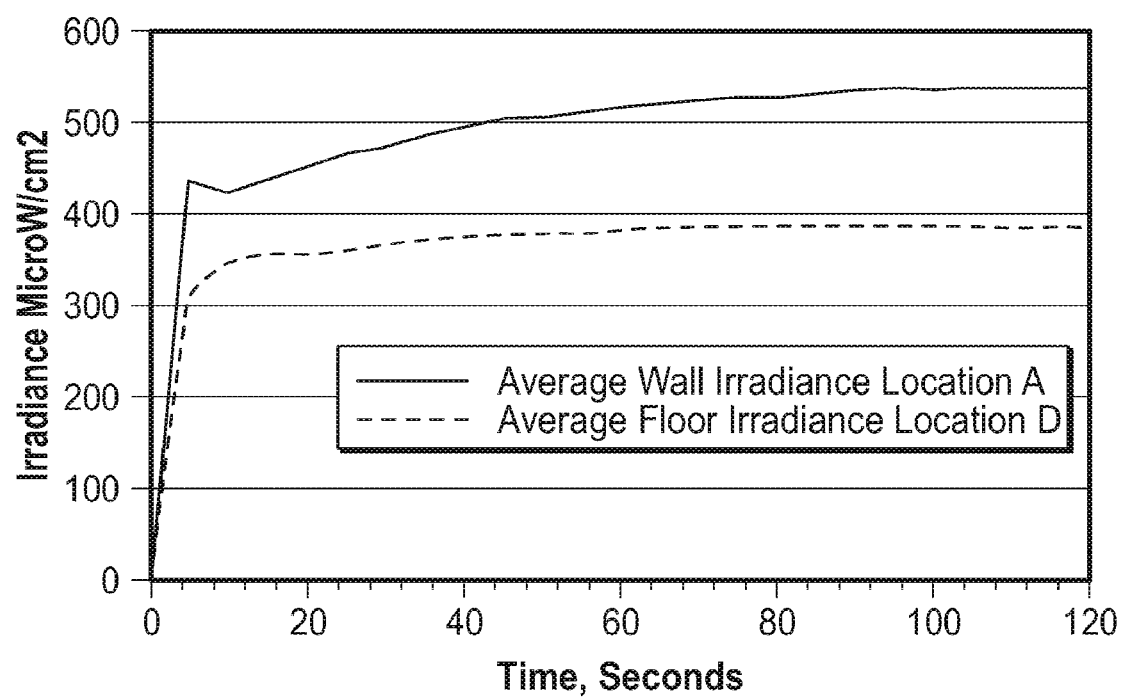

FIG. 41C shows Table 1, which is a summary of the photometric readings on the walls. FIG. 41D shows Table 2, which is a summary of photometric readings on the floor. Data sets from both an ILT meter and a General photometer are displayed. Both these tables show the photometer readings every five seconds over two minutes time at each position using the ILT meter. These values are averaged at the bottom of the table. FIG. 41E shows a profile of irradiance over time for both the walls and the floor, which shows the average irradiance of the four sides at location A of the wall over time, and the average irradiance of the four sides at location D of the floor over time FIG. 41E demonstrates the consistent and homogenous energy matrix at different locations and positions around the example embodiment over time.

Figure 42C:
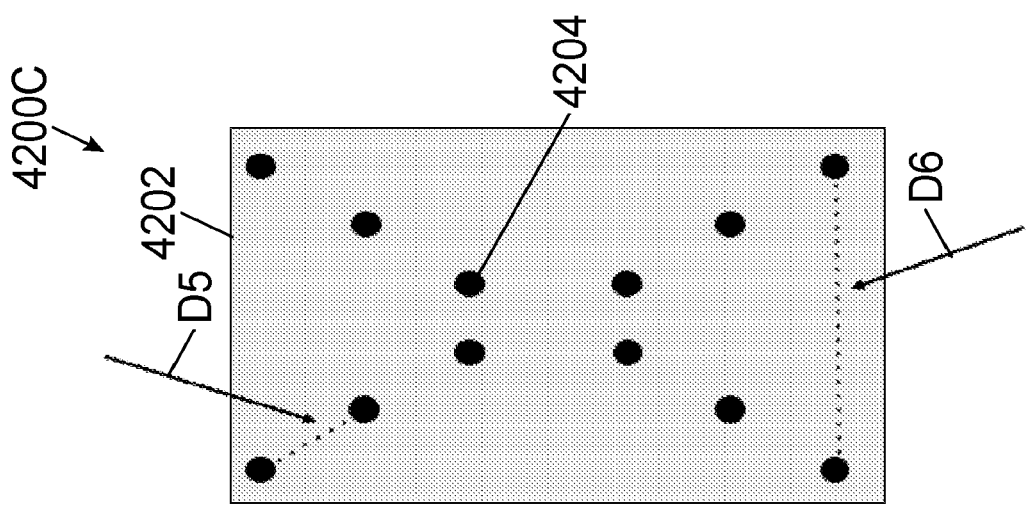
FIGS. 42A-42C illustrate light source arrangements in target volumes, in accordance with at least one example of the present disclosure.
Figure 42B:
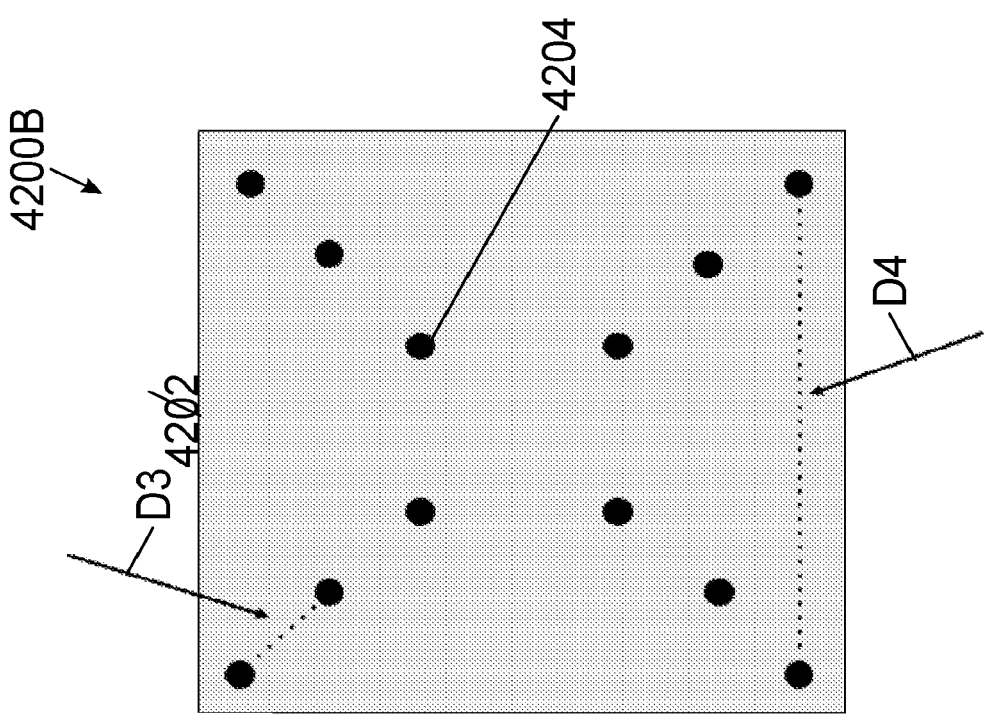
Figure 42A:
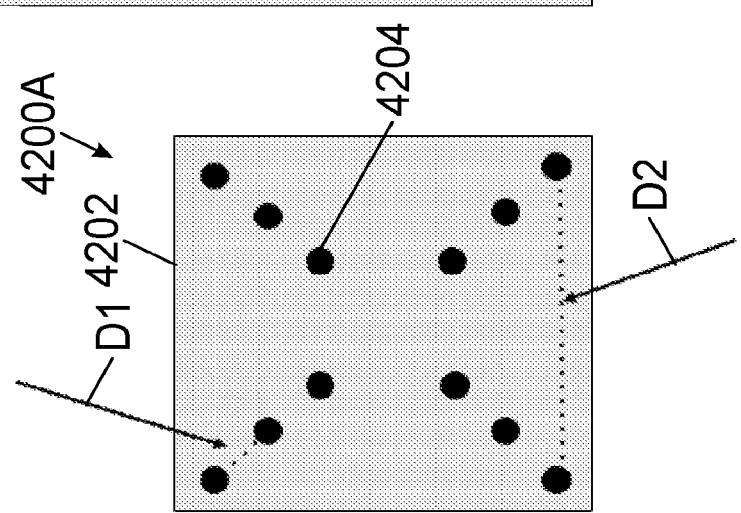
Figure 43A:
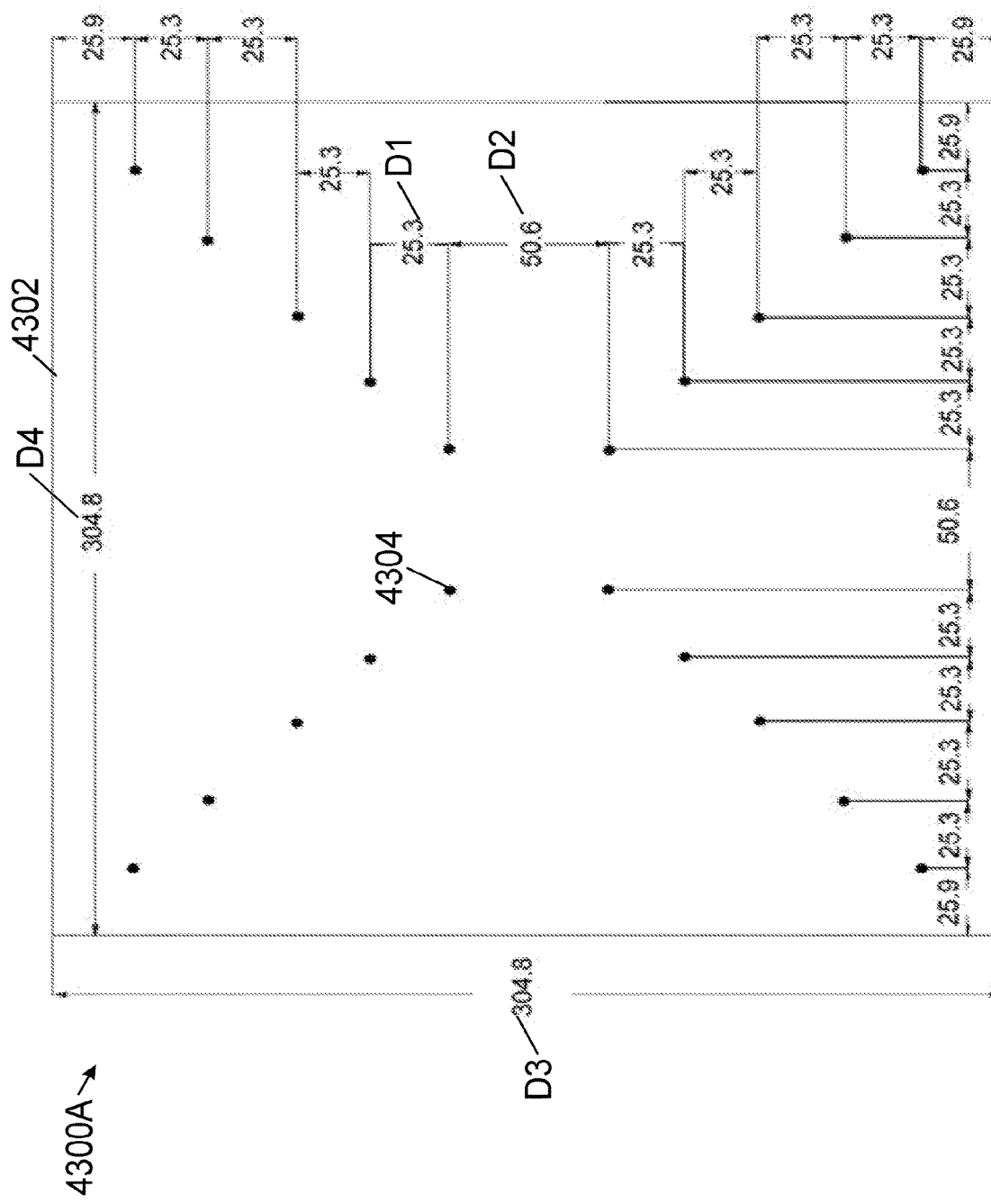
FIGS. 43A-43F illustrate light source spacing arrangements in target volumes, in accordance with at least one example of the present disclosure.
Figure 43B:
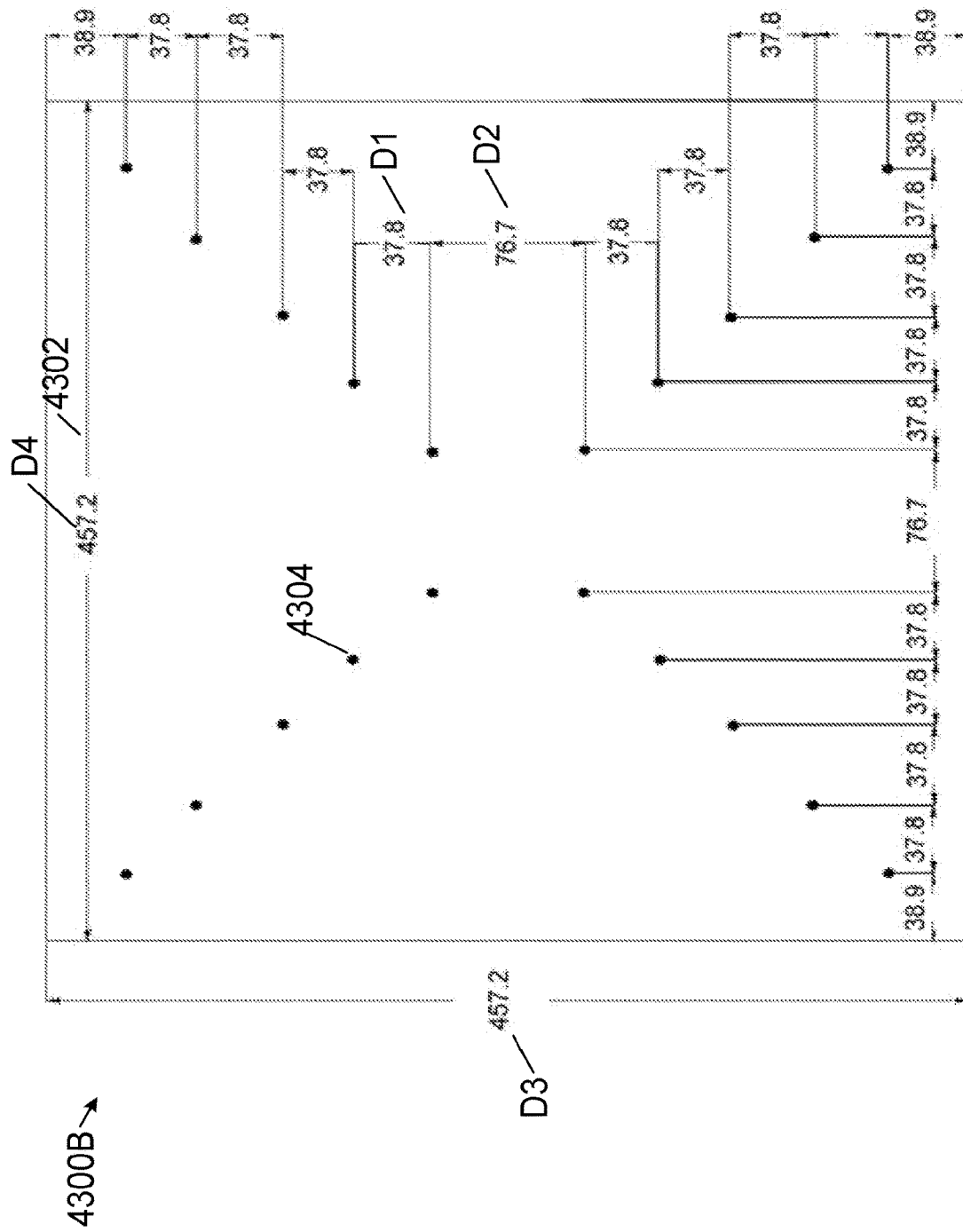
Figure 43C:
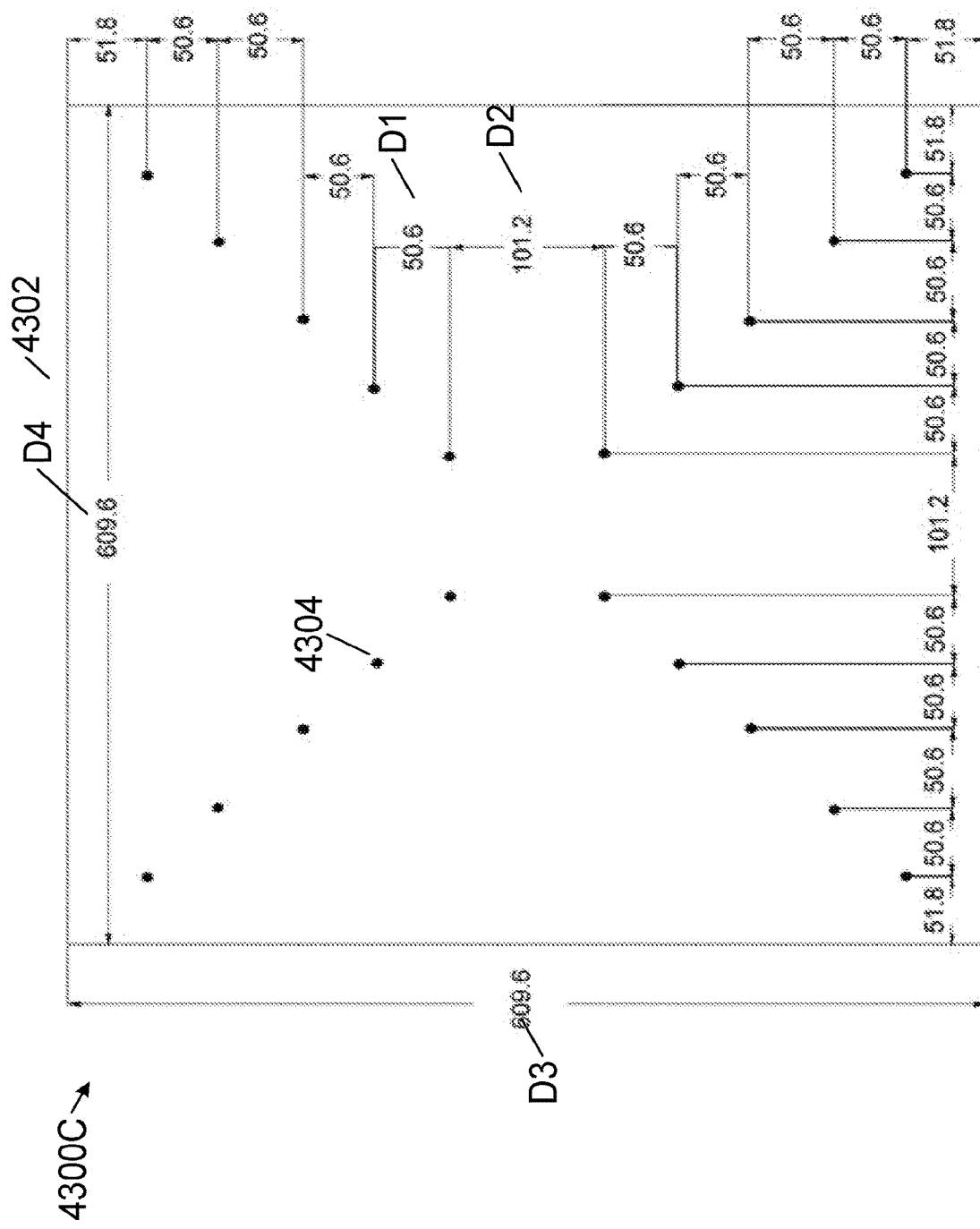
Figure 43D:
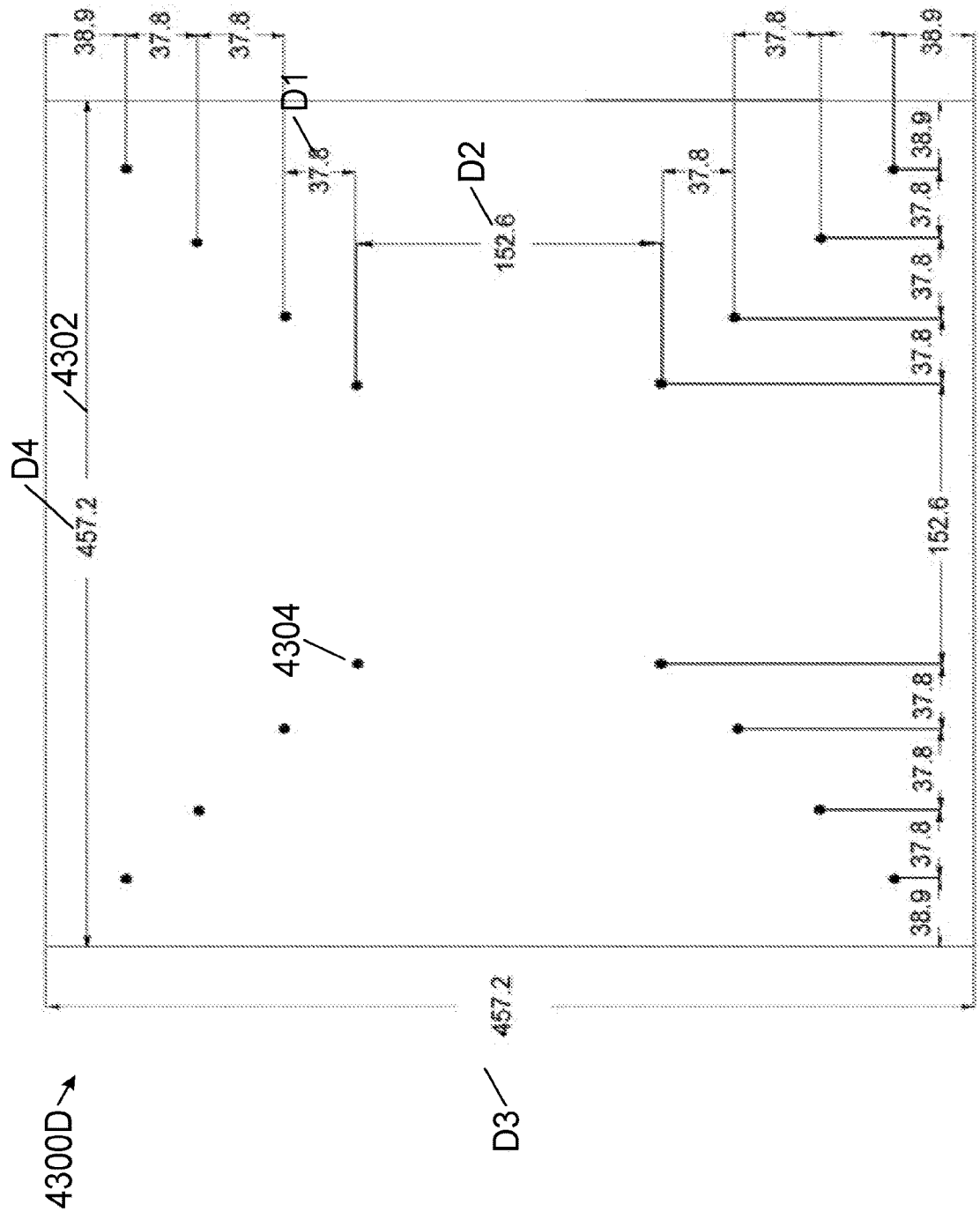
Figure 43E:
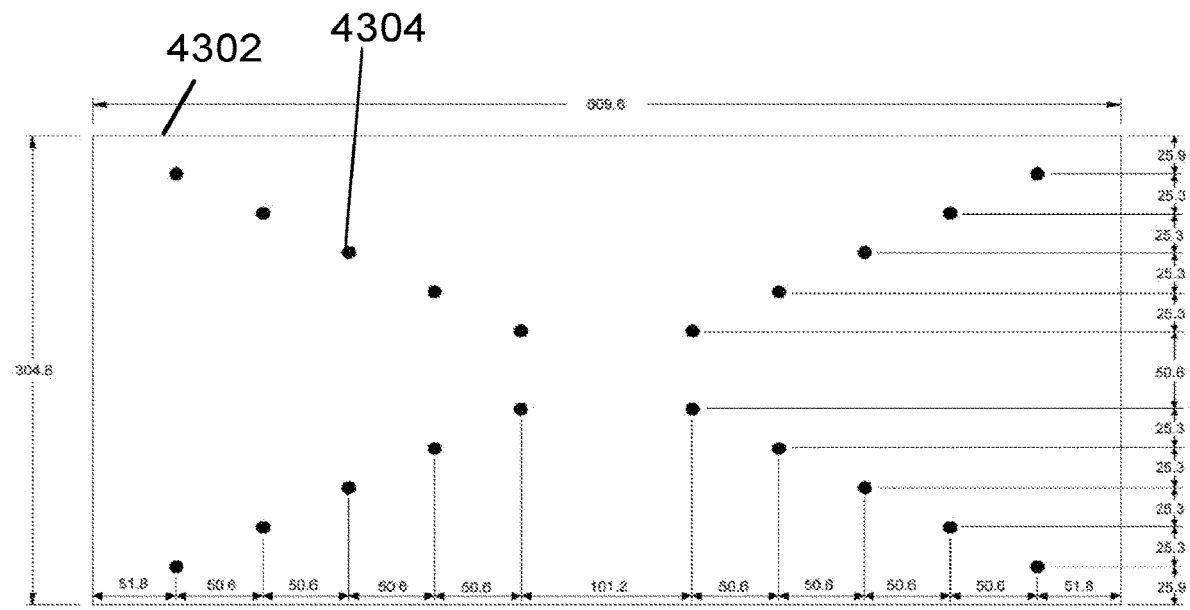
Figure 43F:
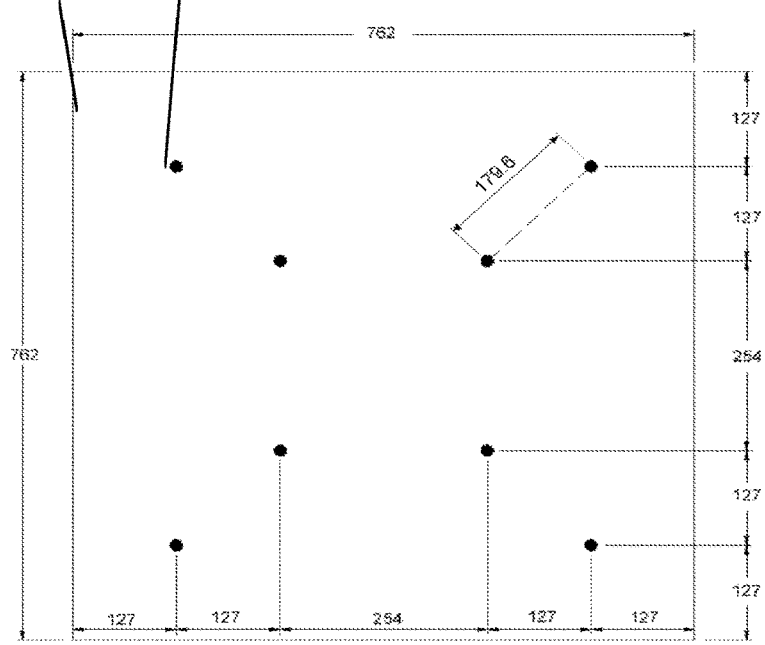

FIGS. 42A-42C illustrate light source arrangements 4200A, 4200B, and 4200C, respectively, in target volumes, in accordance with at least one example of the present disclosure. FIGS. 42A-42C depicts the proportionality of the ultraviolet sources in relation to variable sized rooms and or target volumes.

The arrangement 42A shows the light sources 4204 in a relatively compact arrangement in a target volume 4202A, where each of the light sources 4204 can be spaced linearly at a distance D1 and the distal sources of each line are spaced at a distance of D2. FIG. 42B shows the light sources 4204 of arrangement 4200B where each of the light sources 4204 can be spaced linearly at a distance D3, which is greater than D1 and the distal sources of each line are spaced at a distance of D4, which is greater than D2. Proportionality of the spacing of the light sources 4204 within both of the target volumes 4202A and 4202B can be maintained by any of the disinfection devices of this disclosure discussed in the FIGS. above. Further, FIG. 42C shows the light sources 4204 of arrangement 4200C where each of the light sources 4204 can be spaced linearly at a distance D5, which is greater than D1 smaller than D3, and the distal sources of each line are spaced at a distance of D6, which is greater than D2 and smaller than D4 Proportionality of the spacing of the light sources 4204 within both of the target volumes 4202A-4200C can be maintained by any of the disinfection devices of this disclosure discussed in the FIGS. above.

FIGS. 43A-43F illustrate light source spacing arrangements in target volumes, in accordance with at least one example of the present disclosure. FIG. 43 A shows a target volume 4302 having dimensions D3 of 304.8 centimeters by D4 of 304.8 centimeters. In such an example, a disinfection device can be position within the target volume or room 4302 in an expanded configuration where the light sources 4304 are proportionally spaced at a width of about 35.3 centimeters for each arm and a height, D1, of 25.3 centimeters where the radially inward most light sources from each arm can be spaced from the radially inward most light sources from adjacent arms by a distance D2 of 50.6 centimeters. Such an arrangement is one example of a proportional spacing of the light sources 4304 that can achieve substantially homogenous irradiation through the target volume 4302. FIGS. 43B-43F show further examples of spacing of the light sources 4304 in target volumes 4302, where each example of FIGS. 43B-43F can provide proportional spacing of the light sources 4304 that can achieve substantially homogenous irradiation through the target volume 4302.

FIG. 44 is a block diagram illustrating an example computer system machine upon which any one or more of the previous techniques may be performed or facilitated by. Computer system 4400 specifically may be used in connection with facilitating the operations of the controllers of the sanitizing and disinfection devices discussed above. For example, the computer system 4400 can be a controller for the mobile ultraviolet light devices 2502 and/or for a master controller configured to communicate with the mobile ultraviolet light devices 2502 and/or for a remote controller configured to communicate with the mobile ultraviolet light devices 2502. The computers system 4400 can also be employed in any of the devices configured to emit ultraviolet light discussed above, such as the ultraviolet emitting device 1900, where the computer system 4400 can control one or more devices, such as motors, operable to move the arms 1910, and can include one or more devices to control power output of the light sources 1904. The computer system 4400 can further be included in any controllers discussed above or below. The computer system 4400 can also send and receive signals like text and/or multimedia messages to and from a third party mobile device computer to provide instructions on the status of any of the ultraviolet devices as well as the point at which the operation of a light cycle is initiated and the point at which the operation of a light cycle is completed or terminated. Additionally, the signals can communicate the success of abort of a single or several light cycles that are initiated over time.

In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 4400 includes a processor 4402 (e.g., a central processing unit (CPU), a graphics processing unit (GPU) or both), a main memory 4404 and a static memory 4406, which communicate with each other via a link 1108 (e.g., an interlink, bus, etc.). The computer system 4400 may further include a video display unit 4410, an alphanumeric input device 4412 (e.g., a keyboard), and a user interface (UI) navigation device 4414 (e.g., a mouse). In an example, the video display unit 4410, input device 4412 and UI navigation device 4414 are a touch screen display. The computer system 4400 may additionally include a storage device 4416 (e.g., a drive unit), a signal generation device 4418 (e.g., a speaker), and a network interface device 4420 which may operably communicate with a communications network 4426 using wired or wireless communications hardware. The computer system 4400 may further include one or more input sensors 4428 configured to obtain input (including non-contact human input) in accordance with input recognition and detection techniques. The input sensors 4428 may include a camera, microphone, barcode reader, RFID reader, near field communications reader, proximity sensor, photo sensor, or other sensor producing data for purposes of input. The computer system 4400 may further include an output controller 4430, such as a serial (e.g., universal serial bus (USB), parallel, or other wired or wireless (e.g., infrared (IR)) connection to communicate or control one or more peripheral devices (e.g., a printer, card reader, etc.).

The storage device 4416 may include a machine-readable medium 4422 on which is stored one or more sets of data structures or instructions 4424 (e.g., software) embodying or utilized by any one or more of the methodologies or functions described herein. The instructions 4424 may also reside, completely or at least partially, within the main memory 4404, static memory 4406, and/or within the processor 1102 during execution thereof by the computer system 4400, with the main memory 4404, static memory 4406, and the processor 4402 also constituting machine-readable media.

While the machine-readable medium 4422 is illustrated in an example embodiment to be a single medium, the term "machine-readable medium" may include a single medium or multiple media (e.g., a centralized or distributed database, and/or associated caches and servers) that store the one or more instructions 4424. The term "machine-readable medium" shall also be taken to include any tangible medium (e.g., a non-transitory medium) that is capable of storing, encoding or carrying instructions for execution by the computer system 4400 and that cause the computer system 4400 to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices, magnetic disks such as internal hard disks and removable disks; magneto-optical disks; and CD-ROM and DVD-ROM disks.

The instructions 4424 may further be transmitted or received over a communications network 4426 using a transmission medium via the network interface device 4420 utilizing any one of a number of well-known transfer protocols (e.g., frame relay, internet protocol (IP), transmission control protocol (TCP), user datagram protocol (UDP), hypertext transfer protocol (HTTP)). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or 5G networks).

The term "transmission medium" shall be taken to include any intangible medium that is capable of storing, encoding, or carrying instructions for execution by the computing system 4400, and includes digital or analog communications signals or other intangible medium to facilitate communication of such software.

As an additional example, computing embodiments described herein may be implemented in one or a combination of hardware, firmware, and software. Embodiments may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

Cassette Examples

The present invention generally relates to medical systems, devices and methods, and more particularly relates to the disinfection of medical systems, medical devices, and areas of medical facilities and equipment. An exemplary embodiment of a disinfection system is disclosed in U.S. Pat. No. 9,675,720 incorporated by reference. Needs for healthcare infection control, challenging and versatile demands for disinfection, and rapid disinfection performance plus rapid maintenance of the disinfection equipment as discussed above are directly addressed by the stackable cassette component.

Some examples of the present invention generally relate to a stackable ultraviolet cassette and to methods for disinfecting or sterilizing More specifically, some examples of the present invention relate to a device for disinfection of a space, surface, or structure, and to methods of disinfection of a space in which the cassette or chamber is placed and/or the surfaces and structures within that space.

Examples may address one or more of the problems and deficiencies of the art discussed above. However, the examples may additionally or alternatively prove useful in addressing other problems and deficiencies in a number of technical areas. Therefore, the scope of embodiments should not necessarily be construed as being limited to addressing any of the particular problems or deficiencies discussed herein.

Some embodiments of the presently-disclosed stackable ultraviolet cassette and methods have several features, no single one of which is solely responsible for their desirable attributes. Without limiting the scope of these devices and methods as defined by the claims that follow, their more prominent features will now be discussed briefly. After considering this discussion, and particularly after reading the section of this specification entitled "Detailed Description of the Invention," one of skill in the art will understand how the features of the various embodiments disclosed herein may provide a number of advantages over the current state of the art. In accordance with some embodiments, these advantages may include, without limitation, providing improved stackable ultraviolet cassette and chambers and methods of which may, inter alia, assist in providing disinfected spaces, surfaces, and/or structures, providing a customizable disinfection exposure area; allowing for appropriate exposure, dosage, and disinfection processes of any spaces, surfaces, and/or structures in need of disinfection; combating the spread of diseases that may be communicated via physical contact with infected areas, providing devices and methods that have highly effective ultraviolet disinfection;

providing devices and methods that are easily integrated within, for example, healthcare logistics; and allowing for disinfection in a fast, safe, and effective manner. The presently-disclosed stackable ultraviolet cassette and chamber is designed to be an easily replaceable component of a larger multi-component disinfection system such that failed lamps, ballasts or other integral components may be easily replaced in the field. Once removed from the unit the cassettes may be easily refitted with new lamps, ballasts, or other components and then re-used in other devices. Additional non-limiting unique capabilities of some embodiments of the invention include being buildable and stackable to maximize disinfection field; eradication of 90% or more of pathogenic microorganisms; being compartmentalized to facilitate component replacement; portability, and, being a component that is easily upgradable (i.e. to higher power).

In accordance with examples, a stackable ultraviolet cassette and chamber includes: an ultraviolet source configured to emit ultraviolet light; and, a compartmentalized device capable of being inserted into a larger framework of compartmentalized devices and that, when included in the larger system array, can direct the ultraviolet to the various target surfaces from multiple directions and thereby create a three-dimensional field of multivectored ultraviolet light within which no shadowed areas may harbor microorganisms.

The ultraviolet source may include a plurality of ultraviolet emitting devices such as non-ozone producing low pressure (LP) cylindrical mercury lamps generating a spectral peak at 254 nm wavelength as in the present embodiment or, in future potential embodiments, the ultraviolet light source may be an array of LEDs generating a spectral peak at 250, 251, 252, 253, 254, 255, 260-265-270 nm.

The ultraviolet emitting devices may be inserted in or removed from a larger array of identical devices (cassettes) and the cassettes themselves, which include one or more ultraviolet lamps and UV-reflective backing materials (reflectors), may be considered ultraviolet emitting devices.

The stackable ultraviolet cassette and chamber into which the cassettes are inserted may be selectively reconfigured to achieve a plurality of configurations within the target area.

The stackable ultraviolet cassette and chamber may be controlled by a processor which may be configured to power on a subset of the cassettes while one or more of the other ultraviolet cassettes is powered off.

The cassettes may contain an array of multiple ultraviolet lamps or ultraviolet LEDs. That is, the ultraviolet light source may be a lamp, a cassette composed of multiple lamps, or multiple cassettes. When the system containing the cassettes is extended, ultraviolet light will be emitted in multiple directions and provide considerable ultraviolet exposure to every niche in the room and thereby minimize shadowing effects (or the blockage of ultraviolet light) so as to prevent any potentially hazardous pathogens from surviving the disinfection process.

The stackable ultraviolet cassette and chamber may further include an electronic control system configured to selectively control the amount of ultraviolet radiation emitted from at least one of the cassettes based at least in part on the configuration of the array or number of cassettes within the framework that comprise the chamber.

In accordance with the examples, a method includes: providing a plurality of cassettes that open or extend as part of a larger array of cassettes and framework that will emit ultraviolet into an enclosed or partially enclosed chamber called the Ultraviolet Target Zone (or just the Target Zone) for purposes of disinfection. One or more sets of cassettes will be configured to provide ultraviolet light exposure to all exposed areas of the zone, emitting ultraviolet light from multiple angles and thereby overcoming the problem of shadowing in which pathogens occupying shadowed niches may survive standard room disinfection procedures. The disposition of the cassettes and the arrangement of the ultraviolet lamps on the cassette creates a geometry of surfaces from which light impinges on every exposed point within the Target Zone from multiple directions to create a multivector field of ultraviolet light rays. A minimum of four cassettes may be used to create an enclosed four-sided rectangular area within which ultraviolet radiation can be concentrated on some subject equipment targeted for disinfection. In an alternate embodiment a minimum of three cassettes could be used to enclose a triangular area within which target equipment would be disinfected. For systems with a ceiling or top cassette, a minimum of five cassettes could be utilized to enclose a piece of equipment situated on a floor. For the creation of an enclosed cubical space, a minimum of six cassettes could be utilized.

Specific embodiments of the disclosed device, delivery system, and method will now be described with reference to the drawings. Nothing in this detailed description is intended to imply that any particular component, feature, or step is essential to the invention.

Figure 45:
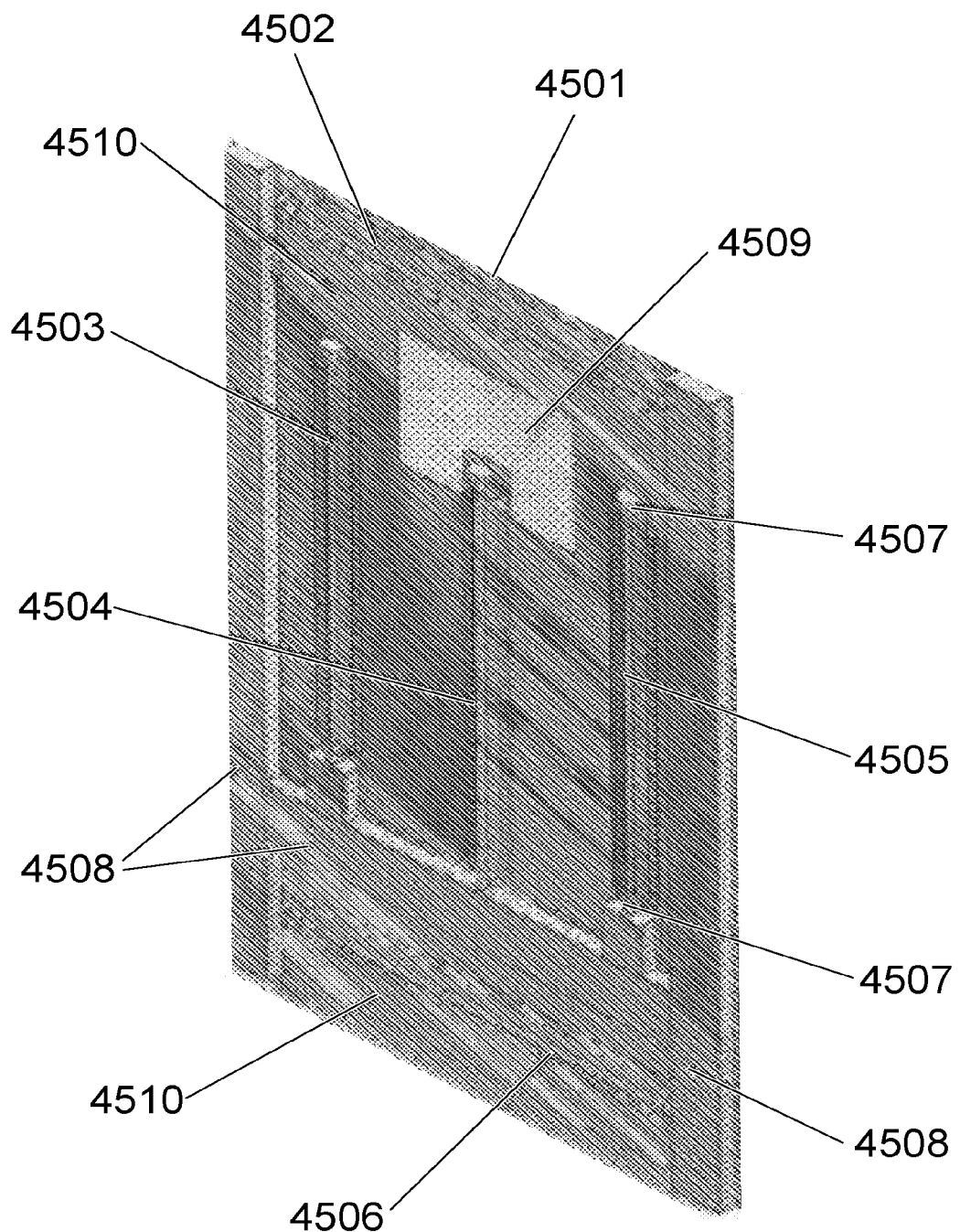
FIG. 45 shows an isometric view of an exemplary embodiment of a modular ultraviolet disinfection cassette.

FIG. 45 shows an isometric view of an exemplary embodiment of a modular ultraviolet disinfection cassette. The cassette 4501 is rectangular and is comprised of five ultraviolet lamps, 4502, 4503, 4504, 4505, and 4506, two-piece lampholders 4507, a set of shells or cover plates 4508, a UV-blocking window 4509 and a reflector plate 4510 made of Alanod™, a polished aluminum sheet that is highly reflective for ultraviolet light. The cassette 4501 in this embodiment is approximately 52 inches (132 centimeters) wide by 71 inches (180 cm) long by 2" (5 cm) thick (maximum) and the other components fit within these dimensions, including the cover plates and the Alanod™ reflector sheet. The ends of the lamps 4502, 4503, 4504, 4505, and 4506 are held on the cassette 4501 by a set of lampholders 4507, which are fixtures in two pieces that hold the lamps at both ends and are bolted or attached by screws to the cassette 4501. The lampholders 4507 are wired at one end and connected to power supplies that provide power. The lampholders 4507 hold the lamps at both ends and thereby hold the lamps parallel to the cassette surface such that the reflective surface reflects and returns the ultraviolet light back towards the Target Zone. The cover plates 4508 are placed over the ballasts and wiring, and are bolted or attached by screws to the cassette 4501. The shape of the cover plates 4508 may be any arbitrary shape that protects the ballasts and wiring, and in this embodiment the cover plates are channels inverted with the concave channel on the inside and the outside smooth and flat. The UV-blocking window 4509, which allows the user to observe the disinfection process, is rectangular, centered, and is disposed in the upper half of the cassette 4501. The UV-blocking window may be of any transparent material that blocks ultraviolet light, including glass and most types of plastic. The ultraviolet lamps in this embodiment are low pressure mercury lamps that generate ultraviolet light at the specific spectrum of 254 nm but can also deploy variations and combinations of wavelengths if desired encompassing the full ultraviolet-C group and/or ultraviolet A and B groups. The five ultraviolet lamps 4502, 4503, 4504, 4505, and 4506 are situated across the surface of the cassette 4501 in a manner that distributes the emitted ultraviolet light across a defined area called the Target Zone, which then concentrates the emitted ultraviolet light on a particular surface. The irradiance field created by the multiplicity of lamps on the several cassettes is such that the ultraviolet light rays will strike any surface within the Target Zone from multiple directions and thereby minimize the shadowed areas that might otherwise allow survival of microbes in the protection of those shadows.

In FIG. 1, the three lamps 4503, 4504, and 4505 have their axes oriented vertically across the approximate center of the cassette and parallel to each other while the remaining two lamps 4502 and 4506 are oriented with their axes horizontally above and below the three vertical lamps 4503, 4504, and 4505 while running parallel to each other and preferably perpendicular to the vertical lamps. Optionally, in this or other embodiments, the cassette 4501 may take a plurality of shapes and sizes, including inter alia, rectangular, square, triangular, circular, shapes with uneven side lengths and angles, etc. Optionally, in this or other embodiments, the surface of the cassette 4501 may be comprised of any material that is highly reflective in the UV spectrum and which enhances the reflected UV light from the lamps, including inter alia, reflective mylar, magnesium hydroxide, calcium carbonate, and ePTFE™ Optionally, in this or other embodiments, the reflectors 4510 of the surface of the cassette may be glued, cemented, bolted or attached by any other comparable means. Optionally, in this or other embodiments, the UV-blocking window 4509 may be any shape and size. Optionally, in this or other embodiments, the UV-blocking window 4509 may be disposed anywhere on the cassette 4501 and may further be made of either UV-blocking glass or plastic. Preferably the embodiment and window placement within or throughout the stackable cassette 4501 will provide visualization of the Target Zone to the operator. Therefore, placement of the window 4509 could be around 50 inches (127 cm) from the ground so an operator of average height can easily view the UV Target Zone through the window 4509 from the non-ultraviolet source side of the stackable cassette. Optionally, in this or other embodiments, the cassette 4501 may comprise one or more lamps of any shape, size, or type although using at least two or more lamps allows the ultraviolet light to be emitted from more than one location on the cassette surface and thereby allows better production of multivectored light. However, in some embodiments the cassette is intended to be part of an array of cassettes that generate multivectored light, there can be 0, 1, 2 and up to 50 number of lamps per cassette if desired depending on the application, build or stackable chamber desired. Quantity of lamps is variable with commercial application. In ideal embodiments for hospital applications, there are 1 to 5 lamps per cassette 4501. Optionally, in this or other embodiments, the one or more lamps may be disposed in virtually any configuration including perpendicular to the cassette surface, although in the current configuration orienting the lamps parallel and close to the cassette reflector 4510 surface is more efficient overall and allows for the thinnest possible cassette and therefore the least weight. Multiple cassettes can be used to create a three-dimensional array of cassettes that deliver ultraviolet light from multiple directions towards a Target Zone. Optionally, in this or other embodiments, some or all of the lamps may be oriented horizontally on the cassette. Optionally, in this or other embodiments, some or all of the lamps may be oriented vertically or protrude away from the cassette surface. Optionally, in this or other embodiment, some or all of the lamps may be oriented transverse to each other. Optionally, in this or other embodiments, the lamps may have multiple orientations and may be configured either parallel or perpendicular to the cassette surface. Optionally, in this or other embodiments, the one or more lamps may comprise non-ozone producing low pressure (LP) cylindrical mercury lamps generating a spectral peak at 254 nm wavelength or may employ MP lamps generating broad spectrum ultraviolet light. Optionally, in this or other embodiments the one or more lamps may be replaced with an ultraviolet source that comprise an array of light emitting diodes (LEDs) generating a spectral peak at 265 nm or any other ultraviolet wavelength. Combinations thereof may also be used in any example.

Figure 46:
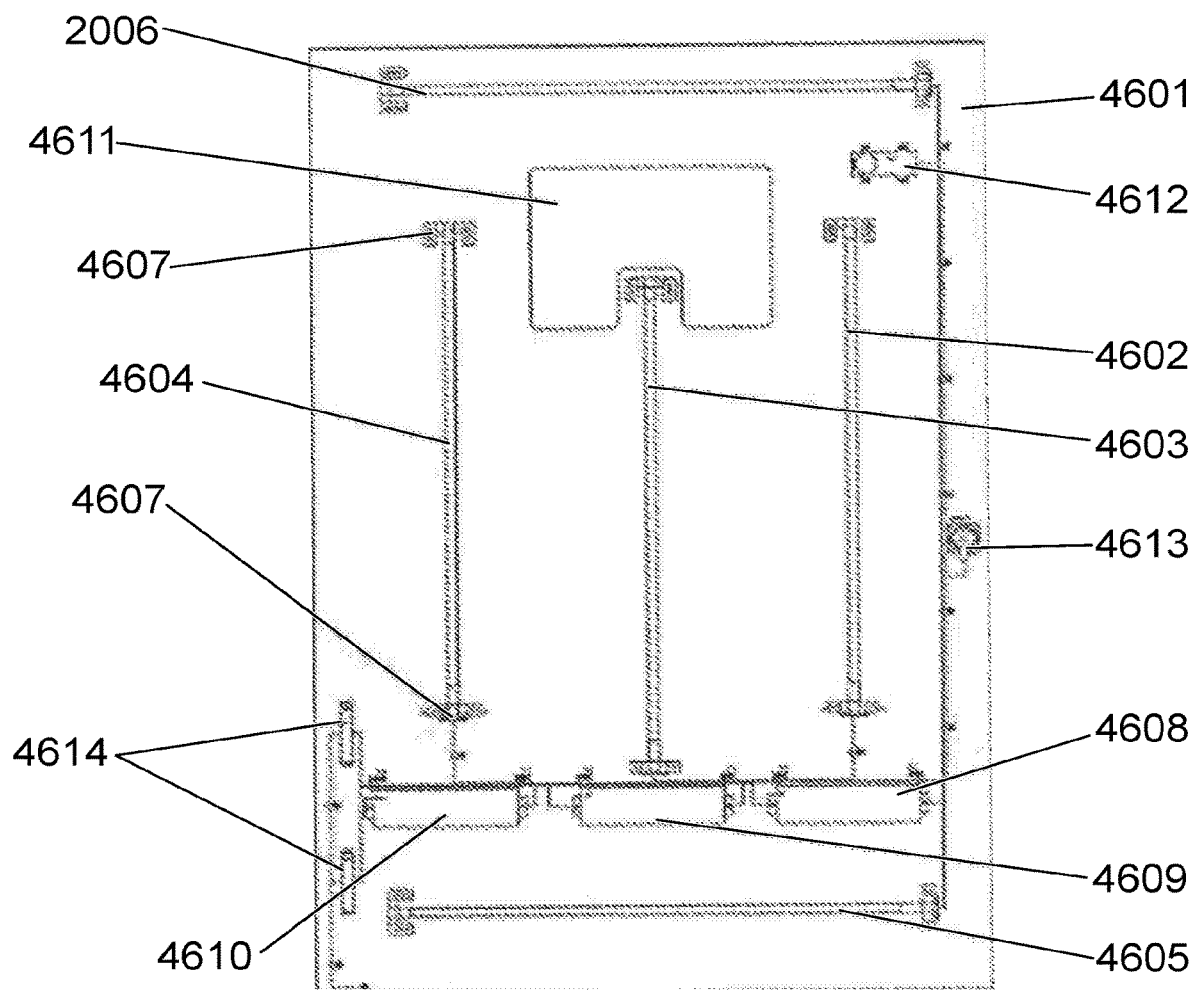
FIG. 46 shows a front view of an exemplary embodiment of a modular ultraviolet disinfection cassette.

FIG. 46 shows a front view of an exemplary embodiment of a modular ultraviolet disinfection cassette without cover plates. The cassette 4601 comprises five ultraviolet lamps 4602, 4603, 4604, 4605, and 4606 along with associated lampholders 4607, which houses the lamp ballasts 4608, 4609 and 4610, associated wiring, and a UV blocking window 4611. The ballasts are attached by bolts or screws to the cassette 4601 and are configured to connect to a main power line. The ballasts are positioned and attached to the surface of the cassette such that the cassette has the lowest possible profile and such that the ballasts can be covered by a cover plate. The ballasts may be disposed in a variety of locations on the cassette but are preferably disposed and located such as to minimize the total amount of wiring necessary and to lower the overall center of gravity of the cassette for purposes of stability of a chamber. The cassette 4601 further comprises a motion sensor 4612, a UV meter 4613, and terminal blocks 4614. The motion sensor is configured to turn the lamps off if someone should appear on the wrong side of the system during operation. The UV meter provides feedback in terms of the level of UV irradiance to help determine whether any part of the system (e.g. lamps or ballasts) has failed during operation. The terminal blocks provide connections for the wiring on board the cassette 4601. The cassette includes various bolt holes or threaded holes for attaching the lampholders 4607, the ballasts 4608, 4609 and 4610, the window 4611, the motion sensor 4612, the UV meter 4613, and a pair of terminal blocks 4614. The bolt holes or screw holes are positioned as necessary to accommodate optimal placement of the various components. In other embodiments the bolt holes or screw holes may be replaced with other attachment methods including snap locks, weldments, and glue, etc. Optionally, in this or any other embodiments, the motion sensor, UV meter, and terminal blocks may be disposed anywhere on the cassette and may be attached by any suitable means including weldments and glue.

Figure 47:
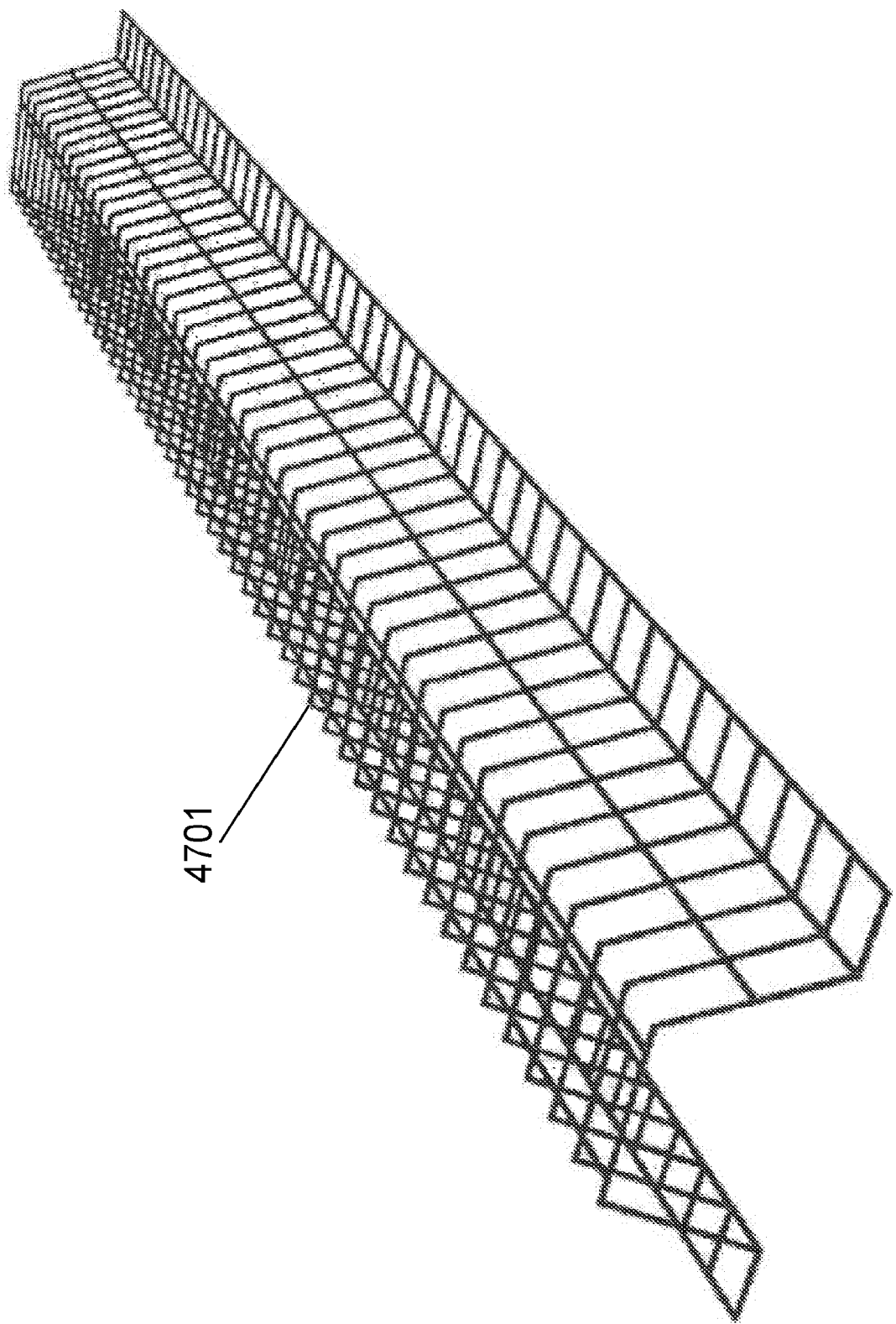
FIG. 47 shows an exemplary embodiment of a wire mesh cage.

FIG. 47 shows an exemplary embodiment of a wire mesh 4701. The wire mesh 4701 is configured to rest over the one or more lamps to protect the lamps from impacts and damage during use. The cage 4701 is made of steel. In this or other embodiments, the one or more lamps on a cassette may be protected by a UV-transparent window made of plastic or fused quartz which would either envelope each individual lamp or else would be a sheet of glass covering all the lamps. In other embodiments this protection may be provided by UV-transparent plastic sheets or by a wire mesh made of UV-reflective materials such as ePTFE™ The wire mesh or protective sheets may sit close to the lamp surface and even be in contact with the lamp surface or may be a few lamp diameters away as in the current embodiment. In other embodiments the protection against the effects of lamp breakage may be provided by currently used and available UV-transparent Teflon or plastic coatings that directly wrap around and seal the lamps.

Figure 48:
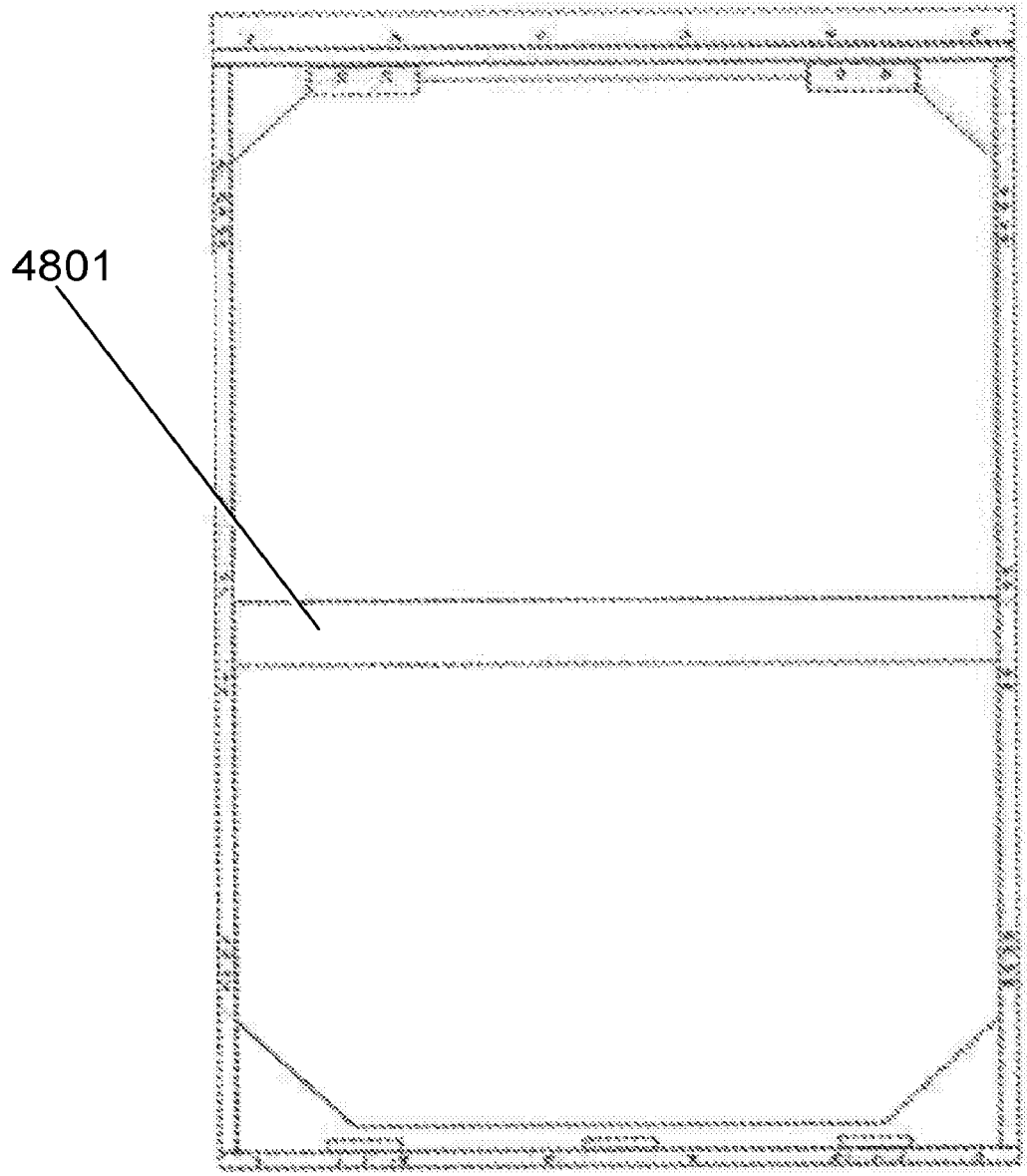
FIG. 48 shows a front view of an exemplary embodiment of a frame to which an exemplary embodiment of a modular ultraviolet disinfection cassette may attach.

FIG. 48 shows a front view of an exemplary embodiment of a frame 4081 to which an exemplary embodiment of a modular ultraviolet disinfection cassette may attach and form a framework by attaching and stacking multiple cassettes. The frame 4801 provides structural support and would, in some embodiments, attach to a central column of a disinfection system by hinges or coupling links or permanently attach to a wall of a building or hospital by methods of the coupling links. The frame 4801 would be supported on casters or by the coupling links and be a floating framework that can create a chamber and be attached to a central column or wall on which a control unit would be mounted. The frame 4801 and framework would be composed of an outer rectangular structure made from fundamental structural components such as box frames, channels or I-beams made from steel, aluminum, plastic or other suitable materials. The frame should include one or more structural beams across the midsection for stability and one or more triangular or other structural components in the corners, as in the current embodiment, to buttress the overall structure orthogonally.

Figure 49:
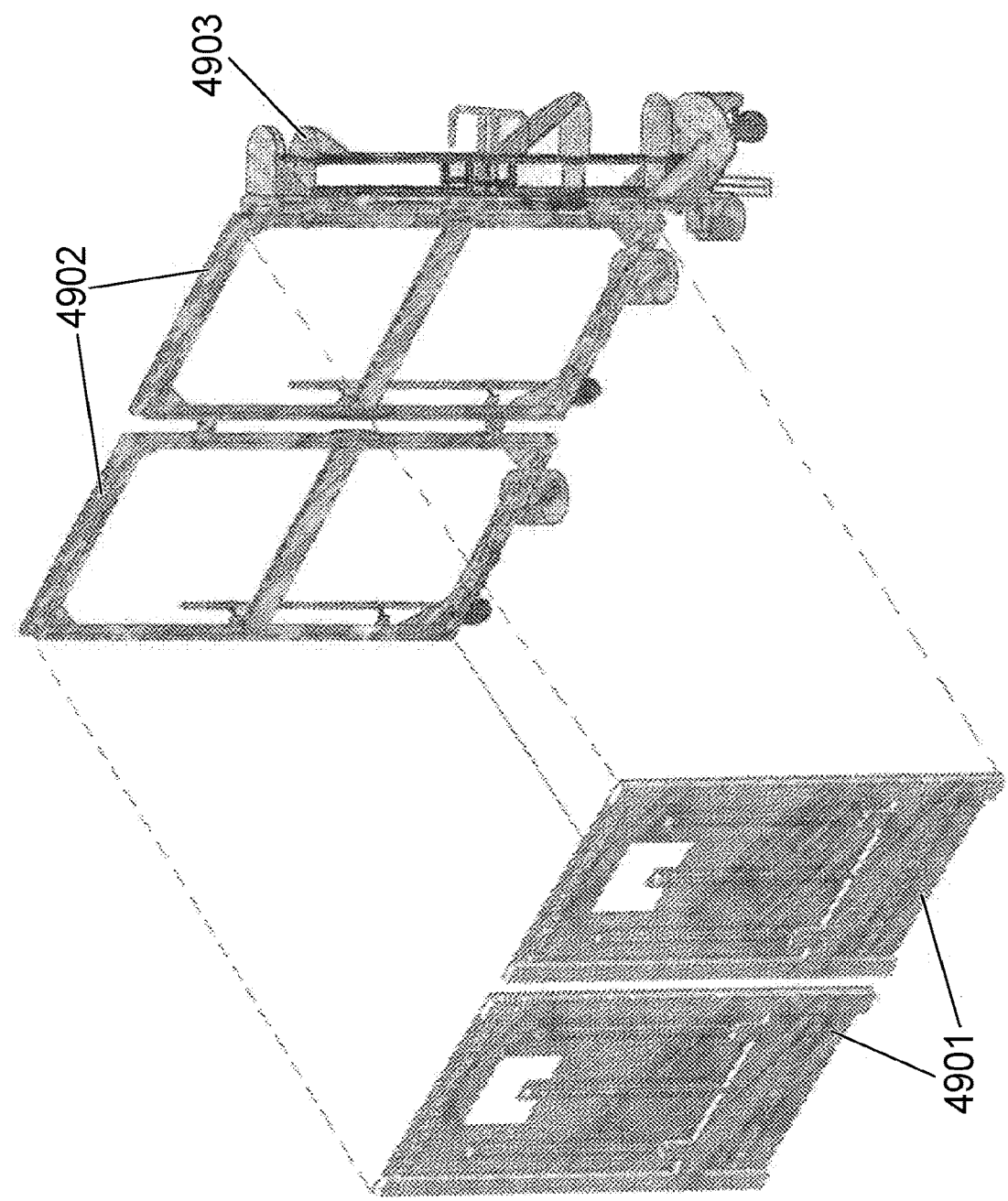
FIG. 49 shows an exemplary embodiment of a cassette being disposed in a frame for a stackable cassette and chamber.

FIG. 49 show an exemplary embodiment of a pair of rectangular cassettes 4901 and the pair of frames 4902 to which they will be attached as part of a mobile framework or chamber that includes a central column 4903. The rectangular cassettes 4901 may be any of the rectangular embodiments described herein. The rectangular frames 4902, may be any of the rectangular embodiments described herein. Each cassette 4901 would attach to a frame 4902 with bolts or screws, or any other suitable attachment method that allows for and facilitates replacement of the cassette and which may include magnetic locks or mechanical snaps that lock the cassette to the frame for easy removal. Attachments would be such that the cassette would be secured to the frame regardless of the position the system is placed, whether it be vertical or hanging from the ceiling in embodiments in which the cassettes are placed overhead as part of a disinfection system. The frames 4902 will attach to the central column 4903 via hinges such that the cassettes 4901 may be oriented at various angles that allow the formation of different geometries suitable for specific disinfection applications, including closed geometries such as squares, rectangles, hexagons, octagons and cubes, and open geometries such as half-circles, rectangular corridors, flat extended walls, or angled walls (open triangles). The hinged connections may be of any type that facilitates the shaping of the intended geometry and may include flexible hinges, axial hinges, or universal joints that may allow cassettes or arrays of cassettes to be turned at multiple angles. The disinfection device as shown in the current embodiment includes casters to facilitate mobility and these casters may or may not be present on each cassette and may or may not be present on the central column as long as there a sufficient minimum number of casters to support the weight of the whole disinfection device in its various configurations, these being the shapes to which the system is conformed for specific applications.

Figure 50:
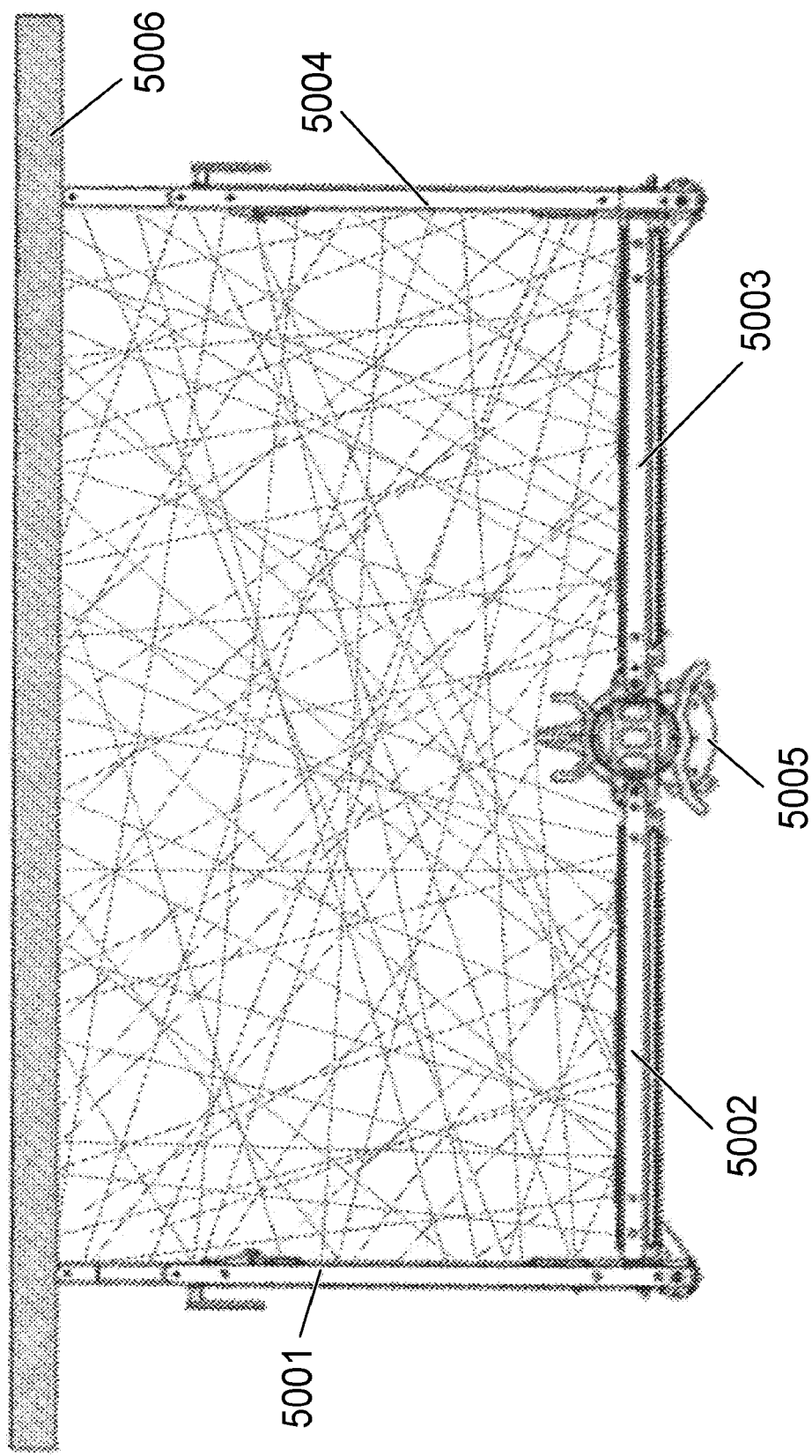
FIG. 50 shows an exemplary embodiment of the cumulative effect of the multivectored light created from a plurality of cassettes.

FIG. 50 shows an exemplary embodiment of the cumulative effect of the multivectored light issuing from a plurality of cassettes and shows figurative rays of light issuing from the cassettes and reflecting off the interior surfaces. The four cassettes 5001, 5002, 5003, and 5004 are connected to a central column 5005, and the four cassettes each produce rays of multivectored light that will reflect off the cassettes and also reflect off the wall 5006 to a degree that depends on the reflectivity of the wall. Together, the four cassettes with their integral ultraviolet lamps create a field so full of multivectored light, or light coming from multiple directions, that shadowed zones are minimized, thereby minimizing the zones where microorganisms might escape the disinfection process. The sum total effect of the sources of ultraviolet light (here, the 5001, 5002, 5003, and 5004 cassettes and the ultraviolet lamps they contain) is to create a volumetric field of multivectored light of fairly even intensity within the Target Zone where the possibility of microbes avoiding UV exposure within shadowed niches is minimized. Optionally, in this or other embodiments, the cassettes may be arranged in squares, rectangles, triangular shapes, or other two-dimensional geometries or, in further embodiments, may be arranged in three-dimensional fully enclosed shapes such as cubes, rectangular boxes, chambers and the like. Optionally, in this or other embodiments, the resulting multivector field is so full of light that no shadowed zones are created in which microorganisms might escape the disinfection process. Optionally, in this or other embodiments, four or more sets of cassettes are configured to provide UV radiation exposure to multiple areas of a room, emitting UV light from multiple angles. Optionally, in this or other embodiments, a minimum of four cassettes is utilized to create an enclosed four-sided rectangular area within which UV-radiation can be concentrated on some subject equipment targeted for disinfection as an example something as small as a medical or surgical tool and the stackable ultraviolet light cassettes and framework can scale to encompass something as large as a space shuttle and large space equipment needing disinfection. Optionally, in this or other embodiments, a minimum of two cassettes may be used to enclose a triangular area within which target equipment, target area, or target surfaces may be disinfected, sterilized, or sanitized. Optionally, in this or other embodiments, five cassettes may be used in a system with a ceiling or top cassette too enclose a piece of equipment or space or target area on a floor or surface. Optionally, in this or other embodiments, six cassettes may be used to create an enclosed cubical or rectangular space. Optionally, in this or other embodiments, the one or more cassettes of a disinfection device may have differing sizes and shapes relative to each other.

Figure 51:
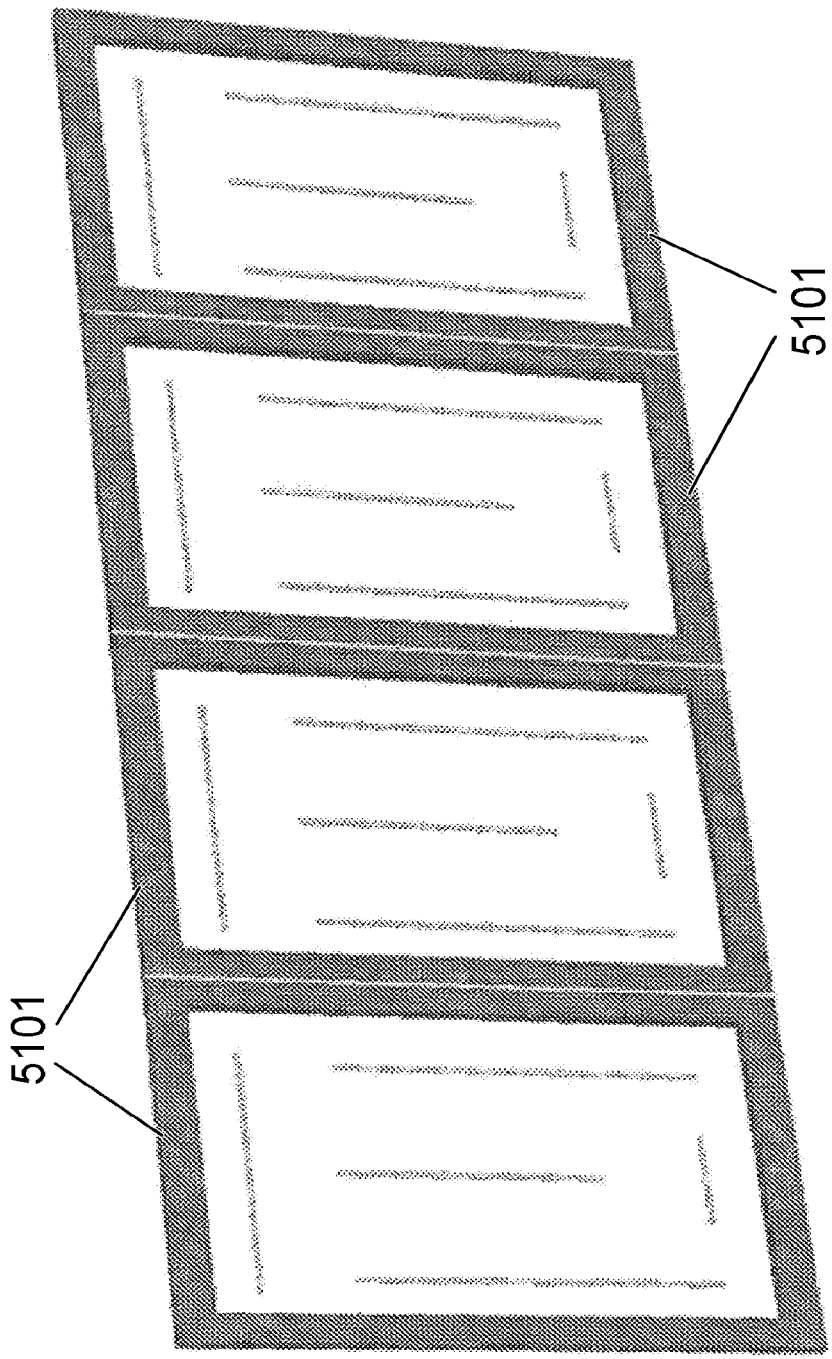
FIG. 51 shows an exemplary embodiment of four (4) rectangular cassettes coupled together in an array framework.

FIG. 51 shows an exemplary embodiment of four (4) rectangular cassettes coupled together in an array framework. In this exemplary embodiment, the four rectangular cassettes 5101 are arranged as a flat wall. The control panel is neglected in this Figure for simplicity. This Figure illustrates the current embodiment of the invention in which four rectangular cassettes form a disinfection device that can be configured to a variety of shapes such as a square or rectangular enclosure, or that can be faced against a wall for disinfection purposes.

Figure 52:
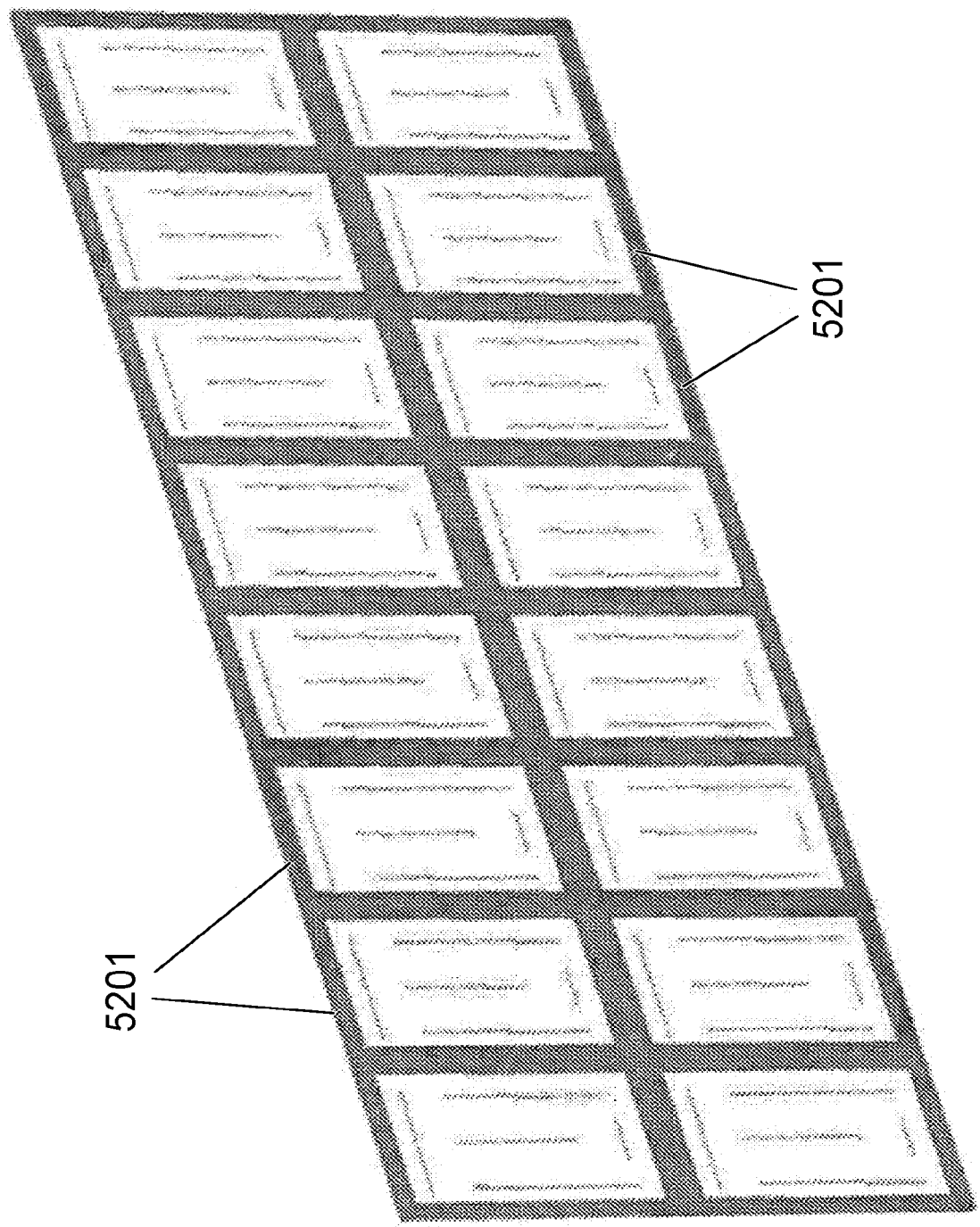
FIG. 52 shows an exemplary embodiment of sixteen (16) rectangular cassettes coupled together in a stacked array framework.

FIG. 52 shows an exemplary embodiment of sixteen (16) rectangular cassettes coupled together in a stacked array framework. In this embodiment, multiple rectangular cassettes 8001 are lined up and stacked to create a much larger surface than FIG. 7. Optionally, in this and other embodiments, stacking of multiple cassettes can be used for large applications or can be used to create large enclosed Ultraviolet Target Zones.

Figure 53:
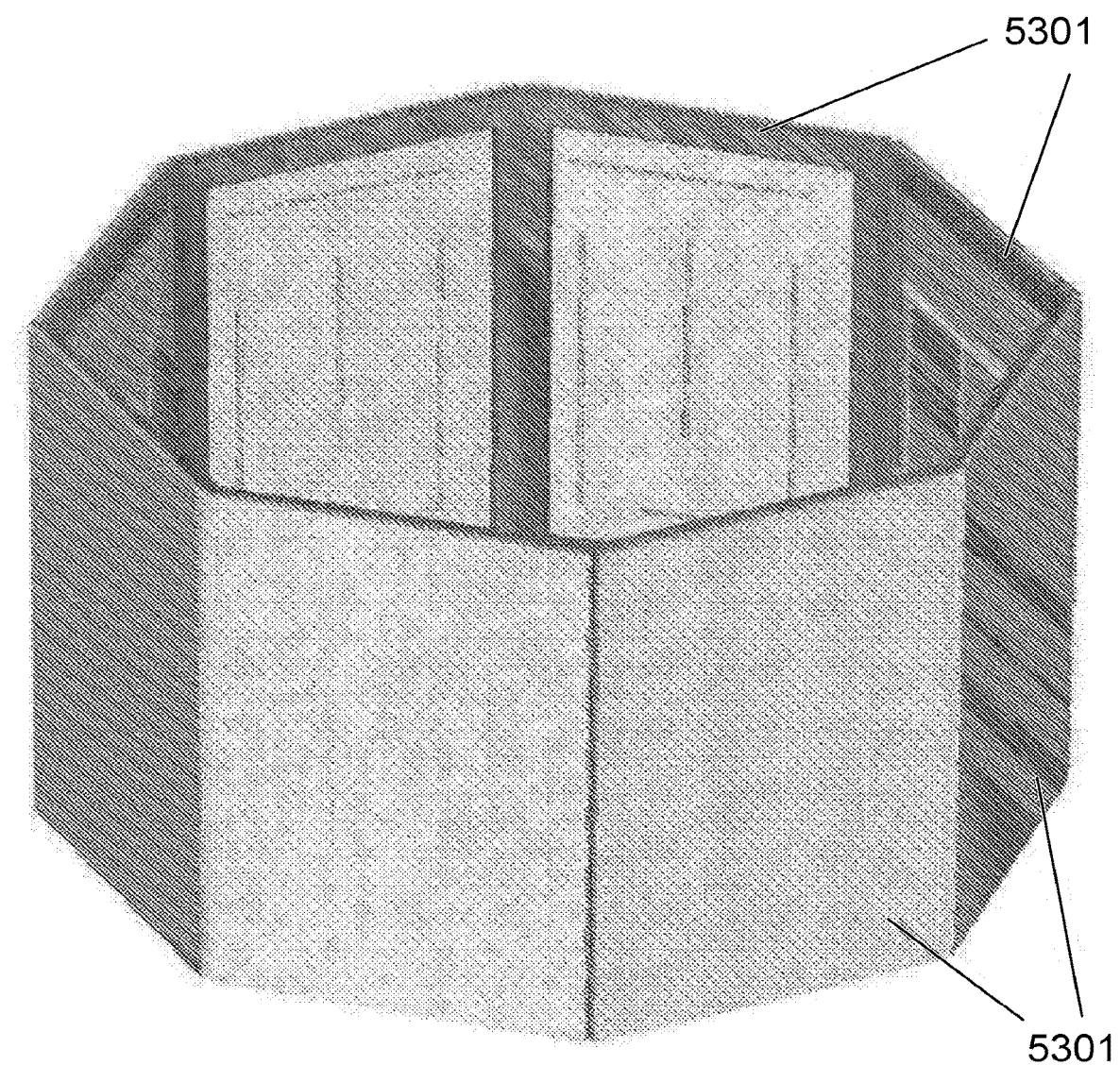
FIG. 53 shows an exemplary embodiment of eight (8) rectangular cassettes coupled together in an octagonal chamber arrangement to create an Ultraviolet Target Zone of concentrated multivector light.

FIG. 53 shows an exemplary embodiment of eight (8) rectangular cassettes coupled together in an octagonal chamber arrangement to create an Ultraviolet Target Zone of concentrated multivector light. In this embodiment, configuration of eight rectangular cassettes 5301 are arranged in an octagon to enclose an Ultraviolet Target Zone.

Figure 54:
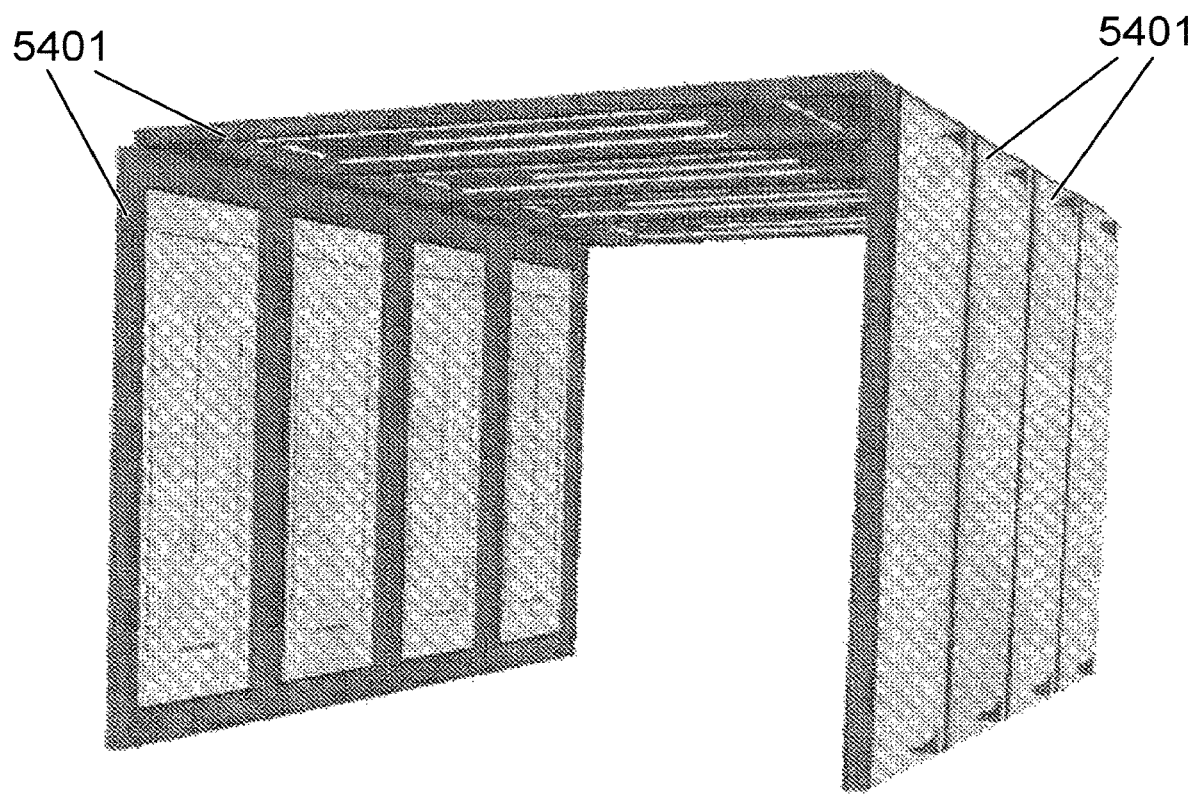
FIG. 54 shows an exemplary embodiment of twelve (12) rectangular cassettes coupled together with four (4) on the left, four (4) on the right, and four (4) overhead to create a corridor chamber through which items may pass and be disinfected.

FIG. 54 shows an exemplary embodiment of twelve rectangular cassettes 5501 arranged with four cassettes on each side and four on the top side to create an enclosed space within which an Ultraviolet Target Zone could be used as a corridor through which equipment could be passed for disinfection. In this and other examples the speed at which the equipment passes through the ultraviolet corridor would determine the ultraviolet dose received. Optionally, in this and other embodiments, the corridor could be lengthened with any number of cassettes necessary to achieve the appropriate ultraviolet dose at any velocity and could be adapted to, for example, assembly lines that operate at a particular speed or velocity.

Figure 55:
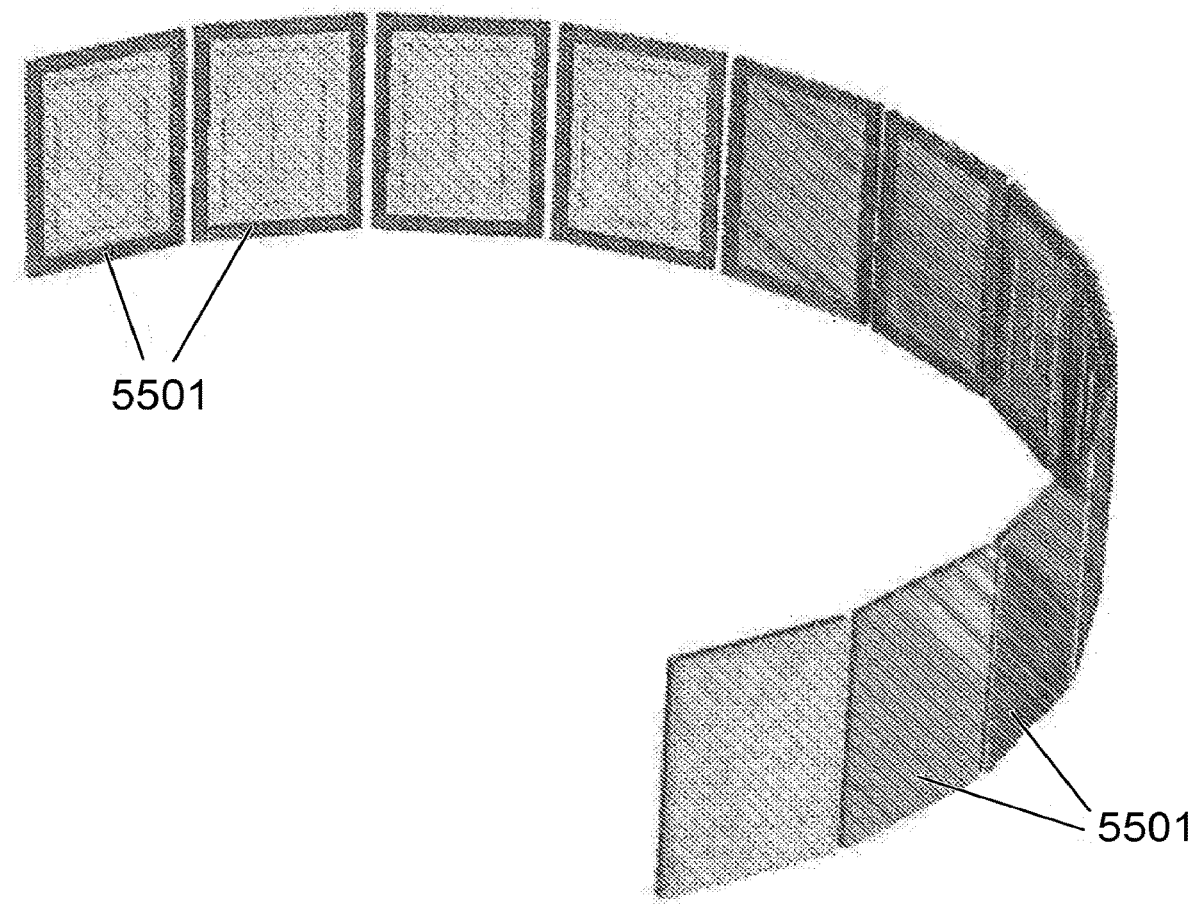
FIG. 55 shows an exemplary embodiment of twelve (12) rectangular cassettes coupled together in a semicircle chamber within which is created an Ultraviolet Target Zone.

FIG. 55 shows an exemplary embodiment of twelve (12) rectangular cassettes coupled together in a semicircle chamber within which is created an Ultraviolet Target Zone. In this embodiment, multiple interlocking rectangular cassettes 5501 could be arranged in a semicircle, or a complete circle if necessary, to provide disinfection of large areas or equipment. Optionally, in this and other embodiments, such circular arrangements could also be stacked to any reasonable height.

Figure 56:
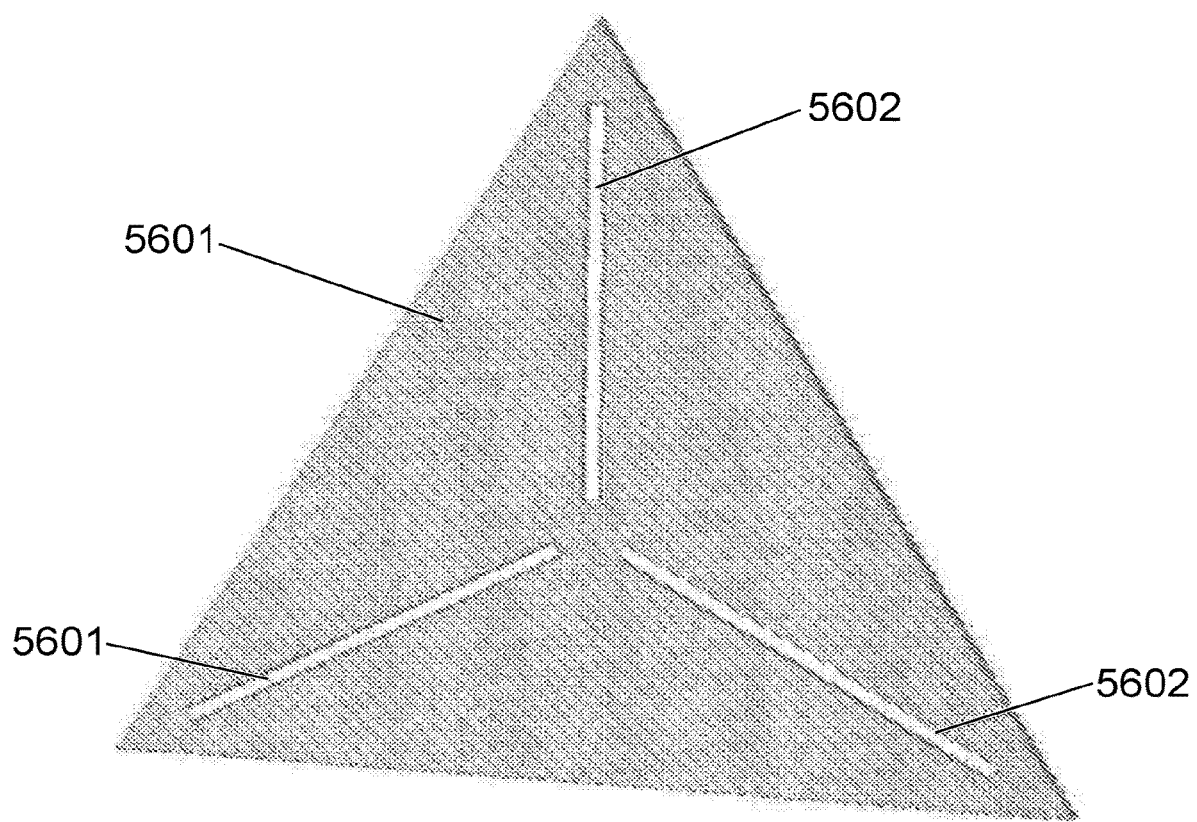
FIG. 56 shows an exemplary embodiment of a triangular cassette containing three ultraviolet lamps which may form a chamber of three-dimensional shapes such as geodesic domes within which is created an Ultraviolet Target Zone.

FIG. 56 shows an exemplary embodiment of a triangular cassette 5601 containing three ultraviolet lamps 5602. This alternate shape for the cassettes, which have heretofore been described as rectangular, could be combined or stacked to create shapes that may not be easily formed from rectangles, including spheres and geodesic domes.

Figure 57:
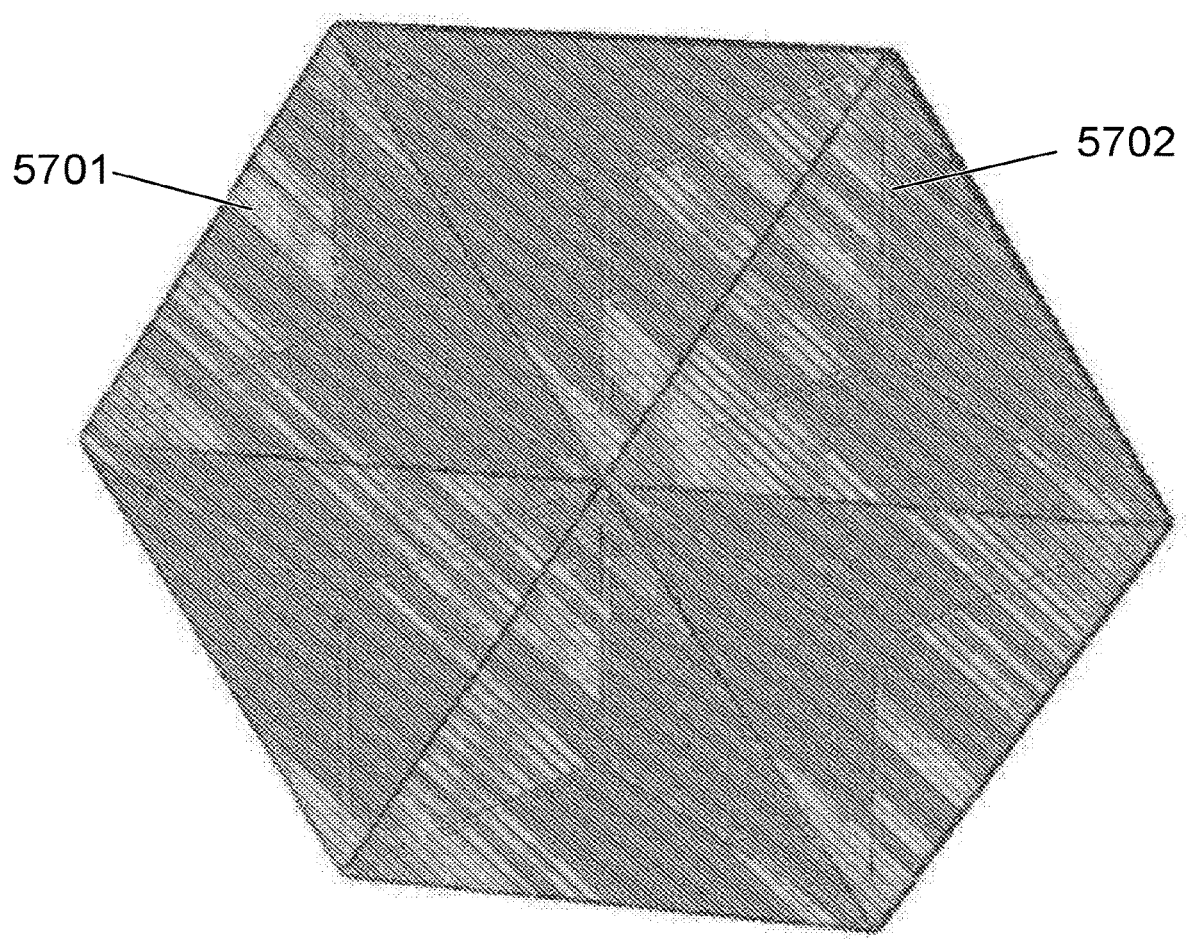
FIG. 57 shows an exemplary embodiment of an array of triangular cassettes forming a hexagonal structure that may form part of a geodesic dome within which is created an Ultraviolet Target Zone.

FIG. 57 shows an exemplary embodiment of how six interlocking triangular cassettes 5701, each containing three ultraviolet lamps 5702, can be used to create a hexagon, either a flat hexagon or a hexagon with a raised center point that can be used to create geodesic domes.

Figure 58:
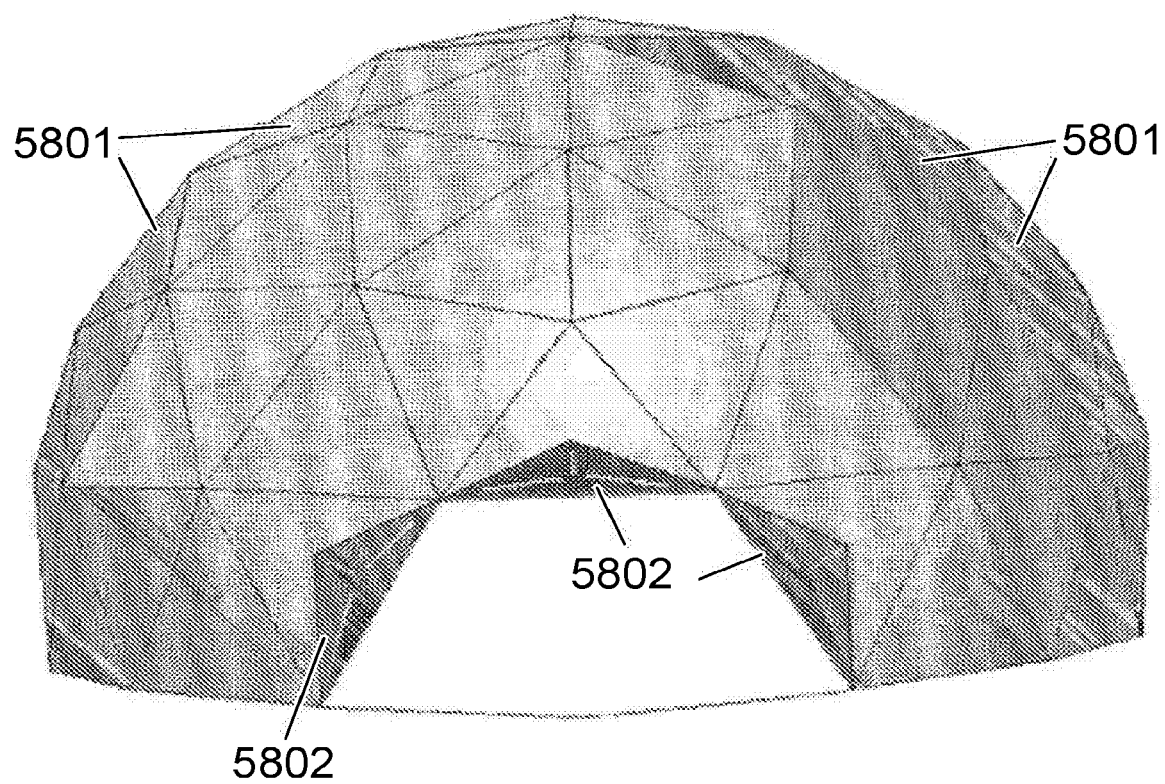
FIG. 58 shows an exemplary embodiment of a geodesic dome composed of triangular cassettes that form a chamber around a completely enclosed Ultraviolet Target Zone.

FIG. 58 shows an exemplary embodiment of how multiple interlocking triangular cassettes 5801 can be combined to create a geodesic dome within which would exist an Ultraviolet Target Zone. This dome would be accessible by doors 5802 created by the unfolding of three triangular cassettes 5801 through which equipment could be brought in. More than three triangular doors could be employed to enclosed very large equipment, or the dome could be assembled around equipment, or even structures that might be contaminated and require disinfection. By creating icosahedrons and extended icosahedrons it is possible to enclose virtually any equipment or structure, including entire buildings.

FIGS. 59A-59D show examples of self-contained interlocking cassettes 5901 and the coupling hinges 5902 & 5903 that would be employed in connecting and stacking arrays of cassettes. FIG. 15A shows a single self-contained cassette 5901 in which ballasts and controls are all included in the cassette itself, and which includes coupling hinges 5902 & 5903 on the sides and top of each cassette such that the cassettes can be coupled to other cassettes and stacked and arranged to enclose any type of three-dimensional space. A male coupled hinge 5902 on the right side of the cassette will couple to a female coupled hinge on the left side of the next cassette, and a male coupled hinge on the top of each cassette will couple to a female coupled hinge on the bottom of a cassette stacked on top of it. In general, the hinge of the coupled hinge can be of hinging that permits a rotation of 180 degrees or more, but other embodiments involving double action hinges that rotate up to 360 degrees can be envisioned that would allow for applying the invention to complex shapes. Various types of hinges can be incorporated in the coupled hinges including strap hinges, Monroe hinges, double action spring hinges, elastic or "natural" hinges, multiple axle hinges, watchband style hinges, double-arm hinges, geared hinges, and universal joint hinges that may be used to rotate cassettes in multiple directions and create non-continuous enclosures. The coupled hinges will be of a type that allows for easy and simple connection or disconnection of two or more cassettes and that may include both power and control connections to link an entire array of multiple cassettes. FIG. 15B shows two self-contained interlocking cassettes 5901 interlocked together in a flat array with male coupled hinges 5902 on the right sides and top, and female coupled hinges on the left and top sides. FIG. 15C shows two self-contained interlocking cassettes 5901 interlocked together in a 90-degree array with male coupled hinges 5902 on the right sides and top, and female coupled hinges 5903 on the left and top sides. In the present embodiment any cassettes could be arranged horizontally or vertically at any angle between 180 degrees and zero degrees (when folded closed) but other embodiments may allow for angles from 0-360 degrees. FIG. 15D shows an example of eight interlocking cassettes 5901 stacked to form a wall and in which each cassette is coupled by the male coupled hinges 5902 on the right side to the female coupled hinges 5903 on the next cassette on the right, and coupled on the top side by the male coupled hinges 5902 to the female coupled hinges 5903 on the cassette above it.

Figure 60A:
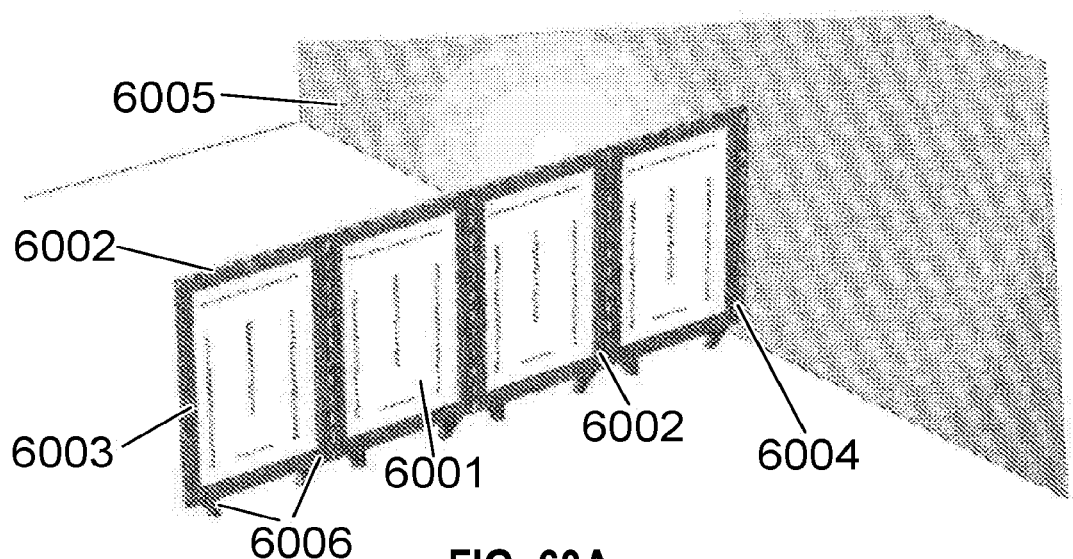
FIGS. 60A-60C show examples of a cassette array employing coupling hinges, and an end-cap for connecting to a wall, illustrated with and without casters, the latter being a free-floating arrangement supported by the wall coupling/interlock, and an image of the cassette array folded up into a compact unit against the wall.
Figure 60B:
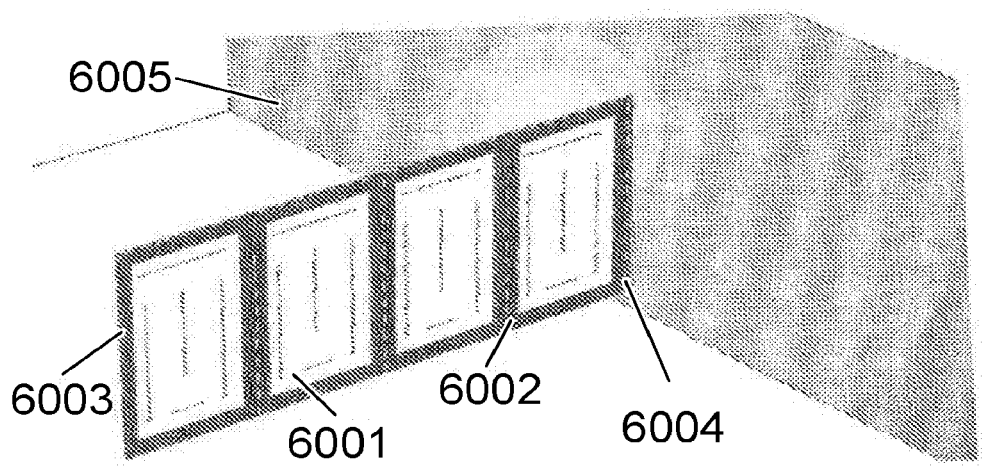
Figure 60C:
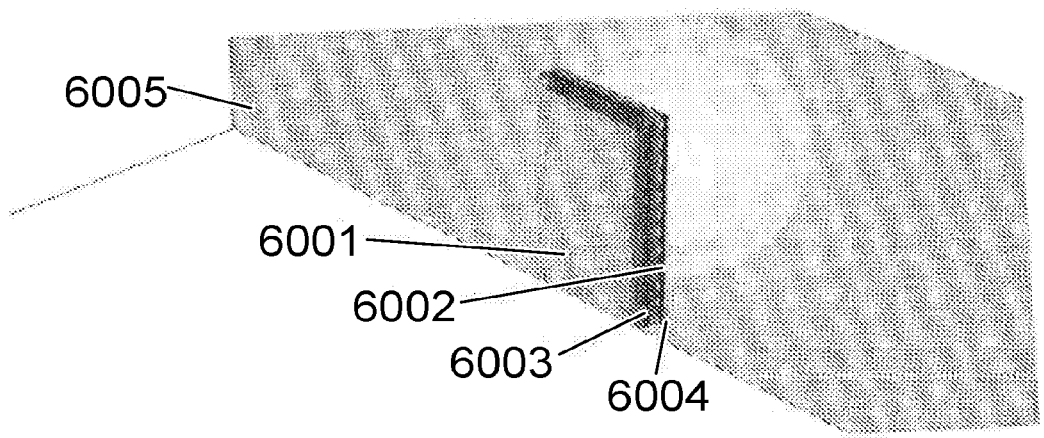

FIG. 60A-C show examples of an array of four cassettes 6001 employing coupling hinges 6002 & 6003, and wall-mounted coupling 6004 for connecting to a wall 6005, illustrated with and without casters 6006, and an image of the array of four cassettes 6001 folded up against the wall for storage. FIG. 60A shows how an array of four interlocking cassettes 6001 employing coupling hinges 6002 & 6003, and which rides or sits on casters 6006, can be mated to a wall 6005 with a wall-mounted coupling 6004 that can facilitate both permanent and temporary installations of the cassette-based disinfection system. The casters 6006 provide mobility and assist the deployment of the cassettes 6001 and support the weight of the cassettes 6001. The casters can also be replaced by structural supports that would be permanently attached or replaceable throughout the frame and or cassettes structures. FIG. 60B shows how an array of four interlocking cassettes 6001 employing coupling hinges 6002 & 6003, can be mated to a wall 6005 with a wall-mounted coupling 6004 that will sit flush with the wall and support the full weight of the cassettes 6001 as they float freely a short distance (i.e. 2, 3, 4, 5, 6, 7, 8, 9 or up to 12 inches) above the floor. FIG. 60C shows how the array of cassettes 6001, either supported by casters as in FIG. 60A or free-floating above the floor as in FIG. 60B can be folded up into a compact arrangement for storage when not in use.

Figure 61:
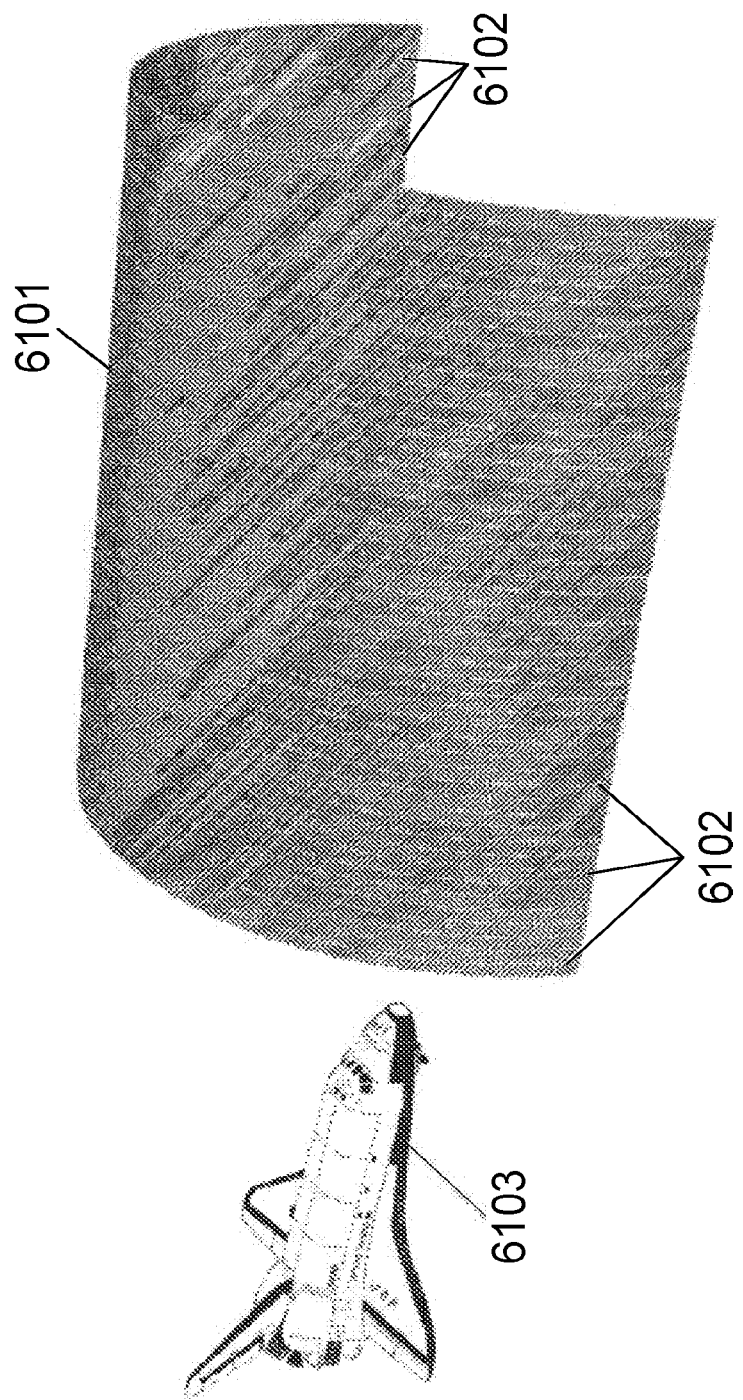
FIG. 61 shows an exemplary embodiment of a figurative application of a large array of self-containing cassettes with coupling hinges stacked and arranged to form a large hangar capable of disinfecting a space shuttle.

FIG. 61 shows a figurative application of a large array of self-contained interlocking cassettes 6102 stacked and constructed to form a large hangar or large chamber 6101 capable of disinfecting a space shuttle 6103.

It should be understood that the functional units or capabilities described in this specification may have been referred to or labeled as components or modules, in order to more particularly emphasize their implementation independence. Component or modules may be implemented in any combination of hardware circuits, programmable hardware devices, other discrete components. Components or modules may also be implemented in software for execution by various types of processors. An identified component or module of executable code may, for instance, comprise one or more physical or logical blocks of computer instructions, which may, for instance, be organized as an object, procedure, or function. Nevertheless, the executables of an identified component or module need not be physically located together but may comprise disparate instructions stored in different locations which, when joined logically together, comprise the component or module and achieve the stated purpose for the component or module. Indeed, a component or module of executable code may be a single instruction, or many instructions, and may even be distributed over several different code segments, among different programs, and across several memory devices.

Similarly, operational data may be identified and illustrated herein within components or modules and may be embodied in any suitable form and organized within any suitable type of data structure. The operational data may be collected as a single data set or may be distributed over different locations including over different storage devices, and may exist, at least partially, merely as electronic signals on a system or network. The components or modules may be passive or active, including agents operable to perform desired functions.

Exemplary embodiments may address one or more of the problems and deficiencies discussed above. However, exemplary embodiments may additionally or alternatively prove useful in addressing other problems and deficiencies in a number of technical areas. Therefore, the scope of embodiments of the present disclosure should not necessarily be construed as being limited to addressing any of the particular problems or deficiencies discussed herein and are only limited by the scope of the claims.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Notes and Examples

The following, non-limiting examples, detail certain aspects of the present subject matter to solve the challenges and provide the benefits discussed herein, among others.

Example 1 is an ultraviolet emitting device comprising, a structure positionable in a target volume and movable between a collapsed position and an expanded position within the target volume; and a plurality of light sources connected to the structure to emit ultraviolet light in a substantially homogenous irradiance within the target volume in any position of the structure between the collapsed position and the expanded position.

In Example 2, the subject matter of Example 1 optionally wherein the plurality of light sources are positioned on the structure to kill at least 90% of organisms within the target volume within a single cycle of operation of the plurality of light sources.

In Example 3, the subject matter of Example 2 optionally includes wherein the single cycle of operation of the plurality of light sources is less than 20 minutes. In Example 4, the subject matter of any one or more of Examples 1-3 optionally include wherein the plurality of light sources are positioned on the structure to kill at least 99.9% of organisms on surfaces within the target volume within a single cycle of operation of the plurality of light sources.

In Example 5, the subject matter of any one or more of Examples 2-4 optionally include wherein the single cycle of operation of the plurality of light sources is less than 3 minutes.

In Example 6, the subject matter of any one or more of Examples 1-5 optionally include wherein the irradiance of every surface in the target volume is substantially homogenous and has a minimum irradiance of between 50 and 800 micro Watts per square centimeter.

In Example 7, the subject matter of any one or more of Examples 1-6 optionally include wherein the target volume is a room having dimensions between 1.5-8 meters in width by 1.5-8 meters in length by 2-5 meters in height.

In Example 8, the subject matter of any one or more of Examples 1-7 optionally include wherein the target volume is a room having dimensions between 6-8 meters in width by 6-8 meters in length by 2-5 meters in height.

In Example 9, the subject matter of any one or more of Examples 1-8 optionally include wherein the structure includes a plurality of arms extendable away from each other to distribute each light source of the plurality of light sources within the target volume such that each light source of each arm is spaced proportionally with respect to the plurality of light sources of that arm.

In Example 10, the subject matter of any one or more of Examples 1-9 optionally include wherein the plurality of light sources is adjustably positionable to emit ultraviolet light in a substantially homogenous irradiance in a plurality of target volumes of various dimensions.

In Example 11, the subject matter of any one or more of Examples 6-10 optionally include wherein the target volume is a room having dimensions of 1.5-6 meters in width by 1.5-6 meters in length by 1.5-6 meters in height, and wherein the plurality of light sources of each arm are spaced from each other along the width every 10-127 centimeters and spaced from each other along the length every 10-127 centimeters.

In Example 12, the subject matter of any one or more of Examples 6-11 optionally include wherein the plurality of light sources of each arm are spaced proportionally from each light source of that arm.

In Example 13, the subject matter of any one or more of Examples 9-12 optionally include wherein the structure includes a base connected to and configured to support each of the plurality of arms such that each of the plurality of arms is extendable away from the base.

In Example 14, the subject matter of Example 13 optionally includes wherein the base and plurality of arms are configured to eliminate shadowing within the target volume when the arms are between the collapsed position and the extended position.

In Example 15, the subject matter of any one or more of Examples 13-14 optionally include wherein the base includes a plurality of compartments, each compartment of the plurality of compartments configured to receive an arm of the plurality of arms therein when the arms are in the collapsed position.

In Example 16, the subject matter of any one or more of Examples 13-15 optionally include wherein the base includes a track extending at least partially around a perimeter of the base and wherein each arm of the plurality of arms is connectable to the track and is configured to move along the track to adjust a position of each of the arms with respect to the plurality of arms.

In Example 17, the subject matter of any one or more of Examples 13-16 optionally include wherein the structure includes a plurality of stands, each stand connected to and configured to support each of the plurality of arms when the plurality of arms is between the collapsed position and the extended position.

In Example 18, the subject matter of Example 17 optionally includes wherein one or more of the base and the plurality of stands includes wheels configured to enable the ultraviolet emitting device to roll within the target volume.

Example 19 is an ultraviolet emitting system comprising: a structure positionable in a target volume and movable between a collapsed position and an expanded position within the target volume; and a plurality of light sources connected to the structure such that each of the light sources of the plurality of light sources is proportionally spaced with respect to each of the light sources as the structure is moved between the collapsed position and the expanded position to emit ultraviolet light in a substantially homogenous irradiance within the target volume in any position between the collapsed position and the expanded position.

In Example 20, the subject matter of Example 19 optionally includes wherein the plurality of light sources are positioned on the structure to kill up to 90% of organisms within the target volume within a single cycle of operation of the plurality of light sources, and wherein the single cycle of operation of the plurality of light sources is less than 300 seconds.

In Example 21, the subject matter of any one or more of Examples 19-20 optionally include a controller connected to and in communication with the plurality of light sources to turn on and off the light sources.

In Example 22, the subject matter of Example 21 optionally includes a motor connected to the structure and in communication with the controller, the controller configured to operate the motor to move the structure between the collapsed position and the expanded position.

In Example 23, the subject matter of Example 22 optionally includes one or more proximity sensors connected to the structure and configured to produce a proximity signal based on a proximity of objects and dimensions of the objects within the target volume relative to the structure.

In Example 24, the subject matter of Example 23 optionally includes wherein the controller is configured to receive the proximity signal from the proximity sensor and to develop a map of objects in the room based on the proximity sensor.

In Example 25, the subject matter of Example 24 optionally includes wherein the controller is configured to operate the motor to move the structure between the collapsed position and the expanded position based on the map of the room.

In Example 26, the subject matter of any one or more of Examples 24-25 optionally include wherein the controller is configured to operate the motor to move the structure between the collapsed position and the expanded position to a predetermined proportionality of the plurality of light sources based on the map of the room.

In Example 27, the subject matter of any one or more of Examples 24-26 optionally include wherein the controller is configured to determine an irradiance set point based on the map and adjust the irradiance emitted by the plurality of light sources based on the irradiance set point.

In Example 28, the subject matter of any one or more of Examples 19-27 optionally include wherein the controller is configured to adjust a power level of individual light sources of the plurality of light sources based on the map and the irradiance set point.

In Example 29, the subject matter of any one or more of Examples 24-28 optionally include wherein the controller is configured to develop a light energy matrix based on a correlation of precise energy and the target volume, and wherein the controller is configured to adjust the irradiance emitted by the plurality of light sources based on the light energy matrix.

In Example 30, the subject matter of any one or more of Examples 21-29 optionally include a tether sensor in communication with the controller, the tether sensor connected to the structure and connectable to a door of the target volume, the tether configured to produce a tether signal based on a position of the door, wherein the controller is configured to disable the light sources with the tether signal indicates that the door is in an open position.

Example 31 is an ultraviolet emitting system comprising, a center support positionable in a target volume and extending along a central axis; a first rail releasably securable to the center support and extending around a periphery of the center support substantially transverse to the central axis; a first arm releasably securable to the first rail and movable along the first rail substantially transverse to the central axis, the first arm movable between a collapsed position and an expanded position; and a first plurality of light sources connected to the first arm such that each of the light sources of the first plurality of light sources is proportionally spaced with respect to each of the light sources as the first arm is moved between the collapsed position and the expanded position.

In Example 32, the subject matter of Example 31 optionally includes wherein the first plurality of light sources is proportionally spaced so as to emit ultraviolet light in a substantially homogenous irradiance within the target volume in any position between the collapsed position and the expanded position.

In Example 33, the subject matter of any one or more of Examples 31-32 optionally include wherein the center support has a geometric shape substantially of a rectangular prism.

In Example 34, the subject matter of any one or more of Examples 31-33 optionally include a second rail releasably securable to the center support and extending around a periphery of the center support substantially transverse to the central axis and substantially parallel to the first rail.

In Example 35, the subject matter of Example 34 optionally includes a second arm releasably securable to the first rail and the second rail and movable along the first rail substantially transverse to the central axis and substantially orthogonally to the first arm, the second arm movable between a collapsed position and expanded position; and a second plurality of light sources connected to the second arm such that each of the light sources of the second plurality of light sources is proportionally spaced with respect to each of the light sources as the second arm is moved between the collapsed position and the expanded position.

In Example 36, the subject matter of Example 35 optionally includes a third arm releasably securable to the first rail and the second rail and movable along the first rail substantially transverse to the central axis, substantially parallel to the first arm, and substantially orthogonally to the second arm, the third arm movable between an expanded position and a collapsed position; and a third plurality of light sources connected to the third arm such that each of the light sources of the third plurality of light sources is proportionally spaced with respect to each of the light sources as the third arm is moved between the collapsed position and the expanded position.

In Example 37, the subject matter of Example 36 optionally includes a fourth arm releasably securable to the first rail and the second rail and movable along the first rail substantially transverse to the central axis, substantially orthogonally to the first arm and the third arm and substantially parallel to the second arm, the fourth arm movable between a collapsed position and the expanded position; and a fourth plurality of light sources connected to the fourth arm such that each of the light sources of the fourth plurality of light sources is proportionally spaced with respect to each of the light sources as the fourth arm is moved between the collapsed position and the expanded position.

In Example 38, the subject matter of any one or more of Examples 31-37 optionally include wherein the first arm includes a plurality of linkages hingeably coupled to each other to enable the first arm to move between the collapsed position and the expanded position.

In Example 39, the subject matter of Example 38 optionally includes wherein the first arm includes a bracket releasably securable to the first rail and connected to the plurality of linkages to connect the first arm to the first rail.

In Example 40, the subject matter of Example 39 optionally includes wherein the first arm includes a second bracket releasably securable to the second rail and connected to the plurality of linkages to connect the second arm to the second rail.

In Example 41, the subject matter of Example 40 optionally includes wherein the first arm includes a cross-member rigidly connecting the first bracket to the second bracket.

In Example 42, the subject matter of any one or more of Examples 39-41 optionally include wherein the first arm includes a roller connected to the first bracket and engageable with the first rail to create a rolling engagement of the first bracket with respect to the first rail to allow translation of the first arm with respect to first rail.

Example 43 is an ultraviolet emitting sanitization system comprising a plurality of mobile ultraviolet light devices, each device comprising: a base positionable in a target volume; a driver connected to the base and engageable with a surface of the target volume; a motor supported by the base and connected to the driver, the motor controllable to operate the driver to cause the base to move with respect to the surface to move the base within the target volume; a light source supported by the base; and a controller in communication with the motor and the light source, the controller operable to position the base within the target volume and configured to operate the light source such that the lights of the plurality of mobile ultraviolet light devices, together, emit ultraviolet light in a substantially homogenous irradiance within the target volume.

In Example 44, the subject matter of Example 43 optionally includes wherein the light sources are positioned with respect to each other to distribute each light source of the plurality of light sources within the target volume such that each light source is spaced proportionally with respect to the plurality of light sources.

In Example 45, the subject matter of any one or more of Examples 43-44 optionally include a central controller in communication with the controller of each of the plurality of mobile ultraviolet light devices, the central controller configured to provide instructions to each of the controllers to; position the mobile ultraviolet light devices within the target volume; position the mobile ultraviolet light devices with respect to each mobile ultraviolet light device; and control ultraviolet light output of each of the light sources.

In Example 46, the subject matter of Example 45 optionally includes wherein each of the plurality of mobile ultraviolet light devices further comprises a proximity sensor connected to the base and configured to transmit a proximity signal to the controller based on a proximity of objects and dimensions of the objects within the target volume.

In Example 47, the subject matter of Example 46 optionally includes wherein the controller is configured to develop a map of the room and objects in the room based on the proximity sensors.

In Example 48, the subject matter of Example 47 optionally includes wherein the controller is configured to operate the motor to move the base within the target volume based on the map of the room.

In Example 49, the subject matter of any one or more of Examples 47-48 optionally include wherein the controller is configured to communicate with the controller of each of the plurality of mobile ultraviolet light devices to develop a destination for each of the plurality of mobile ultraviolet light devices, and is configured to operate the motor to move the base within the target volume based on the map of the room and the destination for each of the plurality of mobile ultraviolet light devices.

In Example 50, the subject matter of any one or more of Examples 44-49 optionally include a remote controller in communication with the controllers of the plurality of mobile ultraviolet light devices and operable to selectively move individual mobile ultraviolet light devices within the target volume, as desired.

In Example 51, the subject matter of any one or more of Examples 43-50 optionally include wherein the plurality of light sources are positioned to kill at least 90% of organisms within the target volume within a single cycle of operation of the plurality of light sources, wherein the single cycle of operation of the plurality of light sources is less than 20 minutes, wherein the substantially homogenous irradiance of every surface in the target volume has a minimum irradiance of between 50 and 800 micro Watts per square centimeter, and wherein the target volume is a room having dimensions between 1.5-8 meters in width by 1.5-8 meters in length by 2-5 meters in height.

Example 52 is a method of sanitizing a target space, the method comprising: positioning a structure in a target volume, and moving the structure between a collapsed position and the expanded position within the target volume to move a plurality of light sources connected to the structure, plurality of light sources configured to emit ultraviolet light in a substantially homogenous irradiance within the target volume in any position between the collapsed position and the expanded position.

In Example 53, the subject matter of Example 52 optionally includes emitting the ultraviolet light to at least 90% of organisms within the target volume in a single cycle of operation of the plurality of light sources, wherein the single cycle of operation of the plurality of light sources is less than 300 seconds, wherein the substantially homogenous irradiance of every surface in the target volume is at least 50 micro Watts per square centimeter.

In Example 54, the subject matter of any one or more of Examples 52-53 optionally include wherein the target volume is a hospital room having dimensions between 2-7 meters in width by 2-7 meters in length by 2-5 meters in height.

In Example 55, the subject matter of any one or more of Examples 52-54 optionally include extending each of the arms of the plurality of arms away from each other to distribute each light source of the plurality of light sources within the target volume such that each light source is spaced proportionally with respect to the plurality of light sources.

In Example 56, the subject matter of Example 55 optionally includes positioning each arm of the plurality of arms in a compartment of a plurality of compartments, when the arms are in the collapsed position.

The method Example 55, further comprising: positioning each arm of the plurality of arms in a compartment of a plurality of compartments, when the arms are in the collapsed position.

In Example 57, the subject matter of any one or more of Examples 55-56 optionally include adjusting a position of each of the arms with respect to the plurality of arms by moving each arm of the plurality of arms along a track connected the base and extending around a perimeter of the base.

In Example 58, the subject matter of any one or more of Examples 55-57 optionally include supporting each arm of the plurality of arms, using a stand, where each stand is configured to support each of the plurality of arms between the collapsed position and the extended position.

In Example 59, the subject matter of any one or more of Examples 52-58 optionally include operating a controller connected to and in communication with the plurality of light sources to turn on and off the light sources.

In Example 60, the subject matter of any one or more of Examples 50-59 optionally include producing, using a proximity sensor connected to the structure, a proximity signal based on a proximity of objects or dimensions of the objects within the target volume.

In Example 61, the subject matter of Example 60 optionally includes developing a map of the room based on the proximity signal.

In Example 62, the subject matter of Example 61 optionally includes operating the motor to move the structure between the collapsed position and the expanded position based on the map of the room.

In Example 63, the subject matter of Example 62 optionally includes determining an irradiance set point based on the map; and adjusting the irradiance emitted by the plurality of light sources based on the irradiance set point.

In Example 64, the subject matter of any one or more of Examples 61-63 optionally include adjusting a power level of individual light sources of the plurality of light sources based on the map and the irradiance set point.

Example 65 is an ultraviolet emitting system for sanitizing a target volume, the system comprising: a plurality of adjustably positionable light sources having a collapsed position and an expanded position, wherein the light sources of the plurality of adjustably positionable light sources are proportionally spaced with respect to each of the light sources as the light sources are moved between the collapsed position and the expanded position to emit ultraviolet light in a substantially homogenous irradiance within the target volume in any position between the collapsed position and the expanded position.

In Example 66, the subject matter of Example 65 optionally includes wherein the plurality of adjustably positionable light sources provides proportionality of the light sources in the expanded position within a plurality of target volumes of various dimensions.

In Example 67, the subject matter of any one or more of Examples 65-66 optionally include wherein the plurality of adjustably positionable light sources further comprises: a base positionable in the target volume; a driver connected to the base and engageable with a surface of the target volume, a motor supported by the base and connected to the driver, the motor controllable to operate the driver to cause the base to move with respect to the surface to move the base within the target volume; a light source supported by the base; and a controller in communication with the motor and the light source, the controller operable to position the base within the target volume.

In Example 68, the subject matter of any one or more of Examples 65-67 optionally include wherein the plurality of adjustably positionable light sources further comprises: a structure positionable in the target volume and operable to move the light sources between the collapsed position and the expanded position within the target volume.

In Example 69, the subject matter of Example 68 optionally includes wherein the base includes a track extending at least partially around a perimeter of the base and wherein each arm of the plurality of arms is connectable to the track and is configured to move along the track to adjust a position of each of the arms with respect to the plurality of arms.

In Example 70, the subject matter of Example 69 optionally includes wherein the structure includes a base connected to and configured to support each of the plurality of arms such that each of the plurality of arms is extendable away from the base.

Example 71 is an ultraviolet emitting device comprising: a structure positionable in a target volume and movable between a collapsed position and the expanded position within the target volume; and a plurality of light sources connected to the structure to emit ultraviolet light in a substantially homogenous irradiance within the target volume in any position between the collapsed position and the expanded position.

In Example 72, the subject matter of Example 71 optionally includes wherein the structure includes a plurality of arms extendable away from each other to distribute each light source of the plurality of light sources within the target volume such that each light source is spaced proportionally with respect to the plurality of light sources.

In Example 73, the subject matter of Example 72 optionally includes wherein the structure includes a base connected to and configured to support each of the plurality of arms such that each of the plurality of arms is extendable away from the base.

In Example 74, the subject matter of Example 73 optionally includes wherein the arms are configured to move between the collapsed position and the expanded position telescopically.

In Example 75, the subject matter of any one or more of Examples 73-74 optionally include wherein each of the arms include a plurality of links hingeably connected.

In Example 76, the subject matter of Example 75 optionally includes wherein the plurality of links are configured to scissor about the hinges to move the arms between the collapsed position and the expanded position.

In Example 77, the subject matter of any one or more of Examples 75-76 optionally include wherein a second arm can be stacked on any of the arms of the plurality of arms.

In Example 78, the subject matter of any one or more of Examples 75-77 optionally include wherein the plurality of arms are movable between the collapsed position and the expanded position to adapt to different room shapes and sizes for a plurality of target volumes.

Example 79 is a modular ultraviolet disinfection assembly comprising: a first cassette comprising: a first coupling element connected to a periphery of the first cassette; and a first plurality of ultraviolet lamps connected to a surface of the first cassette and configured to emit ultraviolet light; and a second cassette comprising: a second coupling element connected to a periphery of the second cassette, the second coupling element releasably couplable to the first coupling element to form a perimeter surrounding and adjacent to a target area to direct ultraviolet light from the first plurality of lamps and the second plurality of lamps to the target area; and a second plurality of ultraviolet lamps connected to a surface of the second cassette and configured to emit ultraviolet light.

In Example 80, the subject matter of Example 79 optionally includes the first cassette further comprising: a plurality of ballasts connected to the surface of the first cassette and electrically connected to the first plurality of ultraviolet lamps to limit current thereto.

In Example 81, the subject matter of any one or more of Examples 79-80 optionally include wherein the first coupling element is a male hinge and the second coupling element is a female hinge.

In Example 82, the subject matter of any one or more of Examples 79-81 optionally include wherein the first coupling element and the second coupling element permit relative rotation of the first cassette by 360 degrees with respect to the second cassette about the first coupling element and the second coupling element when the first coupling element is coupled to the second coupling element.

In Example 83, the subject matter of any one or more of Examples 79-82 optionally include a third cassette comprising: a third coupling element connected to a periphery of the third cassette, and a third plurality of ultraviolet lamps connected to a surface of the third cassette and configured to emit ultraviolet light; wherein the first cassette further comprises an opposing coupling element connected to a periphery of the first cassette opposite the first coupling element, the opposing coupling element releasably couplable to the third coupling element.

In Example 84, the subject matter of Example 83 optionally includes a fourth cassette comprising: a fourth coupling element connected to a periphery the fourth cassette; and a fourth plurality of ultraviolet lamps connected to a surface of the fourth cassette and configured to emit ultraviolet light; wherein the first cassette further comprises a top coupling element connected to a top periphery of the first cassette adjacent the first coupling element and the opposing coupling element, the top coupling element releasably couplable to the fourth coupling element to support the fourth cassette above the first cassette and to permit relative rotation of the fourth cassette with respect to the first cassette when the top coupling element is coupled to the fourth coupling element.

In Example 85, the subject matter of any one or more of Examples 79-84 optionally include wherein the plurality of ultraviolet lamps of the first cassette together with the second plurality of ultraviolet lamps of the second cassette are configured to form an enclosure at least partially around a target area and configured distribute multivectored ultraviolet light around the target area adjacent the first cassette and the second cassette.

Example 86 is a method of arranging multiple ultraviolet lamps within a cassette assembly, the method comprising: providing a first cassette including a first coupling element connected to a periphery the first cassette; connecting a first plurality of ultraviolet lamps to a surface of the first cassette, the first plurality of ultraviolet lamps configured to emit ultraviolet light, providing a second cassette including a second coupling element connected to a periphery of the second cassette; connecting a second plurality of ultraviolet lamps to a surface of the second cassette, the second plurality of ultraviolet lamps configured to emit ultraviolet light; and connecting the first coupling element and the second coupling element to rotatably secure the first cassette to the second cassette.

In Example 87, the subject matter of Example 86 optionally includes connecting a plurality of ballasts to the surface of the first cassette; connecting, electrically, the plurality of ballasts to the first plurality of ultraviolet lamps to limit current thereto.

In Example 88, the subject matter of any one or more of Examples 86-87 optionally include distributing multivectored ultraviolet light within a target area adjacent the first cassette and the second cassette using the first plurality of ultraviolet lamps of the first cassette together with the second plurality of ultraviolet lamps of the second cassette.

In Example 89, the subject matter of any one or more of Examples 86-88 optionally include providing a third cassette including a third coupling element connected to a periphery of the third cassette, and connecting a third plurality of ultraviolet lamps to the surface of the third cassette, the third plurality of lamps configured to emit ultraviolet light.

In Example 90, the subject matter of Example 89 optionally includes connecting an opposing coupling element of the first cassette to the third coupling element, the opposing coupling element connected to a periphery of the first cassette opposite the first coupling element.

In Example 91, the subject matter of any one or more of Examples 86-90 optionally include rotating the first cassette with respect to the second cassette about the first coupling element and the second coupling element when the first coupling element is coupled to the second coupling element.

Example 92 is a modular ultraviolet disinfection assembly comprising: a first cassette comprising a first plurality of ultraviolet lamps connected to a surface of the first cassette and configured to emit ultraviolet light, a second cassette comprising a second plurality of ultraviolet lamps connected to a surface of the second cassette and configured to emit ultraviolet light; and a frame configured to releasably receive and support the first cassette therein and configured to releasably receive and support the second cassette therein adjacent to the first cassette.

In Example 93, the subject matter of Example 92 optionally includes a protective wire mesh cage configured to at least partially enclosed at least one lamp of the first plurality of lamps.

In Example 94, the subject matter of any one or more of Examples 92-93 optionally include a central column connectable to the frame to support the frame, the first cassette, and the second cassette off a floor surface.

In Example 95, the subject matter of Example 94 optionally includes wherein the central column includes a coupling element configured to connect the central column to the frame to allow the frame to rotate with respect to the central column.

In Example 96, the subject matter of any one or more of Examples 94-95 optionally include a plurality of casters connected to the central column and the frame.

In Example 97, the subject matter of any one or more of Examples 94-96 optionally include a third cassette comprising a third plurality of ultraviolet lamps connected to a surface of the third cassette and configured to emit ultraviolet light; a fourth cassette comprising a fourth plurality of ultraviolet lamps connected to a surface of the fourth cassette and configured to emit ultraviolet light; and a second frame configured to releasably receive and support the third cassette therein and configured to releasably receive and support the fourth cassette therein adjacent to the third cassette, the second frame releasably couplable to the frame.

In Example 98, the subject matter of Example 97 optionally includes wherein the second frame includes a hinge connecting the frame to the second frame to allow the frame to rotate with respect to the second frame column.

In Example 99, the devices, systems, and/or method of any one or any combination of Examples 1-98 can optionally be configured such that all elements or options recited are available to use or select from.

The following devices, systems, and/or method can optionally be configured such that all elements or options can be combined with one or more of the examples above.

1) A device with a singular or expandable base structure which can create a physical geometry that translates to a homogenous matrix of light energy emitted by light sources
2) The expandable base is comprised of hinges and coupling joints which allows for a cavity within the base to be formed allowing a space for accommodating a large object for example a hospital bed or surgical table
3) The expandable base structure allows for the simultaneous disinfection of objects and spaces from all sides utilizing one single cycle
4) The expandable base can be utilized for a very small room or scaled for a very large room maintaining a uniform physical geometry 5) The expandable or singular base contains arm which house light sources
6) These arms can be deployed in numerous methods and mechanisms however the mechanisms are designed to proportionally self-adjust the precise distance between the light sources to create a uniform physical geometry dependent on the volume or space being disinfected
7) These arms can telescope
8) These arms can scissor
9) These arms can fold
10) These arms can swivel
11) These arms can layer
12) These arms can build
13) These arms can stack
14) A device with no arms can have a multi base structure containing at least one light source for each base which can be robotically programmed via a controller and logic to scan and identify markers to self-assemble into a predefined uniform physical geometry and achieve this assemble manually or in an automated or robotic method through motors and drivers.
15) A device with a multi base structure can scan with RFID, color schemes, or proximity sensing sensors
16) A device with a multi base, singular base or expandable base structure can accommodate varying dimensions of rooms through adjustable arms in a radial or linear fashion
17) A device with a multi base, singular base or expandable base structure can be motorized to transport, contract and or expand in various rooms based on programmed logic and or indication markers
18) A device with a multi base, singular base or expandable base structure containing light sources create uniform physical geometric delivery systems which construct homogenous volumes of light matrix energy
19) The geometry of the light matrix is self-adjusting to accommodate small rooms or large rooms like a single, double, or sometimes triple hospital room and or small bathrooms
20) The geometry of the light matrix is preprogrammed to achieve precise energy. This precise energy is of varying volumes which are self-adjusting to achieve possible volumes of 250 cubic feet, 4000 cubic feet, and up to 6250 cubic feet 21) Said devices and delivery systems can construct homogenous volumes of energy for different and varying spaces Such spaces can be cylindrical, cube, rectangular, or triangular whereas the delivery system adapts the physical geometry translating to the light energy matrix in correlation with a precise energy calibrate for the precise room or volume
22) Such calibration can be pre-programmed logic or learned logic or intelligence in the room base on spacing or dimension sensors or lasers embedded in the base or arm mechanisms of the device
23) Physical sensors detecting volumes and or physical room can be utilized for calibration
24) Tether sensors can be utilized for dimensions and or safety triggers when fixed to a door of a room and the change in dimension upon a bystander entry will trigger the device to shut down for safety purposes
25) The device can contain a powered motor via A/C or batter operated
26) The device can communicate wirelessly through Wi-Fi or Bluetooth to mobile device and remote monitoring and reporting.

The above detailed description includes references to the accompanying drawings, which form a part of the detailed description. The drawings show, by way of illustration, specific embodiments in which the invention can be practiced. These embodiments are also referred to herein as "examples" Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more" in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An ultraviolet emitting device comprising:
   a center support positionable in a target volume and extending along a central axis;
   a rail coupled to the center support and extending around a periphery of the center support generally transverse to the central axis;
   a first arm coupled to the rail and movable along the rail in a first direction that is generally transverse to the central axis, the first arm movable between a collapsed position and an expanded position;
   a second arm coupled to the rail and movable along the rail in a second direction that is generally transverse to the central axis and generally orthogonal to the first direction, the second arm movable between a collapsed position and an expanded position;
   a first plurality of light sources coupled to the first arm; and
   a second plurality of lights sources coupled to the second arm.

2. The ultraviolet emitting device of claim 1, wherein the first plurality of light sources and the second plurality of light sources are configured to emit ultraviolet light in a substantially homogenous irradiance within the target volume in any position of the first arm and the second arm between their respective collapsed positions and their respective expanded positions.

3. The ultraviolet emitting device of claim 1, wherein an angle of the first arm and the second arm relative to the first rail is adjustable.

4. The ultraviolet emitting device of claim 3, wherein the first plurality of light sources and the second plurality of light sources are configured to emit ultraviolet light in a substantially homogenous irradiance within the target volume for any angle between the first arm and the second arm.

5. The ultraviolet emitting device of claim 1, wherein the first plurality of light sources and the second plurality of light sources are configured to emit ultraviolet light in a substantially homogenous irradiance within the target volume when the first arm and the second arm are symmetric relative to the center support or asymmetric relative to the center support.

6. The ultraviolet emitting device of claim 1, wherein the first plurality of light sources and the second plurality of light sources are configured to emit ultraviolet light in a substantially homogenous irradiance within the target volume for any position of the first arm and the second arm along the rail.

7. The ultraviolet emitting device of claim 1, wherein each one of the first plurality of light sources is proportionally spaced relative to all remaining ones of the first plurality of light sources in any position of the first arm between its collapsed position and its expanded position.

8. The ultraviolet emitting device of claim 7, wherein each one of the second plurality of light sources is proportionally spaced relative to all remaining ones of the second plurality of light sources in any position of the second arm between its collapsed position and its expanded position.

9. The ultraviolet emitting device of claim 1, wherein the first plurality of light sources and the second plurality of light sources are positioned on the first arm and the second arm such that at least 90% of organisms within the target volume are killed within a single cycle of operation of the first plurality of light sources and the second plurality of light sources that is less than 20 minutes.

10. The ultraviolet emitting device of claim 1, wherein an irradiance of a surface in the target volume is substantially homogenous during operation of the first plurality of light sources and the second plurality of light sources, and has a minimum irradiance of between 50 and 800 micro Watts per square centimeter.

11. The ultraviolet emitting device of claim 1, wherein the target volume is a room having dimensions of 1.5-6 meters in width by 1.5-6 meters in length by 1.5-6 meters in height, and wherein the plurality of light sources of each arm are spaced from each other along the width every 10-127 centimeters and spaced from each other along the length every 10-127 centimeters.

12. The ultraviolet emitting device of claim 1, wherein the center support, the first arm, and the second arm are configured to eliminate shadowing within the target volume when the arms are between the collapsed position and the extended position.

13. The ultraviolet emitting device of claim 1, further comprising:
 a controller communicatively coupled to the first plurality of light sources and the second plurality of light sources;
 one or more proximity sensors coupled to the first arm, the second arm, or both, the one or more proximity sensors configured to produce one or more proximity signals based on at least (i) a proximity of one or more foreign objects to the one or more proximity sensors, and (ii) a size of the one or more foreign objects relative to the center support, the first arm, the second arm, or any combination thereof.

14. The ultraviolet emitting device of claim 13, wherein the controller is configured to receive the one or more proximity signals from the one or more proximity sensors and develop a map of the target volume based at least in part on the one or more proximity signals.

15. The ultraviolet emitting device of claim 14, wherein the controller is configured to cause the first plurality of light sources and the second plurality of light sources to achieve a substantially homogeneous irradiance within the target volume by (i) causing the first arm, the second arm, or both the first arm and the second arm to move between their respective collapsed positions and expanded positions based at least in part on the map of the target volume, (ii) adjusting ultraviolet light emitted by one or more of the first plurality of light sources, one or more of the second plurality of light sources, or both, based at least in part on the map of the target volume, or (iii) both (i) and (ii).

16. The ultraviolet emitting device of claim 13, further comprising a tether sensor communicatively coupled to the controller, the tether sensor coupled to the center support and a door of the target volume, the tether sensor configured to produce a tether signal based on a position of the door, the controller configured to disable the first plurality of light sources and the second plurality of light sources in response to the tether signal indicating that the door has moved from a closed position to an open position.

17. The ultraviolet emitting device of claim 1, further comprising an additional rail coupled to the center support and extending around the periphery of the center support generally transverse to the central axis and generally parallel to the first rail, the first arm and the second arm being coupled to the additional rail.

18. The ultraviolet emitting device of claim 1, wherein the center support is configured to receive a center support of an additional ultraviolet emitting device, such that (i) the center support of the ultraviolet emitting device is stacked on top of the center support of the additional ultraviolet emitting device, or (ii) the center support of the additional ultraviolet emitting device is stacked on top of the center support of the ultraviolet emitting device.

19. The ultraviolet emitting device of claim 1, wherein the center support is configured to be coupled to a wall of the target volume, a ceiling of the target volume, or both.

20. An ultraviolet emitting device comprising:
 a cylindrical center support positionable in a target volume and extending along a central axis;
 a generally circular rail coupled to the center support and extending around a circular periphery of the center support;
 a plurality of arms coupled to the rail and movable along the rail in a plane that is generally transverse to the central axis, each of the plurality of arms movable between a collapsed position and an expanded position; and
 a plurality of light sources coupled to the plurality of arms,
 wherein the plurality of light sources is configured to emit ultraviolet light in a substantially homogeneous irradiance within the target volume for any position of each of the plurality of arms between the collapsed position and the expanded position, and for any position of each of the plurality of arms along the circular rail.

* * * * *